US012753163B2

(12) United States Patent
Achab et al.

(10) Patent No.: US 12,753,163 B2
(45) Date of Patent: Oct. 6, 2026

(54) DIAMINOPYRIMIDINE CARBOXAMIDE INHIBITORS OF HPK1

(71) Applicant: MERCK SHARP & DOHME LLC, Rahway, NJ (US)

(72) Inventors: Abdelghani Achab, Melrose, MA (US); David A. Candito, Wrentham, MA (US); Anthony Donofrio, Cambridge, MA (US); Xavier Fradera, Boston, MA (US); Shuhei Kawamura, Cambridge, MA (US); Samuel M. Levi, Medford, MA (US); Bing Li, Towaco, NJ (US); Anilkumar G. Nair, Morganville, NJ (US); Alexander Pasternak, Jamaica Plain, MA (US); Brandon A. Vara, Boston, MA (US); Elsie C. Yu, Brighton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 592 days.

(21) Appl. No.: 18/251,259

(22) PCT Filed: Nov. 4, 2021

(86) PCT No.: PCT/US2021/057971

§ 371 (c)(1),
(2) Date: May 1, 2023

(87) PCT Pub. No.: WO2022/098809

PCT Pub. Date: May 12, 2022

(65) Prior Publication Data

US 2023/0416225 A1 Dec. 28, 2023

Related U.S. Application Data

(60) Provisional application No. 63/111,389, filed on Nov. 9, 2020.

(51) Int. Cl.

| | |
|---|---|
| ***C07D 401/12*** | (2006.01) |
| ***A61K 31/506*** | (2006.01) |
| ***A61K 45/06*** | (2006.01) |
| ***A61P 35/00*** | (2006.01) |
| ***C07D 239/49*** | (2006.01) |
| ***C07D 401/14*** | (2006.01) |
| ***C07D 403/12*** | (2006.01) |
| ***C07D 405/12*** | (2006.01) |
| ***C07D 405/14*** | (2006.01) |
| ***C07D 409/14*** | (2006.01) |
| ***C07D 413/14*** | (2006.01) |

(Continued)

(52) U.S. Cl.

CPC .......... *C07D 401/12* (2013.01); *A61K 31/506* (2013.01); *A61K 45/06* (2013.01); *A61P 35/00* (2018.01); *C07D 239/49* (2013.01); *C07D 401/14* (2013.01); *C07D 403/12* (2013.01); *C07D 405/12* (2013.01); *C07D 405/14* (2013.01); *C07D 409/14* (2013.01); *C07D 413/14* (2013.01); *C07D 417/14* (2013.01); *C07D 451/02* (2013.01); *C07D 471/04* (2013.01); *C07D 487/04* (2013.01); *C07D 498/04* (2013.01)

(58) Field of Classification Search

None

See application file for complete search history.

(56) References Cited

U.S. PATENT DOCUMENTS

| | | | |
|---|---|---|---|
| 6,187,759 | B1 | 2/2001 | Tarpey et al. |
| 10,266,500 | B2 | 4/2019 | Bennett et al. |

FOREIGN PATENT DOCUMENTS

| | | | |
|---|---|---|---|
| CA | 3076276 | A1 | 3/2019 |
| WO | 2009136995 | A2 | 11/2009 |

(Continued)

OTHER PUBLICATIONS

Tolba ((2020), Revolutionizing the landscape of colorectal cancer treatment: The potential role of immune checkpoint inhibitors, Int. J. Cancer., 147, 2996-3006) (Year: 2020).*

(Continued)

*Primary Examiner* — Juliet C Switzer
*Assistant Examiner* — Dawanna Shar-Day White
(74) *Attorney, Agent, or Firm* — Patricia A. Shatynski; John C. Todaro

(57) ABSTRACT

Compounds of the formula I: or the pharmaceutically acceptable salts thereof, are inhibitors of haematopoietic progenitor kinase 1 (HPK1) useful in the treatment of diseases or disorders associated with HPK1. Also disclosed herein are uses of these compounds in the potential treatment or prevention of an HPK1-associated disease or disorder. Also disclosed herein are compositions comprising one or more of the compounds. Further disclosed herein are uses of these compositions in the potential prevention or treatment of an HPK1-associated disease or disorder.

I

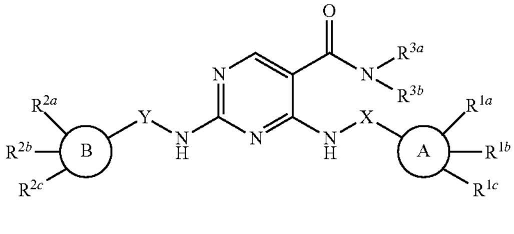

13 Claims, No Drawings

(51) Int. Cl.
*C07D 417/14* (2006.01)
*C07D 451/02* (2006.01)
*C07D 471/04* (2006.01)
*C07D 487/04* (2006.01)
*C07D 498/04* (2006.01)

(56) References Cited

FOREIGN PATENT DOCUMENTS

| | | | |
|---|---|---|---|
| WO | 2012007589 | A1 | 1/2012 |
| WO | 2012145569 | A1 | 10/2012 |
| WO | 2014095956 | A1 | 6/2014 |
| WO | 2018102366 | A1 | 6/2018 |
| WO | 2019090198 | A1 | 5/2019 |

OTHER PUBLICATIONS

Pubchem, SID 403902744, Available Date: Jan. 25, 2020 [retrieved on Jan. 26, 2022]. . . Retrieved from the Internet URL:https://pubchem.ncbi.nlm.nih.gov/substance/403902744 entire document (10 pages).
Pubchem, SID 421133283, Modify Date: Aug. 18, 2020 [retrieved on Dec. 13, 2021].,Retrieved from the Internet URL: https://pubchem.ncbi.nlm.nih.gov/substance/42:1133283 entire document (6 pages).
Vara, Brandon et al., Discovery of Diaminopyrimidine Carboxamide HPK1 Inhibitors as Preclinical Immunotherapy Tool Compounds, ACS Medicinal Chemistry Letters, 2021, 653-661, 12.

* cited by examiner

DIAMINOPYRIMIDINE CARBOXAMIDE INHIBITORS OF HPK1

CROSS-REFERENCE TO RELATED APPLICATIONS

This application is a U.S. National Stage application of International Patent Application No. PCT/US21/057971, filed Nov. 4, 2021, which claims priority to U.S. Provisional Patent Application No. 63/111,389, filed Nov. 9, 2020.

BACKGROUND OF THE INVENTION

Cancer immunotherapy is treatment that uses the human body's own immune system to help fight cancer. This unique approach has witnessed significant clinical successes in the treatment of a variety of tumor types in recent years, particularly with the application of immune checkpoint inhibitors and chimeric antigen T cell therapy. Two of the most investigated checkpoint blockades (i.e., CTLA4 and PD-1 inhibitors) have demonstrated remarkable antitumor activity by overcoming immunosuppressive mechanisms at the tumor site. CTLA4 blockade predominantly enhances T cell activation during the priming phase of the immune response, whereas PD-1 inhibitors appear to release exhausted but otherwise activated effector T cell populations and reduce regulatory T cell function. While these monoclonal antibody-based T cell interventions have proven to be effective, utility of this approach is limited as they can only target receptors on the cell surface. To the contrary, small-molecule T cell activators offer the opportunity to target both extracellular and intracellular immune targets including kinases. Furthermore, inhibiting immune suppressive kinases has the potential to directly activate T cells, thus bypassing checkpoint inhibitory pathways and overcoming intrinsic and acquired resistance to checkpoint receptor blockade.

Haematopoietic progenitor kinase 1 (HPK1; also known as MAP4K1) is a member of the germinal center kinase family of serine/threonine kinases and is mainly expressed by haematopoietic cells. In T cells, it is believed that HPK1 phosphorylates serine 376 of SLP76 after T cell receptor (TCR) triggers and induces the association of SLP76 with 14-3-3 proteins. Knockdown of HPK1 expression in Jurkat T cells has been shown to increase TCR-induced activation of the IL2 gene. Further, antigen-stimulated T cells from HPK1-deficient mice proliferated more vigorously and produced higher amounts of cytokines as compared to antigen-stimulated T-cells from wild-type mice. Importantly. HPK1-deficient mice developed a more severe form of experimental autoimmune encephalomyelitis (EAE), a model of multiple sclerosis. Both in vitro and in vivo, HPK1 knockout dendritic cells (DC) have demonstrated enhanced antigen presentation function. Particularly, both HPK1 knockout T cells and HPK1 knockout DCs have been implicated in tumor rejection in a murine model of lung cancer. These findings have validated HPK1 as a novel target for anti-cancer immunotherapy. Inhibition of HPK1 with small molecule inhibitors therefore has the potential to be a treatment for cancers and other disorders. Compounds disclosed herein are useful in the potential treatment or prevention of HPK1-related diseases.

SUMMARY OF THE INVENTION

Compounds of the formula I:

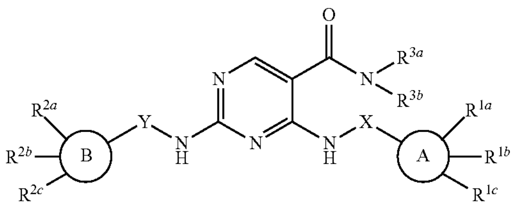

I or pharmaceutically acceptable salts thereof, are inhibitors of haematopoietic progenitor kinase 1 (HPK1) useful in the treatment of diseases or disorders associated with HPK1. Also disclosed herein are uses of these compounds in the potential treatment or prevention of an HPK1-associated disease or disorder. Also disclosed herein are compositions comprising one or more of the compounds. Further disclosed herein are uses of these compositions in the potential prevention or treatment of an HPK1-associated disease or disorder.

DETAILED DESCRIPTION OF THE INVENTION

The present invention is directed to compounds of the formula I:

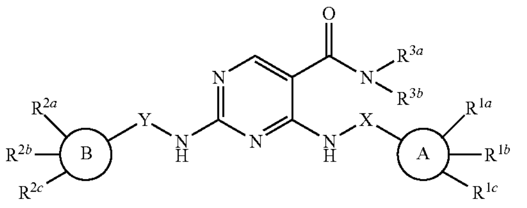

I wherein:

A is a phenyl, cycloalkyl, or heterocyclyl ring;

B is a phenyl, pyrazolyl, pyridyl, pyrimidinyl, benzofuranyl, benzothiophenyl, 2,3-dihydro-indenyl, 2,3-dihydro-isoindolyl, thiazolyl, tetrahydro-benzazepinyl, tetrahydroisoquinolinyl, or $C_{3-6}$cycloalkyl;

X is a bond, or —$C_{1-3}$alkyl-, which is unsubstituted or substituted with hydroxyl;

Y is a bond, —$C_{1-3}$alkyl-, cyclopropyl or —(CO)—, with the proviso that Y is only —(CO)— if B is $C_{3-6}$cycloalkyl;

$R^{1a}$, $R^{1b}$ and $R^{1c}$ as are present are independently selected from:

(1) hydrogen, (2) halogen, (3) hydroxyl, (4) $C_{1-6}$alkyl, which is unsubstituted or substituted with substituents selected from: hydroxy, —O—$C_{1-6}$alkyl, —$NH_2$, —NH($C_{1-6}$alkyl), —N($C_{1-6}$alkyl)$_2$, —CN, —(CO)NH($C_{1-6}$alkyl), —(CO)NH($C_{1-6}$alkyl)$_2$, —(CO)NH($C_{1-6}$alkyl-$CO_2$H), phenyl, and fluoro, (5) —O—$C_{1-6}$alkyl, which is unsubstituted or substituted with substituents selected from: hydroxy, methoxy, —(CO)NH($C_{1-6}$alkyl), —(CO)O($C_{1-6}$alkyl), —CN, and fluoro, (6) —$C_{3-10}$cycloalkyl, which is unsubstituted or substituted with substituents selected from: hydroxy, methoxy, —$C_{1-6}$alkyl, —$C_{2-6}$alkenyl, —$C_{2-6}$alkynyl, —(CO)NH($C_{1-6}$alkyl), —(CO)O($C_{1-6}$alkyl), —CN, and fluoro,
(7) $C_{2-6}$alkynyl,
(8) —$NH_2$,
(9) —NH($C_{1-6}$alkyl),
(10) —N($C_{1-6}$alkyl)$_2$,
(11) —(CO)($C_{1-6}$alkyl),
(12) —(CO)$NH_2$,
(13) —(CO)NH($C_{1-6}$alkyl),
(14) —(CO)NH($C_{3-6}$cycloalkyl),
(15) —NH(CO)($C_{1-6}$alky),
(16) —S—$C_{1-6}$alkyl,
(17) —$SO_2$—$C_{1-6}$alkyl.
(18) —$SO_2NH_2$,
(19) —CN,
(20) keto,
(21) -phenyl,
(22) -pyridyl,
(23) -diazolyl,
(24) -morpholinyl,
(25) -oxazolyl,
(26) -oxadiazolyl.
(27) -piperazinyl.
(28) -piperidinyl,
(29) -pyrazolyl.
(30) -thiazolyl, and
(31) -triazolyl, or $R^{1a}$ and $R^{1b}$ may be joined to form a phenyl, 1,4-dioxanyl, 1,3-dioxolanyl, morpholinyl, oxazolyl, piperidinyl, pyrazolyl, pyrrolidinyl, tetrahydrofuranyl, tetrahydropyranyl, tetrahydroquinolinyl, or thiazolyl ring, which is unsubstituted or substituted with $C_{1-6}$alkyl, or one of $R^{1a}$, $R^{1b}$ and $R^{1c}$ may be joined by a $C_{3-6}$alkyl to one of $R^{2a}$, $R^{2b}$ and $R^{2c}$;

$R^{2a}$, $R^{2b}$ and $R^{2c}$ as are present are independently selected from:
(1) hydrogen,
(2) halogen,
(3) hydroxyl,
(4) $C_{1-6}$alkyl, which is unsubstituted or substituted with substituents selected from: hydroxy, fluoro, —(CO)NH($C_{1-6}$alkyl), —(CO)O($C_{1-6}$alkyl), —$SO_2$—$C_{1-6}$ alkyl, $C_{3-6}$cycloalkyl, —CN, —O—$C_{1-6}$alkyl, —(O—$C_{1-6}$alkyl-)$_3$, —$C_{3-6}$cycloalkyl, $C_{2-6}$alkenyl, phenyl, and pyrazolyl which is unsubstituted or substituted with $C_{1-6}$alkyl,
(5) —O—$C_{1-6}$alkyl, which is unsubstituted or substituted with fluoro,
(6) —$C_{3-6}$cycloalkyl, which is unsubstituted or substituted with substituents selected from: hydroxy, methoxy, —$C_{1-6}$alkyl, —$C_{1-6}$alkyl-OH, —(CO)NH($C_{1-6}$alkyl), —(CO)O($C_{1-6}$alkyl), —CN, and fluoro
(7) —$NH_2$,
(8) —NH($C_{1-6}$alkyl),
(9) —N($C_{1-6}$alkyl)$_2$,
(10) —(CO)$C_{1-6}$alkyl,
(10) —(CO)$C_{1-6}$alkyl-fluoro,
(11) —(CO)$C_{1-6}$alkyl-O—$C_{1-6}$alkyl,
(11) —(CO)$C_{1-6}$alkyl-O—$C_{1-6}$alkyl-O—$C_{1-6}$alkyl-O—$C_{1-6}$alkyl,
(12) —(CO)$C_{3-6}$cycloalkyl-$C_{1-6}$alkyl,
(13) —(CO)$C_{3-6}$cycloalkyl-$C_{1-6}$alkyl-fluoro,
(14) —(CO)$C_{3-6}$cycloalkyl-$C_{1-6}$alkyl-amino,
(15) —(CO)$NH_2$,
(16) —(CO)NH($C_{1-6}$alkyl),
(17) —NH(CO)($C_{1-6}$alkyl),
(18) —$SO_2$—$C_{1-6}$alkyl,
(19) —$SO_2$—NH($C_{1-6}$alkyl),
(20) —$SO_2$—N($C_{1-6}$alkyl)$_2$,
(21) azaspiro[3.3]heptanyl, which is unsubstituted or substituted with —$C_{1-6}$alkyl or oxetanyl, which is unsubstituted or substituted with —$C_{1-6}$alkyl,
(22) azetidinyl, which is unsubstituted or substituted with —$C_{1-6}$alkyl or —(CO)O($C_{1-6}$alkyl),
(23)bicyclopentyl, which is unsubstituted or substituted with —$C_{1-6}$alkyl or —(CO)O($C_{1-6}$alkyl),
(24) oxazolyl,
(25) oxadiazolyl,
(26) oxetanyl, which is unsubstituted or substituted with —$C_{1-6}$alkyl,
(27) piperidinyl, which is unsubstituted or substituted with —$C_{1-6}$alkyl or oxetanyl, which is unsubstituted or substituted with —$C_{1-6}$alkyl,
(28) pyrrolidinyl, which is unsubstituted or substituted with oxo or —$C_{1-6}$alkyl, and
(29) thiazolyl,
(30) keto, or $R^{2b}$ and $R^{2c}$ may be joined to form a pyrrolyl, dihydrospiro[1,4'-pyrazolo[1,5-d][1,4]diazepin]-7'(8'H)-one, or dihydro-4H-pyrazolo[1,5-d][1,4]diazepin-one ring, which is unsubstituted or substituted with —$C_{1-6}$alkyl, —$C_{1-6}$alkyl-OH or —$C_{3-6}$cycloalkyl;

$R^{3a}$ and $R^{3b}$ are independently selected from:
(1) hydrogen,
(2) $C_{1-6}$alkyl, and
(3) —$NH_2$;

or a pharmaceutically acceptable salt thereof.

An embodiment of the present invention includes compounds of the formula Ia:

Ia

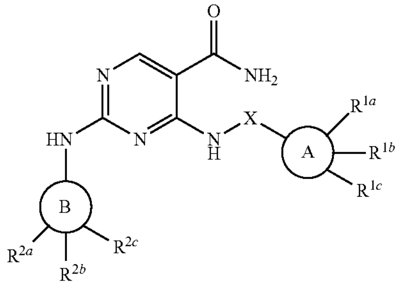

wherein A, B, X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula Ib:

Ib

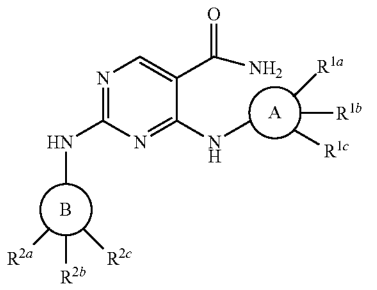

wherein A, B, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula II:

II

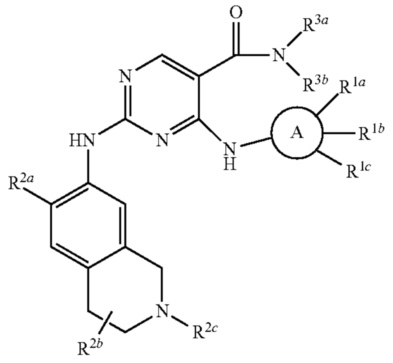

wherein A, $R^{1a}$, $R^{1b}$, $R^{1c}$, $R^{2a}$, $R^{2b}$, $R^{2c}$, $R^{3b}$ and $R^{3b}$ are defined herein; or a pharmaceutically acceptable salt thereof.

An embodiment of the present invention includes compounds of the formula IIa:

IIa

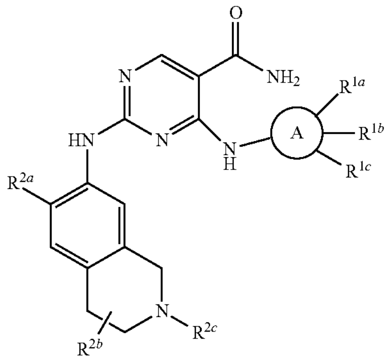

wherein A, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIb:

IId

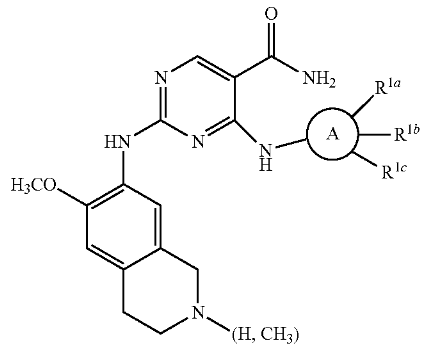

wherein A, $R^{1a}$, $R^{1b}$ and $R^{1c}$ are defined herein, or a pharmaceutically acceptable salt thereof.

An embodiment of the present invention includes compounds wherein A is a phenyl, pyridyl, indenyl, tetrahydronaphthalenyl, tetrahydroisoquinolinyl, pyrazolyl, or 2,3-dihydro-1H-pyrido[2,3-b][1,4]oxazin-7-yl ring. An embodiment of the present invention includes compounds wherein A is a phenyl ring. An embodiment of the present invention includes compounds wherein A is a pyridyl ring. An embodiment of the present invention includes compounds wherein A is an indenyl ring.

An embodiment of the present invention includes compounds wherein B is a tetrahydroisoquinolinyl, phenyl, pyridyl or pyrazolyl ring. An embodiment of the present invention includes compounds wherein B is a tetrahydroisoquinolinyl ring. An embodiment of the present invention includes compounds wherein B is a phenyl ring. An embodiment of the present invention includes compounds wherein B is a pyridyl ring. An embodiment of the present invention includes compounds wherein B is a pyrazolyl ring. An embodiment of the present invention includes compounds wherein B is a pyrazol-4-yl ring. An embodiment of the present invention includes compounds wherein B is a 1H-pyrazol-4-yl ring. An embodiment of the present invention includes compounds wherein B is a thiazolyl ring. An embodiment of the present invention includes compounds wherein B is a 1,2-thiazol-5-yl ring.

An embodiment of the present invention includes compounds wherein X is a bond, or $—(CH_2)—$. An embodiment of the present invention includes compounds wherein X is a bond.

An embodiment of the present invention includes compounds wherein Y is a bond.

An embodiment of the present invention includes compounds wherein $R^{1a}$, $R^{1b}$ and $R^{1c}$ as are present are independently selected from:

(1) hydrogen,
(2) fluoro,
(3) chloro.
(4) bromo,
(5) hydroxyl,
(6) $C_{1-6}$alkyl, which is unsubstituted or substituted with hydroxy, amidoalkyl, amino, aminomethyl, carboxyl, methoxy, phenyl, or one or more fluoro,
(7) —O—$C_{1-6}$alkyl, which is unsubstituted or substituted with one or more fluoro,
(8) $C_{3-6}$cycloalkyl, which is unsubstituted or substituted with cyano, or one or more fluoro,
(9) —S—$C_{1-3}$alkyl,
(10) $—NH_2$,

(11) —NH($C_{1-3}$alkyl),
(12) —N($C_{1-3}$alkyl)$_2$,
(13) —(CO)$NH_2$,
(14) —(CO)NH—$C_{1-6}$alkyl,
(15) keto, and
(16) -phenyl.

An embodiment of the present invention includes compounds wherein $R^{1c}$ is hydrogen and $R^{1a}$ and $R^{1b}$, as are present, are independently selected from:

(1) hydrogen,
(2) fluoro,
(3) bromo,
(4) chloro,
(5) hydroxyl,
(6) —$CH_3$,
(7) —$CHF_2$,
(8) —$CF_3$,
(9) —CN,
(10) —$CH_2OH$,
(11) —$CH_2NH_2$,
(12) —$CH_2CH_3$,
(13) —$CH(CH_3)OH$,
(14) —$CH(CH_3)OCH_3$,
(15) —$CH(CH_3)NH_2$,
(16) —$CH_2CH_2OH$,
(17) —$C(CH_3)_3$,
(18) —$CH_2NH(CH_3)$,
(19) —$CH_2NH(CO)O$—$C(CH_3)_3$,
(20) —$CH_2N(CH_3)CH_2CO_2H$,
(21) —$CH(OCH_3)CH_3$,
(22) —(CO)$NH_2$,
(23) —(CO)$NHCH_3$,
(24) —$OCH_3$,
(25) —$OCF_3$,
(26) —$OCHF_2$,
(27) —$OCH(CH_3)_2$,
(28) —$OCH_2CH_2F$,
(29) —$SCH_3$,
(30) —$N(CH_3)_2$,
(31)cyclopropyl, which is unsubstituted or substituted with —CN, and
(32) phenyl.

An embodiment of the present invention includes compounds wherein $R^{1a}$, $R^{1b}$ and $R^{1c}$ as are present are independently selected from:

(1) hydrogen,
(2) fluoro,
(3) hydroxyl,
(4) —$CH_3$,
(5) —$CHF_2$,
(6) —$CF_3$,
(7) —$CH_2OH$,
(8) —$CH_2CH_3$,
(9) —$C(CH_3)OH$,
(10) —$OCH_3$,
(11) —$OCHF_2$,
(12) —$OCH_2CH_2F$,
(13) —$N(CH_3)_2$,
(14)cyclopropyl, and
(15) phenyl.

An embodiment of the present invention includes compounds wherein $R^{1c}$ is hydrogen, and $R^{1a}$ and $R^{1b}$ may be joined to form a morpholinyl ring.

An embodiment of the present invention includes compounds wherein $R^{1c}$ is methyl, and $R^{1a}$ and $R^{1b}$ may be joined to form a morpholinyl ring.

An embodiment of the present invention includes compounds wherein $R^{1c}$ is hydrogen, and $R^{1a}$ and $R^{1b}$ may be joined to form a tetrahydrofuranyl ring.

An embodiment of the present invention includes compounds wherein $R^{2a}$ is hydrogen, $R^{2b}$ is hydrogen or —$C_{1-6}$alkyl, and $R^{2c}$ is independently selected from:

(1) $C_{1-6}$alkyl, which is unsubstituted or substituted with substituents selected from: hydroxy, —(CO)NH($C_{1-6}$alkyl), —(CO)O($C_{1-6}$alkyl), —$C_{3-6}$cycloalkyl, phenyl and fluoro,
(5) —O—$C_{1-6}$alkyl, which is unsubstituted or substituted with fluoro,
(2) —$C_{3-6}$cycloalkyl, which is unsubstituted or substituted with substituents selected from: hydroxy, methoxy, —$C_{1-6}$alkyl, —(CO)NH($C_{1-6}$alkyl), —(CO)O($C_{1-6}$alkyl), and fluoro,
(3) azaspiro[3.3]heptanyl, which is unsubstituted or substituted with —$C_{1-6}$alkyl or oxetanyl, which is unsubstituted or substituted with —$C_{1-6}$alkyl,
(4) azetidinyl, which is unsubstituted or substituted with —$C_{1-6}$alkyl or —(CO)O($C_{1-6}$alkyl),
(5)bicyclopentyl, which is unsubstituted or substituted with —$C_{1-6}$alkyl or —(CO)O($C_{1-6}$alkyl),
(6) oxazolyl,
(7) oxadiazolyl,
(8) oxetanyl, which is unsubstituted or substituted with —$C_{1-6}$alkyl,
(9) piperidinyl, which is unsubstituted or substituted with —$C_{1-6}$alkyl or oxetanyl, which is unsubstituted or substituted with —$C_{1-6}$alkyl,
(10) pyrrolidinyl, which is unsubstituted or substituted with oxo or —$C_{1-6}$alkyl, and
(11) thiazolyl.

An embodiment of the present invention includes compounds wherein $R^{2a}$ is hydrogen, and $R^{2b}$ and $R^{2c}$ are joined to form a pyrrolyl, dihydrospiro[1,4'-pyrazolo[1,5-d][1,4]diazepin]-7'(8'H)-one, or dihydro-4H-pyrazolo[1,5-d][1,4]diazepin-one ring, which is unsubstituted or substituted with —$C_{1-6}$alkyl, —$C_{1-6}$alkyl-OH or —$C_{3-6}$cycloalkyl.

An embodiment of the present invention includes compounds wherein $R^{2a}$ is hydrogen. $R^{2b}$ is hydrogen or —$C_{1-6}$alkyl, and $R^{2c}$ is independently selected from:

(1) hydrogen,
(2) fluoro,
(3) hydroxyl,
(4) $C_{1-6}$alkyl, and
(5) —O—$C_{1-6}$alkyl.

An embodiment of the present invention includes compounds wherein $R^{2a}$, $R^{2b}$ and $R^{2c}$ as are present are independently selected from:

(1) hydrogen,
(2) halogen,
(3) hydroxyl,
(4) $C_{1-6}$alkyl, and
(5) —O—$C_{1-6}$alkyl.

An embodiment of the present invention includes compounds wherein $R^{2a}$ is hydrogen. An embodiment of the present invention includes compounds wherein $R^{2b}$ is hydrogen. An embodiment of the present invention includes compounds wherein $R^{2a}$ is hydrogen. $R^{2b}$ is methyl, and $R^{2c}$ is methoxy.

An embodiment of the present invention includes compounds wherein $R^{3a}$ is hydrogen and $R^{3b}$ is hydrogen. An embodiment of the present invention includes compounds wherein $R^{3a}$ is hydrogen and $R^{3b}$ is methyl. An embodiment of the present invention includes compounds wherein $R^{3a}$ is methyl and $R^{3b}$ is methyl.

Certain embodiments of the present invention include a compound which is selected from the group consisting of the subject compounds of the Examples herein or a pharmaceutically acceptable salt thereof.

Certain embodiments of the present invention include a compound which is selected from the group consisting of:

4-((3-(hydroxymethyl)phenyl)amino)-2-((6-methoxy-2-methyl-1,2,3,4-tetrahydroisoquinolin-7-yl)amino)pyrimidine-5-carboxamide;

tert-butyl {[3-({5-carbamoyl-2-[(6-methoxy-2-methyl-1,2,3,4-tetrahydroisoquinolin-7-yl)amino]pyrimidin-4-yl}amino)phenyl]methyl}carbamate:

4-{[3-(aminomethyl)phenyl]amino}-2-[(6-methoxy-2-methyl-1,2,3,4-tetrahydroisoquinolin-7-yl)amino]pyrimidine-5-carboxamide;

4-{[2-(aminomethyl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({2-[(methylamino)methyl]phenyl}amino) pyrimidine-5-carboxamide;

4-{[3-(1-aminoethyl)phenyl]amino}-2-[(6-methoxy-2-methyl-1,2,3,4-tetrahydroisoquinolin-7-yl)amino]pyrimidine-5-carboxamide;

4-{[3-(1-aminoethyl)phenyl]amino}-2-[(6-chloro-2-methyl-1,2,3,4-tetrahydroisoquinolin-7-yl)amino]pyrimidine-5-carboxamide;

4-{[3-(1-aminoethyl)phenyl]amino}-2-[(6-fluoro-2-methyl-1,2,3,4-tetrahydroisoquinolin-7-yl)amino]pyrimidine-5-carboxamide;

4-[(3-{[(1-fluorocyclopropane-1-carbonyl)amino] methyl}phenyl)amino]-2-[(6-methoxy-2-methyl-1,2,3,4-tetrahydroisoquinolin-7-yl)amino]pyrimidine-5-carboxamide;

4-((2,6-difluorophenyl)amino)-2-((6-methoxy-2-methyl-1,2,3,4-tetrahydroisoquinolin-7-yl)amino)pyrimidine-5-carboxamide;

4-[(2,6-dimethylphenyl)amino]-2-[(6-methoxy-2-methyl-1,2,3,4-tetrahydroisoquinolin-7-yl)amino]pyrimidine-5-carboxamide;

4-[(2-fluoro-6-methylphenyl)amino]-2-[(6-methoxy-2-methyl-1,2,3,4-tetrahydroisoquinolin-7-yl)amino]pyrimidine-5-carboxamide;

4-[(2-bromo-6-fluorophenyl)amino]-2-[(6-methoxy-2-methyl-1,2,3,4-tetrahydroisoquinolin-7-yl)amino]pyrimidine-5-carboxamide;

2-[(6-chloro-2-methyl-1,2,3,4-tetrahydroisoquinolin-7-yl) amino]-4-[(2-fluoro-6-methylphenyl)amino]pyrimidine-5-carboxamide;

4-[(2-fluoro-6-methylphenyl)amino]-2-[(6-fluoro-2-methyl-1,2,3,4-tetrahydroisoquinolin-7-yl)amino]pyrimidine-5-carboxamide;

4-[(2-fluoro-6-methylphenyl)amino]-2-[(6-methoxy-1,2,3,4-tetrahydroisoquinolin-7-yl)amino]pyrimidine-5-carboxamide;

4-{[2-fluoro-6-(trifluoromethyl)phenyl]amino}-2-[(6-methoxy-2-methyl-1,2,3,4-tetrahydroisoquinolin-7-yl) amino]pyrimidine-5-carboxamide;

4-[(2-cyano-6-fluorophenyl)amino]-2-[(6-methoxy-2-methyl-1,2,3,4-tetrahydroisoquinolin-7-yl)amino]pyrimidine-5-carboxamide;

4-[(2,4-difluorophenyl)amino]-2-[(6-methoxy-2-methyl-1,2,3,4-tetrahydroisoquinolin-7-yl)amino]pyrimidine-5-carboxamide;

4-[(2,5-difluorophenyl)amino]-2-[(6-methoxy-2-methyl-1,2,3,4-tetrahydroisoquinolin-7-yl)amino]pyrimidine-5-carboxamide;

4-[(3-chloro-2-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(2,3,4-trifluorophenyl)amino]pyrimidine-5-carboxamide;

4-[(2-fluoro-3-methylphenyl)amino]-2-[(6-methoxy-2-methyl-1,2,3,4-tetrahydroisoquinolin-7-yl)amino]pyrimidine-5-carboxamide;

4-[(2,6-difluoro-4-methoxyphenyl)amino]-2-[(6-methoxy-2-methyl-1,2,3,4-tetrahydroisoquinolin-7-yl)amino]pyrimidine-5-carboxamide;

4-[(2-chloro-6-fluoro-3-methylphenyl)amino]-2-[(6-methoxy-2-methyl-1,2,3,4-tetrahydroisoquinolin-7-yl) amino]pyrimidine-5-carboxamide;

4-[(2-fluoro-6-hydroxyphenyl)amino]-2-[(6-methoxy-2-methyl-1,2,3,4-tetrahydroisoquinolin-7-yl)amino]pyrimidine-5-carboxamide;

4-[(2-chloro-5-methylphenyl)amino]-2-[(6-methoxy-2-methyl-1,2,3,4-tetrahydroisoquinolin-7-yl)amino]pyrimidine-5-carboxamide;

4-[(2-chloro-4-methylphenyl)amino]-2-[(6-methoxy-2-methyl-1,2,3,4-tetrahydroisoquinolin-7-yl)amino]pyrimidine-5-carboxamide;

4-[(6-chloro-2-fluoro-3-methylphenyl)amino]-2-[(6-methoxy-2-methyl-1,2,3,4-tetrahydroisoquinolin-7-yl) amino]pyrimidine-5-carboxamide;

4-[(2-chloro-4,6-difluorophenyl)amino]-2-[(6-methoxy-2-methyl-1,2,3,4-tetrahydroisoquinolin-7-yl)amino]pyrimidine-5-carboxamide;

2-{[1-(cyclopropylmethyl)-1H-pyrazol-4-yl]amino}-4-[(2-fluoro-6-methylphenyl)amino]pyrimidine-5-carboxamide;

4-[(2-fluoro-6-methylphenyl)amino]-2-{[1-(2-hydroxy-2-methylpropyl)-1H-pyrazol-4-yl]amino}pyrimidine-5-carboxamide;

4-[(2-fluoro-6-methylphenyl)amino]-2-{[1-(2,2,2-trifluoroethyl)-1H-pyrazol-4-yl]amino}pyrimidine-5-carboxamide, 4-[(2-fluoro-6-methylphenyl)amino]-2-{[4-(methylsulfonyl)phenyl]amino}pyrimidine-5-carboxamide;

4-[(2-cyclopropylphenyl)amino]-2-[(6-methoxy-2-methyl-1,2,3,4-tetrahydroisoquinolin-7-yl)amino]pyrimidine-5-carboxamide;

4-[(2-ethylphenyl)amino]-2-[(6-methoxy-2-methyl-1,2,3,4-tetrahydroisoquinolin-7-yl)amino]pyrimidine-5-carboxamide;

4-[(2-tert-butylphenyl)amino]-2-[(6-methoxy-2-methyl-1,2,3,4-tetrahydroisoquinolin-7-yl)amino]pyrimidine-5-carboxamide;

2-[(6-fluoro-2-methyl-1,2,3,4-tetrahydroisoquinolin-7-yl) amino]-4-{[2-fluoro-6-(trifluoromethyl)phenyl] amino}pyrimidine-5-carboxamide;

4-[(4-bromo-2,6-difluorophenyl)amino]-2-[(6-methoxy-2-methyl-1,2,3,4-tetrahydroisoquinolin-7-yl)amino]pyrimidine-5-carboxamide;

4-{[2-(difluoromethoxy)-6-fluorophenyl]amino}-2-[(6-methoxy-2-methyl-1,2,3,4-tetrahydroisoquinolin-7-yl) amino]pyrimidine-5-carboxamide;

4-[(2,2-dimethyl-2,3-dihydro-1-benzofuran-7-yl)amino]-2-[(6-fluoro-2-methyl-1,2,3,4-tetrahydroisoquinolin-7-yl) amino]pyrimidine-5-carboxamide;

4-[(4-cyano-2-fluoro-6-methylphenyl)amino]-2-[(6-methoxy-2-methyl-1,2,3,4-tetrahydroisoquinolin-7-yl) amino]pyrimidine-5-carboxamide;

2-[(3,5-dimethyl-1H-pyrazol-4-yl)amino]-4-[(2-fluoro-6-methylphenyl)amino]pyrimidine-5-carboxamide;

4-[(2-fluoro-6-methylphenyl)amino]-2-[(1-methyl-1H-pyrazol-4-yl)amino]pyrimidine-5-carboxamide;

4-{[2-fluoro-6-(trifluoromethyl)phenyl]amino}-2-{[2-(2-hydroxy-2-methylpropyl)-6-methoxy-1,2,3,4-tetrahydroisoquinolin-7-yl]amino}pyrimidine-5-carboxamide;

4-[(2-fluoro-6-methylphenyl)amino]-2-{[2-(2-hydroxy-2-methylpropyl)-6-methoxy-1,2,3,4-tetrahydroisoquinolin-7-yl]amino}pyrimidine-5-carboxamide;

2-[(6-methoxy-2-methyl-1,2,3,4-tetrahydroisoquinolin-7-yl)amino]-4-(phenylamino)pyrimidine-5-carboxamide;

2-{[4-(methylsulfonyl)phenyl]amino}-4-[(1,2,3,4-tetrahydroisoquinolin-5-yl)amino]pyrimidine-5-carboxamide;

2-[(6-methoxy-2-methyl-1,2,3,4-tetrahydroisoquinolin-7-yl)amino]-4-({2-[(4S)-4-methyl-2-oxo-1,3-oxazolidin-3-yl]phenyl}amino)pyrimidine-5-carboxamide;

4-[(2-bromophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(1,2,3,4-tetrahydroisoquinolin-5-yl)amino]pyrimidine-5-carboxamide;

4-[(1H-benzotriazol-7-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-methylcinnolin-5-yl)amino]pyrimidine-5-carboxamide;

4-[(2,3-dihydro-1-benzofuran-7-yl)amino]-2-[(6-methoxy-2-methyl-1,2,3,4-tetrahydroisoquinolin-7-yl)amino]pyrimidine-5-carboxamide;

2-{[1-(cyclopropylmethyl)-1H-pyrazol-4-yl]amino}-4-[(1,2,3,4-tetrahydroisoquinolin-5-yl)amino]pyrimidine-5-carboxamide;

2-[(3-methoxy-1-methyl-1H-pyrazol-4-yl)amino]-4-[(1,2,3,4-tetrahydroisoquinolin-5-yl)amino]pyrimidine-5-carboxamide;

4-[(2-bromophenyl)amino]-2-{[2-methoxy-4-(piperazin-1-yl)phenyl]amino}pyrimidine-5-carboxamide;

2-[(1-methyl-3-oxo-2,3-dihydro-1H-pyrazol-4-yl)amino]-4-[(1,2,3,4-tetrahydroisoquinolin-5-yl)amino]pyrimidine-5-carboxamide;

2-[(1-methyl-1H-pyrazol-4-yl)amino]-4-[(1,2,3,4-tetrahydroisoquinolin-5-yl)amino]pyrimidine-5-carboxamide;

4-{[2-fluoro-6-(hydroxymethyl)phenyl]amino}-2-[(6-methoxy-2-methyl-1,2,3,4-tetrahydroisoquinolin-7-yl)amino]pyrimidine-5-carboxamide;

4-[(2,2-dimethyl-2,3-dihydro-1-benzofuran-7-yl)amino]-2-[(6-methoxy-2-methyl-1,2,3,4-tetrahydroisoquinolin-7-yl)amino]pyrimidine-5-carboxamide;

2-{[4-(1-cyanocyclopropyl)phenyl]amino}-4-[(1,2,3,4-tetrahydroisoquinolin-5-yl)amino]pyrimidine-5-carboxamide;

2-[(3,4-dihydro-1H-2-benzopyran-7-yl)amino]-4-[(1,2,3,4-tetrahydroisoquinolin-5-yl)amino]pyrimidine-5-carboxamide;

2-{[4-(l-cyanocyclopropyl)phenyl]amino}-4-[(1-oxo-1,2,3,4-tetrahydroisoquinolin-5-yl)amino]pyrimidine-5-carboxamide;

4-[(3-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(trifluoromethyl)phenyl]amino}pyrimidine-5-carboxamide;

2-[(6-methoxy-2-methyl-1,2,3,4-tetrahydroisoquinolin-7-yl)amino]-4-[(2-methylphenyl)amino]pyrimidine-5-carboxamide;

4-[(4-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-methylphenyl)amino]pyrimidine-5-carboxamide;

4-{[2-(butan-2-yl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(4-methylphenyl)amino]pyrimidine-5-carboxamide;

4-[(3-chlorophenyl)amino]-2-[(6-methoxy-2-methyl-1,2,3,4-tetrahydroisoquinolin-7-yl)amino]pyrimidine-5-carboxamide;

4-[(3-cyano-4-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

4-{[2-(2-hydroxy-2-methylpropyl)-1,2,3,4-tetrahydroisoquinolin-5-yl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(2,2,2-trifluoroethyl)-1,2,3,4-tetrahydroisoquinolin-5-yl]amino}pyrimidine-5-carboxamide;

4-[(3-cyano-2-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(methylsulfonyl)-1,2,3,4-tetrahydroisoquinolin-5-yl]amino}pyrimidine-5-carboxamide;

4-{[3-(1-cyanocyclopropyl)phenyl]amino}-2-[(6-methoxy-2-methyl-1,2,3,4-tetrahydroisoquinolin-7-yl)amino]pyrimidine-5-carboxamide;

4-{[2-(hydroxymethyl)phenyl]amino}-2-[(6-methoxy-2-methyl-1,2,3,4-tetrahydroisoquinolin-7-yl)amino]pyrimidine-5-carboxamide;

N-{[3-({5-carbamoyl-2-[(6-methoxy-2-methyl-1,2,3,4-tetrahydroisoquinolin-7-yl)amino]pyrimidin-4-yl}amino)phenyl]methyl}-N-methylglycine 2-[(6-methoxy-2-methyl-1,2,3,4-tetrahydroisoquinolin-7-yl)amino]-4-[(2-methyl-1-oxo-1,2,3,4-tetrahydroisoquinolin-5-yl)amino]pyrimidine-5-carboxamide;

2-[(6-chloro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

2-[(6-fluoro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

2-[(6-methoxy-2-methyl-1,2,3,4-tetrahydroisoquinolin-7-yl)amino]-4-{[3-(methylcarbamoyl)phenyl]amino}pyrimidine-5-carboxamide;

2-[(6-chloro-2-methyl-1,2,3,4-tetrahydroisoquinolin-7-yl)amino]-4-{[3-(methylcarbamoyl)phenyl]amino}pyrimidine-5-carboxamide;

4-[(2-bromo-6-methylphenyl)amino]-2-[(6-methoxy-2-methyl-1,2,3,4-tetrahydroisoquinolin-7-yl)amino]pyrimidine-5-carboxamide;

2-[(6-fluoro-2-methyl-1,2,3,4-tetrahydroisoquinolin-7-yl)amino]-4-{[3-(methylcarbamoyl)phenyl]amino}pyrimidine-5-carboxamide;

2-[(6-fluoro-2-methyl-1,2,3,4-tetrahydroisoquinolin-7-yl)amino]-4-{[2-(hydroxymethyl)phenyl]amino}pyrimidine-5-carboxamide;

2-{[1-(cyclopropylmethyl)-1H-pyrazol-4-yl]amino}-4-[(1-oxo-1,2,3,4-tetrahydroisoquinolin-5-yl)amino]pyrimidine-5-carboxamide;

2-[(1-methyl-1H-pyrazol-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[1-(2,2,2-trifluoroethyl)-1H-pyrazol-4-yl]amino}pyrimidine-5-carboxamide;

2-{[1-(1-cyclopropylethyl)-1H-pyrazol-4-yl]amino}-4-[(1-oxo-1,2,3,4-tetrahydroisoquinolin-5-yl)amino]pyrimidine-5-carboxamide;

2-[(3-methoxy-1-methyl-1H-pyrazol-4-yl)amino]-4-[(1-oxo-1,2,3,4-tetrahydroisoquinolin-5-yl)amino]pyrimidine-5-carboxamide;

2-{[4-(methylsulfonyl)phenyl]amino}-4-[(1-oxo-1,2,3,4-tetrahydroisoquinolin-5-yl)amino]pyrimidine-5-carboxamide;

4-[(2-cyanophenyl)amino]-2-[(6-methoxy-2-methyl-1,2,3,4-tetrahydroisoquinolin-7-yl)amino]pyrimidine-5-carboxamide;

4-[(1-oxo-1,2,3,4-tetrahydroisoquinolin-5-yl)amino]-2-{[1-(propan-2-yl)-1H-pyrazol-4-yl]amino}pyrimidine-5-carboxamide;

2-[(1-cyclobutyl-1H-pyrazol-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[1-(piperidin-4-yl)-1H-pyrazol-4-yl]amino}pyrimidine-5-carboxamide;

4-[(1-oxo-1,2,3,4-tetrahydroisoquinolin-5-yl)amino]-2-[(4,5,6,7-tetrahydropyrazolo[1,5-a]pyridin-3-yl)amino]pyrimidine-5-carboxamide;

2-([5-(difluoromethyl)-1-methyl-1H-pyrazol-4-yl]amino)-4-[(1-oxo-1,2,3,4-tetrahydroisoquinolin-5-yl)amino]pyrimidine-5-carboxamide;

2-{[3-(2,2-difluoroethoxy)-1-methyl-1H-pyrazol-4-yl]amino}-4-[(1-oxo-1,2,3,4-tetrahydroisoquinolin-5-yl)amino]pyrimidine-5-carboxamide;

2-{[1-methyl-5-(trifluoromethyl)-1H-pyrazol-4-yl]amino}-4-[1-oxo-1,2,3,4-tetrahydroisoquinolin-5-yl)amino]pyrimidine-5-carboxamide;

2-[(6,7-dihydro-5H-pyrazolo[5,1-b][1,3]oxazin-3-yl)amino]-4-[(1-oxo-1,2,3,4-tetrahydroisoquinolin-5-yl)amino]pyrimidine-5-carboxamide;

2-[(5,6-dihydro-4H-pyrrolo[1,2-b]pyrazol-2-yl)amino]-4-[(1-oxo-1,2,3,4-tetrahydroisoquinolin-5-yl)amino]pyrimidine-5-carboxamide;

2-({4-[(methylsulfonyl)methyl]phenyl}amino)-4-[(1-oxo-1,2,3,4-tetrahydroisoquinolin-5-yl)amino]pyrimidine-5-carboxamide;

2-({4-[2-(methylsulfonyl)propan-2-yl]phenyl}amino)-4-[(1-oxo-1,2,3,4-tetrahydroisoquinolin-5-yl)amino]pyrimidine-5-carboxamide;

2-{[2-methoxy-5-(methylsulfonyl)phenyl]amino}-4-[(2-methyl-1,2,3,4-tetrahydroisoquinolin-5-yl)amino]pyrimidine-5-carboxamide;

2-{[3-methoxy-1-(2,2,2-trifluoroethyl)-1H-pyrazol-4-yl]amino}-4-[(2-methyl-1,2,3,4-tetrahydroisoquinolin-5-yl)amino]pyrimidine-5-carboxamide;

2-{[2-methoxy-5-(methylsulfonyl)phenyl]amino}-4-[(1,2,3,4-tetrahydroisoquinolin-5-yl)amino]pyrimidine-5-carboxamide;

2-[(2-methyl-3-oxo-2,3-dihydro-1H-isoindol-5-yl)amino]-4-[(1,2,3,4-tetrahydroisoquinolin-5-yl)amino]pyrimidine-5-carboxamide;

4-{[2-fluoro-6-(hydroxymethyl)phenyl]amino}-2-{[4-(methylsulfonyl)phenyl]amino}pyrimidine-5-carboxamide;

2-[(6-methoxy-2-methyl-1,2,3,4-tetrahydroisoquinolin-7-yl)amino]-4-{[7-(trifluoromethyl)-1,2,3,4-tetrahydroisoquinolin-5-yl]amino}pyrimidine-5-carboxamide;

4-({2-[(1S)-1-methoxyethyl]phenyl}amino)-2-[(6-methoxy-2-methyl-1,2,3,4-tetrahydroisoquinolin-7-yl)amino]pyrimidine-5-carboxamide;

4-{[2-(hydroxymethyl)phenyl]amino}-2-({[4-[(methylsulfonyl)methyl]phenyl)amino}pyrimidine-5-carboxamide;

4-({2-[(1R)-1-methoxyethyl]phenyl}amino)-2-[(6-methoxy-2-methyl-1,2,3,4-tetrahydroisoquinolin-7-yl)amino]pyrimidine-5-carboxamide;

4-[(2-iodophenyl)amino]-2-[(6-methoxy-2-methyl-1,2,3,4-tetrahydroisoquinolin-7-yl)amino]pyrimidine-5-carboxamide;

4-[(3-bromophenyl)amino]-2-[(6-methoxy-2-methyl-1,2,3,4-tetrahydroisoquinolin-7-yl)amino]pyrimidine-5-carboxamide;

4-[(4-bromophenyl)amino]-2-[(6-methoxy-2-methyl-1,2,3,4-tetrahydroisoquinolin-7-yl)amino]pyrimidine-5-carboxamide;

4-[(2-chlorophenyl)amino]-2-[(6-methoxy-2-methyl-1,2,3,4-tetrahydroisoquinolin-7-yl)amino]pyrimidine-5-carboxamide;

4-[(2-fluorophenyl)amino]-2-[(6-methoxy-2-methyl-1,2,3,4-tetrahydroisoquinolin-7-yl)amino]pyrimidine-5-carboxamide;

4-{[3-(2-hydroxyethyl)phenyl]amino}-2-[(6-methoxy-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-((2-(2-oxooxazolidin-3-yl)phenyl)amino)pyrimidine-5-carboxamide;

2-[(6-methoxy-2-methyl-1,2,3,4-tetrahydroisoquinolin-7-yl)amino]-4-{[2-(1H-1,2,3-triazol-1-yl)phenyl]amino}pyrimidine-5-carboxamide;

2-[(6-methoxy-2-methyl-1,2,3,4-tetrahydroisoquinolin-7-yl)amino]-4-[(2-sulfamoylphenyl)amino]pyrimidine-5-carboxamide;

4-((1-ethyl-3-methyl-1H-pyrazol-5-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((1,3,5-trimethyl-1H-pyrazol-4-yl)amino)pyrimidine-5-carboxamide;

4-((3-cyclopropyl-1-methyl-1H-pyrazol-4-yl)amino)-2-((6-methoxy-2-methyl-1,2,3,4-tetrahydroisoquinolin-7-yl)amino)pyrimidine-5-carboxamide;

4-((3-cyclopropyl-1-methyl-1H-pyrazol-5-yl)amino)-2-((6-methoxy-2-methyl-1,2,3,4-tetrahydroisoquinolin-7-yl)amino)pyrimidine-5-carboxamide;

4-((3,5-dimethylisoxazol-4-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((2-methyl-2,4,5,6-tetrahydrocyclopenta[c]pyrazol-3-yl)amino)pyrimidine-5-carboxamide;

2-((6-methoxy-2-methyl-1,2,3,4-tetrahydroisoquinolin-7-yl)amino)-4-((2-(3-methylisoxazol-5-yl)phenyl)amino)pyrimidine-5-carboxamide;

2-((6-methoxy-2-methyl-1,2,3,4-tetrahydroisoquinolin-7-yl)amino)-4-((1-methyl-3-(trifluoromethyl)-1H-pyrazol-4-yl)amino)pyrimidine-5-carboxamide;

4-((4-chloro-1-ethyl-1H-pyrazol-3-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((1-methyl-1H-pyrazol-5-yl)amino)pyrimidine-5-carboxamide;

4-((3-(tert-butyl)-1-methyl-1H-pyrazol-5-yl)amino)-2-((6-methoxy-2-methyl-1,2,3,4-tetrahydroisoquinolin-7-yl)amino)pyrimidine-5-carboxamide;

4-((1-(2-hydroxyethyl)-3-methyl-1H-pyrazol-5-yl)amino)-2-((6-methoxy-2-methyl-1,2,3,4-tetrahydroisoquinolin-7-yl)amino)pyrimidine-5-carboxamide;

4-((1-benzyl-3-methyl-1H-pyrazol-5-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((3-methyl-1-phenyl-1H-pyrazol-5-yl)amino)pyrimidine-5-carboxamide;

4-((1-ethyl-4-methyl-1H-pyrazol-5-yl)amino)-2-((6-methoxy-2-methyl-1,2,3,4-tetrahydroisoquinolin-7-yl)amino)pyrimidine-5-carboxamide;

methyl 2-({5-carbamoyl-2-[(6-methoxy-2-methyl-1,2,3,4-tetrahydroisoquinolin-7-yl)amino]pyrimidin-4-yl}amino)benzoate 4-[(2-bromophenyl)amino]-2-[(5-carbamoyl-2-methoxyphenyl)amino]pyrimidine-5-carboxamide;

4-[(2-bromophenyl)amino]-2-[(2,3-dihydro-1-benzofuran-7-yl)amino]pyrimidine-5-carboxamide;

4-{[2-(1,1,1,3,3,3-hexafluoro-2-hydroxypropan-2-yl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(2,2,2-trifluoroethyl)phenyl]amino}pyrimidine-5-carboxamide;

2-[(6-methoxy-2-methyl-1,2,3,4-tetrahydroisoquinolin-7-yl)amino]-4-({2-[(morpholin-4-yl)methyl]phenyl}amino)pyrimidine-5-carboxamide;

4-[(2-bromophenyl)amino]-2-{[4-(1-cyanocyclopropyl)phenyl]amino}pyrimidine-5-carboxamide;

4-([2-(1,1-difluoroethyl)phenyl]amino)-2-[(6-methoxy-2-methyl-1,2,3,4-tetrahydroisoquinolin-7-yl)amino]pyrimidine-5-carboxamide;

4-[(2-ethynylphenyl)amino]-2-[(6-methoxy-2-methyl-1,2,3,4-tetrahydroisoquinolin-7-yl)amino]pyrimidine-5-carboxamide;

4-[(2-bromophenyl)amino]-2-[(1-oxo-1,3-dihydro-2-benzofuran-5-yl)amino]pyrimidine-5-carboxamide;

2-[(6-methoxy-2-methyl-1,2,3,4-tetrahydroisoquinolin-7-yl)amino]-4-[(2-methoxyphenyl)amino]pyrimidine-5-carboxamide;

4-[(2-bromophenyl)amino]-2-(phenylamino)pyrimidine-5-carboxamide;

4-[(2-bromophenyl)amino]-2-[(1-oxo-3,4-dihydro-1H-2-benzopyran-7-yl)amino]pyrimidine-5-carboxamide;

4-[(2-bromophenyl)amino]-2-[(3,4-dihydro-1H-2-benzopyran-7-yl)amino]pyrimidine-5-carboxamide;

2-{[4-(1-cyanocyclopropyl)phenyl]amino}-4-{[2-(hydroxymethyl)phenyl]amino}pyrimidine-5-carboxamide;

2-((6-methoxy-2-methyl-1,2,3,4-tetrahydroisoquinolin-7-yl)amino)-4-((2-(tetrahydrofuran-2-yl)phenyl)amino)pyrimidine-5-carboxamide;

4-{[2-(1-methoxyethyl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({2-[(propan-2-yl)oxy]phenyl}amino)pyrimidine-5-carboxamide;

4-[(2-ethoxyphenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({2-[(trifluoromethyl)sulfanyl]phenyl}amino)pyrimidine-5-carboxamide;

4-{[2-(difluoromethoxy)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(trifluoromethoxy)phenyl]amino}pyrimidine-5-carboxamide;

4-[(2-bromophenyl)amino]-2-({2-methoxy-4-[4-(morpholin-4-yl)piperidin-1-yl]phenyl}amino)pyrimidine-5-carboxamide;

2-((6-methoxy-2-methyl-1,2,3,4-tetrahydroisoquinolin-7-yl)amino)-4-((2-(phenylcarbamoyl)phenyl)amino)pyrimidine-5-carboxamide;

4-((2-(cyclopropylcarbamoyl)phenyl)amino)-2-((6-methoxy-2-methyl-1,2,3,4-tetrahydroisoquinolin-7-yl)amino)pyrimidine-5-carboxamide;

4-[(2-acetyl-1,2,3,4-tetrahydroisoquinolin-5-yl)amino]-2-[(6-methoxy-2-methyl-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide;

4-{[2-(2-hydroxypropan-2-yl)phenyl]amino}-2-[(6-methoxy-2-methyl-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-(phenylamino)pyrimidine-5-carbohydrazide;

10,28-difluoro-23-methoxy-2,4,8,18,29-pentaazapentacyclo-[16.5.3.2~9,12~0.1~3,7~0~21,25~]nonacosa-1(23),3(29),4,6,9,11,21,24,27-nonaene-6-carboxamide;

2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide;

2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide;

4-((2-fluoro-6-(trifluoromethyl)phenyl)amino)-2-((6'-methoxy-2'-methyl-2',3'-dihydro-1'H-spiro[cyclopropane-1,4'-isoquinolin]-7'-yl)amino)pyrimidine-5-carboxamide;

4-((2-bromophenyl)amino)-2-((trans)-2-(1-methyl-1H-pyrazol-4-yl)cyclopropane-1-carboxamido)pyrimidine-5-carboxamide;

4-[(2-bromophenyl)amino]-2-{[(1R,3R)-2-ethyl-3-(1-methyl-1H-pyrazol-4-yl)cyclopropane-1-carbonyl]amino}pyrimidine-5-carboxamide;

4-((2-fluoro-6-(1-methoxyethyl)phenyl)amino)-2-((6-methoxy-2-methyl-1,2,3,4-tetrahydroisoquinolin-7-yl)amino)pyrimidine-5-carboxamide;

4-((2-fluoro-6-(1-hydroxyethyl)phenyl)amino)-2-((6-methoxy-2-methyl-1,2,3,4-tetrahydroisoquinolin-7-yl)amino)pyrimidine-5-carboxamide;

2-((6-methoxy-2,3-dimethyl-1,2,3,4-tetrahydroisoquinolin-7-yl)amino)-4-((2-(trifluoromethyl)phenyl)amino)pyrimidine-5-carboxamide;

2-((6-isopropyl-5-oxo-5,6,7,8-tetrahydro-4H-pyrazolo[1,5-d][1,4]diazepin-2-yl)amino)-4-((1,2,3,4-tetrahydroisoquinolin-5-yl)amino)pyrimidine-5-carboxamide;

4-[(1-oxo-1,2,3,4-tetrahydroisoquinolin-5-yl)amino]-2-(phenylamino)pyrimidine-5-carboxamide;

2-{[4-(1-cyanocyclopropyl)phenyl]amino}-4-[(1-oxo-1,2,3,4-tetrahydroisoquinolin-5-yl)amino]pyrimidine-5-carboxamide;

2-{[3-(2-cyanopropan-2-yl)phenyl]amino}-4-[(1-oxo-1,2,3,4-tetrahydroisoquinolin-5-yl)amino]pyrimidine-5-carboxamide;

2-{[3-(1-cyanocyclopropyl)phenyl]amino}-4-[(1-oxo-1,2,3,4-tetrahydroisoquinolin-5-yl)amino]pyrimidine-5-carboxamide;

2-[(4-fluorophenyl)amino]-4-[(1-oxo-1,2,3,4-tetrahydroisoquinolin-5-yl)amino]pyrimidine-5-carboxamide;

2-[(3-chloro-4-fluorophenyl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[4-(trifluoromethyl)phenyl]amino}pyrimidine-5-carboxamide;

2-{[(1R)-1-(4-fluorophenyl)ethyl]amino}-4-[(1-oxo-1,2,3,4-tetrahydroisoquinolin-5-yl)amino]pyrimidine-5-carboxamide;

2-[(4-ethylphenyl)amino]-4-[(1-oxo-1,2,3,4-tetrahydroisoquinolin-5-yl)amino]pyrimidine-5-carboxamide;

2-[(3-fluorophenyl)amino]-4-[(1-oxo-1,2,3,4-tetrahydroisoquinolin-5-yl)amino]pyrimidine-5-carboxamide;

2-[(2,3-dimethylphenyl)amino]-4-[(1-oxo-1,2,3,4-tetrahydroisoquinolin-5-yl)amino]pyrimidine-5-carboxamide;

2-[(4-cyclopropyl-3-methylphenyl)amino]-4-[(1-oxo-1,2,3,4-tetrahydroisoquinolin-5-yl)amino]pyrimidine-5-carboxamide;

2-[(4-cyclopropylphenyl)amino]-4-[(1-oxo-1,2,3,4-tetrahydroisoquinolin-5-yl)amino]pyrimidine-5-carboxamide;

2-[(naphthalen-1-yl)amino]-4-[(1-oxo-1,2,3,4-tetrahydroisoquinolin-5-yl)amino]pyrimidine-5-carboxamide;

2-[(2-ethylphenyl)amino]-4-[(1-oxo-1,2,3,4-tetrahydroisoquinolin-5-yl)amino]pyrimidine-5-carboxamide;

2-{[3-(difluoromethoxy)phenyl]amino}-4-[(1-oxo-1,2,3,4-tetrahydroisoquinolin-5-yl)amino]pyrimidine-5-carboxamide;

2-[(2,4-difluorophenyl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[3-(trifluoromethyl)phenyl]amino}pyrimidine-5-carboxamide;

2-[(3-methylphenyl)amino]-4-[(1-oxo-1,2,3,4-tetrahydroisoquinolin-5-yl)amino]pyrimidine-5-carboxamide;

2-[(3-tert-butylphenyl)amino]-4-[(1-oxo-1,2,3,4-tetrahydroisoquinolin-5-yl)amino]pyrimidine-5-carboxamide;

2-{[3-chloro-4-(difluoromethoxy)phenyl]amino}-4-[(1-oxo-1,2,3,4-tetrahydroisoquinolin-5-yl)amino]pyrimidine-5-carboxamide;

2-[(3,5-dimethylphenyl)amino]-4-[(1-oxo-1,2,3,4-tetrahydroisoquinolin-5-yl)amino]pyrimidine-5-carboxamide;

2-{[1-(2-fluorophenyl)cyclopropyl]amino}-4-[(1-oxo-1,2,3,4-tetrahydroisoquinolin-5-yl)amino]pyrimidine-5-carboxamide;

2-{[(2,6-dichlorophenyl)methyl]amino}-4-[(1-oxo-1,2,3,4-tetrahydroisoquinolin-5-yl)amino]pyrimidine-5-carboxamide;

2-[(3-cyclopropylphenyl)amino]-4-[(1-oxo-1,2,3,4-tetrahydroisoquinolin-5-yl)amino]pyrimidine-5-carboxamide;

2-[(3-chloro-2-methylphenyl)amino]-4-[(1-oxo-1,2,3,4-tetrahydroisoquinolin-5-yl)amino]pyrimidine-5-carboxamide;

2-{[2-(difluoromethoxy)phenyl]amino}-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[3-(propan-2-yl)phenyl]amino}pyrimidine-5-carboxamide;

2-{[3-methyl-5-(trifluoromethyl)phenyl]amino}-4-[(1-oxo-1,2,3,4-tetrahydroisoquinolin-5-yl)amino]pyrimidine-5-carboxamide;

2-[(4-fluoro-3-methylphenyl)amino]-1-oxo-1,2,3,4-tetrahydroisoquinolin-5-yl)amino]pyrimidine-5-carboxamide;

2-[(3,5-difluorophenyl)amino]-4-[(1-oxo-1,2,3,4-tetrahydroisoquinolin-5-yl)amino]pyrimidine-5-carboxamide;

2-{[2-methyl-5-(trifluoromethyl)phenyl]amino}-4-[(1-oxo-1,2,3,4-tetrahydroisoquinolin-5-yl)amino]pyrimidine-5-carboxamide;

2-[(5-chloro-2-methoxyphenyl)amino]-4-[(1-oxo-1,2,3,4-tetrahydroisoquinolin-5-yl)amino]pyrimidine-5-carboxamide;

2-[(2,3-dihydro-1H-inden-4-yl)amino]-4-[(1-oxo-1,2,3,4-tetrahydroisoquinolin-5-yl)amino]pyrimidine-5-carboxamide;

2-[(4-tert-butylphenyl)amino]-4-[(1-oxo-1,2,3,4-tetrahydroisoquinolin-5-yl)amino]pyrimidine-5-carboxamide;

2-[(2,5-dimethylphenyl)amino]-4-[(1-oxo-1,2,3,4-tetrahydroisoquinolin-5-yl)amino]pyrimidine-5-carboxamide;

2-{[4-fluoro-3-(trifluoromethyl)phenyl]amino}-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-({[4-(trifluoromethyl)phenyl]methyl}amino)pyrimidine-5-carboxamide;

2-[(2,3-difluoro-4-methylphenyl)amino]-4-[(1-oxo-1,2,3,4-tetrahydroisoquinolin-5-yl)amino]pyrimidine-5-carboxamide;

2-[(3,5-difluoro-4-methoxyphenyl)amino]-4-[(1-oxo-1,2,3,4-tetrahydroisoquinolin-5-yl)amino]pyrimidine-5-carboxamide;

2-[(4-fluoro-2-methoxyphenyl)amino]-4-[(1-oxo-1,2,3,4-tetrahydroisoquinolin-5-yl)amino]pyrimidine-5-carboxamide;

2-{[2-fluoro-3-(trifluoromethyl)phenyl]amino}-4-[(1-oxo-1,2,3,4-tetrahydroisoquinolin-5-yl)amino]pyrimidine-5-carboxamide;

2-[(1-benzothiophen-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[4-(2,2,2-trifluoroethyl)phenyl]amino}pyrimidine-5-carboxamide;

2-[(2-methoxypyridin-3-yl)amino]-4-[(1-oxo-1,2,3,4-tetrahydroisoquinolin-5-yl)amino]pyrimidine-5-carboxamide;

4-(cycloheptylamino)-2-[(6-methoxy-2-methyl-1,2,3,4-tetrahydroisoquinolin-7-yl)amino]pyrimidine-5-carboxamide;

4-(cyclohexylamino)-2-[(6-methoxy-2-methyl-1,2,3,4-tetrahydroisoquinolin-7-yl)amino]pyrimidine-5-carboxamide;

4-(cyclopentylamino)-2-[(6-methoxy-2-methyl-1,2,3,4-tetrahydroisoquinolin-7-yl)amino]pyrimidine-5-carboxamide;

4-[(bicyclo[1.1.1]pentan-2-yl)amino]-2-[(6-methoxy-2-methyl-1,2,3,4-tetrahydroisoquinolin-7-yl)amino]pyrimidine-5-carboxamide;

4-[(cis-4-aminocyclohexyl)amino]-2-[(6-methoxy-2-methyl-1,2,3,4-tetrahydroisoquinolin-7-yl)amino]pyrimidine-5-carboxamide;

4-{[(1R)-1-cyclohexylethyl]amino}-2-[(6-methoxy-2-methyl-1,2,3,4-tetrahydroisoquinolin-7-yl)amino]pyrimidine-5-carboxamide;

4-{[(1S)-1-cyclohexylethyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(3R,4S)-4-(methylsulfanyl)oxolan-3-yl]amino}pyrimidine-5-carboxamide;

4-{[(2,3-difluorophenyl)methyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(4aR,7aR)-octahydro-1H-cyclopenta[b]pyridin-5-yl]amino}pyrimidine-5-carboxamide;

4-[(1-cyclopropylpyrrolidin-3-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-phenylcyclopentyl)amino]pyrimidine-5-carboxamide;

methyl 7-({5-carbamoyl-2-[(6-methoxy-2-methyl-1,2,3,4-tetrahydroisoquinolin-7-yl)amino]pyrimidin-4-yl}amino)bicyclo[3.3.1]nonane-3-carboxylate;

4-{[(1S,4R)-bicyclo[2.2.1]heptan-2-yl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(tricyclo[4.2.1.0~2,5~]nonan-3-yl)amino]pyrimidine-5-carboxamide;

2-[(6-methoxy-2-methyl-1,2,3,4-tetrahydroisoquinolin-7-yl)amino]-4-{[4-(trifluoromethyl)cyclohexyl]amino}pyrimidine-5-carboxamide;

4-{[cis-4-(dimethylamino)cyclohexyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({[2-(trifluoromethoxy)phenyl]methyl}amino)pyrimidine-5-carboxamide;

4-{[(1S)-1-(2,3-difluorophenyl)ethyl]amino}-2-[(6-methoxy-2-methyl-1,2,3,4-tetrahydroisoquinolin-7-yl)amino]pyrimidine-5-carboxamide;

4-{[(1R)-1-(2,3-difluorophenyl)ethyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({[2-(trifluoromethyl)phenyl]methyl}amino)pyrimidine-5-carboxamide;

2-[(6-methoxy-2-methyl-1,2,3,4-tetrahydroisoquinolin-7-yl)amino]-4-({1-[2-(trifluoromethyl)phenyl]ethyl}amino)pyrimidine-5-carboxamide;

4-{[(2-ethoxyphenyl)methyl]amino}-2-[(6-methoxy-2-methyl-1,2,3,4-tetrahydroisoquinolin-7-yl)amino]pyrimidine-5-carboxamide;

4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(6-fluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(1R,3r,5S)-8-methyl-8-azabicyclo[3.2.1]octan-3-yl]amino}pyrimidine-5-carboxamide;

4-[(8-azabicyclo[3.2.1]octan-3-yl)amino]-2-[(6-methoxy-2-methyl-1,2,3,4-tetrahydroisoquinolin-7-yl)amino]pyrimidine-5-carboxamide;

4-{[(1R,2S)-2-(methoxymethyl)cyclopentyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(trans-4-methylcyclohexyl)amino]pyrimidine-5-carboxamide;

4-[(3-azabicyclo[3.2.1]octan-8-yl)amino]-2-[(6-methoxy-2-methyl-1,2,3,4-tetrahydroisoquinolin-7-yl)amino]pyrimidine-5-carboxamide;

4-[(4-methoxycyclohexyl)amino]-2-[(6-methoxy-2-methyl-1,2,3,4-tetrahydroisoquinolin-7-yl)amino]pyrimidine-5-carboxamide;

4-{[(1R,2R)-2-(hydroxymethyl)cyclohexyl]amino}-2-[(6-methoxy-2-methyl-1,2,3,4-tetrahydroisoquinolin-7-yl)amino]pyrimidine-5-carboxamide;

4-{[(1R,2R)-2-(difluoromethyl)cyclohexyl]amino}-2-[(6-methoxy-2-methyl-1,2,3,4-tetrahydroisoquinolin-7-yl)amino]pyrimidine-5-carboxamide;

4-[(7-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({[3-(trifluoromethyl)phenyl]methyl}amino)pyrimidine-5-carboxamide;

4-(benzylamino)-2-[(6-methoxy-2-methyl-1,2,3,4-tetrahydroisoquinolin-7-yl)amino]pyrimidine-5-carboxamide;

4-{[(1S)-2,3-dihydro-1H-inden-1-yl]amino}-2-[(6-methoxy-2-methyl-1,2,3,4-tetrahydroisoquinolin-7-yl)amino]pyrimidine-5-carboxamide;

4-[(3,3-difluorocyclopentyl)amino]-2-[(6-methoxy-2-methyl-1,2,3,4-tetrahydroisoquinolin-7-yl)amino]pyrimidine-5-carboxamide;

4-[(cis-4-ethynylcyclohexyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(1R,2R)-2-(prop-2-yn-1-yl)cyclopentyl]amino}pyrimidine-5-carboxamide;

2-[(6-methoxy-2-methyl-1,2,3,4-tetrahydroisoquinolin-7-yl)amino]-4-{[(1R,2S)-2-methylcyclohexyl]amino}pyrimidine-5-carboxamide;

4-{[(1R,2R)-2-(2-hydroxypropan-2-yl)cyclohexyl]amino}-2-[(6-methoxy-2-methyl-1,2,3,4-tetrahydroisoquinolin-7-yl)amino]pyrimidine-5-carboxamide;

4-{[(1S)-2-hydroxy-1-phenylethyl]amino}-2-[(6-methoxy-2-methyl-1,2,3,4-tetrahydroisoquinolin-7-yl)amino]pyrimidine-5-carboxamide;

4-{[(1S)-2-hydroxy-1-phenylethyl]amino}-2-[(1-oxo-1,3-dihydro-2-benzofuran-5-yl)amino]pyrimidine-5-carboxamide;

2-[(6-methoxy-2-methyl-1,2,3,4-tetrahydroisoquinolin-7-yl)amino]-4-{[(2,3,6-trifluorophenyl)methyl]amino}pyrimidine-5-carboxamide;

4-{[(1R)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide;

4-{[(1S)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide;

4-{[(1S)-1-cyclohexyl-2-hydroxyethyl]amino}-2-[(6-methoxy-2-methyl-1,2,3,4-tetrahydroisoquinolin-7-yl)amino]pyrimidine-5-carboxamide;

4-{[(1S)-1-cyclohexyl-2-hydroxyethyl]amino}-2-[(1-methyl-1H-pyrazol-4-yl)amino]pyrimidine-5-carboxamide;

4-[(5,6-difluoro-2,3-dihydro-1H-inden-1-yl)amino]-2-{[1-(piperidin-4-yl)-1H-pyrazol-4-yl]amino}pyrimidine-5-carboxamide;

4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(5,6-difluoro-2,3-dihydro-1H-inden-1-yl)amino]-2-[(1,2,3,4-tetrahydroisoquinolin-7-yl)amino]pyrimidine-5-carboxamide;

4-[(5,6-difluoro-2,3-dihydro-1H-inden-1-yl)amino]-2-[(6-fluoro-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(pyridin-4-yl)methyl]amino}pyrimidine-5-carboxamide;

4-{[(imidazo[1,2-a]pyridin-3-yl)methyl]amino}-2-[(6-methoxy-2-methyl-1,2,3,4-tetrahydroisoquinolin-7-yl)amino]pyrimidine-5-carboxamide;

4-{[(2-hydroxyphenyl)methyl]amino}-2-[(6-methoxy-2-methyl-1,2,3,4-tetrahydroisoquinolin-7-yl)amino]pyrimidine-5-carboxamide;

4-{[(3-cyanophenyl)methyl]amino}-2-[(6-methoxy-2-methyl-1,2,3,4-tetrahydroisoquinolin-7-yl)amino]pyrimidine-5-carboxamide;

4-{[(4-cyanophenyl)methyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(1,3-thiazol-2-yl)methyl]amino}pyrimidine-5-carboxamide;

2-[(6-methoxy-2-methyl-1,2,3,4-tetrahydroisoquinolin-7-yl)amino]-4-({[4-(trifluoromethyl)phenyl]methyl}amino)pyrimidine-5-carboxamide;

4-{[(1R,2R)-2-(hydroxymethyl)-2,3-dihydro-1H-inden-1-yl]amino}-2-[(6-methoxy-2-methyl-1,2,3,4-tetrahydroisoquinolin-7-yl)amino]pyrimidine-5-carboxamide;

4-{[(1S,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide, 4-{[(1R,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;

4-{[(1R,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;

4-{[(1S,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;

4-{[(1R)-2,3-dihydro-1H-inden-1-yl]amino}-2-[(6-methoxy-2-methyl-1,2,3,4-tetrahydroisoquinolin-7-yl)amino]pyrimidine-5-carboxamide;

4-[(5,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(6-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(4,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(6-methyl-2,3-dihydro-1H-inden-1-yl)amino]pyrimidine-5-carboxamide; and 2-[(6-methoxy-2-methyl-1,2,3,4-tetrahydroisoquinolin-7-yl)amino]-4-{[(piperidin-4-yl)methyl]amino}pyrimidine-5-carboxamide;

or a pharmaceutically acceptable salt thereof.

Alternate embodiments of the present invention may also exclude any of the compounds which are recited in the list above.

In one embodiment, the present invention is a composition comprising a compound of formula I, II, IIa, IIb, IIc, IId, III, IIIa, IIIb, IIIc, IIId, IV, IVa, IVb, or a pharmaceutically acceptable salt thereof, and at least one pharmaceutically acceptable carrier.

In another embodiment, the present invention is a method of treating cancer, metastasis, inflammation and auto-immune pathogenesis comprising administering to a patient in need thereof a composition of formula I, II, IIa, IIb, IIc, IId, III, IIIa, IIIb, IIIc, IIId, IV, IVa, IVb, or a pharmaceutically acceptable salt thereof.

In another embodiment, the present invention is the use of a compound of formula I, II, IIa, IIb, IIc, IId, III, IIIa, IIIb, IIc, IIId, IV, IVa, IVb, or a pharmaceutically acceptable salt thereof, in the manufacture of a medicament for treating cancer, metastasis, inflammation and auto-immune pathogenesis.

In another embodiment, the present invention includes compounds of formula I, II, IIa, IIb, IIc, IId, III, IIIa, IIIb, IIIc, IIId, IV, IVa, IVb, or a pharmaceutically acceptable salt thereof, for use in the treatment of cancer, metastasis, inflammation and auto-immune pathogenesis.

Also disclosed herein is a method of inhibiting activity of haematopoietic progenitor kinase 1 (HPK1) comprising contacting HPK1 with a compound disclosed herein, or a pharmaceutically acceptable salt thereof.

Also disclosed herein is a method of treating cancer, metastasis, inflammation and auto-immune pathogenesis, comprising administering to a patient suffering from at least one of said diseases or disorder an effective amount of a compound disclosed herein, or a pharmaceutically acceptable salt thereof.

Also disclosed herein is a method of treating melanoma in a patient comprising administering to said patient an effective amount of a compound disclosed herein, or a pharmaceutically acceptable salt thereof.

The present invention relates to compounds and compositions that are capable of inhibiting the activity of HPK1. The invention features methods of treating, preventing or ameliorating a disease or disorder in which HPK1 plays a role by administering to a patient in need thereof a therapeutically effective amount of a compound of Formula (I), or a pharmaceutically acceptable salt thereof. The invention also features methods of treating, preventing or ameliorating a disease or disorder in which HPK1 plays a role by administering to a patient in need thereof a therapeutically effective amount of a compound of Formula (I), or a pharmaceutically acceptable thereof. The methods of the present invention can be used in the treatment of a variety of HPK1 dependent diseases and disorders by inhibiting the activity of HPK1 enzymes. Inhibition of HPK1 provides a novel approach to the treatment, prevention, or amelioration of diseases including, but not limited to, cancer and metastasis Further disclosed herein is a compound disclosed herein, or a pharmaceutically acceptable salt thereof, for use in therapy. In one embodiment, disclosed herein is the use of a compound disclosed herein, or a pharmaceutically acceptable salt thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Cycloalkyl" refers to a non-aromatic ring system comprising from 3 to 6 ring carbon atoms. Non-limiting examples of monocyclic cycloalkyl include cyclopropyl, cyclobutyl, cyclopentyl. Non-limiting examples of cycloalkyl additionally include bicyclic spiro-cycloalkyl including spirohexane (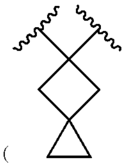).

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

'H' refers to hydrogen.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydro-pyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein, "Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

"Celite®" (Fluka) diatomite is diatomaceous earth and can be referred to as "celite".

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

Regarding stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated based on the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. A basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH═C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^{2}H$ (i.e., Deuterium or "D"), $^{3}H$, $^{11}C$, $^{13}C$, $^{14}C$, $^{14}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Substitution with positron emitting isotopes, such as $^{11}C$, $^{18}F$, $^{15}O$ and $^{13}N$, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline. N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of haematopoietic progenitor kinase 1 (HPK1). For example, the compounds disclosed herein can potentially be used to inhibit activity of HPK1 in cell or in an individual in need of modulation of the enzyme by administering an effective amount of a compound.

Also disclosed herein are methods of treating diseases associated with activity or expression, including abnormal activity and/or overexpression, of HPK1 in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the HPK1 enzyme, such as over expression or abnormal activity. An HPK1-associated disease can also include any disease, disorder or condition that may be prevented, ameliorated, or cured by modulating enzyme activity.

Examples of HPK1-associated diseases include cancer, metastasis, inflammation and auto-immune pathogenesis. Example cancers potentially treatable by the methods herein include cancer of the colon, pancreas, breast, prostate, lung, brain, ovary, cervix, testes, renal, head and neck, lymphoma, leukemia, melanoma, and the like. In some embodiments, the cancer is selected from liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma. Another aspect of the invention relates to a method of inducing cell cycle arrest, apoptosis in tumor cells, and/or enhanced tumor-specific T cell immunity. The method comprises contacting the cells with an effective amount of a compound of Formula (I). In another embodiment, the present invention relates to a compound of Formula (I) or a pharmaceutical composition comprising a compound of the present invention and a pharmaceutically acceptable carrier used for the treatment of cancers including, but not limited to, liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma. In some embodiments, administration of a compound of Formula (I) or a pharmaceutical composition comprising a compound of the present invention and a pharmaceutically acceptable carrier induces a change in the cell cycle or cell viability As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the HPK1 enzyme with a compound disclosed herein includes the administration of a compound of the present invention to an individual or patient, such as a human, as well as, for example, introducing a compound of the invention into a sample containing a cellular or purified preparation containing the HPK1 enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with HPK1 enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit HPK1 enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an HPK1 enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or overtime as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with HPK1 enzyme activity comprising administration of an effective amount of a compound disclosed herein to a subject in need of treatment thereof. In one embodiment, the disease or disorder associated with an HPK1 enzyme is a cell proliferation disorder.

In one embodiment, disclosed herein is the use of a compound disclosed herein in a therapy. The compound may be useful in a method of inhibiting HPK1 enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to HPK1 enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartarmidephenol, or polyethyleneoxidepolylysine substituted with palmitoyl residues. Furthermore, the compounds of the invention may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared using a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient, and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be vaned and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein, and other active agents will generally also be within the aforementioned range, but in each case, an effective dose of each active agent should be used. In such combinations, the compound disclosed herein, and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with HPK1 enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with HPK1 enzyme activity, wherein the medicament is prepared for administration with another active agent. The invention also provides the use of another active agent for treating a disease or disorder associated with an HPK1 enzyme, wherein the medicament is adminstered with a compound disclosed herein.

The invention also provides the use of a compound disclosed herein for treating a disease or disorder associated with HPK1 enzyme activity, wherein the patient has previously (e.g. within 24 hours) been treated with another active agent. The invention also provides the use of another therapeutic agent for treating a disease or disorder associated with HPK1 enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM. L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as daunorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxy-adenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, $F(ab')_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US201110271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL PROCEDURES

The following examples are intended to be illustrative only and not limiting in any way. Abbreviations not indicated below have their meanings as conventionally used in the art unless specifically stated otherwise.

| | |
|---|---|
| ACN or MeCN | acetonitrile |
| AcOH | acetic acid |
| t-AmOH or tert-AmOH | tert-Amyl alcohol |
| BrettPhos-Pd-G3 | [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |
| t-BuBrettPhos | 2-(di-tert-butylphosphino)-2',4',6'-triisopropyl-3,6-dimethoxy-1,1'-biphenyl |
| t-BuBrettPhos-Pd-G3 | [(2-di-tert-butylphosphino-3,6-dimethoxy-2',4',6'-triisopropyl-1,1'-biphenyl)-2-(2'-amino-1,1'-biphenyl)]palladium(II) methanesulfonate |
| BisPin | bis(pinacolato)diboron |
| Boc | tert-butoxy carbamate |
| $Boc_2O$ | di-tert-butyl dicarbonate |
| DCM | dichloromethane |
| DIEA | diisopropylethylamine |
| DMA | dimethylacetamide |
| DMF | dimethylformamide |
| DMSO | dimethylsulfoxide |
| EI | electron ionization |
| EIOAc | ethyl acetate |
| EtOH | ethanol |
| $^1$H NMR | proton nuclear magnetic resonance (data) |
| HPLC | high performance liquid chromatography |
| KOAc | potassium acetate |
| $K_3PO_4$ | potassium phosphate |
| LC/MS | liquid chromatography coupled to mass spectrometer |
| LiHMDS | lithium hexamethyldisilazide or lithium bis(trimethylsilyl)amide |
| MeCN | acetonitrile |
| MeOH | methanol |
| MHz | megahertz |
| MS | mass spectrum (data) |
| NBS | N-bromosuccinimide |
| NCS | N-chlorosuccinimide |
| MTBE | methyl tert-butyl ether |
| $N(Et)_3$ | triethylamine |
| NMR | nuclear magnetic resonance (data) |
| $Na_2SO_4$ | sodium sulfate |
| $NaBH(OAc)_3$ | sodium triacetoxyborohydride |
| NaOAc | sodium acetate |
| $PdCl_2$(dppf) | 1,1'-bis(diphenylphosphino)ferrocene-palladium(II)dichloride |
| $PdCl_2$(dtbpf) | [1,1'-bis(di-tert-butylphosphino)ferrocene]dichloropalladium(II) |
| $Pd(PPh_3)_4$ | tetrakis(triphenylphosphine)palladium(0) |
| $Pd[(t\text{-}Bu)_3P]_2$ | bis(tri-tert-butylphosphine)palladium(0) |
| $Pd_2(dba)_3$ | tris(dibenzylideneacetone) dipalladium(0) |
| $Pd(PPh_3)_2Cl_2$ | bis(triphenylphosphine)palladium(II) dichloride |
| PMB | para-methoxybenzyl |
| PPA | polyphosphoric acid |
| i-$Pr_2$Net | N,N-diisopropylethylamine |
| RT | room temperature |
| TFA | trifluoroacetic acid |
| THF | tetrahydrofuran |
| TMSCl | trimethylsilyl chloride |
| TLC | thin layer chromatography |
| Xphos | 2-dicyclohexylphosphino-2',4',6'-triisopropylbiphenyl |
| G2-XPhos Precatalyst | chloro(2-dicyclohexylphosphino-2',4',6'-triisopropyl-1,1'-biphenyl)[2-(2'-amino-1,1'-biphenyl)]palladium(II) |

General Synthetic Schemes

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

While the present invention has been described in conjunction with the specific examples set forth below, many alternatives, modifications, and variations thereof will be apparent to those of ordinary skill in the art. All such alternatives, modifications, and variations are intended to fall within the spirit and scope of the present invention.

Methods of Synthesis

The compounds in the present invention can be prepared according to the following general schemes using appropriate materials and are further exemplified by the subsequent specific examples. The compounds illustrated in the examples are not to be construed as forming the only genus that is considered as the invention. The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated, all reactions were stirred (mechanically, stir bar/stir plate, or shaken) and conducted under an inert atmosphere of nitrogen or argon unless specifically stated otherwise. All temperatures are degrees Celsius (° C.) unless otherwise noted. Ambient temperature is 15-25° C. Most compounds were purified by reverse-phase preparative HPLC, MPLC on silica gel, recrystallization and/or trituration (suspension in a solvent followed by filtration of the solid). The course of the reactions was followed by thin layer chromatography (TLC) and/or LC/MS and/or NMR and reaction times are given for illustration only. All end products were analyzed by NMR and LC/MS. Intermediates were analyzed by NMR and/or TLC and/or LC/MS.

General Syntheses

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

While the present invention has been described in conjunction with the specific examples set forth below, many alternatives, modifications, and variations thereof will be apparent to those of ordinary skill in the art. All such alternatives, modifications, and variations are intended to fall within the spirit and scope of the present invention.

General Synthetic Schemes

Several synthetic methods were employed to provide the compounds described herein. Final compounds were evaluated for biological activity in the kinase activity assay in either the neutral form, as a TFA salt, or as a HCl salt, and were screened in the kinase activity assay as either the racemate or as resolved enantiomers and diastereomers. The chiral separations were conducted on either the final compounds or on a synthetic intermediate. Chiral separation conditions are noted where appropriate.

Scheme G-1

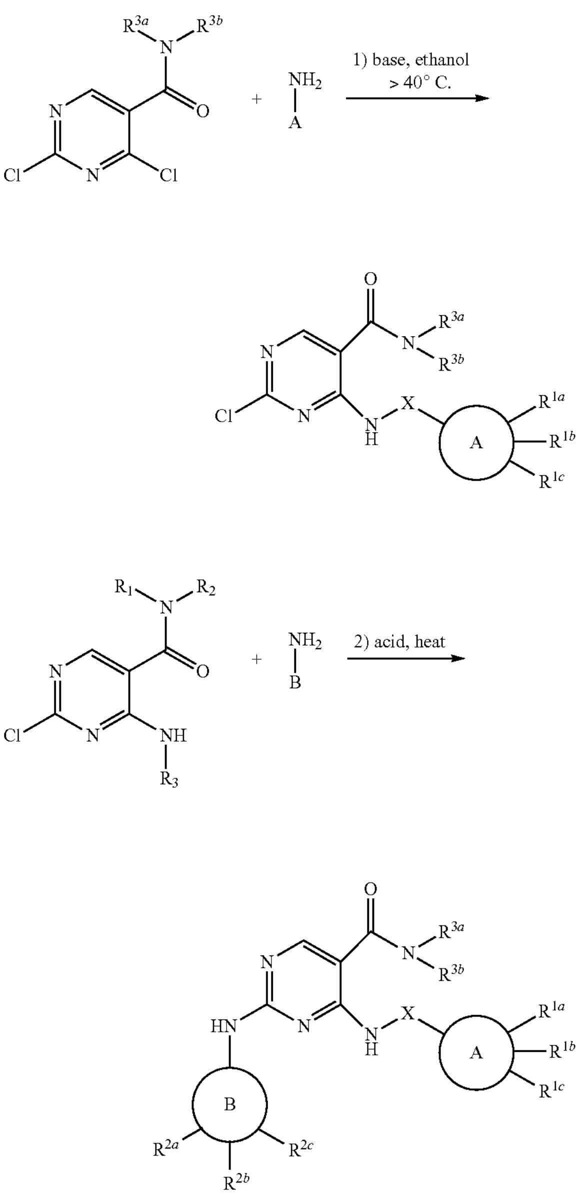

A general synthetic approach to access the small molecules described herein can be found in Scheme G-1 Beginning from commercial material, 2,4-dichloropyrimidine-5-carboxamide, for example, the righthand amine (alkyl, aryl, or benzylamine) can be installed using a base-mediated SnAr reaction (C—N bond forming reaction). The subsequent material can then be modified to afford the final compound following an acid-mediated (usually, but not limited to, HCl or TsOH) SnAr reaction (C—N bond forming reaction) under more forcing (>60° C.) heating conditions described herein. Those skilled in the art will readily understand that known variations of the conditions and processes of the such procedures can be used to prepare the subject compounds.

Synthesis of Common Intermediates

Intermediate I-1. Preparation of tert-butyl 7-Amino-6-methoxy-1,2,3,4-tetrahydroisoquinoline-2-carboxylate

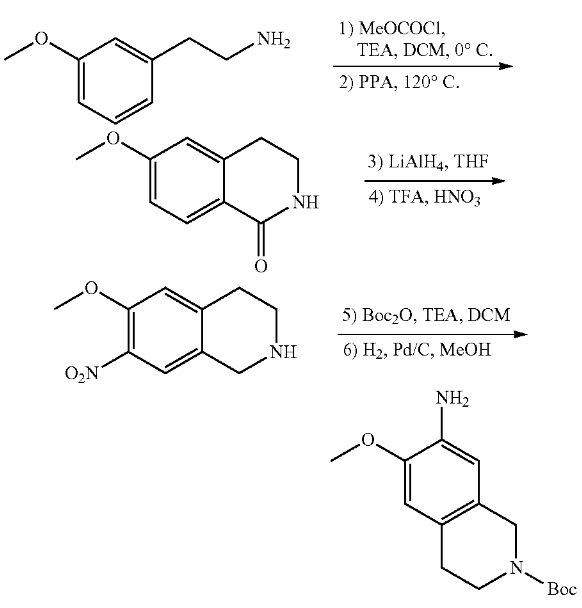

I-1

Step 1. To a stirred solution of 2-(3-methoxyphenyl)ethan-1-amine (300 g, 1.98 mol) and TEA (602 g, 5.95 mol) in DCM (4 L) was added dropwise at 0° C. methyl carbonochloridate (206 g, 2.18 mol) under nitrogen atmosphere. The resulting mixture was stirred for 4 h at 0° C., then quenched by the addition of water (2 L). The resulting mixture was extracted with DCM (2×3 L). The combined organic layers were washed with 1 N HCl (3 L), water (3 L) and brine (3 L), dried ($Na_2SO_4$), and concentrated under reduced pressure, giving methyl N-[2-(3-methoxyphenyl)ethyl]carbamate (250 g).

Step 2. A 5 L 3-necked round-bottom flask was charged with methyl N-[2-(3-methoxyphenyl)ethyl]-carbamate (250 g, 1.19 mol) and polyphosphoric acid (2 L). The resulting mixture was stirred for 4 h at 120° C. under a nitrogen atmosphere. The mixture was cooled to RT and poured into 500 mL of ice/water. The resulting mixture was extracted with EtOAc (5 L). The organic layers were washed with water (3 L) and brine (3 L), dried over anhydrous $Na_2SO_4$, and concentrated under reduced pressure. The residue was purified by silica gel column chromatography (3:1 hexane/EtOAc) to afford 6-methoxy-1,2,3,4-tetrahydroisoquinolin-1-one (180 g).

Step 3. To a stirred solution of 6-methoxy-1,2,3,4-tetrahydroisoquinolin-1-one (180 g, 1.02 mol) in THF (3 L) was added $LiAlH_4$ (62.8 g, 1.66 mol) portionwise. The resulting mixture was stirred for 2 h. The reaction was quenched with 500 mL of water and the aqueous layer was extracted with EtOAc (3 L). The organic phase was washed with 1 N NaOH (500 mL), brine (1 L), dried over anhydrous $Na_2SO_4$, and concentrated under reduced pressure. The residue was purified by silica gel column chromatography (20:1 $CH_2Cl_2$/MeOH) to afford 6-methoxy-1,2,3,4-tetrahydroisoquinoline (150 g).

Step 4. To a stirred solution of 6-methoxy-1,2,3,4-tetrahydroisoquinoline (150 g, 919 mmol) in TFA (3 L) was added $HNO_3$ (100 mL) dropwise under a nitrogen atmosphere. The resulting mixture was stirred for 3 h at room temperature. The reaction was diluted with DCM (4 L), washed with saturated aqueous $NaHCO_3$ (4 L), water (4 L), brine (4 L), dried ($Na_2SO_4$), and concentrated under reduced pressure. This resulted in 6-methoxy-7-nitro-1,2,3,4-tetrahydroisoquinoline (170 g).

Step 5. To a stirred mixture of 6-methoxy-7-nitro-1,2,3,4-tetrahydroisoquinoline (170 g, 816 mmol) and TEA (163 g, 1.61 mol) in DCM (3 L) was added $Boc_2O$ (176 g, 815 mmol) portionwise. The resulting mixture was stirred for 2 h. The mixture was diluted with DCM (2 L), washed with 1 N HCl (500 mL), water (500 mL), brine (500 mL), dried ($Na_2SO_4$), and concentrated under reduced pressure. The residue was purified by silica gel column chromatography (8:1 petroleum ether/EtOAc) to afford tert-butyl 6-methoxy-7-nitro-1,2,3,4-tetrahydroisoquinoline-2-carboxylate (70 g).

Step 6. A 3 L 3-necked round-bottom flask was charged with tert-butyl 6-methoxy-7-nitro-1,2,3,4-tetrahydroisoquinoline-2-carboxylate (70.0 g, 227 mmol), MeOH (1 L) and Pd/C (10.0 g, 93.9 mmol). To this mixture $H_2$ (gas) was introduced and the resulting mixture was stirred for 5 h. The mixture was filtered, and the filtrate concentrated under reduced pressure. The crude product was re-crystallized from petroleum/EtOAc (8:1) to afford tert-butyl 7-amino-6-methoxy-1,2,3,4-tetrahydroisoquinoline-2-carboxylate (50.7 g). $^1H$ NMR (400 MHz, DMSO-$d_6$) δ 6.56 (s, 1H), 6.37 (s, 1H), 4.56 (s, 2H), 4.29 (s, 2H), 3.73 (s, 3H), 3.49 (m, 2H), 2.61 (m, 2H), 1.42 (s, 9H). MS (EI) m/z calc'd for $C_{15}H_{23}N_2O_3$ $[M+H]^+$, 279, found 279.

Intermediate I-2. Preparation of 6-methoxy-2-methyl-1,2,3,4-tetrahydroisoquinolin-7-amine

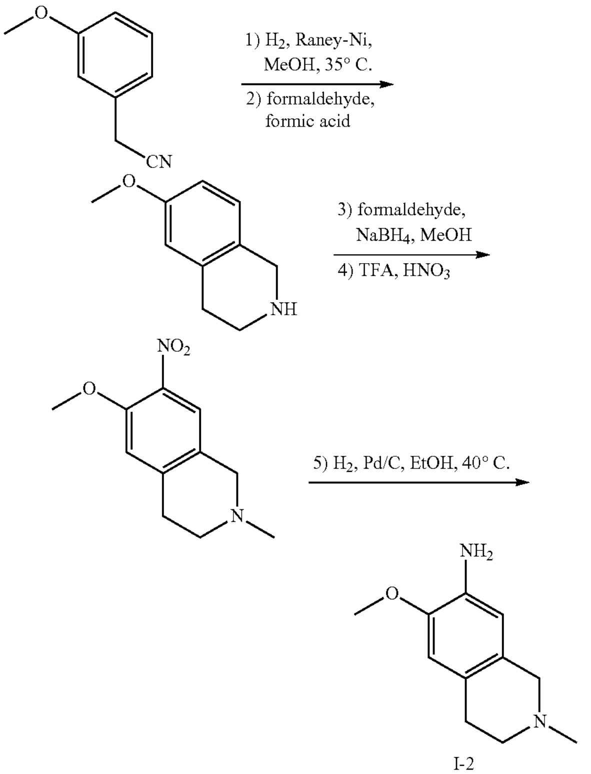

I-2

Step 1. A 20-L pressure reactor was charged with Raney-Ni (200 g), MeOH (10 L) and 2-(3-methoxyphenyl)acetonitrile (1000 g). The resulting solution was stirred overnight at 35° C. under an atmosphere of $H_2$ (30 atm). The resulting mixture was filtered and concentrated in vacuo, giving 740 g of 2-(3-methoxyphenyl)ethanamine.

Step 2. A 20-L 4-necked round-bottom flask was charged with 2-(3-methoxyphenyl)-ethanamine (740 g, 4.89 mol), formic acid (7.4 L), $H_2O$ (740 mL), formaldehyde (151 g, 5.04 mol). The resulting solution was stirred overnight, concentrated in vacuo. To this, acetyl chloride (370 mL) in MeOH (6 L) was added and the mixture stirred for 30 minutes. The mixture was concentrated and then triturated with EtOAc (1 L) to provide the desired product, 6-methoxy-1,2,3,4-tetrahydroisoquinoline (370 g).

Step 3. A 5-L 4-necked round-bottom flask was charged with 6-methoxy-1,2,3,4-tetrahydroisoquinoline (370 g, 2.27 mol), MeOH (4.0 L) and formaldehyde (1.1 L) was added slowly at 0° C. The resulting solution was stirred for 15 min, then $NaBH_4$ (300 g, 7.93 mol) was added in portions at 0° C. The resulting solution was stirred for 3 h, and quenched with water (1 L). The resulting mixture was stirred for 30 min, then concentrated under reduced pressure. The resulting mixture was diluted with water (5 L) and extracted with DCM (3×3 L). The combined organic layers were concentrated in vacuo, giving 6-methoxy-2-methyl-1,2,3,4-tetrahydroisoquinoline (260 g).

Step 4. A 5-L 4-necked round-bottom flask was charged with TFA (2.0 L), 6-methoxy-2-methyl-1,2,3,4-tetrahydroisoquinoline (260 g, 1.47 mol), and $HNO_3$ (150 g, 2.38 mmol). The resulting solution was stirred for 1 h and concentrated in vacuo. The residue was diluted with water (3 L), adding 4 N NaOH to adjust the pH to 10. The resulting solution was extracted with DCM (3×3 L) and concentrated. The residue was purified by chromatography on $SiO_2$ (5% MeOH/DCM) to provide 6-methoxy-2-methyl-7-nitro-1,2,3,4-tetrahydroisoquinoline (130 g).

Step 5. A 3-L 4-necked round-bottom flask was charged with 6-methoxy-2-methyl-7-nitro-1,2,3,4-tetrahydroisoquinoline (130 g, 593 mmol), Pd/C (20 g, 188 mmol), MeOH (1.5 L). The flask was evacuated and flushed three times with nitrogen, followed by flushing with hydrogen gas. The mixture was stirred 3 h at 40° C. under an atmosphere of hydrogen (balloon). The mixture was filtered and the filtrate concentrated in vacuo, providing 6-methoxy-2-methyl-1,2,3,4-tetrahydroisoquinolin-7-amine (97 g). MS (EI) m, calc'd for $C_{11}H_{17}N_2O$ $[M+H]^+$ 193, found 193. $^1H$ NMR (300 MHz, $CDCl_3$) δ 6.53 (s, 1H), 6.39 (s, 1H), 3.83 (s, 3H), 3.62 (bs, 2H), 3.46 (d, J=1.2 Hz, 2H), 2.83 (m, 2H), 2.67 (m, 2H), 2.45 (s, 3H).

INTERMEDIATE TABLE 1

| Compound Number | Structure | Name | Exact Mass |
|---|---|---|---|
| I-3 | 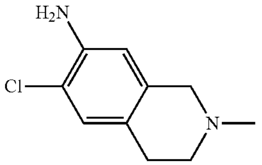 | 6-chloro-2-methyl-1,2,3,4-tetrahydro-isoquinolin-7-amine | Calc'd 197, found 197 |
| I-4 | 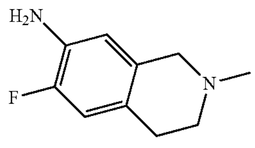 | 6-fluoro-2-methyl-1,2,3,4-tetrahydroi-soquinolin-7-amine | Calc'd 181, found 181 |

Intermediate I-5. Preparation of 6-methoxy-2,3-dimethyl-1,2,3,4-tetrahydroisoquinolin-7-amine

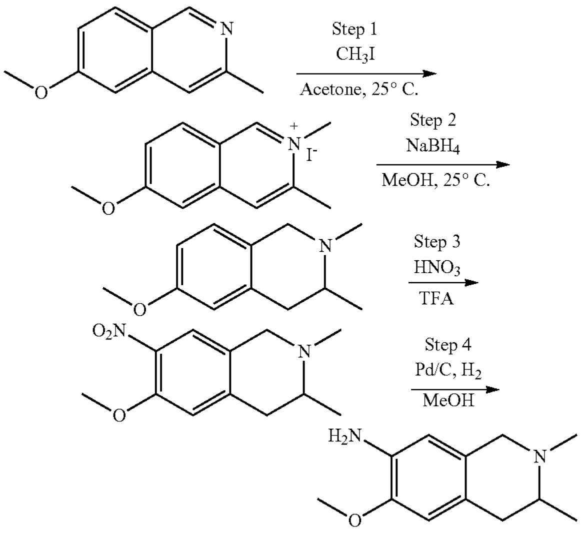

I-5

Step 1. To a solution of 6-methoxy-3-methylisoquinoline (700 mg, 4.04 mmol) in acetone (10 mL) was added iodomethane (1.3 mL, 20.88 mmol) at 25° C. under $N_2$ atmosphere. The mixture was stirred at 25° C. for 16 h. LCMS showed desired product. The mixture was evaporated under reduced pressure to give the product of 6-methoxy-2,3-dimethylisoquinolin-2-ium (760 mg).

Step 2. To a solution of 6-methoxy-2,3-dimethyl-1,2-dihydroisoquinoline (700 mg, 3.70 mmol) in MeOH (18 mL) was added $NaBH_4$ (1119 mg, 29.6 mmol) at 0° C. After the addition was finished, the mixture was stirred at 25° C. for 3 h. The mixture was diluted with water (40 mL), and extracted with DCM (40 mL×2). The organic layer was washed with brine (40 mL), dried over $Na_2SO_4$. After filtration, the filtrate was concentrated under reduced pressure to give 6-methoxy-2,3-dimethyl-1,2,3,4-tetrahydroisoquinoline as a solid. The crude was taken to next step without purification.

Step 3. To a solution of 6-methoxy-2,3-dimethyl-1,2,3,4-tetrahydroisoquinoline (710 mg, crude) in TFA (7 mL) was added nitric acid (0.261 mL, 4.08 mmol) at 0° C. After the addition was finished, the mixture was stirred at 25° C. for 16 h. The mixture was concentrated in vacuum to remove the TFA. The residue was slowly diluted with sat. aq $Na_2CO_3$ (100 mL), and extracted with DCM (50 mL*2). The combined organic layers were washed with brine (50 mL), dried ($Na_2SO_4$), filtered and concentrated. The residue was purified by flash silica gel chromatography eluenting with 0~20% MeOH @ 60 m/min to give 6-methoxy-2,3-dimethyl-7-nitro-1,2,3,4-tetrahydroisoquinoline.

Step 4. To a solution of 6-methoxy-2,3-dimethyl-7-nitro-1,2,3,4-tetrahydroisoquinoline (200 mg, 0.846 mmol) in MeOH (20 mL) was added Pd—C (180 mg)(10% wt) at 25° C. The mixture was stirred under $H_2$ balloon (15 psi) at 25° C. for 3 h. The mixture was filtered through a celite pad, the filtrate was concentrated under reduced pressure to give 6-methoxy-2,3-dimethyl-1, 2, 3, 4-tetrahydroisoquinolin-7-amine. MS (ESI) m z calc'd for $C_{12}H_{19}N_2O$ $(M+H)^+$ 207, found 207.

Intermediate I-6. Preparation of 2-fluoro-6-(1-methoxyethyl)aniline

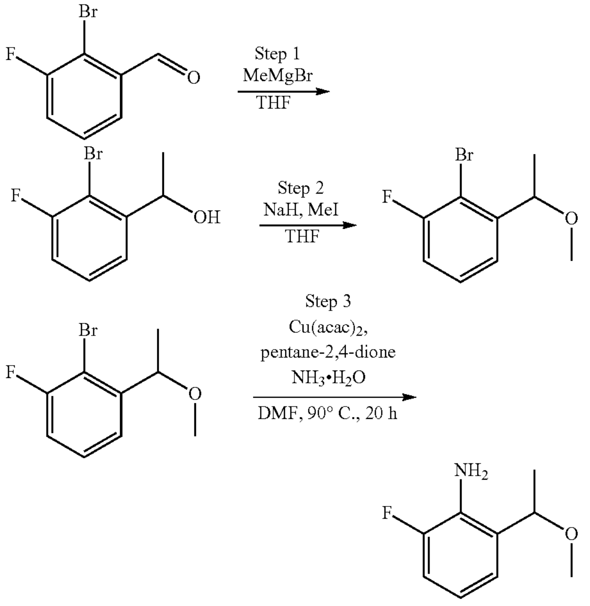

I-6

Step 1. To a solution of 2-bromo-3-fluorobenzaldehyde (3.0 g, 14.8 mmol) in dry THF (30 mL) was added methylmagnesium bromide (9.85 mL, 29.6 mmol) dropwise at −30° C. under $N_2$ atmosphere. The mixture was stirred at −30° C. for 10 min then allowed to warm to 25° C. for 3 h. TLC ($SiO_2$; petroleum ether:ethyl acetate=5:1) showed reaction completed. The mixture was quenched with water (10 mL), extracted with EtOAc (30 mL×2), dried ($Na_2SO_4$) filtered, and the solvent was evaporated under reduced pressure to give 1-(2-bromo-3-fluorophenyl)ethanol, which was used directly.

Step 2. To a solution of 1-(2-bromo-3-fluorophenyl)ethanol (1.0 g, 4.57 mmol) in THF (10 mL) was added NaH (0.274 g, 6.85 mmol) and iodomethane (0.811 mL, 13.03 mmol) at 0° C. under $N_2$ atmosphere. The mixture was stirred at 25° C. for 2 h. The reaction was monitored by TLC, ($SiO_2$, Pet. ether/EtOAc=311) showed complete conversion. The mixture was diluted with $NH_4Cl$ (30 mL), extracted with EtOAc (30 mL×2), dried ($Na_2SO_4$), filtered, and the solvent was evaporated under reduced pressure to give 2-bromo-1-fluoro-3-(1-methoxyethyl)benzene, which was used directly in the next step.

Step 3. A mixture of ammonium hydroxide (5.28 mL, 38.0 mmol), pentane-2,4-dione (0.260 mL, 2.53 mmol), copper (II) acetylacetonate (66.3 mg, 0.253 mmol), 2-bromo-1-fluoro-3-(1-methoxyethyl)benzene (590 mg, 2.53 mmol) and $Cs_2CO_3$ (1650 mg, 5.06 mmol) in DMF (10 mL) was degassed and backfilled with $N_2$ (three times). The reaction mixture was stirred at 90° C. for 20 h. TLC ($SiO_2$, EtOAc/Pet. Ether=1/10) showed starting material consumed and product formed. Water (20 mL) was added and to the resulting mixture was added EtOAc (20 mL). The organic layer was separated and the aqueous was extracted with EtOAc (20 mL×3). The combined organic layers were washed with brine (20 mL), dried ($Na_2SO_4$), filtered, and concentrated to give a residue which was purified by flash silica gel chromatography (Silica Flash Column (12 g), Eluent of 0~3% EtOAc/Pet. ether gradient @30 mL/min) to give 2-fluoro-6-(1-methoxyethyl)aniline. MS (ESI) m/z calc'd for $C_9H_{13}FNO$ $(M+H)^+$ 170, found 170. $^1H$ NMR (400 MHz, $CDCl_3$): δ 6.90-6.93 (m, 1H), 6.78 (d, J=7.2 Hz, 1H), 6.61 (dt, J=5.2, 8.0 Hz, 1H), 4.41 (q, J=6.8 Hz 1H), 4.36 (br s, 2H), 3.28 (s, 3H), 1.54 (d, J=7.2 Hz, 3H).

INTERMEDIATE TABLE 2

| Compound Number | Structure | Name | Exact Mass $[M+H]^+$ |
|---|---|---|---|
| I-7 | 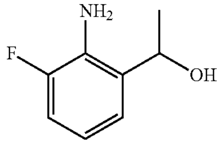 | 1-(2-amino-3-fluorophenyl)ethan-1-ol | Calc'd 156, found 156 |

Intermediate I-8. Preparation of 7-Bromo-1-cyclopropyl-6-methoxy-2-methyl-1,2,3,4-tetrahydroisoquinoline

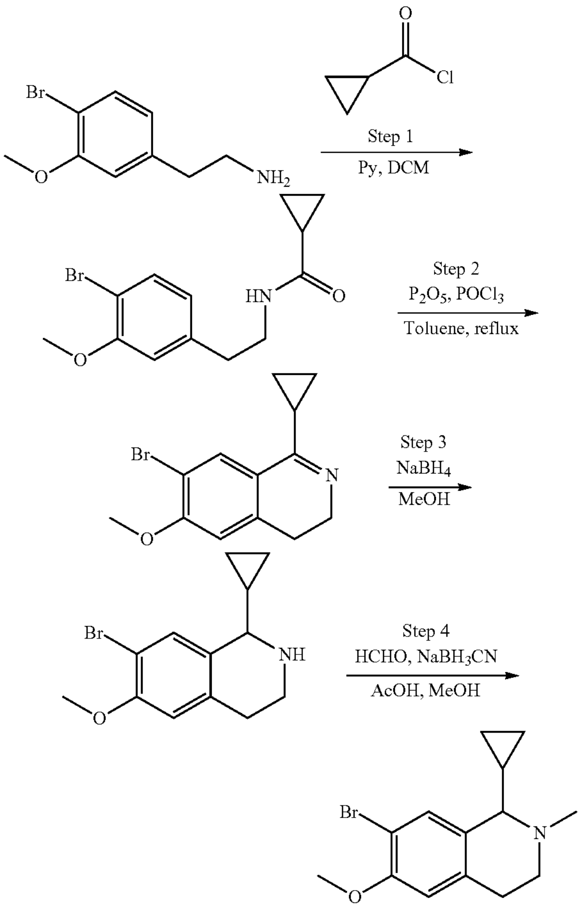

I-8

Step 1. To a mixture of 2-(4-bromo-3-methoxyphenyl) ethanamine (530 mg, 2.30 mmol) and pyridine (0.279 ml, 3.45 mmol) in $CH_2Cl_2$ (10 mL) was slowly added cyclopropanecarbonyl chloride (289 mg, 2.76 mmol) at 0° C. under $N_2$. After addition, the mixture was stirred at 25° C. for 2 h. The mixture was diluted with 30 mL of water and extracted with 30 mL of $CH_2Cl_2$. The organic layer was washed with 30 mL of brine, dried ($Na_2SO_4$), filtered and concentrated to give crude N-(4-bromo-3-methoxyphenethyl)cyclopropanecarboxamide (900 mg), which was used for next step directly.

Step 2. To a mixture of N-(4-bromo-3-methoxyphenethyl) cyclopropanecarboxamide (900 mg, 2.20 mmol) and phosphorus pentoxide (626 mg, 4.41 mmol) in toluene (15 mL) was slowly added $POCl_3$ (1.027 ml, 11.02 mmol) under $N_2$ at 25° C. Then the mixture was stirred at 110° C. under $N_2$ for 2 h. LCMS showed complete conversion to desired product. The mixture was slowly poured into stirred water (50 mL) at 0° C. The aq. NaOH (2M) was added to adjust the pH to 8~10, then DCM (50 mL) was added. The organic layer was separated and the aqueous was re-extracted with $CH_2Cl_2$ (50 mL×3). The combined organic layers were washed with brine (50 mL), dried ($Na_2SO_4$), filtered and concentrated in vacuum to give crude 7-bromo-1-cyclopropyl-6-methoxy-3,4-dihydroisoquinoline (600 mg), which was used in next step directly.

Step 3. To a solution of 7-bromo-1-cyclopropyl-6-methoxy-3,4-dihydroisoquinoline (600 mg, 2.14 mmol) in MeOH (10 mL) was $NaBH_4$ (162 mg, 4.28 mmol) at 0° C. under $N_2$. Then it was stirred at 25° C. for 2 h. The LCMS showed the desired product was formed. After finished, water (20 mL) and EtOAc (20 mL) was added. The organic layer was separated and the aqueous was re-extracted with EtOAc (20 mL×3). The combined organic layers were washed with brine (20 mL), dried ($Na_2SO_4$), filtered and concentrated in vacuum to give crude 7-bromo-1-cyclopropyl-6-methoxy-1,2,3,4-tetrahydroisoquinoline (500 mg), which was used in next step directly.

Step 4. A mixture of 7-bromo-1-cyclopropyl-6-methoxy-1,2,3,4-tetrahydroisoquinoline (500 mg, 1.77 mmol) and formaldehyde (518 mg, 6.38 mmol) was added a drop of AcOH (0.5 mL) in MeOH (5 mL). The mixture was stirred at 25° C. for 10 min, then $NaBH_3CN$ (301 mg, 4.78 mmol) was added and the mixture was stirred at 25° C. for 4 h under $N_2$. Solvent was removed under reduced pressure. The residue was diluted with water (10 mL) and extracted with EtOAc (10 mL×3). The organic layers were washed with brine (10 mL), dried ($Na_2SO_4$), filtered and concentrated in vacuum. The residue was purified by flash silica gel chromatography (Silica Flash Column (12 g), eluent of 0~30% $MeOH/CH_2Cl_2$ @ 30 mL/min) to give 7-bromo-1-cyclopropyl-6-methoxy-2-methyl-1,2,3,4-tetrahydroisoquinoline (280 mg). MS (ESI) m/z calc'd for $C_{14}H_{19}BrNO$ $(M+H)^+$ 298, found 298. $^1H$ NMR (400 MHz, $CDCl_3$) δ 7.57 (s, 1H), 6.64 (s, 1H), 3.88 (s, 3H), 3.36 (m, 1H), 3.09 (br d, J=8.8 Hz, 1H), 3.00 (br dd, J=6.4, 12.4 Hz, 1H), 2.88-2.93 (m, 2H), 2.63 (s, 3H), 0.98-1.07 (m, 1H), 0.72-0.85 (m, 2H), 0.60 (m, 1H), 0.44-0.51 (m, 1H).

Intermediate I-9. Preparation of 4-((2-bromophenyl) amino)-2-chloropyrimidine-5-carboxamide

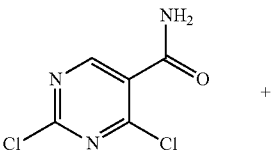

-continued

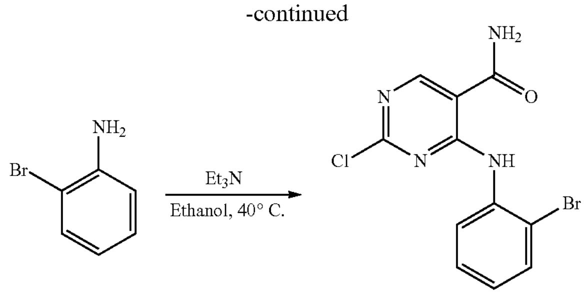

I-9

To a stirred solution of 2,4-dichloropyrimidine-5-carboxamide (19.5 g, 102 mmol) in EtOH (200 ml) under an argon atmosphere were added 2-bromoaniline (18.3 mg, 2.08 mmol) and triethylamine (31 ml, 222 mmol) at room temperature. The reaction mixture was stirred at 40° C. for 16 hrs. Reaction mixture was diluted with water (75 mL) and extracted with EtOAc (50 mL×3). The combined organic extracts were dried ($Na_2SO_4$), filtered, and concentrated in vacuo. The residue was sufficiently pure and carried on crude to give methyl 2-((5-carbamoyl-2-chloropyrimidin-4-yl)amino)benzoate. MS (ESI) m/z calcd for $C_{11}H_9BrClN_4O$ $[M+H]^+$327 found 327.

INTERMEDIATE TABLE 3

| Compound Number | Structure | Name | Exact Mass $[M + H]^+$ |
|---|---|---|---|
| I-10 | 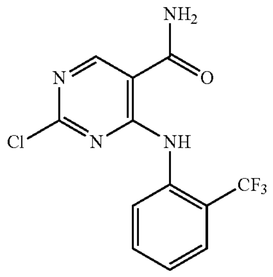 [SMILES: NC(=O)c1cnc(Cl)nc1Nc1ccccc1C(F)(F)F] | 2-chloro-4-((2-(trifluoromethyl) phenyl)amino) pyrimidine-5-carboxamide | Calc'd 317, found 317 |
| I-11 | 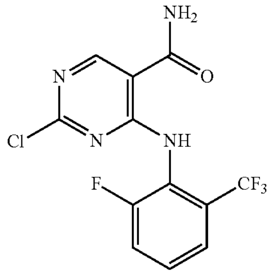 [SMILES: NC(=O)c1cnc(Cl)nc1Nc1c(F)cccc1C(F)(F)F] | 2-chloro-4-((2-fluoro-6-(trifluoromethyl) phenyl)amino) pyrimidine-5-carboxamide | Calc'd 335, found 335 |

Intermediate I-12. Preparation of 2-chloro-4-((2-(4-methyl-2-oxooxazolidin-3-yl)phenyl)amino)pyrimidine-5-carboxamide

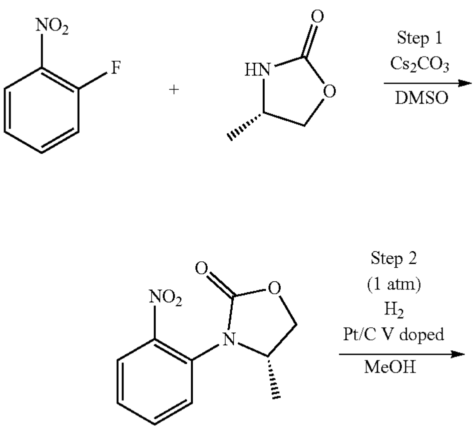

-continued

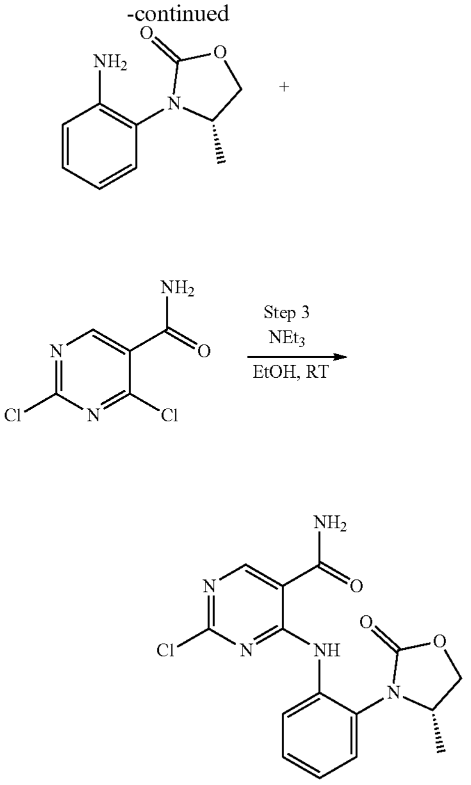

I-12

Step 1. A solution of (S)-4-methyloxazolidin-2-one (860 mg, 8.50 mmol), 1-fluoro-2-nitrobenzene (860 mg, 8.50 mmol) and cesium carbonate (4.62 g, 14.2 mmol) in DMSO (30 mL) was heated to 70° C. and the reaction was stirred overnight. The mixture was cooled, diluted with ethyl acetate (50 mL), washed with brine (saturated, 3×100 mL), dried ($Na_2SO_4$), filtered and the solvent was evaporated under reduced pressure. The residue was purified by column chromatography on silica gel eluting with (3:1 EtOAc/EtOH)/Hexanes (0% to 100%) to give 4-methyl-3-(2-nitrophenyl)oxazolidin-2-one. MS (ESI) m/z calc'd for $C_{10}H_{11}N_2O_4$ $[M+H]^+$ 223, found 223.

Step 2. A vial was charged with 1% Platinum on Carbon doped with 2% vanadium (1000 mg, 0.041 mmol), the vial was evacuated and backfilled with argon (3×), then a solution of (S)-5-methyl-1-(2-nitrophenyl)pyrrolidin-2-one (1.36 g, 6.18 mmol) in methanol (25 mL) was added, the vial was evacuated and backfilled with hydrogen (3×) from a balloon then reaction was stirred under 1 atm of hydrogen overnight. The reaction was filtered over celite pad and concentrated to give 3-(2-aminophenyl)-4-methyloxazolidin-2-one which was used without further purification. MS (ESI) m/z calc'd for $C_{10}H_{13}N_2O_2$ $[M+H]^+$ 193 found 193.

Step 3. (S)-3-(2-Aminophenyl)-4-methyloxazolidin-2-one (106 mg, 0.550 mmol), 2,4-dichloropyrimidine-5-carboxamide (96 mg, 0.5 mmol) and triethylamine (174 μL, 1.250 mmol) in ethanol (2000 μL) were heated to 50° C. overnight. The reaction was diluted with DMSO (2 mL), filtered and purified via mass directed reverse-phase prep-HPLC (Purification Method A) to yield 2-chloro-4-((2-(4-methyl-2-oxooxazolidin-3-yl)phenyl)amino)pyrimidine-5-carboxamide. MS (ESI) m/z calc'd for $C_{15}H_{15}ClN_5O_3$ $[M+H]^+$ 348, found 348.

Intermediate I-13. Preparation of 7'-bromo-6'-methoxy-2'-methyl-2',3'-dihydro-1'H-spiro[cyclopropane-1,4'-isoquinoline]

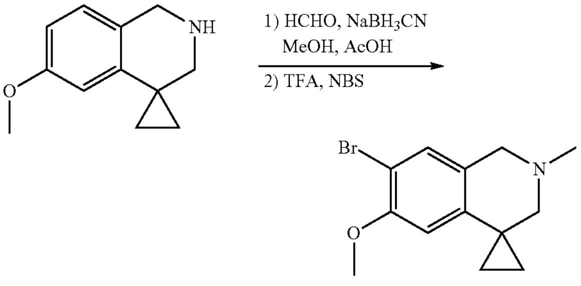

I-13

Step 1. To a mixture of 6'-methoxy-2',3'-dihydro-1'H-spiro[cyclopropane-1,4'-isoquinoline] (500 mg, 2.64 mmol) in MeOH (5 mL) was added formaldehyde (37%) (860 mg, 11 mmol) and AcOH (0.5 mL). The mixture was stirred at 15° C. for 10 min, then $NaCNBH_3$ (498 mg, 7.93 mmol) was added and stirred at 15° C. for 4 h under nitrogen. Solvent was removed under reduced pressure. The residue was added water (30 mL), and extracted with EtOAc (3×50 mL). The organic layers were washed with brine (50 mL), dried over $Na_2SO_4$, filtered and concentrated in vacuum to give the desired product which was used in next step directly.

Step 2. To the crude mixture (500 mg, crude) in TFA (5 mL) was added NBS (482 mg, 2.71 mmol) at 25° C. Then the mixture was stirred at 25° C. for 1 h. LC-MS showed desired product was formed. Then it was added water (10 mL) and $NaHCO_3$ to adjust the pH to 8-9, a solution of 10% MeOH/DCM (50 mL) was added. The organic layer was separated and the aqueous was re-extracted with 10% MeOH/DCM (2×30 mL). The combined organic layers were washed with brine (80 mL), dried over anhydrous $Na_2SO_4$, filtered and concentrated. The residue was purified by Pre-TLC (silica gel, DCM:MeOH=10:1) to give 7'-bromo-6'-methoxy-2'-methyl-2',3'-dihydro-1'H-spiro[cyclopropane-1,4'-isoquinoline]. $^1H$ NMR (400 MHz, $CDCl_3$) δ 7.19 (s, 1H), 6.16 (m, 1H), 3.80 (s, 3H), 3.62 (s, 2H), 2.50 (s, 2H), 2.43 (s, 3H), 0.99-1.06 (m, 2H), 0.88-0.98 (m, 2H).

EXAMPLES

Example 1-1. 4-((3-(Hydroxymethyl)phenyl)amino)-2-((6-methoxy-2-methyl-1,2,3,4-tetrahydroisoquinolin-7-yl)amino)pyrimidine-5-carboxamide

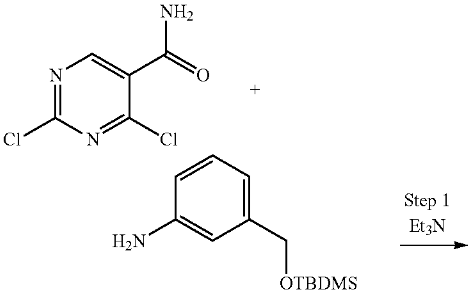

-continued

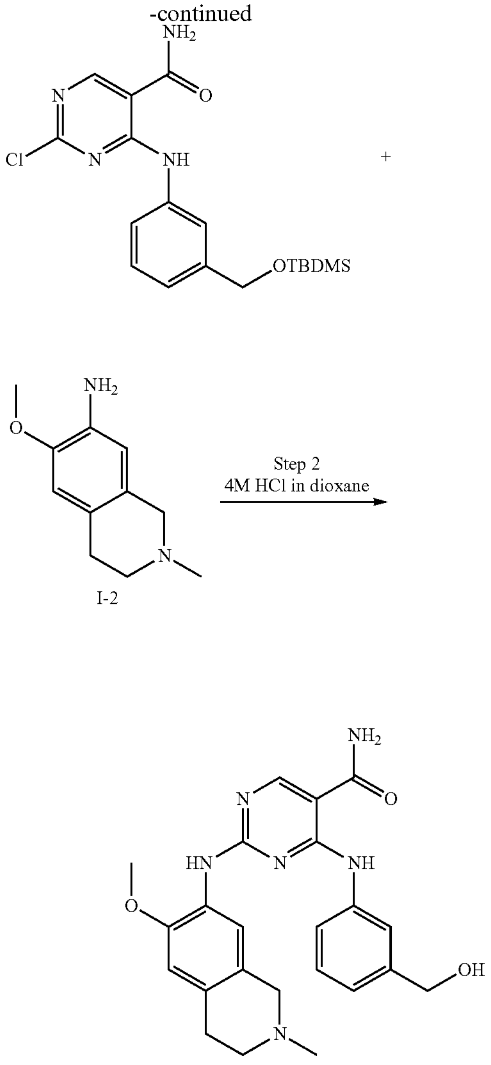

I-2

1-1

Step 1. To a stirred solution of 2,4-dichloropyrimidine-5-carboxamide (1000.0 mg, 5.21 mmol) in Ethanol (10 ml) under an argon atmosphere were added 3-(((tert-butyldimethylsilyl)-oxy)methyl)aniline (1237 mg, 5.21 mmol) and triethylamine (1.452 ml, 10.42 mmol) and reaction was stirred at 70° C. for 12 h. Reaction mixture was diluted with water and extracted with EtOAc (2×). The combined organic extracts were dried ($Na_2SO_4$), filtered, and concentrated in vacuo. The crude material was purified by silica column chromatography (10% to 20% MeOH in DCM) yielding 4-((3-(((tert-butyldimethylsilyl)oxy)methyl)phenyl)amino)-2-chloropyrimidine-5-carboxamide. MS (ESI) m/z calc'd for $C_{18}H_{25}ClN_4O_2Si$ $[M+H]^+$ 393, found 393.

Step 2. A mixture of 4-((3-(((tert-butyldimethylsilyl)oxy) methyl)phenyl)amino)-2-chloropyrimidine-5-carboxamide (200 mg, 0.509 mmol), 6-methoxy-2-methyl-1,2,3,4-tetrahydroisoquinolin-7-amine (98 mg, 0.509 mmol) in DMF (4.0 ml) was added 4 M HCl in dioxane (1.272 ml, 5.09 mmol) and the resulting mixture was heated at 100° C. for 6 h. The mixture was filtered and concentrated in vacuo to dryness. The crude material was purified by mass-directed reverse phase chromatography (Purification Method B) to give 4-((3-(hydroxymethyl)phenyl)amino)-2-((6-methoxy-2-methyl-1,2,3,4-tetrahydroisoquinolin-7-yl)amino)pyrimidine-5-carboxamide. MS (ESI) m/z calc'd for $C_{23}H_{27}N_6O_3Si$ $[M+H]^+$ 435, found 435. 1H NMR (499 MHz, DMSO-d6) δ 11.55 (s, 1H), 8.66 (s, 1H), 8.33 (s, 1H), 8.09-7.90 (br, 2H), 7.40 (s, 1H), 7.31 (br s, 1H), 7.22 (t, J=7.8 Hz, 1H), 7.02 (d, J=7.5 Hz, 1H), 6.79 (s, 1H), 5.25 (br s, 1H), 4.41 (s, 2H), 3.78 (s, 3H), 3.30 (s, 2H), 2.84-2.81 (m, 2H), 2.60-2.57 (m, 2H), 2.34 (s, 3H).

TABLE 1

Compounds listed in the table below were prepared using the synthetic methods described in the aforementioned Example 1-1. The table provides the compound structure, the name, the calculated and observed masses.

| Example | Structure | Name | Exact Mass $[M + H]^+$ |
| --- | --- | --- | --- |
| 1-1 | 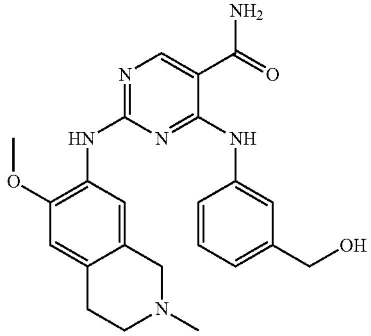 [SMILES: COc1cc2c(cc1Nc1ncc(C(N)=O)c(Nc3cccc(CO)c3)n1)CN(C)CC2] | 4-((3-(hydroxymethyl)phenyl)amino)-2-((6-methoxy-2-methyl-1,2,3,4-tetrahydroisoquinolin-7-yl)amino)pyrimidine-5-carboxamide | Calc'd 435, found 435 |

Example 2-1 and 2-2. tert-Butyl (3-((5-carbamoyl-2-((6-methoxy-2-methyl-1,2,3,4-tetrahydroisoquinolin-7-yl)amino)pyrimidin-4-yl)amino)benzyl)carbamate and 4-((3-(aminomethyl)phenyl)amino)-2-((6-methoxy-2-methyl-1,2,3,4-tetrahydroisoquinolin-7-yl)amino)pyrimidine-5-carboxamide

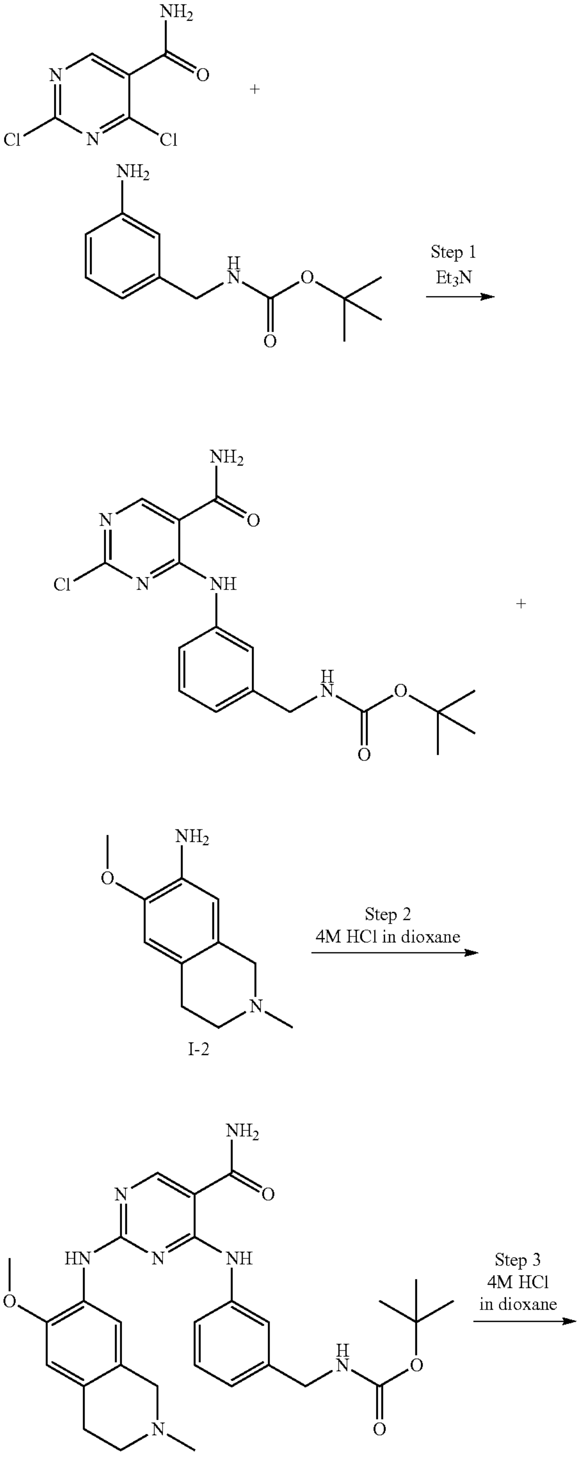

2-1

-continued

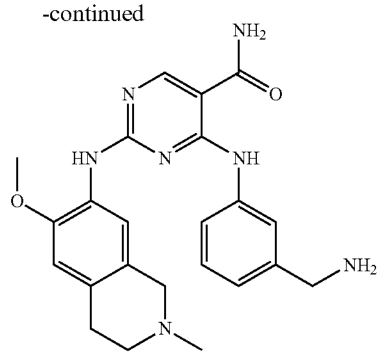

2-2

Step 1. To a stirred solution of 2,4-dichloropyrimidine-5-carboxamide (85 mg, 0.443 mmol) in Ethanol (3.0 ml) under an argon atmosphere were added tert-butyl (3-aminobenzyl) carbamate (98 mg, 0.443 mmol) and triethylamine (0.123 ml, 0.885 mmol) at RT. The reaction mixture was stirred at 70° C. for 1 h. Reaction mixture was diluted with water and extracted with EtOAc (15 mL×2). The combined organic extracts were dried ($Na_2SO_4$), filtered, and concentrated in vacuo. The crude material was purified by silica column chromatography (10% to 20% MeOH in DCM) yielding tert-butyl (3-((5-carbamoyl-2-chloropyrimidin-4-yl)amino) benzyl)carbamate. MS (ESI) m/z calc'd for $C_{17}H_{20}ClN_5O_3$ $[M+H]^+$ 378, found 378.

Step 2. A mixture of tert-butyl (3-((5-carbamoyl-2-chloropyrimidin-4-yl)amino)benzyl)carbamate-(3) (70 mg, 0.185 mmol), 6-methoxy-2-methyl-1,2,3,4-tetrahydroisoquinolin-7-amine (1-2) (35.6 mg, 0.185 mmol) in DMF (2000 μl) was added 4 M HCl in dioxane (139 μl, 0.556 mmol) and the resulting mixture was heated at 100° C. for 6 h. LCMS showed complete conversion to 2-1. The crude material was purified by mass-directed reverse phase chromatography (Purification method B) to give 4-((3-(aminomethyl)phenyl)amino)-2-((6-methoxy-2-methyl-1,2,3,4-tetrahydroisoquinolin-7-yl)amino)pyrimidine-5-carboxamide (2-1). MS (ESI) m/z calc'd for $C_{23}H_{27}N_7O_2$ $[M+H]^+$ 434, found 434. $^1$H NMR (499 MHz, DMSO-d6) δ 11.54 (s, 1H), 8.75-8.54 (m, 1H), 8.35 (s, 1H), 8.01 (s, 1H), 7.61 (s, 1H), 7.42 (s, 2H), 7.35-7.09 (m, 2H), 6.92 (d, J=7.5 Hz, 1H), 6.79 (s, 1H), 4.02 (s, 2H), 3.91-3.63 (m, 3H), 3.30 (s, 2H), 2.81 (s, 2H), 2.58 (s, 2H), 2.32 (s, 3H), 1.40 (s, 9H).

Step 3.

To the previous reaction mixture, was added an additional 4 M HCl in dioxane (139 μl, 0.556 mmol) was added to the remaining mixture and heated to 100° C. for 2 h. The reaction was concentrated, diluted with DMSO (2 mL), filtered and purified via mass directed reverse-phase prep-HPLC (Purification Method B). This provided tert-butyl (3-((5-carbamoyl-2-((6-methoxy-2-methyl-1,2,3,4-tetrahydroisoquinolin-7-yl)amino)pyrimidin-4-yl)amino)benzyl) carbamate (2-2). MS (ESI) m/z calc'd for $C_{28}H_{35}N_7O_4$ $[M+H]^+$ 535, found 535. $^1$H NMR (499 MHz, DMSO-d6) δ 11.51 (s, 1H), 8.65 (s, 1H), 8.31 (s, 1H), 8.00 (s, 1H), 7.56 (s, 1H), 7.44 (s, 1H), 7.36 (s, 2H), 7.19 (t, J=7.7 Hz, 1H), 7.01 (d, J=7.3 Hz, 1H), 6.79 (s, 1H), 3.80-3.73 (m, 3H), 3.64 (s, 2H), 3.29 (s, 2H), 2.81 (s, 2H), 2.58 (t, J=5.3 Hz, 2H), 2.32 (s, 3H).

TABLE 2

Compounds listed in the table below were prepared using the synthetic methods described in the aforementioned Example 2-1. The table provides the compound structure, the name, the calculated and observed masses.

| Example | Structure | Name | Exact Mass $[M + H]^+$ |
|---|---|---|---|
| 2-1 | 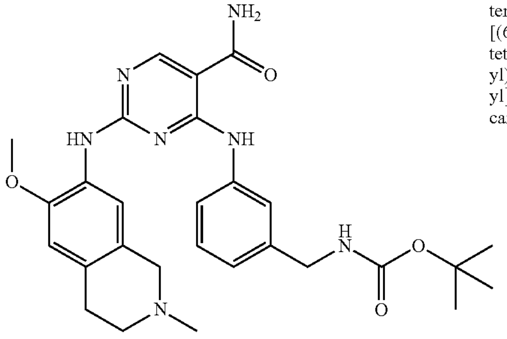 | tert-butyl {[3-({5-carbamoyl-2-[(6-methoxy-2-methyl-1,2,3,4-tetrahydroisoquinolin-7-yl)amino]pyrimidin-4-yl}amino)phenyl methyl} carbamate | Calc'd 534, found 534 |
| 2-2 | 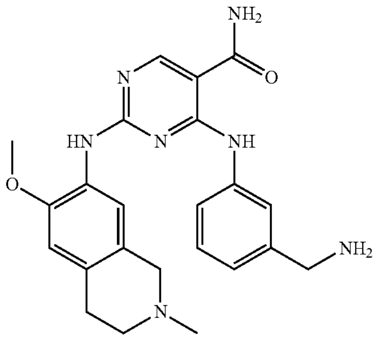 [SMILES: COc1cc2c(cc1Nc1ncc(C(N)=O)c(Nc3cccc(CN)c3)n1)CN(C)CC2] | 4-{[3-(aminomethyl)phenyl]-amino}-2-[(6-methoxy-2-methyl-1,2,3,4-tetrahydroisoquinolin-7-yl)amino]pyrimidine-5-carboxamide | Calc'd 434, found 434 |
| 2-3 | 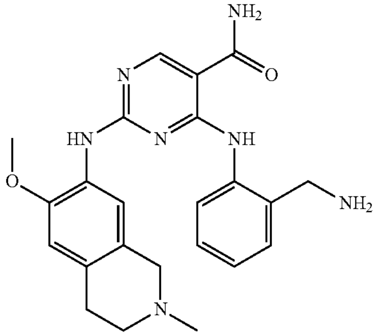 [SMILES: COc1cc2c(cc1Nc1ncc(C(N)=O)c(Nc3ccccc3CN)n1)CN(C)CC2] | 4-{[2-(aminomethyl)phenyl]-amino}-2-[(6-methoxy-2-methy1-1,2,3,4-tetrahydroisoquinolin-7-yl)amino]pyrimidine-5-carboxamide | Calc'd 434, found 434 |
| 2-4 | 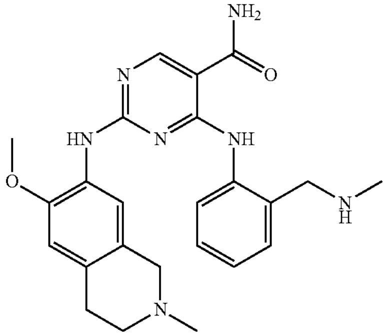 [SMILES: CNCc1ccccc1Nc1nc(Nc2cc3c(cc2OC)CCN(C)C3)ncc1C(N)=O] | 2-[(6-methoxy-2-methyl-1,2,3,4-tetrahydroisoquinolin~7-yl)amino ]-4-({2-[(methylamino)methyl]-phenyl}amino)pyrimidine-5-carboxamide | Calc'd 448, found 448 |

TABLE 2-continued

Compounds listed in the table below were prepared using the synthetic methods described in the aforementioned Example 2-1. The table provides the compound structure, the name, the calculated and observed masses.

| Example | Structure | Name | Exact Mass $[M + H]^+$ |
|---|---|---|---|
| 2-5 | 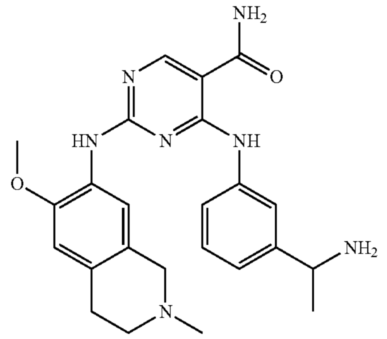 [SMILES: COc1cc2c(cc1Nc1ncc(C(N)=O)c(Nc3cccc(C(C)N)c3)n1)CN(C)CC2] | 4-{[3-(1-aminoethyl)phenyl]-amino}-2-[(6-methoxy-2-methyl-1,2,3,4-tetrahydroisoquinolin-7-yl)amino]pyrimidine-5-carboxamide | Calc'd 448, found 448 |
| 2-6 | 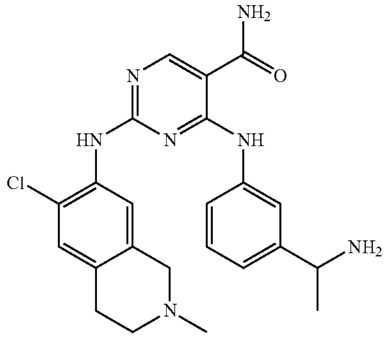 [SMILES: CC(N)c1cccc(Nc2nc(Nc3cc4c(cc3Cl)CCN(C)C4)ncc2C(N)=O)c1] | 4-{[3-(1-aminoethyl)phenyl]-amino}-2-[(6-chloro-2-methyl-1,2,3,4-tetrahydroisoquinolin-7-yl)amino]pyrimidine-5-carboxamide | Calc'd 452, found 452 |
| 2-7 | 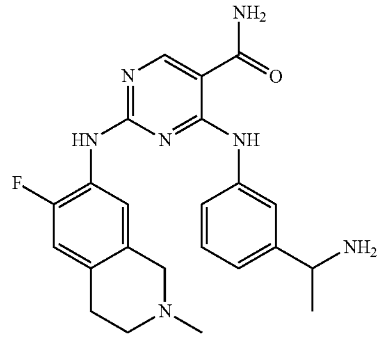 [SMILES: CC(N)c1cccc(Nc2nc(Nc3cc4c(cc3F)CCN(C)C4)ncc2C(N)=O)c1] | 4-{[3-(1-aminoethyl)phenyl]-amino}-2-[(6-fluoro-2-methyl-1,2,3,4-tetrahydroisoquinolin-7-yl)amino]pyrimidine-5-carboxamide | Calc'd 436, found 436 |

Example 1-1. 4-((3-((1-Fluorocyclopropane-1-carboxamido)methyl)phenyl)amino)-2-((6-methoxy-2-methyl-1,2,3,4-tetrahydroisoquinolin-7-yl)amino) pyrimidine-5-carboxamide

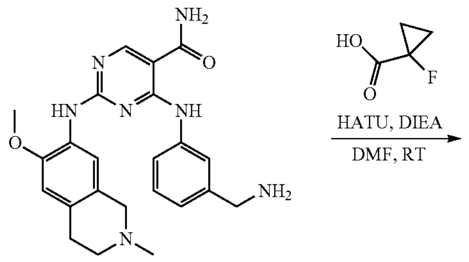

2-2

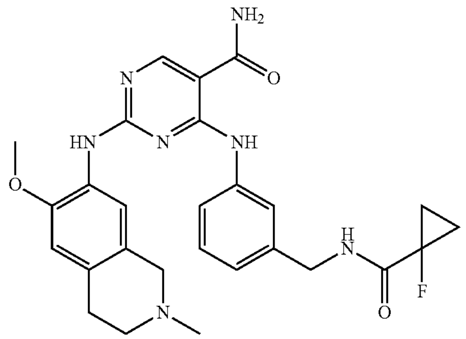

3-1

A 20 mL vial containing 1-fluorocyclopropane-1-carboxylic acid (4.80 mg, 0.046 mmol) in DMF (1.0 ml), was added with stirring HATU (21.05 mg, 0.055 mmol) and reaction was stirred for few minutes then was added 4-((3-(aminomethyl)phenyl)amino)-2-((6-methoxy-2-methyl-1,2,3,4-tetrahydroisoquinolin-7-yl)amino)pyrimidine-5-carboxamide 5 (2-2, 20.0 mg, 0.046 mmol), DIEA (0.016 ml, 0.092 mmol) and the reaction was stirred for 4 h at RT. The reaction was quenched with ethyl acetate and extracted with 3 portions of 1 N aq HCl, 2 portion of water, 1 portion of brine, 1 portion of sat. aq. $NaHCO_3$. The organics were dried ($Na_2SO_4$), filtered, and concentrated. The crude material was purified by mass-directed reverse phase chromatography (Purification Method B) to give 4-((3-((1-fluorocyclopropane-1-carboxamido)methyl)phenyl)-amino)-2-((6-methoxy-2-methyl-1,2,3,4-tetrahydroisoquinolin-7-yl)amino) pyrimidine-5-carboxamide. MS (ESI) m/z calc'd for $C_{27}H_{30}FN_7O_3$ $[M+H]^+$ 520, found 520. $^1H$ NMR (499 MHz, DMSO-d6) δ 11.55 (s, 1H), 8.96 (t, J=6.1 Hz, 1H), 8.67 (s, 1H), 8.34 (s, 1H), 8.02 (s, 1H), 7.63 (d, J=7.4 Hz, 1H), 7.42 (d, J=16.0 Hz, 2H), 7.28-7.16 (m, 1H), 6.95 (d, J=7.5 Hz, 1H), 6.79 (s, 1H), 4.27 (d, J=5.4 Hz, 2H), 3.77 (s, 3H), 3.30 (s, 2H), 2.81 (t, J=5.7 Hz, 2H), 2.58 (t, J=5.8 Hz, 2H), 2.32 (s, 3H), 1.35-1.23 (m, 2H), 1.22-1.18 (m, 2H).

TABLE 3

Compounds listed in the table below were prepared using the synthetic methods described in the aforementioned Example 3-1. The table provides the compound structure, the name, the calculated and observed masses.

| Example | Structure | Name | Exact Mass $[M + H]^+$ |
|---|---|---|---|
| 3-1 | 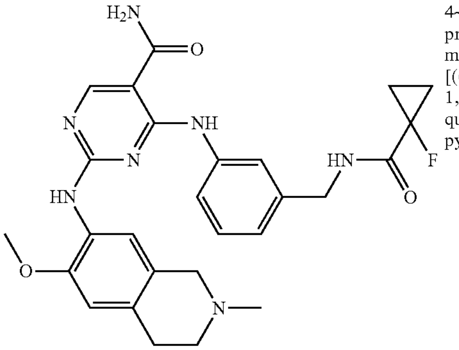 | 4~[(3~{[(1-fluorocyclopropane-1-carbonyl)amino]-methyl} phenyl)amino]-2-[(6-methoxy-2-methyl-1,2,3,4-tetrahydroisoquinolin-7-yl)amino]-pyrimidine-5-carboxamide | Calc'd 520, found 520 |

Example 4-1. 4-((2,6-Difluorophenyl)amino)-2-((6-methoxy-2-methyl-1,2,3,4-tetrahydroisoquinolin-7-yl)amino)pyrimidine-5-carboxamide

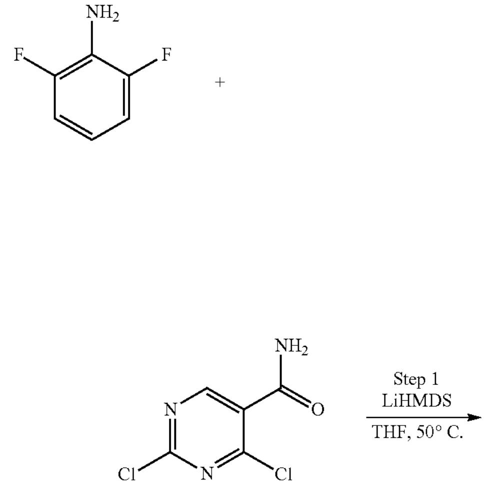

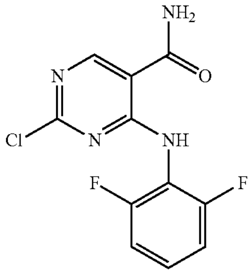

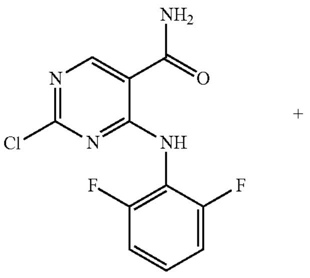

-continued

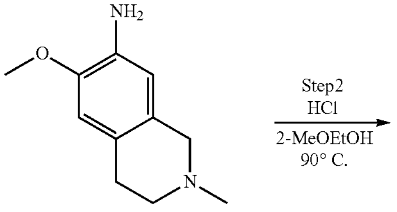

I-2

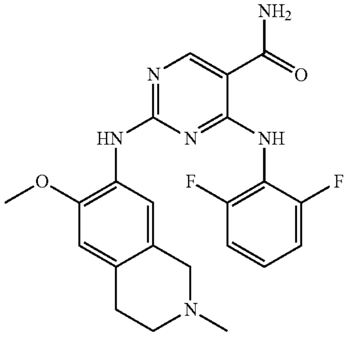 [SMILES: COc1cc2c(cc1Nc1ncc(C(N)=O)c(Nc3c(F)cccc3F)n1)CN(C)CC2]

4-1

Step 1. Fresh LiHMDS (1M THF) (521 μl, 0.521 mmol) was added via syringe to a solution of 2,6-difluoroaniline (25.5 μl, 0.253 mmol) and 2,4-dichloropyrimidine-5-carboxamide (50 mg, 0.260 mmol) in dry THF (868 μl) and the mixture was stirred at 50° C. for 2 h. The mixture was cooled, and the solvent was evaporated. The resulting residue was diluted with DCM (10 mL) and sat. aq $NH_4Cl$ (10 mL), and stirred for an additional 15 min. The aqueous layer was extracted with DCM (2×10 mL), filtered through a phase separator, and concentrated to afford 2-chloro-4-((2,6-difluorophenyl)amino)pyrimidine-5-carboxamide as solid. The material was sufficiently pure (97%) by LCMS and carried forward crude without purification. MS (ESI) m/z calc'd for $C_{11}H_8ClF_2N_4O$ $[M+H]^+$ 285, found 285.

Step 2. 2-Chloro-4-((2,6-difluorophenyl)amino)pyrimidine-5-carboxamide (70 mg, 0.246 mmol) was added to a 2 dram vial containing 6-methoxy-2-methyl-1,2,3,4-tetrahydroisoquinolin-7-amine (52.0 mg, 0.271 mmol) in 2-MethoxyEthanol (820 μl). HCl (1.25 M in ethanol) (590 μl, 0.738 mmol) was added via syringe and the mixture was sealed and stirred at 90° C. overnight. The mixture was cooled, diluted with DMA (1.5 mL), filtered through a frit, and the mixture was purified via mass directed reverse-phase prep-HPLC (Purification Method B), to give 4-((2,6-difluorophenyl)amino)-2-((6-methoxy-2-methyl-1,2,3,4-tetrahydroisoquinolin-7-yl)amino)pyrimidine-5-carboxamide as a solid after dry down. MS (ESI) m/z calc'd for $C_{22}H_{23}F_2N_6O_2$ $[M+H]^+$ 441. found 441. $^1$H NMR (499 MHz, DMSO-d6) δ 10.70 (s, 1H), 8.69 (br s, 1H), 8.07 (s, 1H), 7.87 (s, 1H), 7.59-7.33 (m, 3H), 7.28-7.25 (m, 2H), 6.69 (s, 1H), 3.79 (s, 3H), 3.01 (s, 2H), 2.71 (t, J=5.6 Hz, 2H), 2.52-2.50 (m, 2H), 2.34 (s, 3H).

TABLE 4

Compounds listed in the table below were prepared using the synthetic methods described in the aforementioned Example 4-1. The table provides the compound structure, the name, the calculated and observed masses.

| Example | Structure | Name | Exact Mass $[M + H]^+$ |
|---|---|---|---|
| 4-1 | 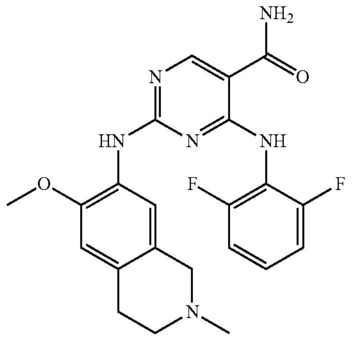 | 4-((2,6-difluorophenyl)amino)-2-((6-methoxy-2-methyl-1,2,3,4-tetrahydroisoquinolin-7-yl)amino)pyrimidine-5-carboxamide | Calc'd 441, found 441 |
| 4-2 | 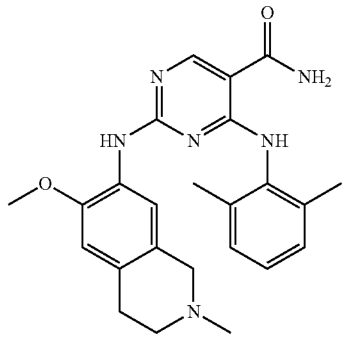 | 4-[(2,6-dimethylphenyl)amino]-2-[(6-methoxy-2-methyl-1,2,3,4-tetrahydroisoquinolin-7-yl)amino]pyrimidine-5-carboxamide | Calc'd 433, found 433 |
| 4-3 | 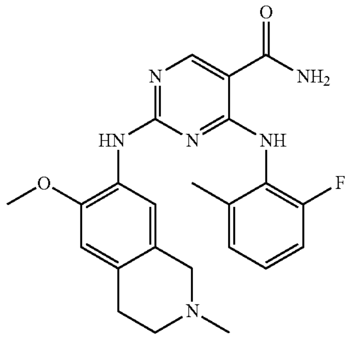 [SMILES: COc1cc2c(cc1Nc1ncc(C(N)=O)c(Nc3c(C)cccc3F)n1)CN(C)CC2] | 4-[(2-fluoro-6-methylphenyl)amino]-2-1(6-methoxy-2-methyl-1,2,3,4-tetrahydroisoquinolin-7-yl)amino]pyrimidine-5-carboxamide | Calc'd 437, found 437 |
| 4-4 | 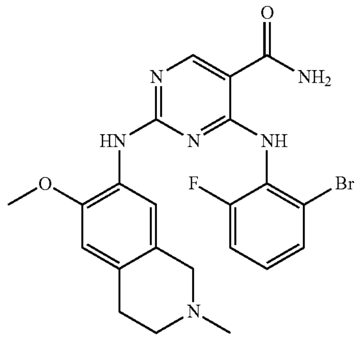 [SMILES: COc1cc2c(cc1Nc1ncc(C(N)=O)c(Nc3c(F)cccc3Br)n1)CN(C)CC2] | 4-[(2-bromo-6-fluorophenyl)amino]-2-[(6-methoxy-2-methyl-1,2,3,4-tetrahydroisoquinolin-7-yl)amino]pyrimidine-5-carboxamide | Calc'd 501, found 501 |

TABLE 4-continued

| Compounds listed in the table below were prepared using the synthetic methods described in the aforementioned Example 4-1. The table provides the compound structure, the name, the calculated and observed masses. | | | |
|---|---|---|---|
| Example | Structure | Name | Exact Mass [M + H]$^+$ |
| 4-5 | 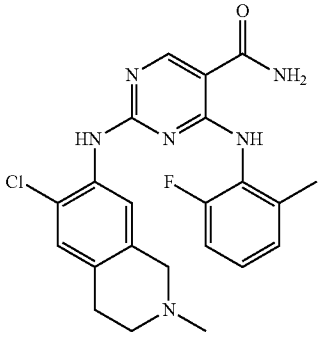 [SMILES: Cc1cccc(F)c1Nc1nc(Nc2cc3c(cc2Cl)CCN(C)C3)ncc1C(N)=O] | 2-[(6-chloro-2-methyl-1,2,3,4-tetrahydroisoquinolin-7-yl)amino]-4-[(2-fluoro-6-methylphenyl)amino] pyrimidine-5-carboxamide | Calc'd 441, found 441 |
| 4-6 | 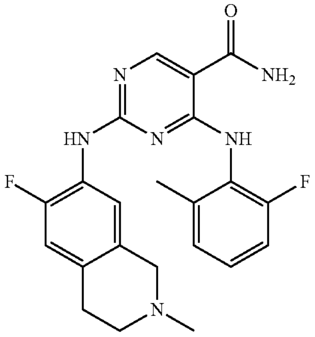 [SMILES: Cc1cccc(F)c1Nc1nc(Nc2cc3c(cc2F)CCN(C)C3)ncc1C(N)=O] | 4-[(2-fluoro-6-methylphenyl)amino]-2-[(6-fluoro-2-methyl-1,2,3,4-tetrahydroisoquinolin-7-yl)amino]pyrimidine-5-carboxamide | Calc'd 425, found 425 |
| 4-7 | 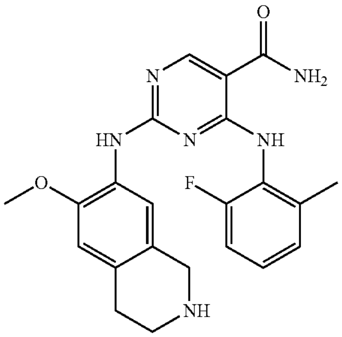 | 4-[(2-fluoro-6-methylphenyl)amino]-2-[(6-methoxy-1,2,3,4-tetrahydroisoquinolin-7-yl)amino]pyrimidine-5-carboxamide | Calc'd 423, found 423 |
| 4-8 | 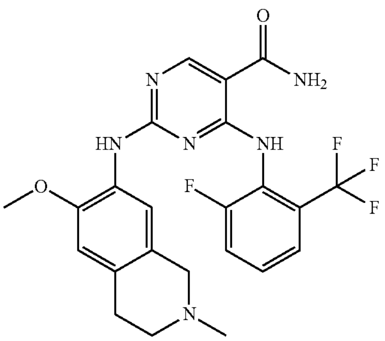 [SMILES: COc1cc2c(cc1Nc1ncc(C(N)=O)c(Nc3c(F)cccc3C(F)(F)F)n1)CN(C)CC2] | 4-{[2-fluoro-6-(trifluoromethyl)phenyl]amino}-2-[(6-methoxy-2-methyl-1,2,3,4-tetrahydroisoquinolin-7-yl)amino]pyrimidine-5-carboxamide | Calc'd 491.0, found 491 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass [M + H]+ |
|---|---|---|---|
| 4-9 | 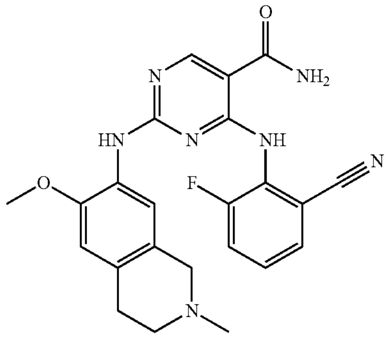 [SMILES: COc1cc2c(cc1Nc1ncc(C(N)=O)c(Nc3c(F)cccc3C#N)n1)CN(C)CC2] | 4-[(2-cyano-6-fluorophenyl)amino]-2-[(6-methoxy-2-methyl-1,2,3,4-tetrahydroisoquinolin-7-yl)amino]pyrimidine-5-carboxamide | Calc'd 448, found 448 |
| 4-10 | 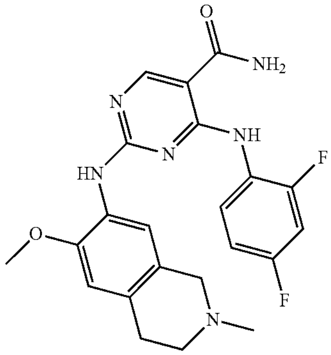 [SMILES: COc1cc2c(cc1Nc1ncc(C(N)=O)c(Nc3ccc(F)cc3F)n1)CN(C)CC2] | 4-[(2,4-difluorophenyl)amino]-2-[(6-methoxy-2-methyl-1,2,3,4-tetrahydroisoquinolin-7-yl)amino]pyrimidine-5-carboxamide | Calc'd 441, found 441 |
| 4-11 | 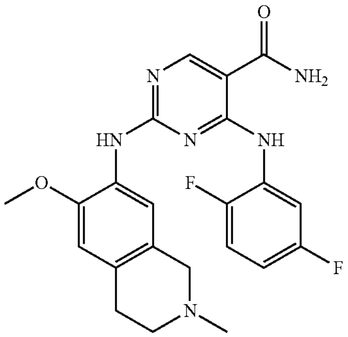 [SMILES: COc1cc2c(cc1Nc1ncc(C(N)=O)c(Nc3cc(F)ccc3F)n1)CN(C)CC2] | 4-[(2,5-difluorophenyl)amino]-2-[(6-methoxy-2-methyl-1,2,3,4-tetrahydroisoquinolin-7-yl)amino]pyrimidine-5-carboxamide | Calc'd 441, found 441 |
| 4-12 | 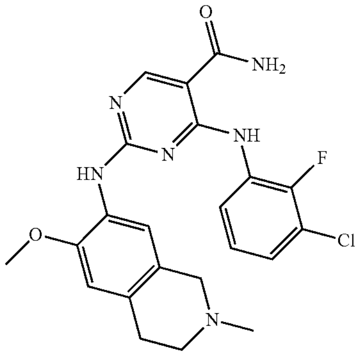 [SMILES: COc1cc2c(cc1Nc1ncc(C(N)=O)c(Nc3cccc(Cl)c3F)n1)CN(C)CC2] | 4-[(3-chloro-2-fluorophenyl)amino]-2-[(6-methoxy-2-methyl-1,2,3,4-tetrahydroisoquinolin-7-yl)amino]pyrimidine-5-carboxamide | Calc'd 457, found 457 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass [M + H]$^+$ |
|---|---|---|---|
| 4-13 | 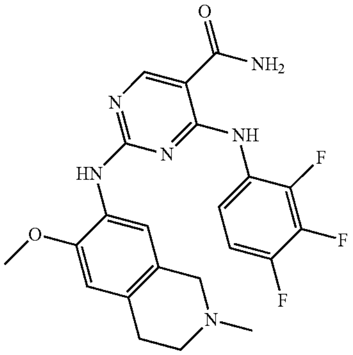 [SMILES: COc1cc2c(cc1Nc1ncc(C(N)=O)c(Nc3ccc(F)c(F)c3F)n1)CN(C)CC2] | 2-[(6-methoxy-2-methyl-1,2,3,4-tetrahydroisoquinolin-7-yl)amino]-4-[(2,3,4-trifluorophenyl)amino] pyrimidine-5-carboxamide | Calc'd 459, found 459 |
| 4-14 | 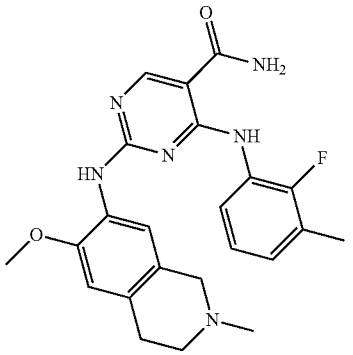 | 4-[(2-fluoro-3-methylpheny1)amino]-2-[(6-methoxy-2-methyl-1,2,3,4-tetrahydroisoquinolin-7-yl)amino]pyrimidine-5-carboxamide | Calc'd 437, found 437 |
| 4-15 | 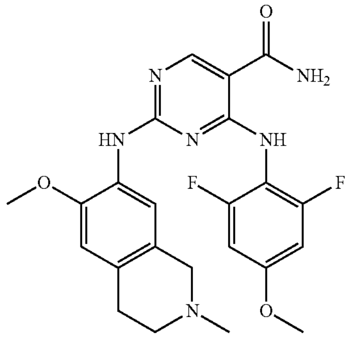 [SMILES: COc1cc(F)c(Nc2nc(Nc3cc4c(cc3OC)CCN(C)C4)ncc2C(N)=O)c(F)c1] | 4-[(2,6-difluoro-4-methoxyphenyl)amino]-2-[(6-methoxy-2-methyl-1,2,3,4-tetrahydroisoquinolin-7-yl)amino]pyrimidine-5-carboxamide | Calc'd 471, found 471 |
| 4-16 | 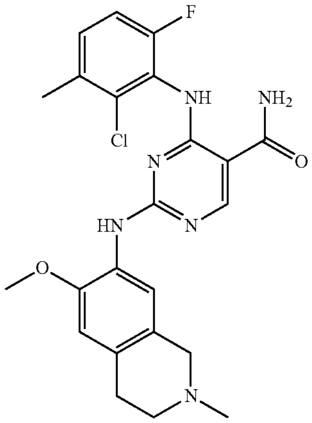 [SMILES: COc1cc2c(cc1Nc1ncc(C(N)=O)c(Nc3c(F)ccc(C)c3Cl)n1)CN(C)CC2] | 4-[(2-chloro-6-fluoro-3-methylphenyl)amino]-2-[(6-methoxy-2-methyl-1,2,3,4-tetrahydroisoquinolin-7-yl)amino]pyrimidine-5-carboxamide | Calc'd 471, found 471 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass [M + H]+ |
|---|---|---|---|
| 4-17 | 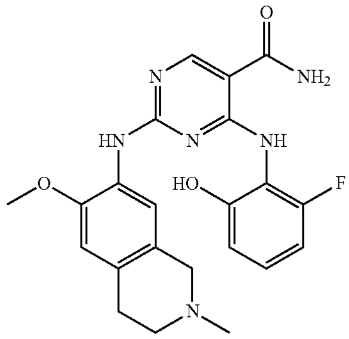 [SMILES: COc1cc2c(cc1Nc1ncc(C(N)=O)c(Nc3c(O)cccc3F)n1)CN(C)CC2] | 4-[(2-fluoro-6-hydroxyphenyl)amino]-2-[(6-methoxy-2-methyl-1,2,3,4-tetrahydroisoquinolin-7-yl)amino]pyrimidine-5-carboxamide | Calc'd 439, found 439 |
| 4-18 | 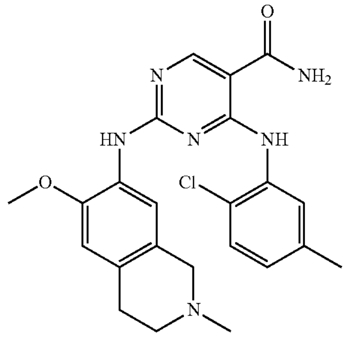 | 4-[(2-chloro-5-methylphenyl)amino]-2-[(6-methoxy-2-methyl-1,2,3,4-tetrahydroisoquinolin-7-yl)amino]pyrimidine-5-carboxamide | Calc'd 453, found 453 |
| 4-19 | 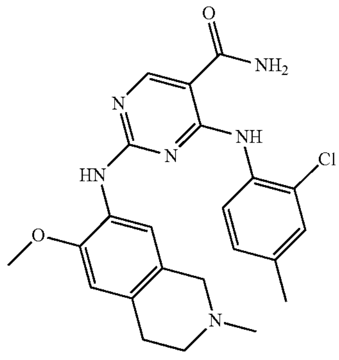 [SMILES: COc1cc2c(cc1Nc1ncc(C(N)=O)c(Nc3ccc(C)cc3Cl)n1)CN(C)CC2] | 4-[(2-chloro-4-methylpheny 1)amino]-2-[(6-methoxy-2-methyl-1,2,3,4-tetrahydroisoquinolin-7-yl)amino]pyrimidine-5-carboxamide | Calc'd 453, found 453 |
| 4-20 | 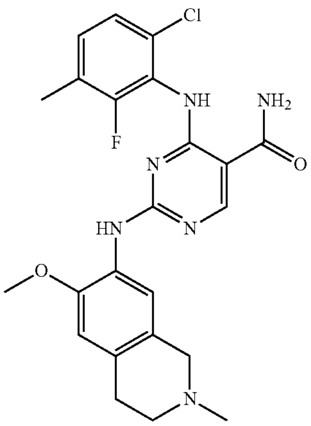 [SMILES: COc1cc2c(cc1Nc1ncc(C(N)=O)c(Nc3c(Cl)ccc(C)c3F)n1)CN(C)CC2] | 4-[(6-chloro-2-fluoro-3-methylphenyl)amino]-2-[(6-methoxy-2-methyl-1,2,3,4-tetrahydroisoquinolin-7-yl)amino]pyrimidine-5-carboxamide | Calc'd 471, found 471 |

TABLE 4-continued

| Compounds listed in the table below were prepared using the synthetic methods described in the aforementioned Example 4-1. The table provides the compound structure, the name, the calculated and observed masses. | | | |
|---|---|---|---|
| Example | Structure | Name | Exact Mass $[M + H]^+$ |
| 4-21 | 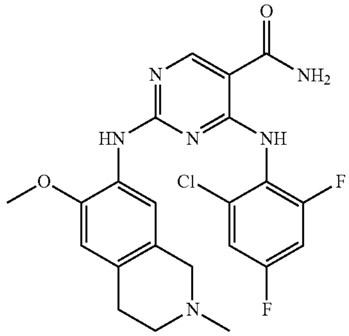 [SMILES: COc1cc2c(cc1Nc1ncc(C(N)=O)c(Nc3c(F)cc(F)cc3Cl)n1)CN(C)CC2] | 4-[(2-chloro-4,6-difluorophenyl)amino]-2-[(6-methoxy-2-methyl-1,2,3,4-tetrahydroisoquinolin-7-yl)amino]pyrimidine-5-carboxamide | Calc'd 475, found 475 |
| 4-22 | 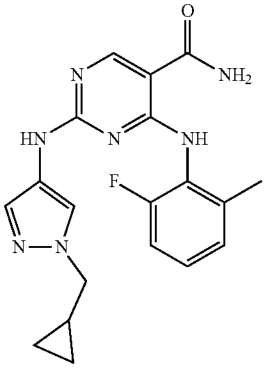 [SMILES: Cc1cccc(F)c1Nc1nc(Nc2cnn(CC3CC3)c2)ncc1C(N)=O] | 2-{[1]-(cyclopropylmethyl)-1H-pyrazol-4-yl]amino}-4-[(2-fluoro-6-methylphenyl)amino] pyrimidine-5-carboxamide | Calc'd 382, found 382 |
| 4-23 | 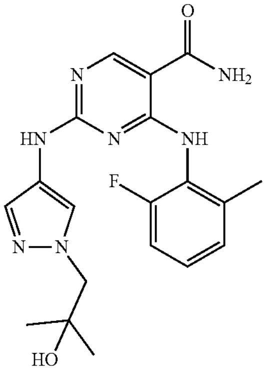 [SMILES: Cc1cccc(F)c1Nc1nc(Nc2cnn(CC(C)(C)O)c2)ncc1C(N)=O] | 4-[(2-fluoro-6-methylphenyl)amino]-2-{[1-(2-hydroxy-2-methylpropyl)-1H-pyrazol-4-yl]amino}pyrimidine-5-carboxamide | Calc'd 400, found 400 |
| 4-24 | 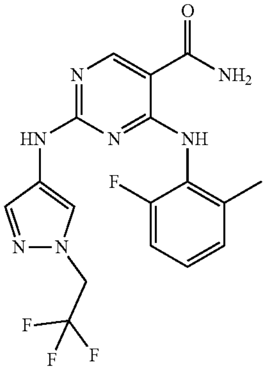 [SMILES: Cc1cccc(F)c1Nc1nc(Nc2cnn(CC(F)(F)F)c2)ncc1C(N)=O] | 4-[(2-fluoro-6-methylphenyl)amino]-2-{[1-(2,2,2-trifluoroethyl)-1H-pyrazol-4-yl]amino}pyrimidine-5-carboxamide | Calc'd 410, found 410 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass [M + H]$^+$ |
|---|---|---|---|
| 4-25 | 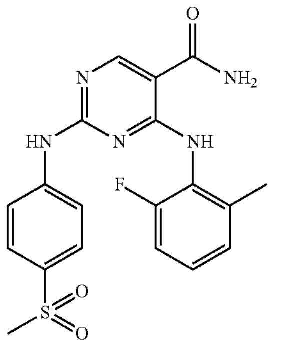 [SMILES: Cc1cccc(F)c1Nc1nc(Nc2ccc(S(C)(=O)=O)cc2)ncc1C(N)=O] | 4-[(2-fluoro-6-methylphenyl)amino]-2-{[4-(methylsulfonyl)phenyl]amino}pyrimidine-5-carboxamide | Calc'd 416, found 416 |
| 4-26 | 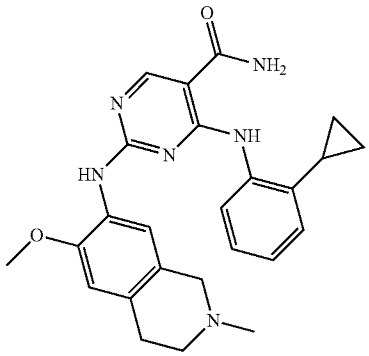 [SMILES: COc1cc2c(cc1Nc1ncc(C(N)=O)c(Nc3ccccc3C3CC3)n1)CN(C)CC2] | 4-[(2-cyclopropylphenyl)amino]-2-[(6-methoxy-2-methyl-1,2,3,4-tetrahydroisoquinolin-7-yl)amino]pyrimidine-5-carboxamide | Calc'd 445, found 445 |
| 4-27 | 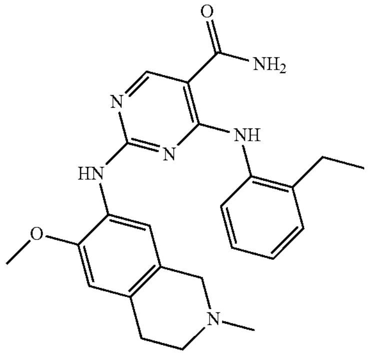 [SMILES: CCc1ccccc1Nc1nc(Nc2cc3c(cc2OC)CCN(C)C3)ncc1C(N)=O] | 4-[(2-ethylphenyl)amino]-2-[(6-methoxy-2-methyl-1,2,3,4-tetrahydroisoquinolin-7-yl)amino]pyrimidine-5-carboxamide | Calc'd 433, found 433 |
| 4-28 | 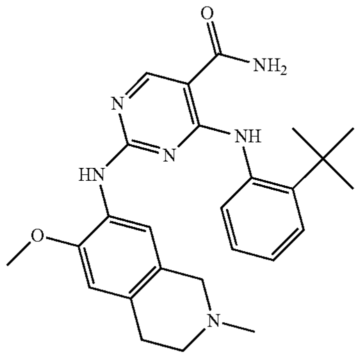 [SMILES: COc1cc2c(cc1Nc1ncc(C(N)=O)c(Nc3ccccc3C(C)(C)C)n1)CN(C)CC2] | 4-[(2-tert-butylphenyl)amino]-2-[(6-methoxy-2-methyl-1,2,3,4-tetrahydroisoquinolin-7-yl)amino]pyrimidine-5-carboxamide | Calc'd 461, found 461 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass $[M + H]^+$ |
|---|---|---|---|
| 4-29 | 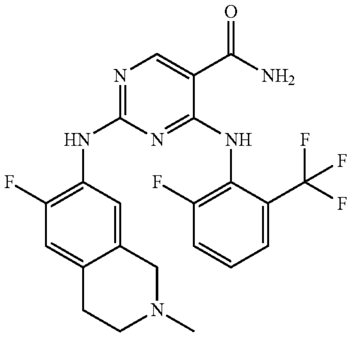 [SMILES: CN1CCc2cc(F)c(Nc3ncc(C(N)=O)c(Nc4c(F)cccc4C(F)(F)F)n3)cc2C1] | 2-[(6-fluoro-2-methyl-1,2,3,4-tetrahydroisoquinolin-7-yl)amino]-4-{[2-fluoro-6-(trifluoromethyl)phenyl]amino}pyrimidine-5-carboxamide | Calc'd 479, found 479 |
| 4-30 | 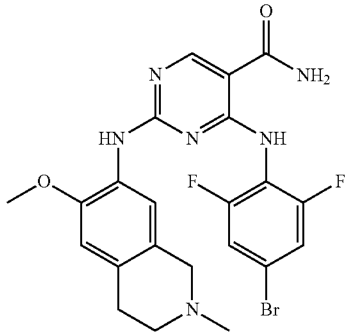 [SMILES: COc1cc2c(cc1Nc1ncc(C(N)=O)c(Nc3c(F)cc(Br)cc3F)n1)CN(C)CC2] | 4-[(4-bromo-2,6-difluorophenyl)amino]-2-[(6-methoxy-2-methyl-1,2,3,4-tetrahydroisoquinolin-7-yl)amino]pyrimidine-5-carboxamide | Calc'd 519, found 519 |
| 4-31 | 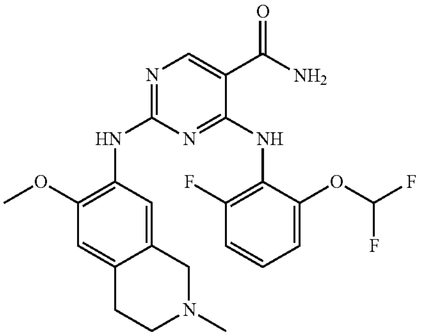 [SMILES: COc1cc2c(cc1Nc1ncc(C(N)=O)c(Nc3c(F)cccc3OC(F)F)n1)CN(C)CC2] | 4-{[2-(difluoromethoxy)-6-fluorophenyl]amino}-2-1(6-methoxy-2-methyl-1,2,3,4-tetrahydroisoquinolin-7-yl)amino|pyrimidine-5-carboxamide | Calc'd 489, found 489 |
| 4-32 | 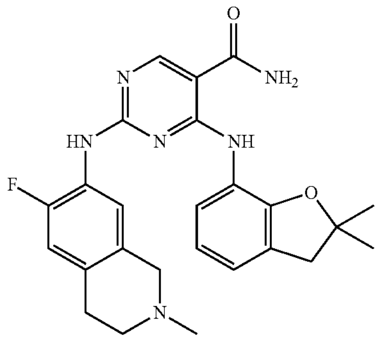 [SMILES: CN1CCc2cc(F)c(Nc3ncc(C(N)=O)c(Nc4cccc5c4OC(C)(C)C5)n3)cc2C1] | 4-[(2,2-dimethyl-2,3-dihydro-1-benzofuran-7-yl)amino]-2-[(6-fluoro-2-methyl-1,2,3,4-tetrahydroisoquinolin-7-yl)amino]pyrimidine-5-carboxamide | Calc'd 463, found 463 |

TABLE 4-continued

Compounds listed in the table below were prepared using the synthetic methods described in the aforementioned Example 4-1. The table provides the compound structure, the name, the calculated and observed masses.

| Example | Structure | Name | Exact Mass $[M + H]^+$ |
|---|---|---|---|
| 4-33 | 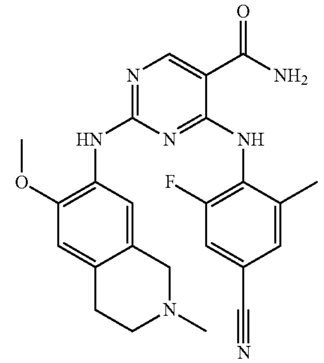 [SMILES: COc1cc2c(cc1Nc1ncc(C(N)=O)c(Nc3c(C)cc(C#N)cc3F)n1)CN(C)CC2] | 4-[(4-cyano-2-fluoro-6-methylphenyl)amino]-2-[(6-methoxy-2-methyl-1,2,3,4-tetrahydroisoquinolin-7-yl)amino]pyrimidine-5-carboxamide | Calc'd 462, found 462 |
| 4-34 | 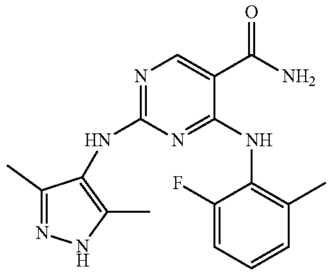 | 2-[(3,5-dimethyl-1H-pyrazol-4-yl)amino]-4-[(2-fluoro-6-methylphenyl)amino] pyrimidine-5-carboxamide | Calc'd 356, found 356 |
| 4-35 | 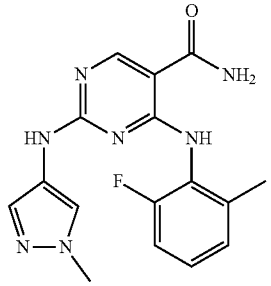 [SMILES: Cc1cccc(F)c1Nc1nc(Nc2cnn(C)c2)ncc1C(N)=O] | 4-[(2-fluoro-6-methylphenyl)amino]-2-[(1-methyl-1H-pyrazol-4-yl)amino]pyrimidine-5-carboxamide | Calc'd 342, found 342 |

Example 5-1. 4-((2-Fluoro-6-(trifluoromethyl)phenyl)amino)-2-((2-(2-hydroxy-2-methylpropyl)-6-methoxy-1,2,3,4-tetrahydroisoquinolin-7-yl)amino)pyrimidine-5-carboxamide

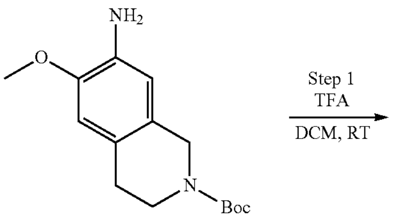

I-1

-continued

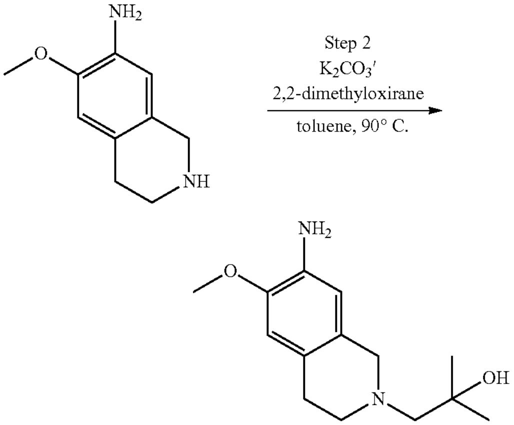

-continued

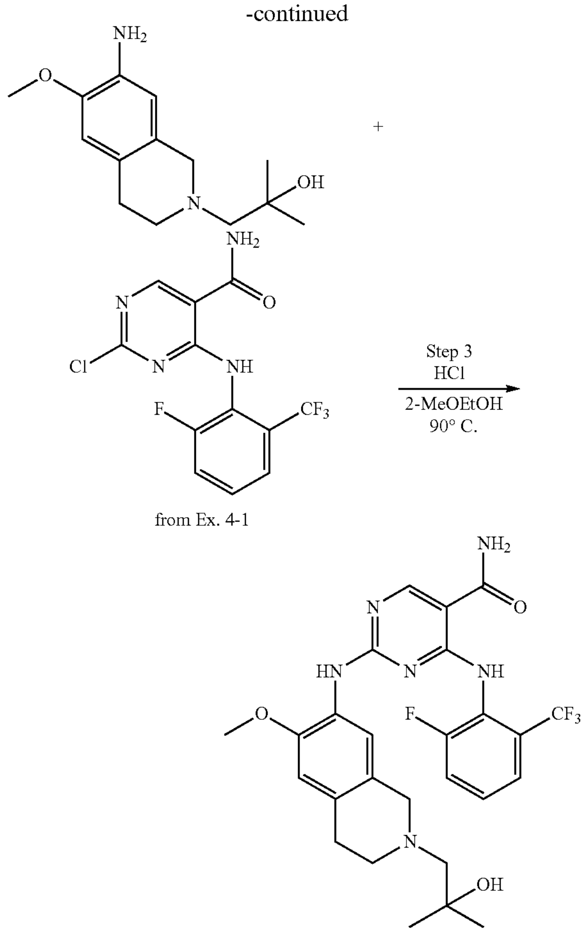

5-1

Step 1. tert-Butyl-7-amino-6-methoxy-3,4-dihydroisoquinoline-2(1H)-carboxylate (1.5 g, 5.39 mmol) was added to a 50 mL flask in DCM (7.19 mL). TFA (1.246 ml, 16.17 mmol) was added in one portion via syringe and stirred for 1 h at RT. The material was concentrated to give 6-methoxy-1,2,3,4-tetrahydroisoquinolin-7-amine (TFA salt) as a crude oil, which was carried into the next step crude. MS (ESI) m-z calc'd for $C_{10}H_{15}N_2O$ $[M+H]^+$ 179, found 179.

Step 2. 6-Methoxy-1,2,3,4-tetrahydroisoquinolin-7-amine (0.959 g, 5.39 mmol) was added to a 100 mL flask and dissolved in toluene (17.19 ml). Potassium carbonate (2.234 g, 16.17 mmol) was added in one portion followed by 2,2-dimethyloxirane (0.521 ml, 5.93 mmol) at RT and vigorously. The mixture was heated to 90° C. and stirred for 4 h. The mixture was cooled and diluted in water (20 mL), and extracted with ethyl acetate (2×20 mL). The organics were collected, dried (MgSO4), filtered and concentrated under reduced pressure. The residue was purified by column chromatography on silica gel 12 g column, eluting with EtOAc/EtOH (3:1) in hexanes (5-50%) to give 1-(7-amino-6-methoxy-3,4-dihydroisoquinolin-2(1H)-yl)-2-methylpropan-2-ol as a pale yellow solid (850 mg). MS (ESI) m/z calc'd for $C_{14}H_{23}N_2O_2$$[M+H]^+$ 251, found 251.

Step 3. 1-(7-Amino-6-methoxy-3,4-dihydroisoquinolin-2(1H)-yl)-2-methylpropan-2-ol (16.46 mg, 0.066 mmol) and 2-chloro-4-((2-fluoro-6-(trifluoromethyl)phenyl)amino)-pyrimidine-5-carboxamide (preparation from Ex. 4-1) (20 mg, 0.060 mmol) were added in 2-MethoxyMethanol (171 μl) under argon. Hydrogen chloride (1.25M in Ethanol) (143 μl, 0.179 mmol) was added and contents were heated to 95° C. for 90 min. Upon reaction completion as monitored by LCMS, the mixture was cooled and diluted in DMSO. The mixture was filtered through a frit and purified via mass directed reverse-phase prep-HPLC (Purification Method B), to give 4-((2-fluoro-6-(trifluoromethyl)phenyl)amino)-2-((2-(2-hydroxy-2-methylpropyl)-6-methoxy-1,2,3,4-tetrahydroisoquinolin-7-yl)amino)pyrimidine-5-carboxamide as a solid after dry down. MS (ESI) m/z calc'd for $C_{26}H_{29}F_4N_6O_3$ $[M+H]^+$ 549, found 549. $^1H$ NMR (499 MHz, DMSO-d6) δ 11.10 (s, 1H), 8.71 (s, 1H), 8.08 (br s, 1H), 7.88 (s, 1H), 7.77-7.73 (m, 1H), 7.69 (d, J=7.6 Hz, 1H), 7.66-7.57 (m, 1H), 7.47 (s, 1H), 7.27 (s, 1H), 6.67 (s, 1H), 4.21 (s, 1H), 3.78 (s, 3H), 3.25-3.23 (m, 2H) m 2.79-2.66 (m, 4H), 2.35 (s, 2H), 1.15 (s, 6H).

TABLE 5

Compounds listed in the table below were prepared using the synthetic methods described in the aforementioned Example 5-1. The table provides the compound structure, the name, the calculated and observed masses.

| Example | Structure | Name | Exact Mass $[M + H]^+$ |
|---|---|---|---|
| 5-1 | 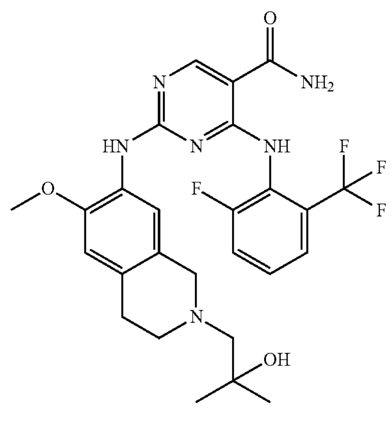 [SMILES: COc1cc2c(cc1Nc1ncc(C(N)=O)c(Nc3c(F)cccc3C(F)(F)F)n1)CN(CC(C)(C)O)CC2] | 4-{[2-fluoro-6-(trifluoromethyl)phenyl]amino}-2-{[2-(2-hydroxy-2-methylpropyl)-6-methoxy-1,2,3,4-tetrahydroisoquinolin-7-yl]amino}pyrimidine-5-carboxamide | Calc'd 549, found 549 |

TABLE 5-continued

| Compounds listed in the table below were prepared using the synthetic methods described in the aforementioned Example 5-1. The table provides the compound structure, the name, the calculated and observed masses. | | | |
|---|---|---|---|
| Example | Structure | Name | Exact Mass [M + H]+ |
| 5-2 | 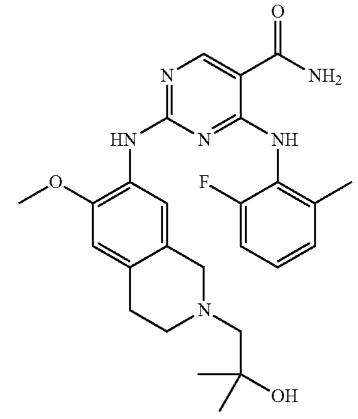 | 4-[(2-fluoro-6-methylphenyl)amino]-2-{[2-(2-hydroxy-2-methylpropyl)-6-methoxy-1,2,3,4-tetrahydroisoquinolin-7-yllamino}pyrimidine-5-carboxamide | Calc'd 495, found 495 |

Example 6-1. 2-((6-Methoxy-2-methyl-1,2,3,4-tetrahydroisoquinolin-7-yl)amino)-4-(phenylamino)pyrimidine-5-carboxamide

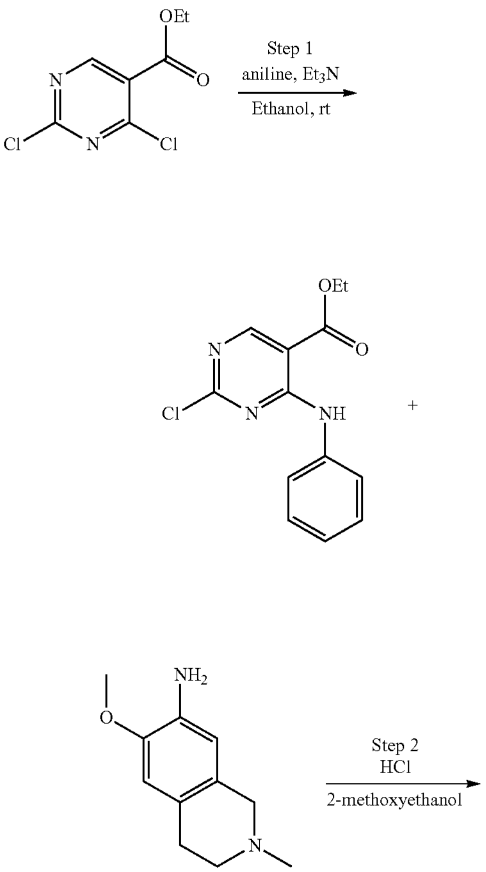

I-2

-continued

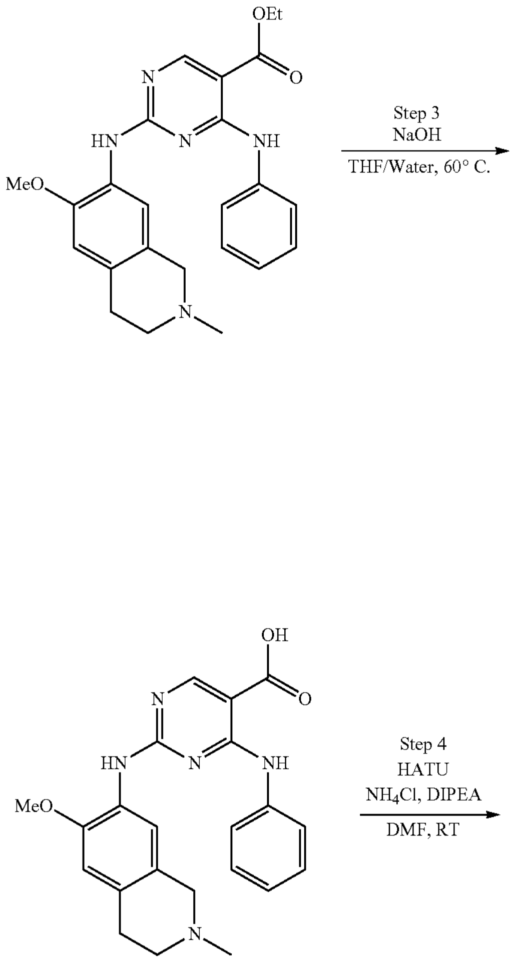

-continued

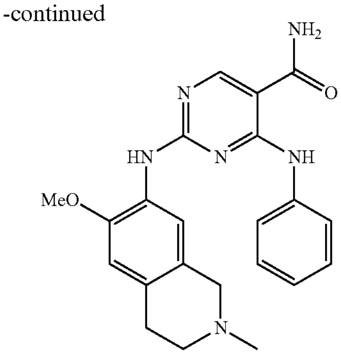

6-1

Step 1. Aniline (4.36 ml, 48.2 mmol) was added to a solution of ethyl 2,4-dichloro-pyrimidine-5-carboxylate (10.1 g, 45.9 mmol) and triethylamine (12.8 ml, 92 mmol) in ethanol (92 mL) at 0° C. After the addition the reaction was allowed to reach room temperature and stirred overnight. Water was added (200 mL) and a solid precipitated. The solid was filtered and dried under a stream of nitrogen. This ethyl 2-chloro-4-(phenylamino)pyrimidine-5-carboxylate which was used without further purification. MS (ESI) m/z calc'd for $C_{13}H_{13}ClN_3O_2$ $[M+H]^+$ 278, found 278.

Step 2. A 500 mL 3-necked round bottomed flask with reflux condenser was charged with 6-methoxy-2-methyl-1,2,3,4-tetrahydroisoquinolin-7-amine (1-2, 7.37 g, 38.3 mmol) and ethyl 2-chloro-4-(phenylamino)pyrimidine-5-carboxylate (9.68 g, 34.9 mmol). 2-methoxylethanol (100 mL) and was added followed by HCl (70 mL, 87 mmol, 1.25 M in ethanol) and the reaction was stirred at 110° C. overnight. The reaction was cooled in an ice bath and neutralized with $NaOH_{(aq)}$ (approx. 50 mL, litmus test pH 7), solid began precipitate, distilled water (250 mL) was added and the reaction was stirred for 10 minutes. The solid was filtered off and dried under a stream of nitrogen. This provided ethyl 2-((6-methoxy-2-methyl-1,2,3,4-tetrahydroisoquinolin-7-yl)amino)-4-(phenylamino)pyrimidine-5-carboxylate which was used without further purification. MS (ESI) m/z calc'd for $C_{24}H_{28}N_5O_3$ $[M+H]^+$ 434, found 434.

Step 3. A 20 mL Biotage microwave vial was charged with ethyl 2-((6-methoxy-2-methyl-1,2,3,4-tetrahydroisoquinolin-7-yl)amino)-4-(phenylamino)pyrimidine-5-carboxylate (1 g, 2 mmol). THF/water (14 mL, 1:1) was added followed by solid sodium hydroxide (0.48 g, 12 mmol). The reaction was heated to 60° C. and stirred for 3 d. The reaction was cooled, neutralized with $HCl_{(aq)}$ (2 M, litmus test), concentrated to remove the organic solvent. The solid was filtered, dried by azeotroping with isopropanol (3×50 mL) and further dried under high vacuum. This provided 2-((6-methoxy-2-methyl-1,2,3,4-tetrahydroisoquinolin-7-yl)amino)-4-(phenylamino)pyrimidine-5-carboxylic acid which was used without further purification. MS (ESI) m/z calc'd for $C_{22}H_{24}N_5O_3$ $[M+H]^+$ 406, found 406.

Step 4. A 40 mL vial was charged with 2-((6-methoxy-2-methyl-1,2,3,4-tetrahydroisoquinolin-7-yl)amino)-4-(phenylamino)pyrimidine-5-carboxylic acid (0.77 g, 1.89 mmol), DMF (5 mL) was added followed by DIPEA (0.99 ml, 5.7 mmol) and HATU (1.44 g, 3.78 mmol) at room temperature. Additional DMF (10 mL) was added followed by ammonium chloride (0.20 g, 3.78 mmol) and the reaction was stirred at room temperature overnight. The contents of the reaction were transferred to a Erlenmeyer flask and water (150 mL) was added, the solution was stirred until a precipitate had formed. The solid was collected by filtration and the filter cake was slurried with MeOH (5 mL) and filtered, the process was repeated 1 more time and the solid was dried overnight under a stream of nitrogen. This provided 2-((6-methoxy-2-methyl-1,2,3,4-tetrahydroisoquinolin-7-yl)amino)-4-(phenylamino)pyrimidine-5-carboxamide. MS (ESI) m/z calc'd for $C_{22}H_{25}N_6O_2$ $[M+H]^+$ 405, found 405. $^1H$ NMR (499 MHz, DMSO-$d_6$) δ 11.55 (s, 1H), 10.69 (s, 1H), 8.68 (s, 1H), 8.38 (s, 1H), 8.06 (s, 1H), 7.65 (s, 1H), 7.60-7.52 ((m, 2H), 7.48-7.29 (m, 3H), 7.14-7.03 (m, 1H), 6.94 (s, 1H), 4.24-4.02 (m, 2H), 3.81 (s, 3H), 3.59-3.20 (m, 2H), 3.17-2.98 (m, 2H), 2.88 (s, 3H).

TABLE 6

Compounds listed in the table below were prepared using the synthetic methods described in the aforementioned Example 6-1. The table provides the compound structure, the name, the calculated and observed masses.

| Example | Structure | Name | Exact Mass $[M + H]^+$ |
|---|---|---|---|
| 6-1 | 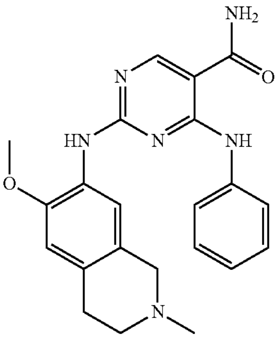 [SMILES: COc1cc2c(cc1Nc1ncc(C(N)=O)c(Nc3ccccc3)n1)CN(C)CC2] | 2-[(6-methoxy-2-methyl-1,2,3,4-tetrahydroisoquinolin-7-yl)amino]-4-(phenylamino)pyrimidine-5-carboxamide | Calc'd 405, found 405 |

Example 7-1. tert-Butyl 5-((5-carbamoyl-2-chloropyrimidin-4-yl)amino)-3,4-dihydroisoquinoline-2(1H)-carboxylate Example 7-2. (S)-2-((6-Methoxy-2-methyl-1,2,3,4-tetrahydroisoquinolin-7-yl)amino)-4-((2-(4-methyl-2-oxooxazolidin-3-yl)phenyl)amino)pyrimidine-5-carboxamide Example 7-3.4-[(2-Bromophenyl)amino]-2-[(6-methoxy-2-methyl-1,2,3,4-tetrahydroisoquinolin-7-yl)amino]pyrimidine-5-carboxamide

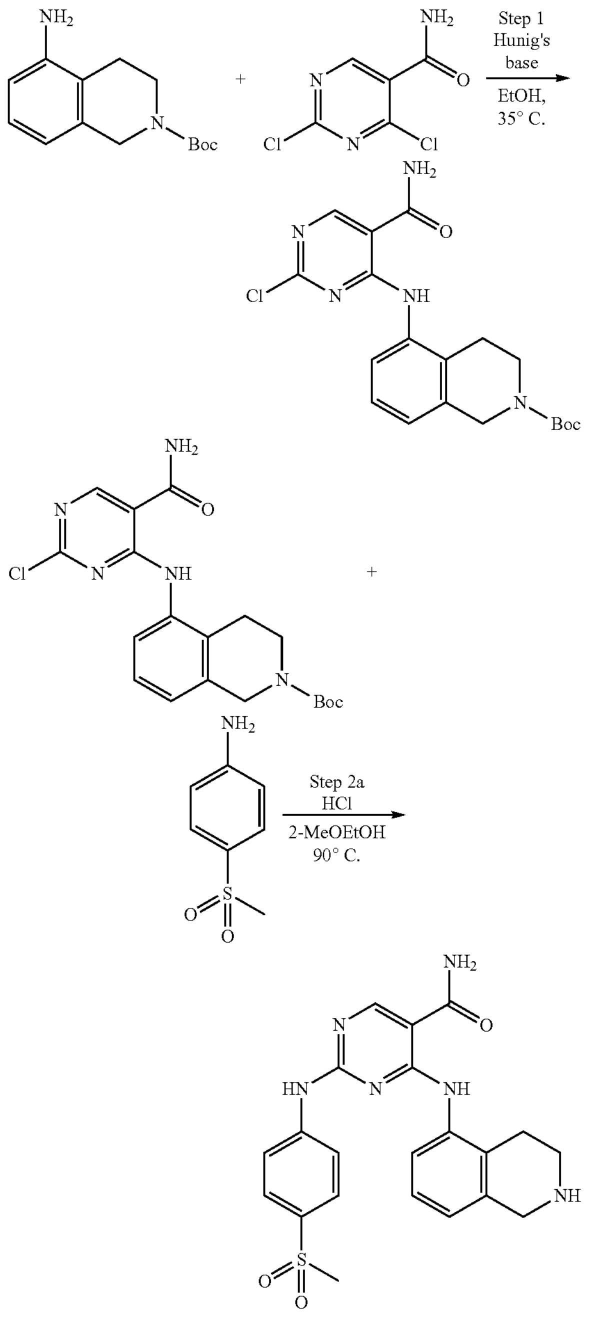

7-1

-continued

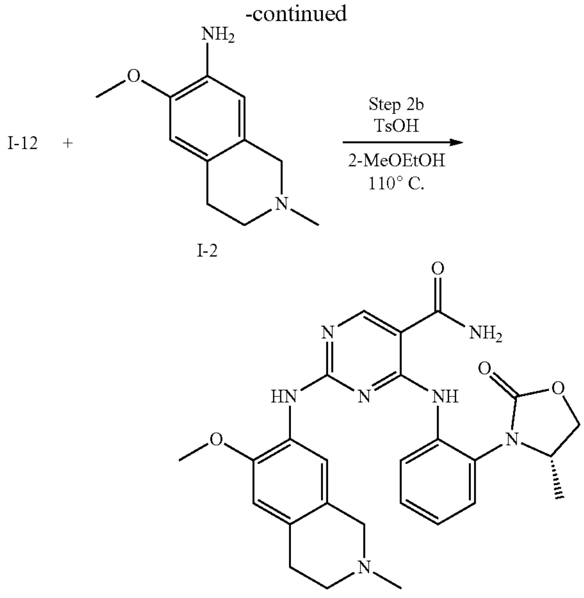

7-2

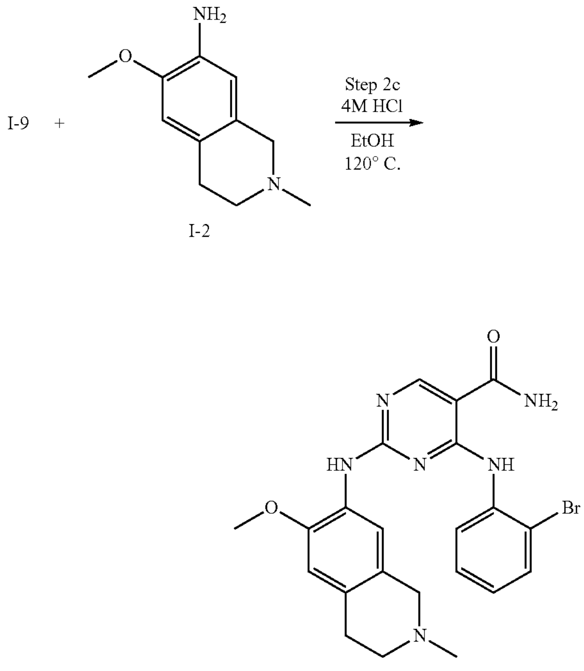

7-3

Step 1. N-Ethyl-N-isopropylpropan-2-amine (512 µl, 2.93 mmol) was added to a solution of tert-butyl 5-amino-3,4-dihydroisoquinoline-2(1H)carboxylate (485 mg, 1.953 mmol) and 2,4-dichloropyrimidine-5-carboxamide (375 mg, 1.953 mmol) in ethanol (5580 µl) and the mixture was capped and stirred at 35° C. for 2 h. The mixture was cooled, diluted with water (15 mL), and extracted with DCM (2×15 mL). The organics were combined, dried (MgSO4), filtered, and concentrated to give tert-butyl 5-((5-carbamoyl-2-chloropyrimidin-4-yl)amino)-3,4-dihydroisoquinoline-2(1H)-carboxylate as a solid. The compound was sufficiently pure (87%) and was carried forward crude. MS (ESI) m/z calc'd for $C_{19}H_{23}ClN_5O_3$ $[M+H]^+$ 404. found 404.

Step 2a (Prep 2a in Table 7). 2-((4-(Methylsulfonyl)phenyl)amino)-4-((1,2,3,4-tetrahydroisoquinolin-5-yl)amino)pyrimidine-5-carboxamide (Example 7-1)

4-(Methylsulfonyl)aniline (13.99 mg, 0.082 mmol) was added to a vial containing tert-butyl 5-((5-carbamoyl-2-chloropyrimidin-4-yl)amino)-3,4-dihydroisoquinoline-2(1H)-carboxylate (30 mg, 0.074 mmol) in 2-MethoxyEthanol (495 μl). HCl (1.25 M in ethanol)(296 μl, 0.370 mmol) was added via syringe and the mixture was stirred at 90° C. overnight. The mixture was cooled and diluted in DMA/DMSO (2 mL) and filtered through a frit. The residue was purified via mass directed reverse-phase prep-HPLC (Purification Method B), to give 2-((4-(methylsulfonyl)-phenyl)amino)-4-((1,2,3,4-tetrahydroisoquinolin-5-yl)amino)pyrimidine-5-carboxamide as a solid following dry down. MS (ESI) m/z calc'd for $C_{21}H_{23}N_6O_3S$ $[M+H]^+$439, found 439. $^1H$ NMR (499 MHz, DMSO-d6) δ 11.26 (s, 1H), 10.12 (s, 1H), 8.77 (s, 1H), 8.11 (br s, 1H), 7.92 (d, J=8.8 Hz, 2H), 7.84 (s, 1H), 7.69 (d, J=8.8 Hz, 2H), 7.48 (s, 1H), 7.21 (t, J=7.8 Hz, 1H), 6.92 (d, J=7.5 Hz, 1H), 3.88 (s, 2H), 3.25 (br s, 1H), 3.14 (s, 3H), 2.98 (m, 2H), 2.58 (m, 2H).

Step 2b (Prep 2b in Table 7). 2-((4-(Methylsulfonyl)phenyl)amino)-4-((1,2,3,4-tetrahydroisoquinolin-5-yl)amino)pyrimidine-5-carboxamide (Example 7-2)

6-Methoxy-2-methyl-1,2,3,4-tetrahydroisoquinolin-7-amine (42.0 mg, 0.218 mmol), (S)-2-chloro-4-((2-(4-methyl-2-oxooxazolidin-3-yl)phenyl)amino)pyrimidine-5-carboxamide (69 mg, 0.20 mmol) were charged in a vial, 2-methoxyethanol (2000 μL) was added followed by tosic acid (56.6 mg, 0.298 mmol). The reaction was heated to 110° C. overnight. The crude was diluted with DMSO (2 mL), filtered and purified via mass directed reverse-phase prep-HPLC (Purification Method A). This provided (S)-2-((6-methoxy-2-methyl-1,2,3,4-tetrahydroisoquinolin-7-yl)amino)-4-((2-(4-methyl-2-oxooxazolidin-3-yl)phenyl)amino)-pyrimidine-5-carboxamide. MS (ESI) m/z calc'd for $C_{26}H_{30}N_7O_4$ $[M+H]^+$ 504 found 504. $^1H$ NMR (499 MHz, DMSO-d6) δ 12.07 (s, 1H), 8.78-8.58 (m, 1H), 8.36 (s, 1H), 8.15 (s, 1H), 7.65 (s, 1H), 7.50 (d, J=5.0 Hz, 1H), 7.47 (d, J=8.1 Hz, 1H), 7.40-7.36 (m, 1H), 7.32 (t, J=7.7 Hz, 1H), 7.20-7.13 (m, 1H), 7.11 (d, J=7.8 Hz, 1H), 7.03 (s, 1H), 4.68 (t, J=8.1 Hz, 1H), 4.44-4.29 (m, 2H), 4.23-4.12 (m, 1H), 4.07 (t, J=7.9 Hz, 1H), 3.81 (s, 3H), 3.74-3.65 (m, 1H), 3.42-3.29 (m, 1H), 3.19-3.03 (m, 2H), 2.95 (d, J=3.9 Hz, 3H), 1.09 (d, J=6.2 Hz, 3H).

Step 2c (Prep 2c in Table 7). 4-[(2-Bromophenyl)amino]-2-[(6-methoxy-2-methyl-1,2,3,4-tetrahydroisoquinolin-7-yl)amino]pyrimidine-5-carboxamide (Example 7-3)

A vial was charged with 4-((2-bromophenyl)amino)-2-chloropyrimidine-5-carboxamide (500 mg, 1.523 mmol, I-9), 6-methoxy-2-methyl-1,2,3,4-tetrahydroisoquinolin-7-amine (293 mg, 1.53 mmol), 20 drops of 4M aq. HCl, and ethanol (10.18 ml). The mixture was heated in a microwave vial to 120° C. for 2 h. then allowed to crystallize at RT and filtered with ethanol to afford 4-((2-bromophenyl)amino)-2-((6-methoxy-2-methyl-1,2,3,4-tetrahydroisoquinolin-7-yl)aminopyrimidine-5-carboxamide, hydrochloride. MS (ESI) m/z calc'd for $C_{22}H_{24}BrN_6O_2$ $[M+H]^+$ 483 found 483. 1H NMR (499 MHz, DMSO-d6) δ 11.67 (s, 1H), 8.71 (s, 1H), 8.35 (s, 1H), 8.21 (s, 1H), 8.03 (s, 1H), 7.69-7.65 (m, 2H), 7.41 (s, 1H), 7.26 (s, 1H), 7.04 (t, J=7.6 Hz, 1H), 6.78 (s, 1H), 3.77 (s, 3H), 3.27 (s, 2H), 2.80 (s, 2H), 2.58 (s, 2H), 2.34 (s, 3H).

TABLE 7

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-1 | 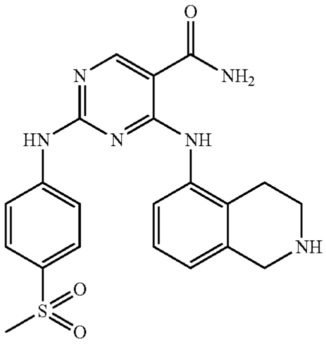 [SMILES: CS(=O)(=O)c1ccc(Nc2ncc(C(N)=O)c(Nc3cccc4c3CCNC4)n2)cc1] | 2-{[4-(methylsulfonyl)phenyl]amino}-4-[(1,2,3,4-tetrahydroisoquinolin-5-yl)amino]pyrimidine-5-carboxamide | Calc'd 439, found 439 (Prep 2a) |

TABLE 7-continued

| Compounds listed in the table below were prepared using the synthetic methods described in the aforementioned Example 7-1, 7-2, or 7-3. The table provides the compound structure, the name, the calculated and observed masses, and Prep procedure details in the Prep Column. | | | |
|---|---|---|---|
| Example | Structure | Name | Exact Mass $[M + H]^+$ & Prep |
| 7-2 | 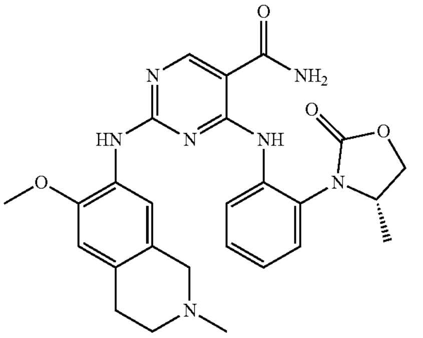 [SMILES: COc1cc2c(cc1Nc1ncc(C(N)=O)c(Nc3ccccc3N3C(=O)OC[C@@H]3C)n1)CN(C)CC2] | 2-[(6-methoxy-2-methyl-1,2,3,4-tetrahydroisoquinolin-7-yl)amino]-4-({2-[(4S)-4-methyl-2-oxo-1,3-oxazolidin-3-yl]phenyl}amino)pyrimidine-5-carboxamide | Calc'd 504, found 504 (Prep 2b) |
| 7-3 | 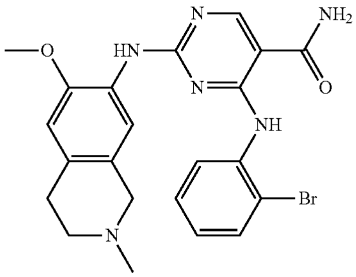 [SMILES: COc1cc2c(cc1Nc1ncc(C(N)=O)c(Nc3ccccc3Br)n1)CN(C)CC2] | 4-[(2-bromophenyl)amino]-2-[(6-methoxy-2-methyl-1,2,3,4-tetrahydroisoquinolin-7-yl)amino]pyrimidine-5-carboxamide | Calc'd 483, found 483 (Prep 2b) |
| 7-4 | 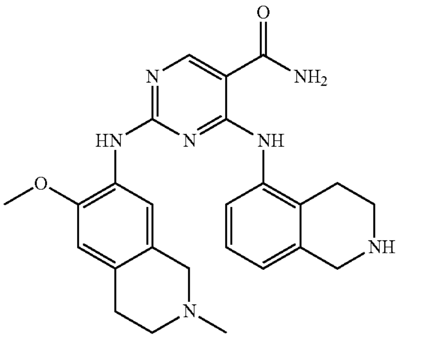 [SMILES: COc1cc2c(cc1Nc1ncc(C(N)=O)c(Nc3cccc4c3CCNC4)n1)CN(C)CC2] | 2-[(6-methoxy-2-methyl-1,2,3,4-tetrahydroisoquinolin-7-yl)amino]-4-[(1,2,3,4-tetrahydroisoquinolin-5-yl)amino]pyrimidine-5-carboxamide | Calc'd 460, found 460 (Prep 2a) |
| 7-5 | 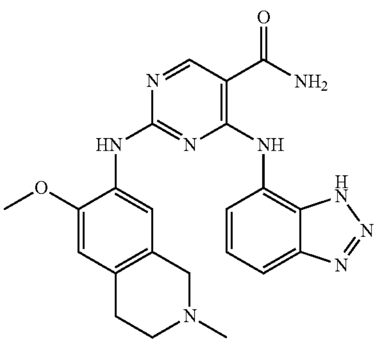 [SMILES: COc1cc2c(cc1Nc1ncc(C(N)=O)c(Nc3cccc4nn[nH]c34)n1)CN(C)CC2] | 4-[(1H-benzotriazol-7-yl)amino]-2-[(6-methoxy-2-methyl-1,2,3,4-tetrahydroisoquinolin-7-yl)amino]pyrimidine-5-carboxamide | Calc'd 446, found 446 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-6 | 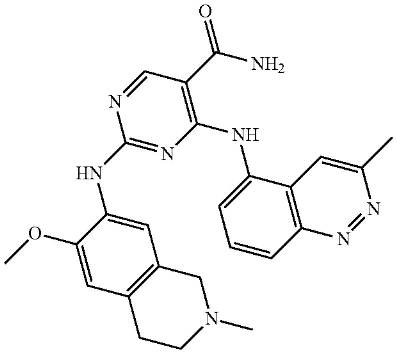 | 2-[(6-methoxy-2-methyl-1,2,3,4-tetrahydroisoquinolin-7-yl)amino]-4-[(3-methylcinnolin-5-yl)amino]pyrimidine-5-carboxamide | Calc'd 471, found 471 (Prep 2a) |
| 7-7 | 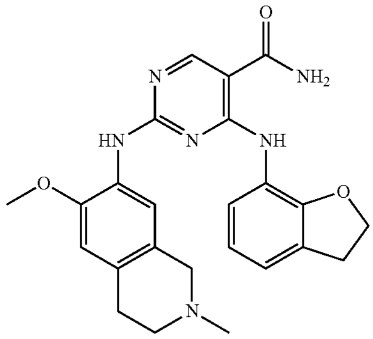 [SMILES: COc1cc2c(cc1Nc1ncc(C(N)=O)c(Nc3cccc4c3OCC4)n1)CN(C)CC2] | 4-[(2,3-dihydro-1-benzofuran-7-yl)amino]-2-[(6-methoxy-2-methyl-1,2,3,4-tetrahydroisoquinolin-7-yl)amino]pyrimidine-5-carboxamide | Calc'd 447, found 447 (Prep 2a) |
| 7-8 | 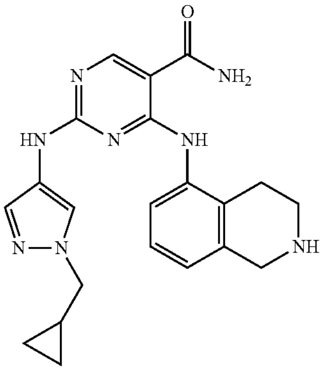 [SMILES: NC(=O)c1cnc(Nc2cnn(CC3CC3)c2)nc1Nc1cccc2c1CCNC2] | 2-{[1-(cyclopropylmethyl)-1H-pyrazol-4-yl]amino}-4-[(1,2,3,4-tetrahydroisoquinolin-5-yl)amino]pyrimidine-5-carboxamide | Calc'd 405, found 405 (Prep 2a) |
| 7-9 | 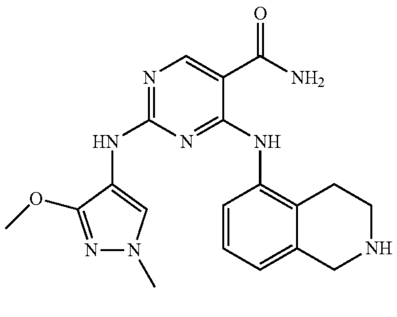 [SMILES: COc1nn(C)cc1Nc1ncc(C(N)=O)c(Nc2cccc3c2CCNC3)n1] | 2-[(3-methoxy-1-methyl-1H-pyrazol-4-yl)amino]-4-[(1,2,3,4-tetrahydroisoquinolin-5-yl)amino]pyrimidine-5-carboxamide | Calc'd 395, found 395 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-10 | 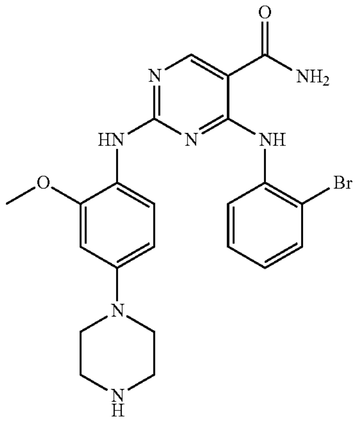 [SMILES: COc1cc(N2CCNCC2)ccc1Nc1ncc(C(N)=O)c(Nc2ccccc2Br)n1] | 4-[(2-bromophenyl)amino]-2-{[2-methoxy-4-(piperazin-1-yl)phenyl]amino}pyrimidine-5-carboxamide | Calc'd 498, found 498 (Prep 2c) |
| 7-11 | 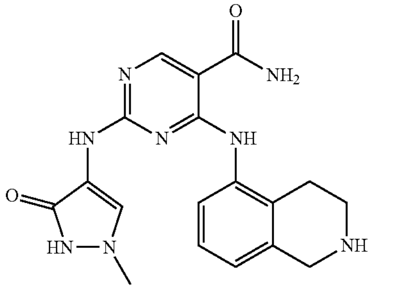 [SMILES: Cn1cc(Nc2ncc(C(N)=O)c(Nc3cccc4c3CCNC4)n2)c(=O)[nH]1] | 2-[(1-methyl-3-oxo-2,3-dihydro-1H-pyrazol-4-yl)amino]-4-[(1,2,3,4-tetrahydroisoquinolin-5-yl)amino]pyrimidine-5-carboxamide | Calc'd 381, found 381 (Prep 2a) |
| 7-12 | 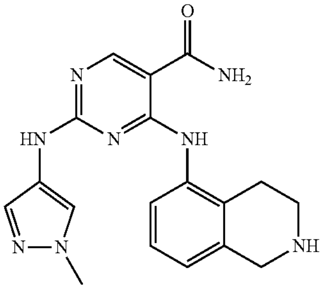 [SMILES: Cn1cc(Nc2ncc(C(N)=O)c(Nc3cccc4c3CCNC4)n2)cn1] | 2-[(1-methyl-1H-pyrazol-4-yl)amino]-4-[(1,2,3,4-tetrahydroisoquinolin-5-yl)amino]pyrimidine-5-carboxamide | Calc'd 365, found 365 (Prep 2a) |
| 7-13 | 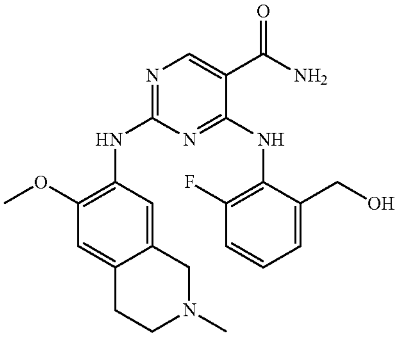 [SMILES: COc1cc2c(cc1Nc1ncc(C(N)=O)c(Nc3c(F)cccc3CO)n1)CN(C)CC2] | 4-{[2-fluoro-6-(hydroxymethyl)phenyl]amino}-2-[(6-methoxy-2-methyl-1,2,3,4-tetrahydroisoquinolin-7-yl)amino]pyrimidine-5-carboxamide | Calc'd 453, found 453 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-14 | 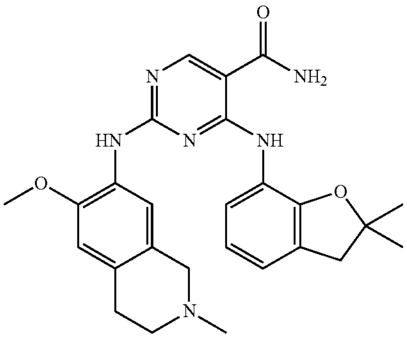 | 4-[(2,2-dimethyl-2,3-dihydro-1-benzofuran-7-yl)amino]-2-[(6-methoxy-2-methyl-1,2,3,4-tetrahydroisoquinolin-7-yl)amino]pyrimidine-5-carboxamide | Calc'd 475, found 475 (Prep 2a) |
| 7-15 | 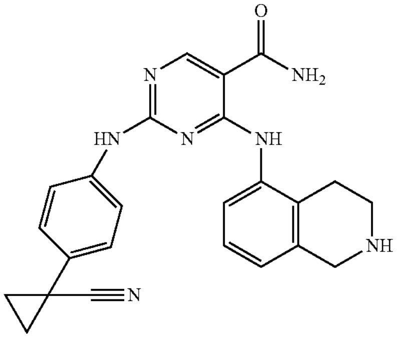 [SMILES: N#CC1(c2ccc(Nc3ncc(C(N)=O)c(Nc4cccc5c4CCNC5)n3)cc2)CC1] | 2-{[4-(1-cyanocyclopropyl)phenyl]amino}-4-[(1,2,3,4-tetrahydroisoquinolin-5-yl)amino]pyrimidine-5-carboxamide | Calc'd 426, found 426 (Prep 2c) |
| 7-16 | 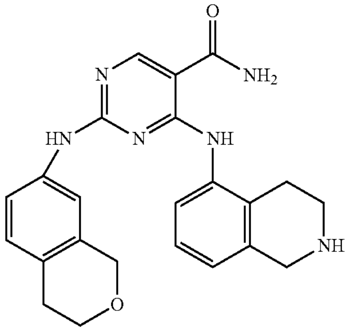 [SMILES: NC(=O)c1cnc(Nc2ccc3c(c2)COCC3)nc1Nc1cccc2c1CCNC2] | 2-[(3,4-dihydro-1H-2-benzopyran-7-yl)amino]-4-[(1,2,3,4-tetrahydroisoquinolin-5-yl)amino]pyrimidine-5-carboxamide | Calc'd 417, found 417 (Prep 2c) |
| 7-17 | 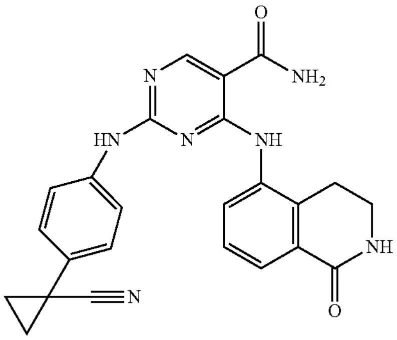 [SMILES: N#CC1(c2ccc(Nc3ncc(C(N)=O)c(Nc4cccc5c4CCNC5=O)n3)cc2)CC1] | 2-{[4-(1-cyanocyclopropyl)phenyl]amino}-4-[(1-oxo-1,2,3,4-tetrahydroisoquinolin-5-yl)amino]pyrimidine-5-carboxamide | Calc'd 440, found 440 (Prep 2c) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-18 | 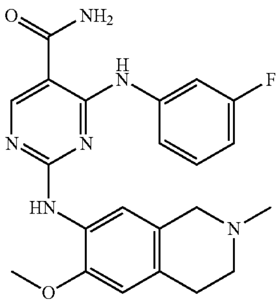 [SMILES: COc1cc2c(cc1Nc1ncc(C(N)=O)c(Nc3cccc(F)c3)n1)CN(C)CC2] | 4-[(3-fluorophenyl)amino]-2-[(6-methoxy-2-methyl-1,2,3,4-tetrahydroisoquinolin-7-yl)amino]pyrimidine-5-carboxamide | Calc'd 423, found 423 (Prep 2a) |
| 7-19 | 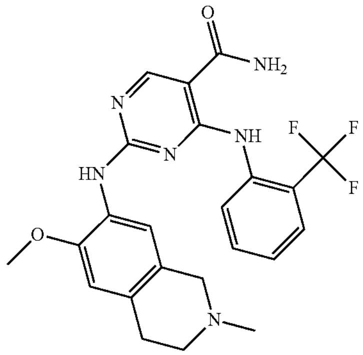 [SMILES: COc1cc2c(cc1Nc1ncc(C(N)=O)c(Nc3ccccc3C(F)(F)F)n1)CN(C)CC2] | 2-[(6-methoxy-2-methyl-1,2,3,4-tetrahydroisoquinolin-7-yl)amino]-4-{[2-(trifluoromethyl)phenyl]amino}pyrimidine-5-carboxamide | Calc'd 473, found 473 (Prep 2b) |
| 7-20 | 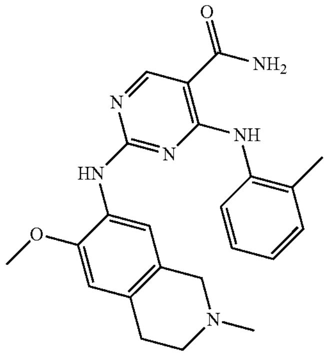 | 2-[(6-methoxy-2-methyl-1,2,3,4-tetrahydroisoquinolin-7-yl)amino]-4-[(2-methylphenyl)amino]pyrimidine-5-carboxamide | Calc'd 419, found 419 (Prep 2b) |
| 7-21 | 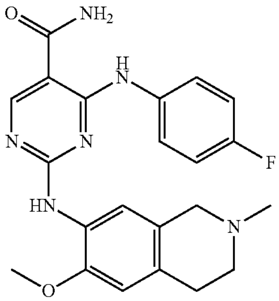 [SMILES: COc1cc2c(cc1Nc1ncc(C(N)=O)c(Nc3ccc(F)cc3)n1)CN(C)CC2] | 4-[(4-fluorophenyl)amino]-2-[(6-methoxy-2-methyl-1,2,3,4-tetrahydroisoquinolin-7-yl)amino]pyrimidine-5-carboxamide | Calc'd 423, found 423 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-22 | 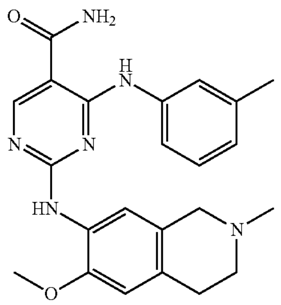 [SMILES: COc1cc2c(cc1Nc1ncc(C(N)=O)c(Nc3cccc(C)c3)n1)CN(C)CC2] | 2-[(6-methoxy-2-methyl-1,2,3,4-tetrahydroisoquinolin-7-yl)amino]-4-[(3-methylphenyl)amino]pyrimidine-5-carboxamide | Calc'd 419, found 419 (Prep 2a) |
| 7-23 | 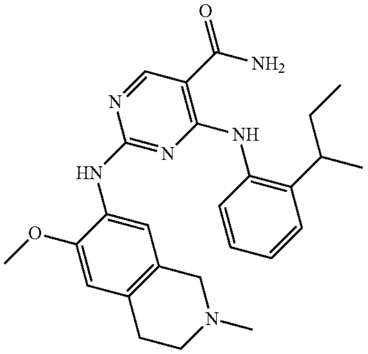 [SMILES: CCC(C)c1ccccc1Nc1nc(Nc2cc3c(cc2OC)CCN(C)C3)ncc1C(N)=O] | 4-{[2-(butan-2-yl)phenyl]amino}-2-[(6-methoxy-2-methyl-1,2,3,4-tetrahydroisoquinolin-7-yl)amino]pyrimidine-5-carboxamide | Calc'd 461, found 461 (Prep 2b) |
| 7-24 | 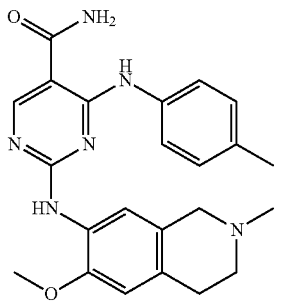 [SMILES: COc1cc2c(cc1Nc1ncc(C(N)=O)c(Nc3ccc(C)cc3)n1)CN(C)CC2] | 2-[(6-methoxy-2-methyl-1,2,3,4-tetrahydroisoquinolin-7-yl)amino]-4-[(4-methylphenyl)amino]pyrimidine-5-carboxamide | Calc'd 419, found 419 (Prep 2a) |
| 7-25 | 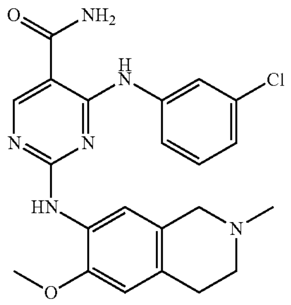 [SMILES: COc1cc2c(cc1Nc1ncc(C(N)=O)c(Nc3cccc(Cl)c3)n1)CN(C)CC2] | 4-[(3-chlorophenyl)amino]-2-[(6-methoxy-2-methyl-1,2,3,4-tetrahydroisoquinolin-7-yl)amino]pyrimidine-5-carboxamide | Calc'd 439, found 439 (Prep 2a) |

TABLE 7-continued

| Compounds listed in the table below were prepared using the synthetic methods described in the aforementioned Example 7-1, 7-2, or 7-3. The table provides the compound structure, the name, the calculated and observed masses, and Prep procedure details in the Prep Column. | | | |
|---|---|---|---|
| Example | Structure | Name | Exact Mass $[M + H]^+$ & Prep |
| 7-26 | 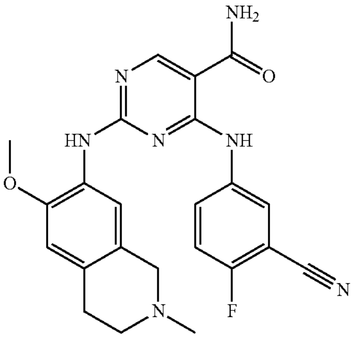 [SMILES: COc1cc2c(cc1Nc1ncc(C(N)=O)c(Nc3ccc(F)c(C#N)c3)n1)CN(C)CC2] | 4-[(3-cyano-4-fluorophenyl)amino]-2-[(6-methoxy-2-methyl-1,2,3,4-tetrahydroisoquinolin-7-yl)amino]pyrimidine-5-carboxamide | Calc'd 448, found 448 (Prep 2a) |
| 7-27 | 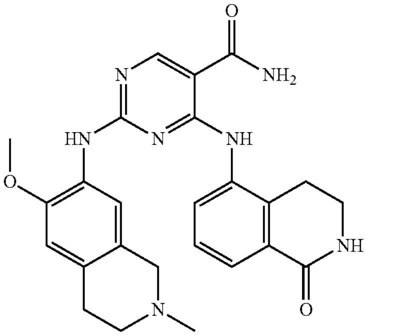 [SMILES: COc1cc2c(cc1Nc1ncc(C(N)=O)c(Nc3cccc4c3CCNC4=O)n1)CN(C)CC2] | 2-[(6-methoxy-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide | Calc'd 474, found 474 (Prep 2a) |
| 7-28 | 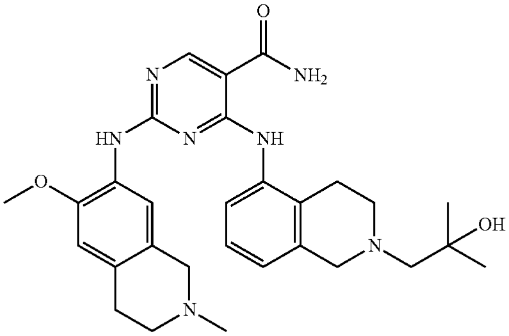 [SMILES: COc1cc2c(cc1Nc1ncc(C(N)=O)c(Nc3cccc4c3CCN(CC(C)(C)O)C4)n1)CN(C)CC2] | 4-{[2-(2-hydroxy-2-methylpropyl)-1,2,3,4-tetrahydroisoquinolin-5-yl]amino}-2-[(6-methoxy-2-methyl-1,2,3,4-tetrahydroisoquinolin-7-yl)amino]pyrimidine-5-carboxamide | Calc'd 532, found 532 (Prep 2a) |
| 7-29 | 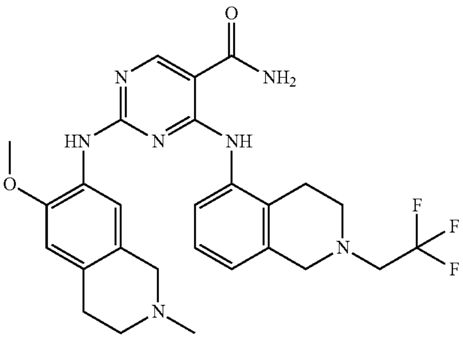 [SMILES: COc1cc2c(cc1Nc1ncc(C(N)=O)c(Nc3cccc4c3CCN(CC(F)(F)F)C4)n1)CN(C)CC2] | 2-[(6-methoxy-2-methyl-1,2,3,4-tetrahydroisoquinolin-7-yl)amino]-4-{[2-(2,2,2-trifluoroethyl)-1,2,3,4-tetrahydroisoquinolin-5-yl]amino}pyrimidine-5-carboxamide | Calc'd 542, found 542 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-30 | 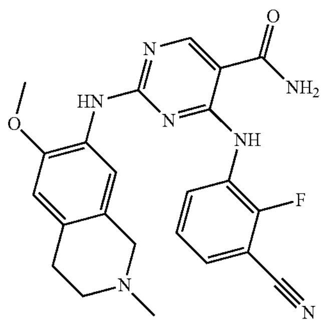 [SMILES: COc1cc2c(cc1Nc1ncc(C(N)=O)c(Nc3cccc(C#N)c3F)n1)CN(C)CC2] | 4-[(3-cyano-2-fluorophenyl)amino]-2-[(6-methoxy-2-methyl-1,2,3,4-tetrahydroisoquinolin-7-yl)amino]pyrimidine-5-carboxamide | Calc'd 448, found 448 (Prep 2a) |
| 7-31 | 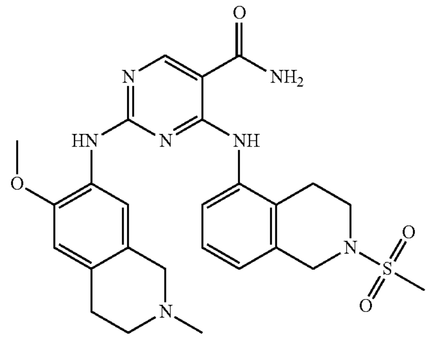 [SMILES: COc1cc2c(cc1Nc1ncc(C(N)=O)c(Nc3cccc4c3CCN(S(C)(=O)=O)C4)n1)CN(C)CC2] | 2-[(6-methoxy-2-methyl-1,2,3,4-tetrahydroisoquinolin-7-yl)amino]-4-{[2-(methylsulfonyl)-1,2,3,4-tetrahydroisoquinolin-5-yl]amino}pyrimidine-5-carboxamide | Calc'd 538, found 538 (Prep 2a) |
| 7-32 | 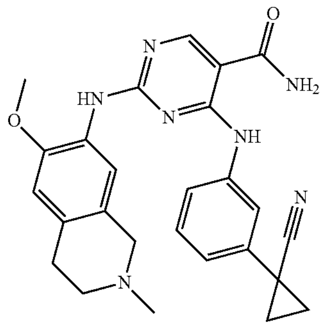 [SMILES: COc1cc2c(cc1Nc1ncc(C(N)=O)c(Nc3cccc(C4(C#N)CC4)c3)n1)CN(C)CC2] | 4-{[3-(1-cyanocyclopropyl)phenyl]amino}-2-[(6-methoxy-2-methyl-1,2,3,4-tetrahydroisoquinolin-7-yl)amino]pyrimidine-5-carboxamide | Calc'd 470, found 470 (Prep 2a) |
| 7-33 | 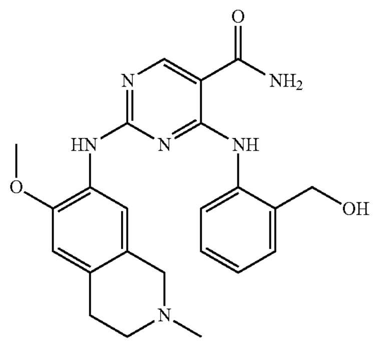 [SMILES: COc1cc2c(cc1Nc1ncc(C(N)=O)c(Nc3ccccc3CO)n1)CN(C)CC2] | 4-{[2-(hydroxymethyl)phenyl]amino}-2-[(6-methoxy-2-methyl-1,2,3,4-tetrahydroisoquinolin-7-yl)amino]pyrimidine-5-carboxamide | Calc'd 435, found 435 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-34 | 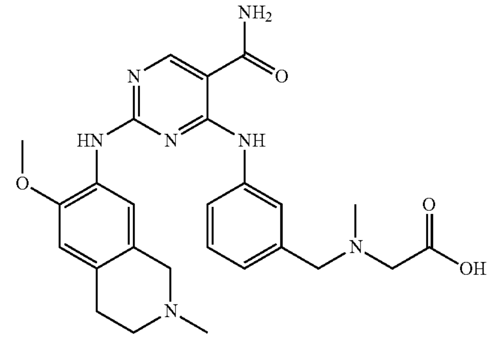 [SMILES: COc1cc2c(cc1Nc1ncc(C(N)=O)c(Nc3cccc(CN(C)CC(=O)O)c3)n1)CN(C)CC2] | N-{[3-({5-carbamoyl-2-[(6-methoxy-2-methyl-1,2,3,4-tetrahydroisoquinolin-7-yl)amino]pyrimidin-4-yl}amino)phenyl]methyl}-N-methylglycine | Calc'd 405, found 506 (Prep 2a) |
| 7-35 | 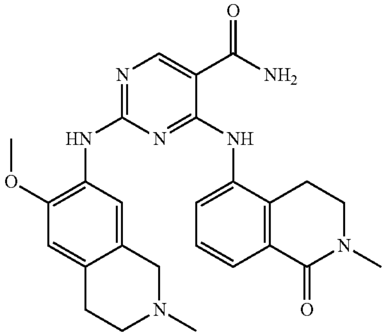 [SMILES: COc1cc2c(cc1Nc1ncc(C(N)=O)c(Nc3cccc4c3CCN(C)C4=O)n1)CN(C)CC2] | 2-[(6-methoxy-2-methyl-1,2,3,4-tetrahydroisoquinolin-7-yl)amino]-4-[(2-methyl-1-oxo-1,2,3,4-tetrahydroisoquinolin-5-yl)amino]pyrimidine-5-carboxamide | Calc'd 488, found 488 (Prep 2a) |
| 7-36 | 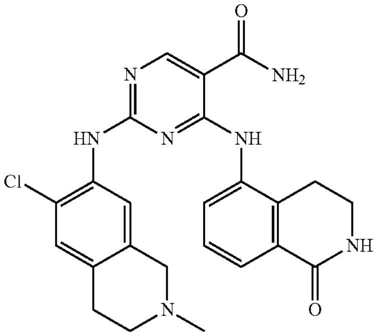 [SMILES: CN1CCc2cc(Cl)c(Nc3ncc(C(N)=O)c(Nc4cccc5c4CCNC5=O)n3)cc2C1] | 2-[(6-chloro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide | Calc'd 478, found 478 (Prep 2a) |
| 7-37 | 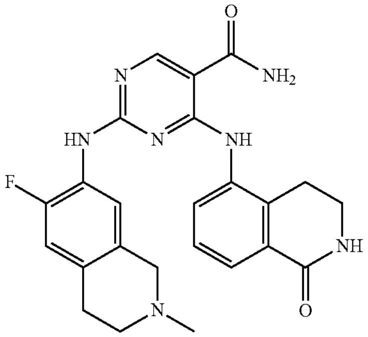 | 2-[(6-fluoro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide | Calc'd 462, found 462 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-38 | 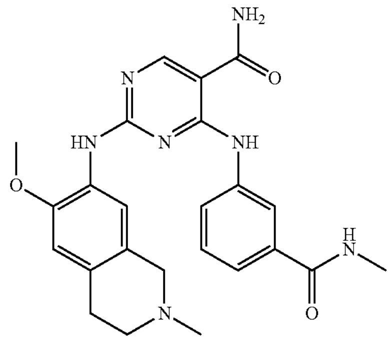 [SMILES: CNC(=O)c1cccc(Nc2nc(Nc3cc4c(cc3OC)CCN(C)C4)ncc2C(N)=O)c1] | 2-[(6-methoxy-2-methyl-1,2,3-tetrahydroisoquinolin-7-yl)amino]-4-{[3-(methylcarbamoyl)phenyl]amino}pyrimidine-5-carboxamide | Calc'd 462, found 462 (Prep 2a) |
| 7-39 | 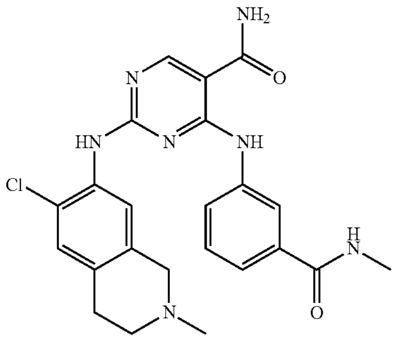 [SMILES: CNC(=O)c1cccc(Nc2nc(Nc3cc4c(cc3Cl)CCN(C)C4)ncc2C(N)=O)c1] | 2-[(6-chloro-2-methyl-1,2,3,4-tetrahydroisoquinolin-7-yl)amino]-4-{[3-(methylcarbamoyl)phenyl]amino}pyrimidine-5-carboxamide | Calc'd 466, found 466 (Prep 2a) |
| 7-40 | 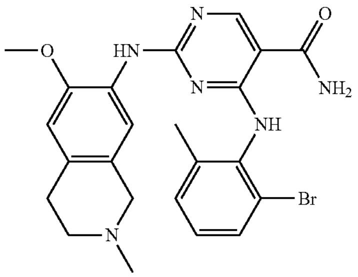 [SMILES: COc1cc2c(cc1Nc1ncc(C(N)=O)c(Nc3c(C)cccc3Br)n1)CN(C)CC2] | 4-[(2-bromo-6-methylphenyl)amino]-2-[(6-methoxy-2-methyl-1,2,3,4-tetrahydroisoquinolin-7-yl)amino]pyrimidine-5-carboxamide | Calc'd 497, found 497 (Prep 2c) |
| 7-41 | 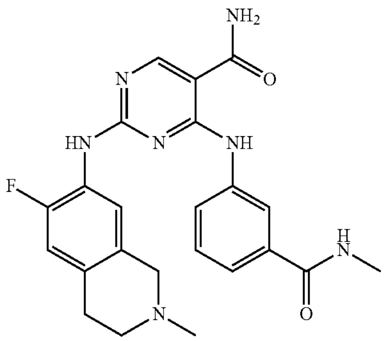 [SMILES: CNC(=O)c1cccc(Nc2nc(Nc3cc4c(cc3F)CCN(C)C4)ncc2C(N)=O)c1] | 2-[(6-fluoro-2-methyl-1,2,3,4-tetrahydroisoquinolin-7-yl)amino]-4-{[3-(methylcarbamoyl)phenyl]amino}pyrimidine-5-carboxamide | Calc'd 450, found 450 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-42 | 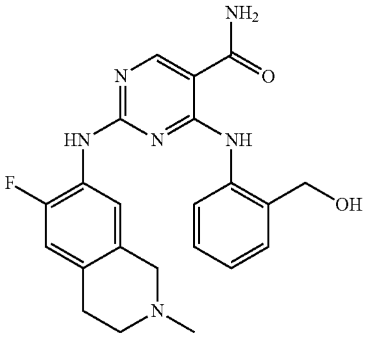 [SMILES: CN1CCc2cc(F)c(Nc3ncc(C(N)=O)c(Nc4ccccc4CO)n3)cc2C1] | 2-[(6-fluoro-2-methyl-1,2,3,4-tetrahydroisoquinolin-7-yl)amino]-4-{[2-(hydroxymethyl)phenyl]amino}pyrimidine-5-carboxamide | Calc'd 423, found 423 (Prep 2a) |
| 7-43 | 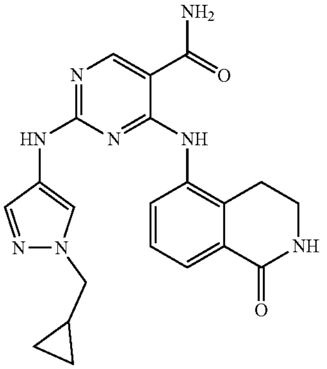 [SMILES: NC(=O)c1cnc(Nc2cnn(CC3CC3)c2)nc1Nc1cccc2c1CCNC2=O] | 2-{[1-(cyclopropylmethyl)-1H-pyrazol-4-yl]amino}-4-[(1-oxo-1,2,3,4-tetrahydroisoquinolin-5-yl)amino]pyrimidine-5-carboxamide | Calc'd 419, found 419 (Prep 2a) |
| 7-44 | 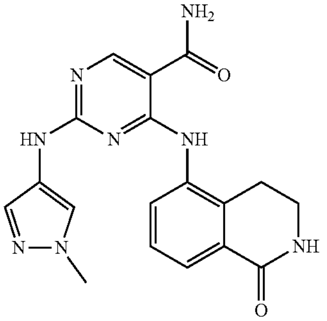 [SMILES: Cn1cc(Nc2ncc(C(N)=O)c(Nc3cccc4c3CCNC4=O)n2)cn1] | 2-[(1-methyl-1H-pyrazol-4-yl)amino]-4-[(1-oxo-1,2,3,4-tetrahydroisoquinolin-5-yl)amino]pyrimidine-5-carboxamide | Calc'd 379, found 379 (Prep 2a) |
| 7-45 | 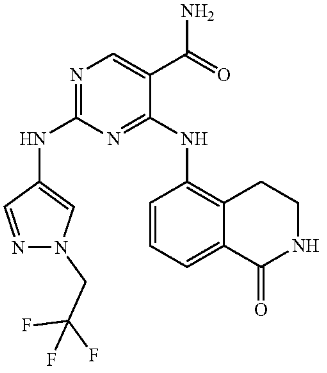 [SMILES: NC(=O)c1cnc(Nc2cnn(CC(F)(F)F)c2)nc1Nc1cccc2c1CCNC2=O] | 4-[(1-oxo-1,2,3,4-tetrahydroisoquinolin-5-yl)amino]-2-{[1-(2,2,2-trifluoroethyl)-1H-pyrazol-4-yl]amino}pyrimidine-5-carboxamide | Calc'd 447, found 447 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-46 | 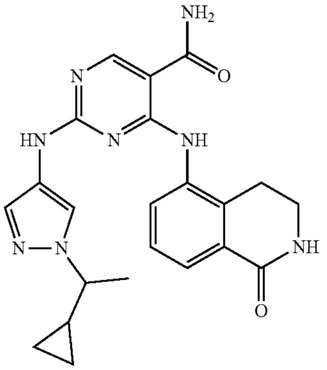 [SMILES: CC(C1CC1)n1cc(Nc2ncc(C(N)=O)c(Nc3cccc4c3CCNC4=O)n2)cn1] | 2-{[1-(1-cyclopropylethyl)-1H-pyrazol-4-yl]amino}-4-[(1-oxo-1,2,3,4-tetrahydroisoquinolin-5-yl)amino]pyrimidine-5-carboxamide | Calc'd 433, found 433 (Prep 2a) |
| 7-47 | 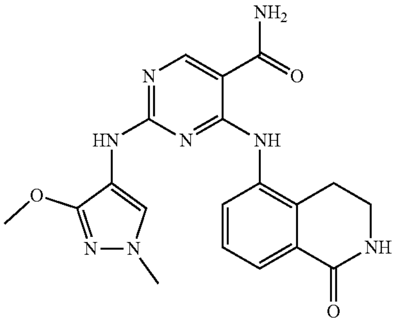 [SMILES: COc1nn(C)cc1Nc1ncc(C(N)=O)c(Nc2cccc3c2CCNC3=O)n1] | 2-[(3-methoxy-1-methyl-1H-pyrazol-4-yl)amino]-4-[(1-oxo-1,2,3,4-tetrahydroisoquinolin-5-yl)amino]pyrimidine-5-carboxamide | Calc'd 409, found 409 (Prep 2a) |
| 7-48 | 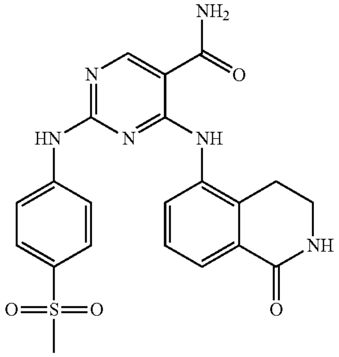 [SMILES: CS(=O)(=O)c1ccc(Nc2ncc(C(N)=O)c(Nc3cccc4c3CCNC4=O)n2)cc1] | 2-{[4-(methylsulfonyl)phenyl]amino}-4-[(1-oxo-1,2,3,4-tetrahydroisoquinolin-5-yl)amino]pyrimidine-5-carboxamide | Calc'd 453, found 453 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-49 | 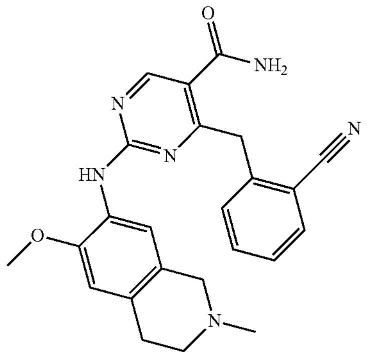 [SMILES: COc1cc2c(cc1Nc1ncc(C(N)=O)c(Cc3ccccc3C#N)n1)CN(C)CC2] | 4-[(2-cyanophenyl)amino]-2-[(6-methoxy-2-methyl-1,2,3,4-tetrahydroisoquinolin-7-yl)amino]pyrimidine-5-carboxamide | Calc'd 430, found 430 (Prep 2b) |
| 7-50 | 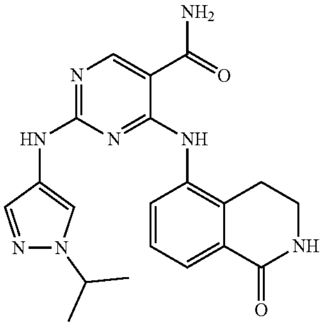 [SMILES: CC(C)n1cc(Nc2ncc(C(N)=O)c(Nc3cccc4c3CCNC4=O)n2)cn1] | 4-[(1-oxo-1,2,3,4-tetrahydroisoquinolin-5-yl)amino]-2-{[1-(propan-2-yl)-1H-pyrazol-4-yl]amino}pyrimidine-5-carboxamide | Calc'd 407, found 407 (Prep 2a) |
| 7-51 | 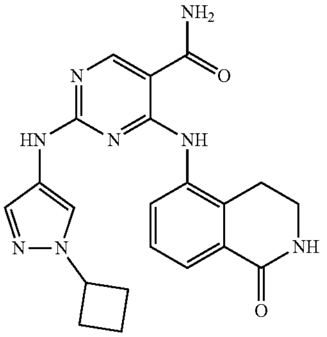 [SMILES: NC(=O)c1cnc(Nc2cnn(C3CCC3)c2)nc1Nc1cccc2c1CCNC2=O] | 2-[(1-cyclobutyl-1H-pyrazol-4-yl)amino]-4-[(1-oxo-1,2,3,4-tetrahydroisoquinolin-5-yl)amino]pyrimidine-5-carboxamide | Calc'd 419, found 419 (Prep 2a) |
| 7-52 | 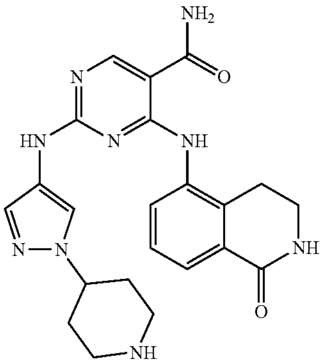 [SMILES: NC(=O)c1cnc(Nc2cnn(C3CCNCC3)c2)nc1Nc1cccc2c1CCNC2=O] | 4-[(1-oxo-1,2,3,4-tetrahydroisoquinolin-5-yl)amino]-2-{[1-(piperidin-4-yl)-1H-pyrazol-4-yl]amino}pyrimidine-5-carboxamide | Calc'd 448, found 448 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-53 | 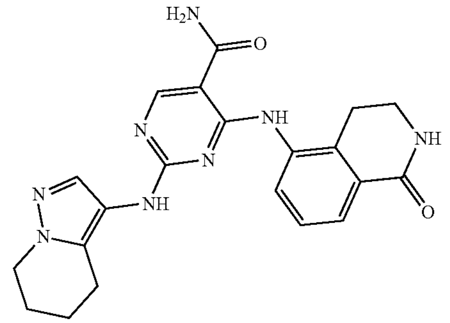 [SMILES: NC(=O)c1cnc(Nc2cnn3c2CCCC3)nc1Nc1cccc2c1CCNC2=O] | 4-[(1-oxo-1,2,3,4-tetrahydroisoquinolin-5-yl)amino]-2-[(4,5,6,7-tetrahydropyrazolo[1,5-a]pyridin-3-yl)amino]pyrimidine-5-carboxamide | Calc'd 419, found 419 (Prep 2a) |
| 7-54 | 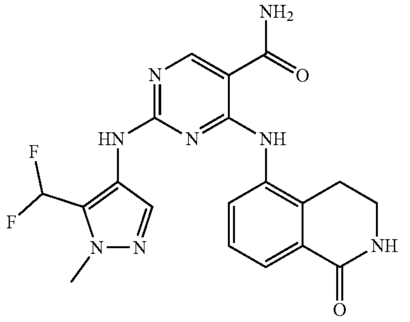 [SMILES: Cn1ncc(Nc2ncc(C(N)=O)c(Nc3cccc4c3CCNC4=O)n2)c1C(F)F] | 2-{[5-(difluoromethyl)-1-methyl-1H-pyrazol-4-yl]amino}-4-[(1-oxo-1,2,3,4-tetrahydroisoquinolin-5-yl)amino]pyrimidine-5-carboxamide | Calc'd 429, found 429 (Prep 2a) |
| 7-55 | 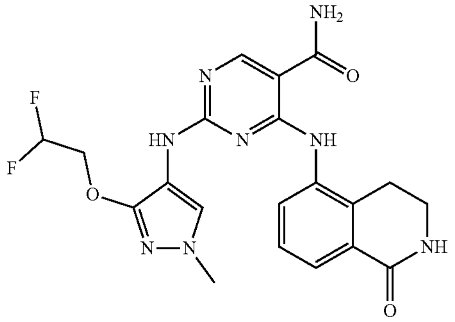 [SMILES: Cn1cc(Nc2ncc(C(N)=O)c(Nc3cccc4c3CCNC4=O)n2)c(OCC(F)F)n1] | 2-{[3-(2,2-difluoroethoxy)-1-methyl-1H-pyrazol-4-yl]amino}-4-[(1-oxo-1,2,3,4-tetrahydroisoquinolin-5-yl)amino]pyrimidine-5-carboxamide | Calc'd 459, found 459 (Prep 2a) |
| 7-56 | 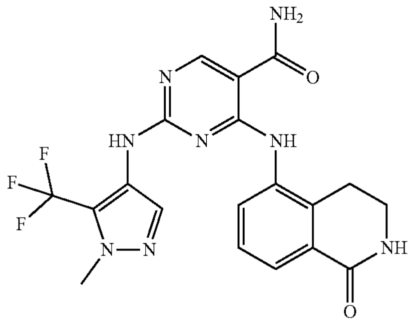 [SMILES: Cn1ncc(Nc2ncc(C(N)=O)c(Nc3cccc4c3CCNC4=O)n2)c1C(F)(F)F] | 2-{[1-methyl-5-(trifluoromethyl)-1H-pyrazol-4-yl]amino}-4-[(1-oxo-1,2,3,4-tetrahydroisoquinolin-5-yl)amino]pyrimidine-5-carboxamide | Calc'd 447, found 447 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-57 | 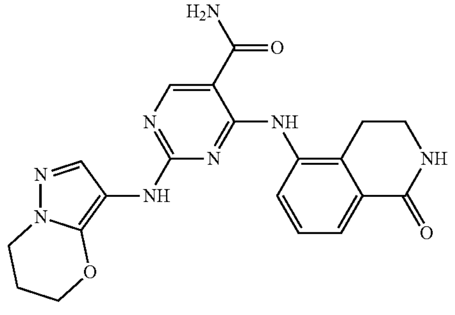 [SMILES: NC(=O)c1cnc(Nc2cnn3c2OCCC3)nc1Nc1cccc2c1CCNC2=O] | 2-[(6,7-dihydro-5H-pyrazolo[5,1-b][1,3]oxazin-3-yl)amino]-4-[(1-oxo-1,2,3,4-tetrahydroisoquinolin-5-yl)amino]pyrimidine-5-carboxamide | Calc'd 421, found 421 (Prep 2a) |
| 7-58 | 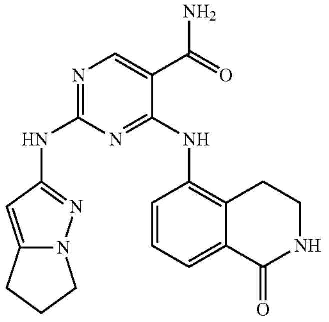 [SMILES: NC(=O)c1cnc(Nc2cc3n(n2)CCC3)nc1Nc1cccc2c1CCNC2=O] | 2-[(5,6-dihydro-4H-pyrrolo[1,2-b]pyrazol-2-yl)amino]-4-[(1-oxo-1,2,3,4-tetrahydroisoquinolin-5-yl)amino]pyrimidine-5-carboxamide | Calc'd 405, found 405 (Prep 2a) |
| 7-59 | 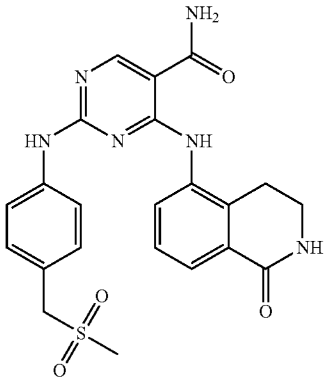 [SMILES: CS(=O)(=O)Cc1ccc(Nc2ncc(C(N)=O)c(Nc3cccc4c3CCNC4=O)n2)cc1] | 2-({4-[(methylsulfonyl)methyl]phenyl}amino)-4-[(1-oxo-1,2,3,4-tetrahydroisoquinolin-5-yl)amino]pyrimidine-5-carboxamide | Calc'd 467, found 467 (Prep 2a) |
| 7-60 | 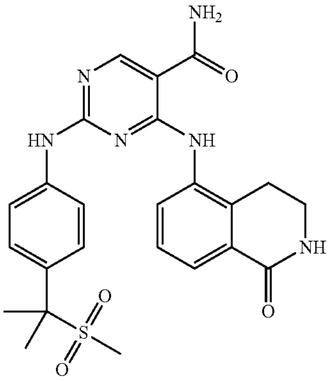 [SMILES: CC(C)(c1ccc(Nc2ncc(C(N)=O)c(Nc3cccc4c3CCNC4=O)n2)cc1)S(C)(=O)=O] | 2-({4-[2-(methylsulfonyl)propan-2-yl]phenyl}amino)-4-[(1-oxo-1,2,3,4-tetrahydroisoquinolin-5-yl)amino]pyrimidine-5-carboxamide | Calc'd 495, found 495 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass [M + H]$^+$ & Prep |
|---|---|---|---|
| 7-61 | 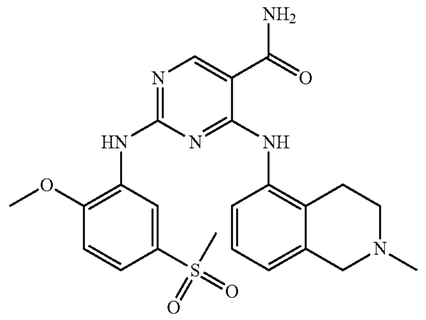 | 2-{[2-methoxy-5-(methylsulfonyl)phenyl]amino}-4-[(2-methyl-1,2,3,4-tetrahydroisoquinolin-5-yl)amino]pyrimidine-5-carboxamide | Calc'd 483, found 483 (Prep 2a) |
| 7-62 | 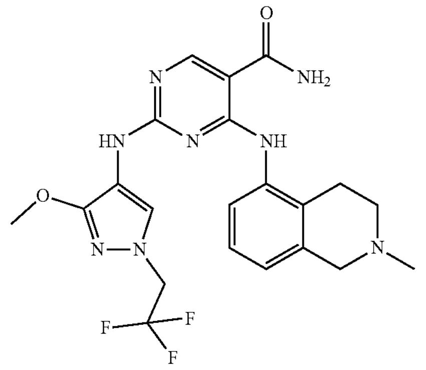 | 2-{[3-methoxy-1-(2,2,2-trifluoroethyl)-1H-pyrazol-4-yl]amino}-4-[(2-methyl-1,2,3,4-tetrahydroisoquinolin-5-yl)amino]pyrimidine-5-carboxamide | Calc'd 477, found 477 (Prep 2a) |
| 7-63 | 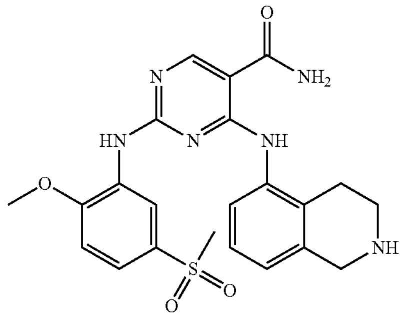 [SMILES: COc1ccc(S(C)(=O)=O)cc1Nc1ncc(C(N)=O)c(Nc2cccc3c2CCNC3)n1] | 2-{[2-methoxy-5-(methylsulfonyl)phenyl]amino}-4-[(1,2,3,4-tetrahydroisoquinolin-5-yl)amino]pyrimidine-5-carboxamide | Calc'd 469, found 469 (Prep 2a) |
| 7-64 | 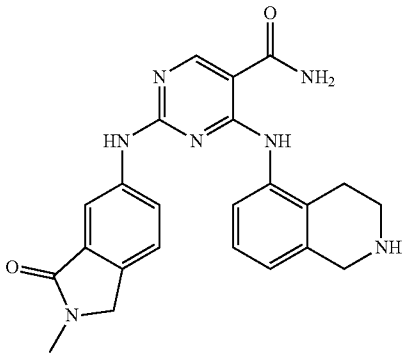 [SMILES: CN1Cc2ccc(Nc3ncc(C(N)=O)c(Nc4cccc5c4CCNC5)n3)cc2C1=O] | 2-[(2-methyl-3-oxo-2,3-dihydro-1H-isoindolin-5-yl)amino]-4-[(1,2,3,4-tetrahydroisoquinolin-5-yl)amino]pyrimidine-5-carboxamide | Calc'd 430, found 430 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-65 | 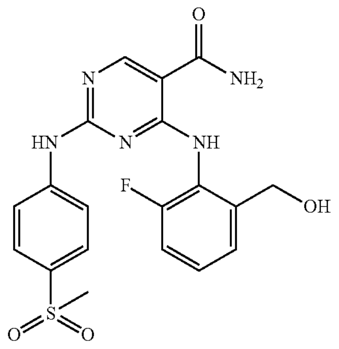 [SMILES: CS(=O)(=O)c1ccc(Nc2ncc(C(N)=O)c(Nc3c(F)cccc3CO)n2)cc1] | 4-{[2-fluoro-6-(hydroxymethyl)phenyl]amino}-2-{[4-(methylsulfonyl)phenyl]amino}pyrimidine-5-carboxamide | Calc'd 432, found 432 (Prep 2a) |
| 7-66 | 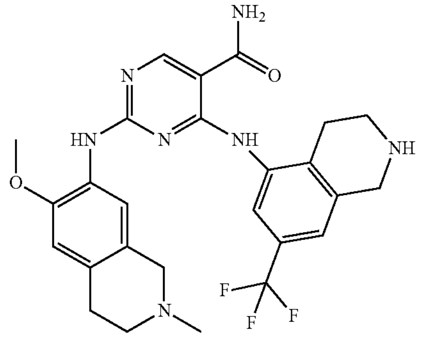 [SMILES: COc1cc2c(cc1Nc1ncc(C(N)=O)c(Nc3cc(C(F)(F)F)cc4c3CCNC4)n1)CN(C)CC2] | 2-[(6-methoxy-2-methyl-1,2,3,4-tetrahydroisoquinolin-7-yl)amino]-4-{[7-(trifluoromethyl)-1,2,3,4-tetrahydroisoquinolin-5-yl]amino}pyrimidine-5-carboxamide | Calc'd 528, found 528 (Prep 2a) |
| 7-67 | 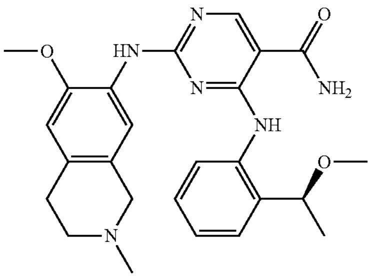 | 4-({2-[(1S)-1-methoxyethyl]phenyl}amino)-2-[(6-methoxy-2-methyl-1,2,3,4-tetrahydroisoquinolin-7-yl)amino]pyrimidine-5-carboxamide | Calc'd 463, found 463 (Prep 2c) |
| 7-68 | 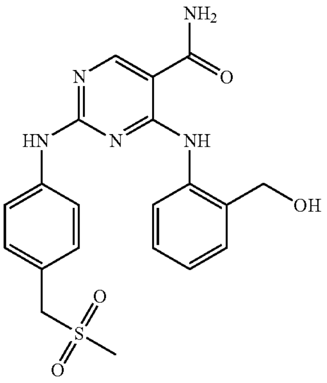 [SMILES: CS(=O)(=O)Cc1ccc(Nc2ncc(C(N)=O)c(Nc3ccccc3CO)n2)cc1] | 4-{[2-(hydroxymethyl)phenyl]amino}-2-({4-[(methylsulfonyl)methyl]phenyl}amino)pyrimidine-5-carboxamide | Calc'd 428, found 428 (Prep 2a) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-69 | 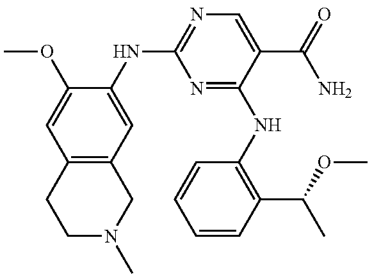 | 4-({2-[(1R)-1-methoxyethyl]phenyl}amino)-2-[(6-methoxy-2-methyl-1,2,3,4-tetrahydroisoquinolin-7-yl)amino]pyrimidine-5-carboxamide | Calc'd 463, found 463 (Prep 2c) |
| 7-70 | 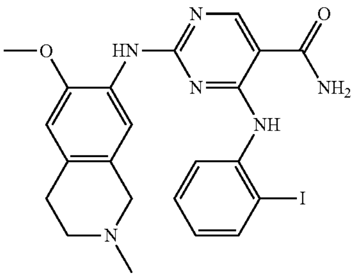 [SMILES: COc1cc2c(cc1Nc1ncc(C(N)=O)c(Nc3ccccc3I)n1)CN(C)CC2] | 4-[(2-iodophenyl)amino]-2-[(6-methoxy-2-methyl-1,2,3,4-tetrahydroisoquinolin-7-yl)amino]pyrimidine-5-carboxamide | Calc'd 531, found 531 (Prep 2c) |
| 7-71 | 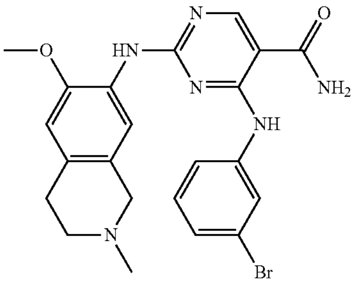 [SMILES: COc1cc2c(cc1Nc1ncc(C(N)=O)c(Nc3cccc(Br)c3)n1)CN(C)CC2] | 4-[(3-bromophenyl)amino]-2-[(6-methoxy-2-methyl-1,2,3,4-tetrahydroisoquinolin-7-yl)amino]pyrimidine-5-carboxamide | Calc'd 483, found 483 (Prep 2c) |
| 7-72 | 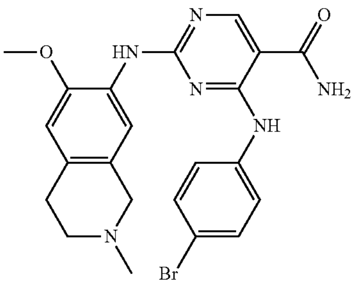 [SMILES: COc1cc2c(cc1Nc1ncc(C(N)=O)c(Nc3ccc(Br)cc3)n1)CN(C)CC2] | 4-[(4-bromophenyl)amino]-2-[(6-methoxy-2-methyl-1,2,3,4-tetrahydroisoquinolin-7-yl)amino]pyrimidine-5-carboxamide | Calc'd 483, found 483 (Prep 2c) |
| 7-73 | 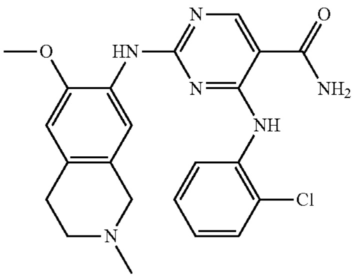 [SMILES: COc1cc2c(cc1Nc1ncc(C(N)=O)c(Nc3ccccc3Cl)n1)CN(C)CC2] | 4-[(2-chlorophenyl)amino]-2-[(6-methoxy-2-methyl-1,2,3,4-tetrahydroisoquinolin-7-yl)amino]pyrimidine-5-carboxamide | Calc'd 439, found 439 (Prep 2c) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-74 | 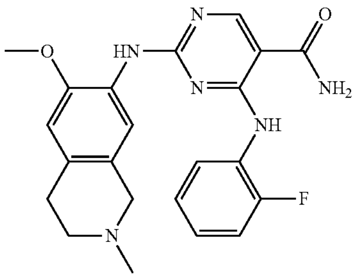 | 4-[(2-fluorophenyl)amino]-2-[(6-methoxy-2-methyl-1,2,3,4-tetrahydroisoquinolin-7-yl)amino]pyrimidine-5-carboxamide | Calc'd 423, found 423 (Prep 2c) |
| 7-75 | 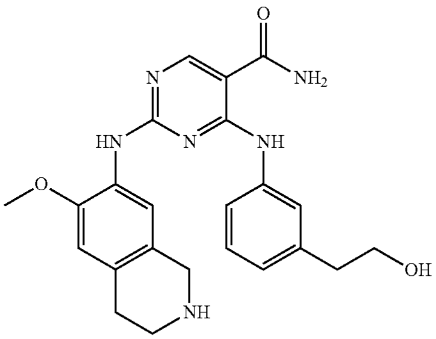 [SMILES: COc1cc2c(cc1Nc1ncc(C(N)=O)c(Nc3cccc(CCO)c3)n1)CNCC2] | 4-{[3-(2-hydroxyethyl)phenyl]amino}-2-[(6-methoxy-1,2,3,4-tetrahydroisoquinolin-7-yl)amino]pyrimidine-5-carboxamide | Calc'd 435, found 435 (Prep 2c) |
| 7-76 | 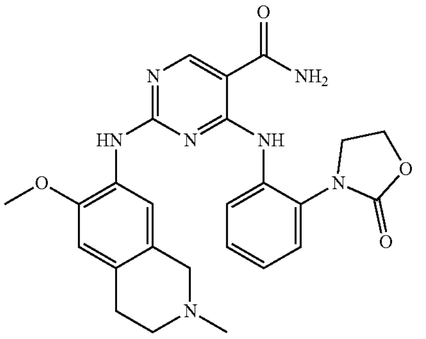 [SMILES: COc1cc2c(cc1Nc1ncc(C(N)=O)c(Nc3ccccc3N3CCOC3=O)n1)CN(C)CC2] | 2-((6-methoxy-2-methyl-1,2,3,4-tetrahydroisoquinolin-7-yl)amino)-4-((2-(2-oxooxazolidin-3-yl)phenyl)amino)pyrimidine-5-carboxamide | Calc'd 490, found 490 (Prep 2b) |
| 7-77 | 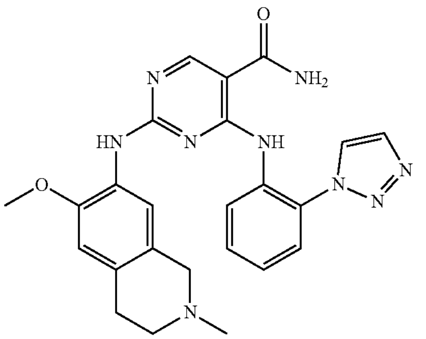 [SMILES: COc1cc2c(cc1Nc1ncc(C(N)=O)c(Nc3ccccc3-n3ccnn3)n1)CN(C)CC2] | 2-[(6-methoxy-2-methyl-1,2,3,4-tetrahydroisoquinolin-7-yl)amino]-4-{[2-(1H-1,2,3-triazol-1-yl)phenyl]amino}pyrimidine-5-carboxamide | Calc'd 472, found 472 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-78 | 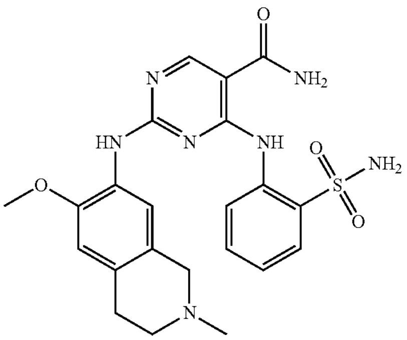 [SMILES: COc1cc2c(cc1Nc1ncc(C(N)=O)c(Nc3ccccc3S(N)(=O)=O)n1)CN(C)CC2] | 2-[(6-methoxy-2-methyl-1,2,3,4-tetrahydroisoquinolin-7-yl)amino]-4-[(2-sulfamoylphenyl)amino]pyrimidine-5-carboxamide | Calc'd 484, found 484 (Prep 2b) |
| 7-79 | 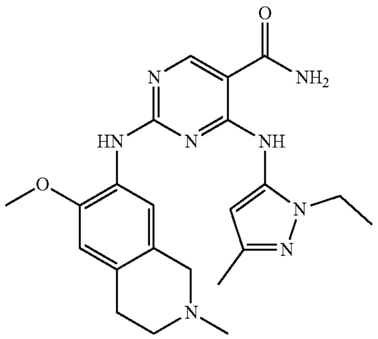 [SMILES: CCn1nc(C)cc1Nc1nc(Nc2cc3c(cc2OC)CCN(C)C3)ncc1C(N)=O] | 4-((1-ethyl-3-methyl-1H-pyrazol-5-yl)amino)-2-((6-methoxy-2-methyl-1,2,3,4-tetrahydroisoquinolin-7-yl)amino)pyrimidine-5-carboxamide | Calc'd 437, found 437 (Prep 2b) |
| 7-80 | 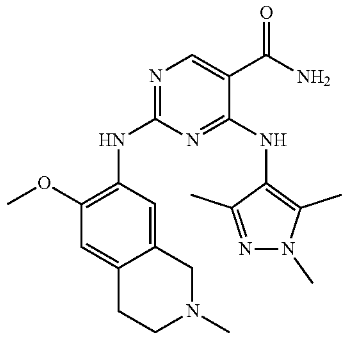 | 2-((6-methoxy-2-methyl-1,2,3,4-tetrahydroisoquinolin-7-yl)amino)-4-((1,3,5-trimethyl-1H-pyrazol-4-yl)amino)pyrimidine-5-carboxamide | Calc'd 437, found 437 (Prep 2b) |
| 7-81 | 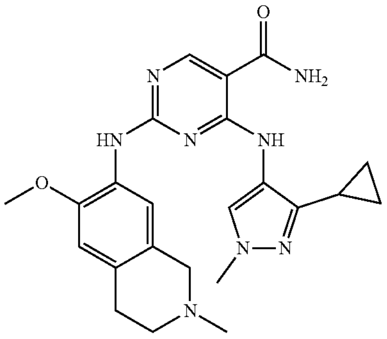 [SMILES: COc1cc2c(cc1Nc1ncc(C(N)=O)c(Nc3cn(C)nc3C3CC3)n1)CN(C)CC2] | 4-((3-cyclopropyl-1-methyl-1H-pyrazol-4-yl)amino)-2-((6-methoxy-2-methyl-1,2,3,4-tetrahydroisoquinolin-7-yl)amino)pyrimidine-5-carboxamide | Calc'd 449, found 449 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-82 | 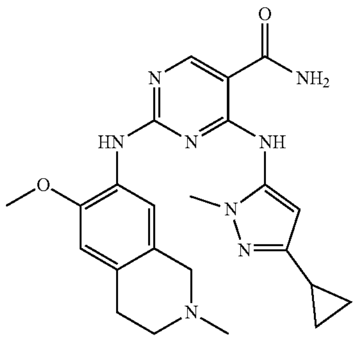 [SMILES: COc1cc2c(cc1Nc1ncc(C(N)=O)c(Nc3cc(C4CC4)nn3C)n1)CN(C)CC2] | 4-((3-cyclopropyl-1-methyl-1H-pyrazol-5-yl)amino)-2-((6-methoxy-2-methyl-1,2,3,4-tetrahydroisoquinolin-7-yl)amino)pyrimidine-5-carboxamide | Calc'd 449, found 449 (Prep 2b) |
| 7-83 | 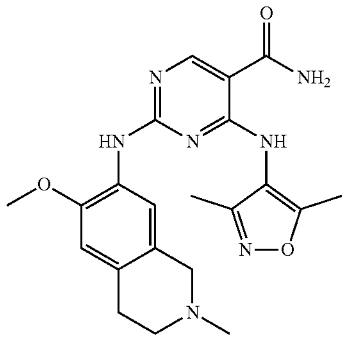 | 4-((3,5-dimethylisoxazol-4-yl)amino)-2-((6-methoxy-2-methyl-1,2,3,4-tetrahydroisoquinolin-7-yl)amino)pyrimidine-5-carboxamide | Calc'd 424, found 424 (Prep 2b) |
| 7-84 | 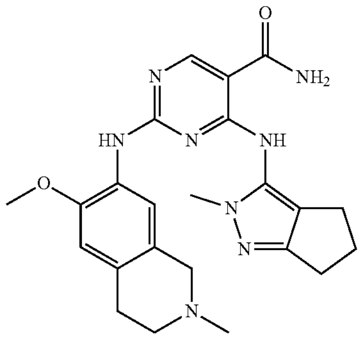 [SMILES: COc1cc2c(cc1Nc1ncc(C(N)=O)c(Nc3c4c(nn3C)CCC4)n1)CN(C)CC2] | 2-((6-methoxy-2-methyl-1,2,3,4-tetrahydroisoquinolin-7-yl)amino)-4-((2-methyl-2,4,5,6-tetrahydrocyclopenta[c]pyrazol-3-yl)amino)pyrimidine-5-carboxamide | Calc'd 449, found 449 (Prep 2b) |
| 7-85 | 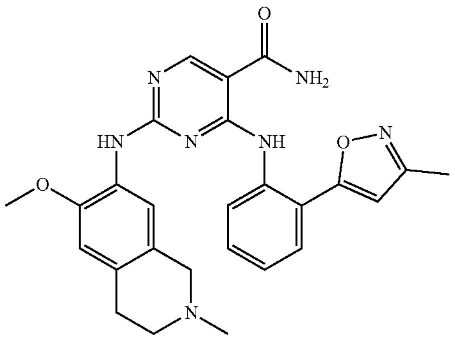 | 2-((6-methoxy-2-methyl-1,2,3,4-tetrahydroisoquinolin-7-yl)amino)-4-((2-(3-methylisoxazol-5-yl)phenyl)amino)pyrimidine-5-carboxamide | Calc'd 486, found 486 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-86 | 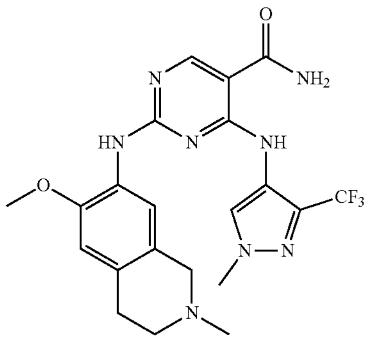 [SMILES: COc1cc2c(cc1Nc1ncc(C(N)=O)c(Nc3cn(C)nc3C(F)(F)F)n1)CN(C)CC2] | 2-((6-methoxy-2-methyl-1,2,3,4-tetrahydroisoquinolin-7-yl)amino)-4-((1-methyl-3-(trifluoromethyl)-1H-pyrazol-4-yl)amino)pyrimidine-5-carboxamide | Calc'd 477, found 477 (Prep 2b) |
| 7-87 | 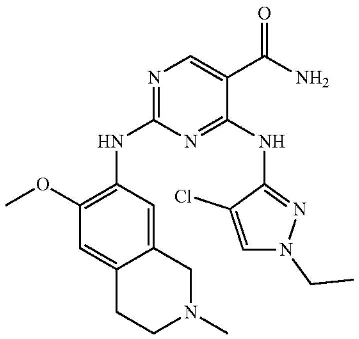 [SMILES: CCn1cc(Cl)c(Nc2nc(Nc3cc4c(cc3OC)CCN(C)C4)ncc2C(N)=O)n1] | 4-((4-chloro-1-ethyl-1H-pyrazol-3-yl)amino)-2-((6-methoxy-2-methyl-1,2,3,4-tetrahydroisoquinolin-7-yl)amino)pyrimidine-5-carboxamide | Calc'd 457, found 457 (Prep 2b) |
| 7-88 | 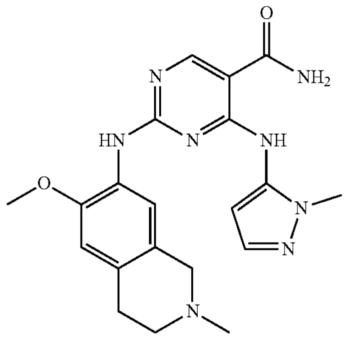 | 2-((6-methoxy-2-methyl-1,2,3,4-tetrahydroisoquinolin-7-yl)amino)-4-((1-methyl-1H-pyrazol-5-yl)amino)pyrimidine-5-carboxamide | Calc'd 409, found 409 (Prep 2b) |
| 7-89 | 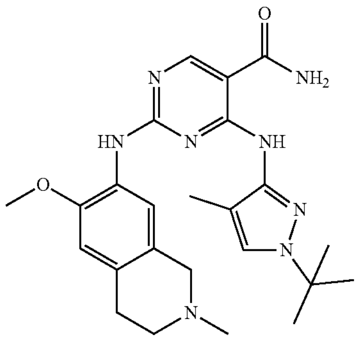 [SMILES: COc1cc2c(cc1Nc1ncc(C(N)=O)c(Nc3nn(C(C)(C)C)cc3C)n1)CN(C)CC2] | 4-((3-(tert-butyl)-1-methyl-1H-pyrazol-5-yl)amino)-2-((6-methoxy-2-methyl-1,2,3,4-tetrahydroisoquinolin-7-yl)amino)pyrimidine-5-carboxamide | Calc'd 465, found 465 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-90 | 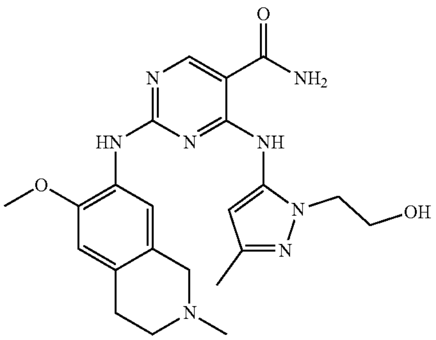 [SMILES: COc1cc2c(cc1Nc1ncc(C(N)=O)c(Nc3cc(C)nn3CCO)n1)CN(C)CC2] | 4-((1-(2-hydroxyethyl)-3-methyl-1H-pyrazol-5-yl)amino)-2-((6-methoxy-2-methyl-1,2,3,4-tetrahydroisoquinolin-7-yl)amino)pyrimidine-5-carboxamide | Calc'd 453, found 453 (Prep 2b) |
| 7-91 | 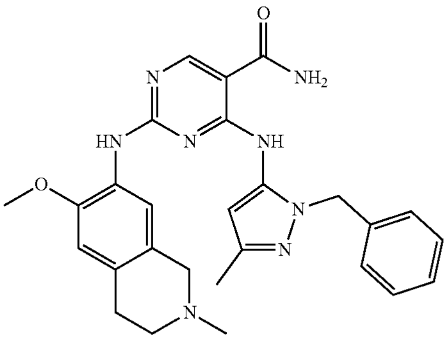 [SMILES: COc1cc2c(cc1Nc1ncc(C(N)=O)c(Nc3cc(C)nn3Cc3ccccc3)n1)CN(C)CC2] | 4-((1-benzyl-3-methyl-1H-pyrazol-5-yl)amino)-2-((6-methoxy-2-methyl-1,2,3,4-tetrahydroisoquinolin-7-yl)amino)pyrimidine-5-carboxamide | Calc'd 499, found 499 (Prep 2b) |
| 7-92 | 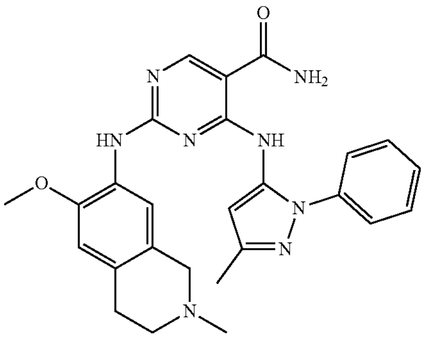 [SMILES: COc1cc2c(cc1Nc1ncc(C(N)=O)c(Nc3cc(C)nn3-c3ccccc3)n1)CN(C)CC2] | 2-((6-methoxy-2-methyl-1,2,3,4-tetrahydroisoquinolin-7-yl)amino)-4-((3-methyl-1-phenyl-1H-pyrazol-5-yl)amino)pyrimidine-5-carboxamide | Calc'd 485, found 485 (Prep 2b) |
| 7-93 | 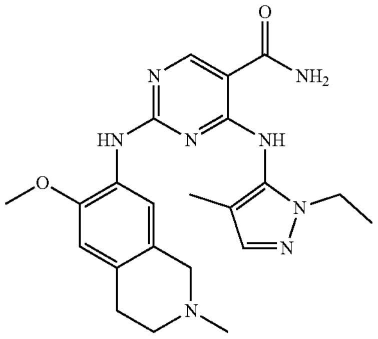 [SMILES: CCn1ncc(C)c1Nc1nc(Nc2cc3c(cc2OC)CCN(C)C3)ncc1C(N)=O] | 4-((1-ethyl-4-methyl-1H-pyrazol-5-yl)amino)-2-((6-methoxy-2-methyl-1,2,3,4-tetrahydroisoquinolin-7-yl)amino)pyrimidine-5-carboxamide | Calc'd 437, found 437 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-94 | 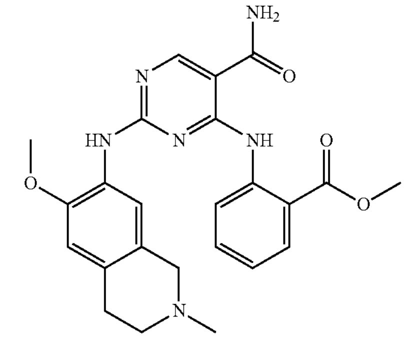 [SMILES: COC(=O)c1ccccc1Nc1nc(Nc2cc3c(cc2OC)CCN(C)C3)ncc1C(N)=O] | methyl 2-({5-carbamoyl-2-[(6-methoxy-2-methyl-1,2,3,4-tetrahydroisoquinolin-7-yl)amino]pyrimidin-4-yl}amino)benzoate | Calc'd 463, found 463 (Prep 2b) |
| 7-95 | 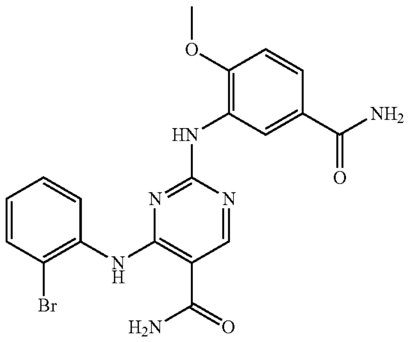 [SMILES: COc1ccc(C(N)=O)cc1Nc1ncc(C(N)=O)c(Nc2ccccc2Br)n1] | 4-[(2-bromophenyl)amino]-2-[(5-carbamoyl-2-methoxyphenyl)amino]pyrimidine-5-carboxamide | Calc'd 457, found 457 (Prep 2b) |
| 7-96 | 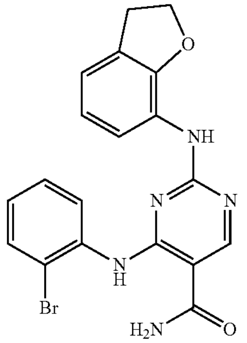 [SMILES: NC(=O)c1cnc(Nc2cccc3c2OCC3)nc1Nc1ccccc1Br] | 4-[(2-bromophenyl)amino]-2-[(2,3-dihydro-1-benzofuran-7-yl)amino]pyrimidine-5-carboxamide | Calc'd 426, found 426 (Prep 2b) |
| 7-97 | 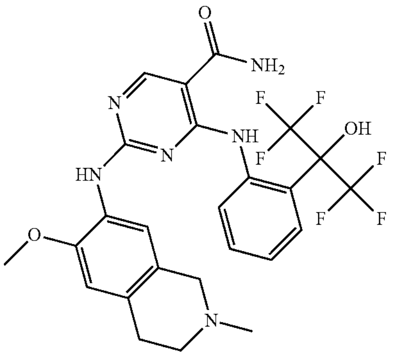 [SMILES: COc1cc2c(cc1Nc1ncc(C(N)=O)c(Nc3ccccc3C(O)(C(F)(F)F)C(F)(F)F)n1)CN(C)CC2] | 4-{[2-(1,1,1,3,3,3-hexafluoro-2-hydroxypropan-2-yl)phenyl]amino}-2-[(6-methoxy-2-methyl-1,2,3,4-tetrahydroisoquinolin-7-yl)amino]pyrimidine-5-carboxamide | Calc'd 471, found 571 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-98 | 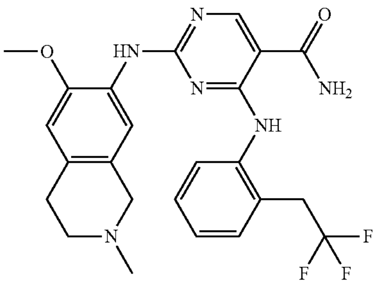 [SMILES: COc1cc2c(cc1Nc1ncc(C(N)=O)c(Nc3ccccc3CC(F)(F)F)n1)CN(C)CC2] | 2-[(6-methoxy-2-methyl-1,2,3,4-tetrahydroisoquinolin-7-yl)amino]-4-{[2-(2,2,2-trifluoroethyl)phenyl]amino}pyrimidine-5-carboxamide | Calc'd 487, found 487 (Prep 2c) |
| 7-99 | 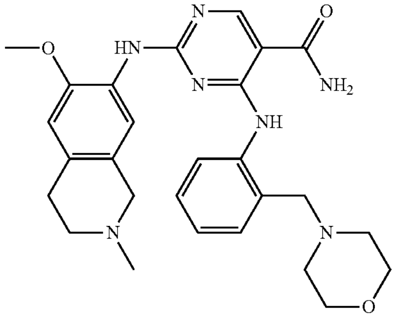 [SMILES: COc1cc2c(cc1Nc1ncc(C(N)=O)c(Nc3ccccc3CN3CCOCC3)n1)CN(C)CC2] | 2-[(6-methoxy-2-methyl-1,2,3,4-tetrahydroisoquinolin-7-yl)amino]-4-({2-[(morpholin-4-yl)methyl]phenyl}amino)pyrimidine-5-carboxamide | Calc'd 504, found 504 (Prep 2c) |
| 7-100 | 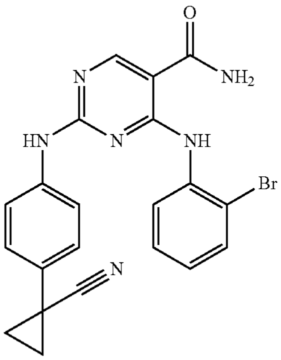 [SMILES: N#CC1(c2ccc(Nc3ncc(C(N)=O)c(Nc4ccccc4Br)n3)cc2)CC1] | 4-[(2-bromophenyl)amino]-2-{[4-(1-cyanocyclopropyl)phenyl]amino}pyrimidine-5-carboxamide | Calc'd 449, found 449 (Prep 2c) |
| 7-101 | 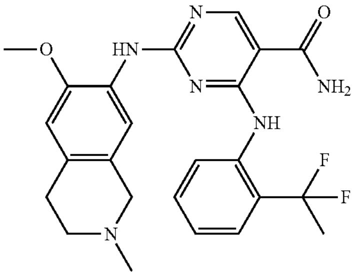 [SMILES: COc1cc2c(cc1Nc1ncc(C(N)=O)c(Nc3ccccc3C(C)(F)F)n1)CN(C)CC2] | 4-{[2-(1,1-difluoroethyl)phenyl]amino}-2-[(6-methoxy-2-methyl-1,2,3,4-tetrahydroisoquinolin-7-yl)amino]pyrimidine-5-carboxamide | Calc'd 469, found 469 (Prep 2c) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-102 | 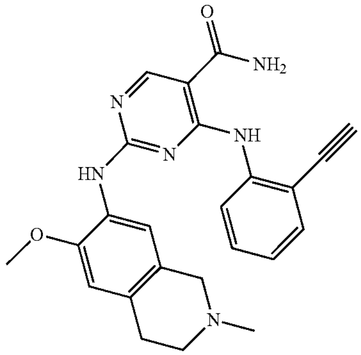 [SMILES: C#Cc1ccccc1Nc1nc(Nc2cc3c(cc2OC)CCN(C)C3)ncc1C(N)=O] | 4-[(2-ethynylphenyl)amino]-2-[(6-methoxy-2-methyl-1,2,3,4-tetrahydroisoquinolin-7-yl)amino]pyrimidine-5-carboxamide | Calc'd 429, found 429 (Prep 2b) |
| 7-103 | 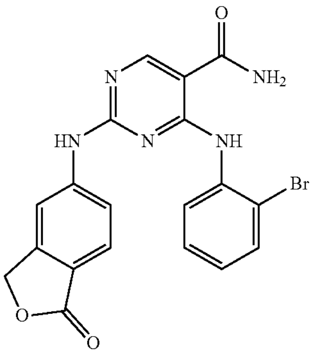 [SMILES: NC(=O)c1cnc(Nc2ccc3c(c2)COC3=O)nc1Nc1ccccc1Br] | 4-[(2-bromopehnyl)amino]-2-[(1-oxo-1,3-dihydro-2-benzofuran-5-yl)amino]pyrimidine-5-carboxamide | Calc'd 440, found 440 (Prep 2c) |
| 7-104 | 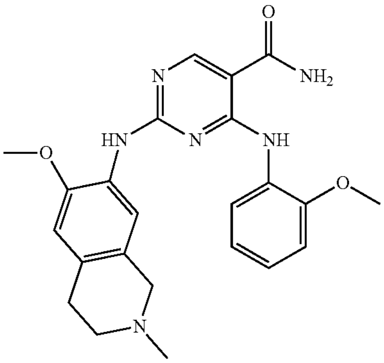 | 2-[(6-methoxy-2-methyl-1,2,3,4-tetrahydroisoquinolin-7-yl)amino]-4-[(2-methoxyphenyl)amino]pyrimidine-5-carboxamide | Calc'd 435, found 435 (Prep 2c) |
| 7-105 | 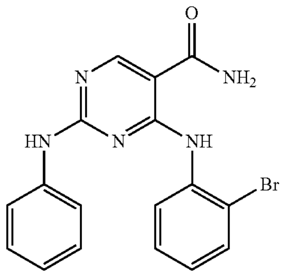 [SMILES: NC(=O)c1cnc(Nc2ccccc2)nc1Nc1ccccc1Br] | 4-[(2-bromophenyl)amino]-2-(phenylamino)pyrimidine-5-carboxamide | Calc'd 384, found 384 (Prep 2c) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-106 | 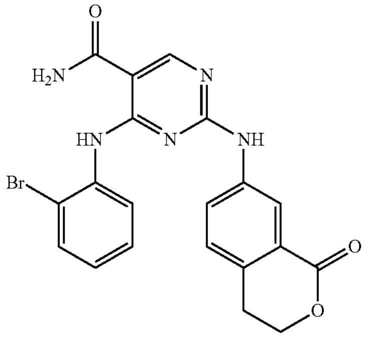 [SMILES: NC(=O)c1cnc(Nc2ccc3c(c2)C(=O)OCC3)nc1Nc1ccccc1Br] | 4-[(2-bromophenyl)amino]-2-[(1-oxo-3,4-dihydro-1H-2-benzopyran-7-yl)amino]pyrimidine-5-carboxamide | Calc'd 454, found 454 (Prep 2b) |
| 7-107 | 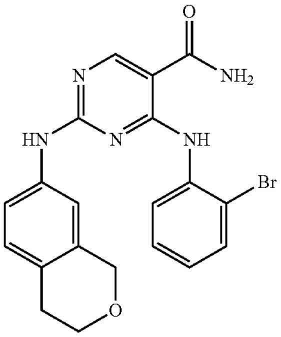 [SMILES: NC(=O)c1cnc(Nc2ccc3c(c2)COCC3)nc1Nc1ccccc1Br] | 4-[(2-bromophenyl)amino]-2-[(3,4-dihydro-1H-2-benzopyran-7-yl)amino]pyrimidine-5-carboxamide | Calc'd 440, found 440 (Prep 2b) |
| 7-108 | 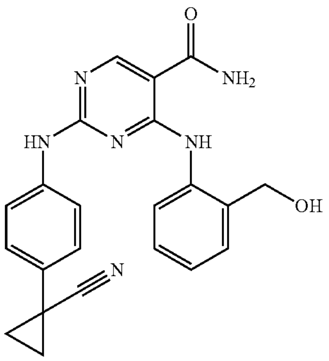 [SMILES: N#CC1(c2ccc(Nc3ncc(C(N)=O)c(Nc4ccccc4CO)n3)cc2)CC1] | 2-{[4-(1-cyanocyclopropyl)phenyl]amino}-4-{[2-(hydroxymethyl)phenyl]amino}pyrimidine-5-carboxamide | Calc'd 401, found 401 (Prep 2c) |
| 7-109 | 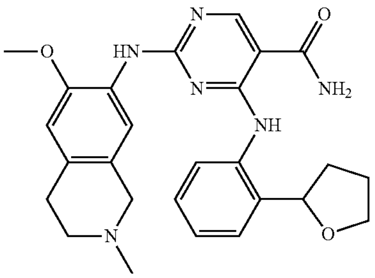 [SMILES: COc1cc2c(cc1Nc1ncc(C(N)=O)c(Nc3ccccc3C3CCCO3)n1)CN(C)CC2] | 2-((6-methoxy-2-methyl-1,2,3,4-tetrahydroisoquinolin-7-yl)amino)-4-((2-(tetrahydrofuran-2-yl)phenyl)amino)pyrimidine-5-carboxamide | Calc'd 475, found 475 (Prep 2c) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-110 | 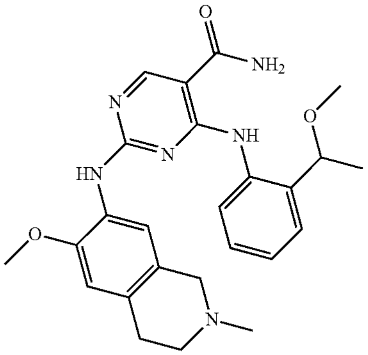 [SMILES: COc1cc2c(cc1Nc1ncc(C(N)=O)c(Nc3ccccc3C(C)OC)n1)CN(C)CC2] | 4-{[2-(1-methoxyethyl)phenyl]amino}-2-[(6-methoxy-2-methyl-1,2,3,4-tetrahydroisoquinolin-7-yl)amino]pyrimidine-5-carboxamide | Calc'd 463 found 463 (Prep 2b) |
| 7-111 | 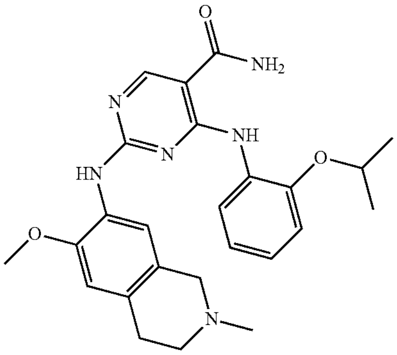 [SMILES: COc1cc2c(cc1Nc1ncc(C(N)=O)c(Nc3ccccc3OC(C)C)n1)CN(C)CC2] | 2-[(6-methoxy-2-methyl-1,2,3,4-tetrahydroisoquinolin-7-yl)amino]-4-({2-[(propan-2-yl)oxy]phenyl}amino)pyrimidine-5-carboxamide | Calc'd 463, found 463 (Prep 2b) |
| 7-112 | 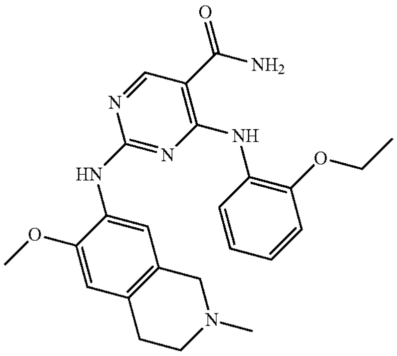 [SMILES: CCOc1ccccc1Nc1nc(Nc2cc3c(cc2OC)CCN(C)C3)ncc1C(N)=O] | 4-[(2-ethoxyphenyl)amino]-2-[(6-methoxy-2-methyl-1,2,3,4-tetrahydroisoquinolin-7-yl)amino]pyrimidine-5-carboxamide | Calc'd 449, found 449 (Prep 2b) |
| 7-113 | 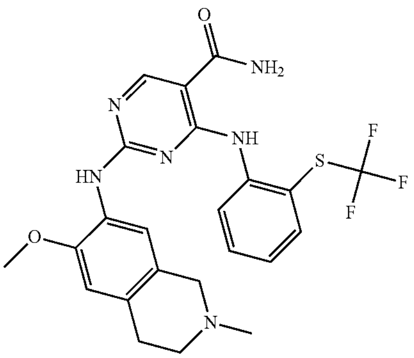 [SMILES: COc1cc2c(cc1Nc1ncc(C(N)=O)c(Nc3ccccc3SC(F)(F)F)n1)CN(C)CC2] | 2-[(6-methoxy-2-methyl-1,2,3,4-tetrahydroisoquinolin-7-yl)amino]-4-({2-[(trifluoromethyl)sulfanyl]phenyl}amino)pyrimidine-5-carobxamide | Calc'd 505, found 505 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass $[M + H]^+$ & Prep |
|---|---|---|---|
| 7-114 | 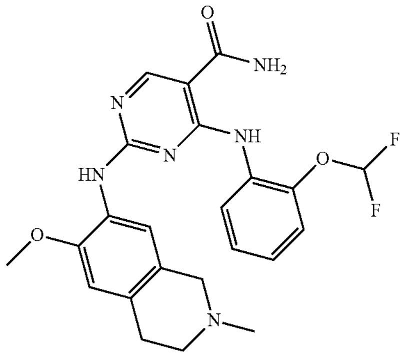 [SMILES: COc1cc2c(cc1Nc1ncc(C(N)=O)c(Nc3ccccc3OC(F)F)n1)CN(C)CC2] | 4-{[2-(difluoromethoxy)phenyl]amino}-2-[(6-methoxy-2-methyl-1,2,3,4-tetrahydroisoquinolin-7-yl)amino]pyrimidine-5-carboxamide | Calc'd 471, found 471 (Prep 2b) |
| 7-115 | 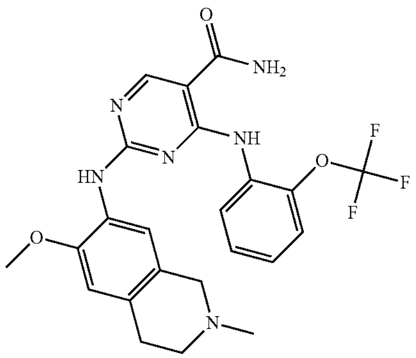 [SMILES: COc1cc2c(cc1Nc1ncc(C(N)=O)c(Nc3ccccc3OC(F)(F)F)n1)CN(C)CC2] | 2-[(6-methoxy-2-methyl-1,2,3,4-tetrahydroisoquinolin-7-yl)amino]-4-{[2-(trifluoromethoxy)phenyl]amino}pyrimidine-5-carboxamide | Calc'd 489, found 489 (Prep 2b) |
| 7-116 | 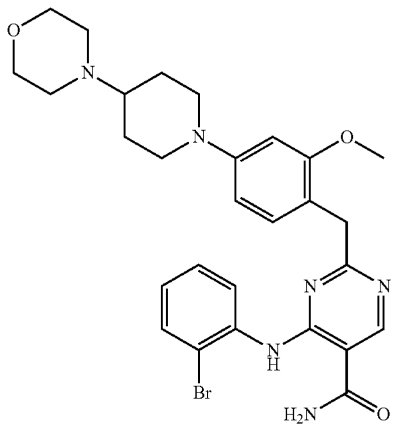 [SMILES: COc1cc(N2CCC(N3CCOCC3)CC2)ccc1Cc1ncc(C(N)=O)c(Nc2ccccc2Br)n1] | 4-[(2-bromophenyl)amino]-2-({2-methoxy-4-[4-(morpholin-4-yl)piperidin-1-yl]phenyl}amino)pyrimidine-5-carboxamide | Calc'd 582, found 582 (Prep 2b) |

TABLE 7-continued

Compounds listed in the table below were prepared using the synthetic methods described in the aforementioned Example 7-1, 7-2, or 7-3. The table provides the compound structure, the name, the calculated and observed masses, and Prep procedure details in the Prep Column.

| Example | Structure | Name | Exact Mass [M + H]+ & Prep |
|---|---|---|---|
| 7-117 | 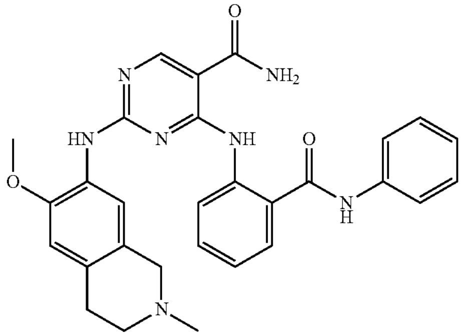 [SMILES: COc1cc2c(cc1Nc1ncc(C(N)=O)c(Nc3ccccc3C(=O)Nc3ccccc3)n1)CN(C)CC2] | 2-((6-methoxy-2-methyl-1,2,3,4-tetrahydroisoquinolin-7-yl)amino)-4-((2-(phenylcarbamoyl)phenyl)amino)pyrimidine-5-carboxamide | Calc'd 524, found 524 (Prep 2b) |
| 7-118 | 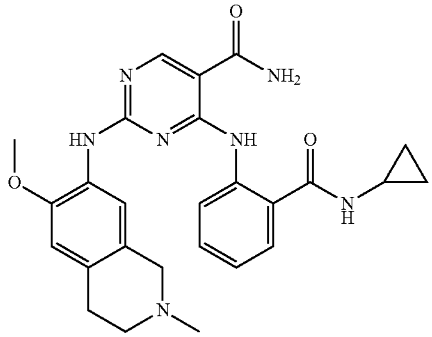 [SMILES: COc1cc2c(cc1Nc1ncc(C(N)=O)c(Nc3ccccc3C(=O)NC3CC3)n1)CN(C)CC2] | 4-((2-(cyclopropylcarbamoyl)phenyl)amino)-2-((6-methoxy-2-methyl-1,2,3,4-tetrahydroisoquinolin-7-yl)amino)pyrimidine-5-carboxamide | Calc'd 488, found 488 (Prep 2b) |

Example 8-1. 2-((2-Methoxy-4-(pyrrolidin-2-yl)phenyl)amino)-4-((2-(trifluoromethyl)phenyl)amino)pyrimidine-5-carboxamide

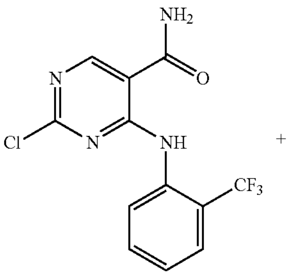

I-10

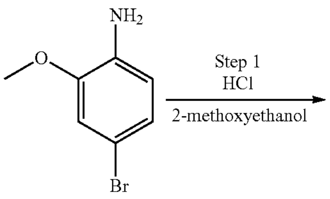

-continued

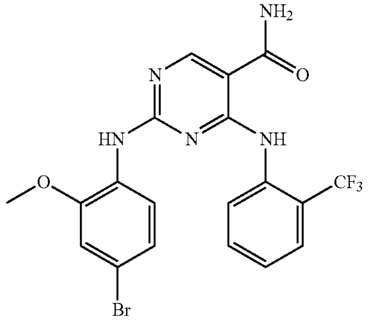

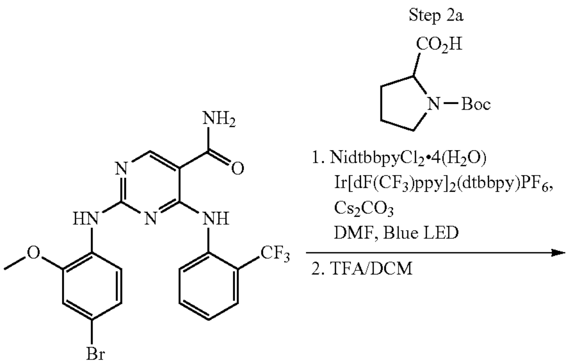

-continued

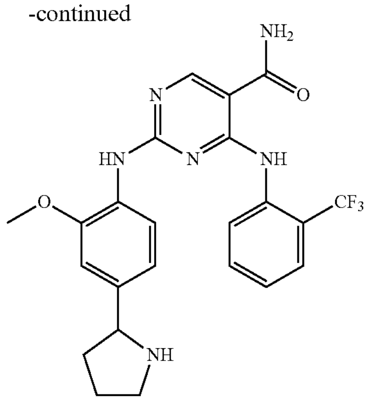

8-1

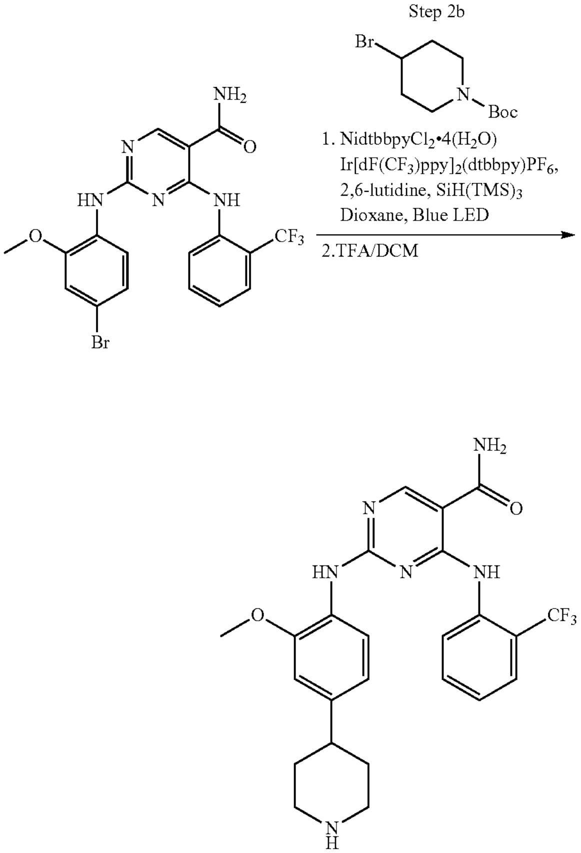

8-2

Step 1. 4-Bromo-2-methoxyaniline (228 mg, 1.13 mmol), 2-chloro-4-((2 (trifluoromethyl)-phenyl)amino)pyrimidine-5-carboxamide (325 mg, 1.03 mmol) were charged in a vial, 2-methoxyethanol (4.1 mL) was added followed by tosic acid (293 mg, 1.54 mmol). The reaction was heated to 110° C. overnight. The reaction was concentrated, diluted with EtOAc (20 mL), neutralized with saturated aqueous $NaHCO_3$ (10 mL), the layers were separated, and the organic layer was washed with brine (1×50 mL), dried over sodium sulfate, filtered and concentrated. The residue was purified by column chromatography on silica gel eluting with (3:1 EtOAc/EtOH)/Hexanes (0% to 100%). This provided 2-((4-bromo-2-methoxy phenyl)amino)-4-((2-(trifluoromethyl) phenyl)amino)pyrimidine-5-carboxamide. MS (ESI) m/z calc'd for $C_{19}H_{16}BrF_3N_5O_2$ [M+H]$^+$ 482, found 482.

Step 2a (Prep 2a in Table 8). 2-((2-Methoxy-4-(pyrrolidin-2-yl)phenyl)amino)-4-((2-(trifluoromethyl)phenyl) amino)pyrimidine-5-carboxamide (Example 8-1) 2-((4-Bromo-2-methoxyphenyl)amino)-4-((2-(trifluoromethyl) phenyl)amino)pyrimidine-5-carboxamide (24 mg, 0.05 mmol), (tert-butoxycarbonyl)proline (22 mg, 0.100 mmol), NidtbbpyCl$_2$·4(H$_2$O) (5 mg, 10 μmol), (Ir[dF(CF$_3$)ppy]$_2$ (dtbbpy))PF$_6$ (1 mg, 1 μmol) and cesium carbonate (41 mg, 0.13 mmol) were charged in 2 dram vial, the vial was evacuated and backfilled with argon (3×), DMF (1 mL) was added and the reaction was irradiated at 100% intensity with blue LEDs overnight. The reaction diluted with DCM (5 mL) and washed with brine (5 mL), the layers were separated using a phase separator with hydrophobic frit. The filtrate was concentrated and dissolved in DCM (1 mL). The solution was treated with TFA (1 mL) and stirred for 2 h at room temperature. The reaction was concentrated, diluted with DMSO (2 mL), filtered and purified via mass directed reverse-phase prep-HPLC (Purification Method A). This provided 2-((2-methoxy-4-(pyrrolidin-2-yl)phenyl)amino)-4-((2-(trifluoromethyl)phenyl)amino)pyrimidine-5-carboxamide MS (ESI) m/z calc'd for $C_{23}H_{24}F_3N_6O_2$ [M+H]$^+$ 473, found 473. $^1$H NMR (499 MHz, DMSO-d6) δ 11.79 (s, 1H), 9.33 (s, 1H), 8.74 (s, 1H), 8.59 (s, 1H), 8.48 (s, 1H), 8.12 (d, J=8.5 Hz, 2H), 7.83 (d, J=8.2 Hz, 1H), 7.75 (d, J=7.4 Hz, 1H), 7.66 (t, J=7.8 Hz, 1H), 7.51 (s, 1H), 7.37 (t, J=7.6 Hz, 1H), 7.21-7.14 (m, 2H), 7.10 (s, 1H), 6.99 (s, 1H), 6.89 (d, J=8.7 Hz, 1H), 4.52 (s, 1H), 2.36 (d, J=9.9 Hz, 3H), 2.13 (d, J=5.4 Hz, 2H), 2.10-1.98 (m, 3H).

Step 2b (Prep 2b in Table 8). 2-((2-Methoxy-4-(piperidin-4-yl)phenyl)amino)-4-((2-(trifluoromethyl)phenyl)amino)pyrimidine-5-carboxamide (Example 8-2)

2-((4-Bromo-2-methoxyphenyl)amino)-4-((2-(trifluoromethyl)phenyl)amino)pyrimidine-5-carboxamide (48 mg, 0.1 mmol), NidtbbpyCl$_2$·4(H$_2$O) (5 mg, 10 μmol), (Ir[dF (CF$_3$)ppy]$_2$(dtbbpy))PF$_6$ (2 mg, 2 μmol), tert-butyl 4-bromopiperidine-1-carboxylate (40 mg, 0.15 mmol), 2,6-lutidine (0.058 mL, 0.50 mmol) and tris(trimethylsilyl)silane (0.032 mL, 0.10 mmol) were charged in 2 dram vial, dioxane (0 mL) was added, and the reaction was degassed by bubbling a stream of nitrogen through for 5 minutes. The reaction was then irradiated at 100% intensity with blue LEDs. The reaction diluted with DCM (5 mL) and washed with brine (5 mL), the layers were separated using a phase separator with hydrophobic frit. The filtrate was concentrated and dissolved in DCM (1 mL). The solution was treated with TFA (1 mL) and stirred for 2 h at room temperature. The reaction was concentrated, diluted with DMSO (2 mL), filtered and purified via mass directed reverse-phase prep-HPLC (Purification Method A). This provided 2-((2-methoxy-4-(piperidin-4-yl)phenyl)amino)-4-((2-(trifluoromethyl)phenyl)amino)pyrimidine-5-carboxamide as a solid. MS (ESI) m/z calc'd for $C_{24}H_{26}F_3N_6O_2$ [M+H]$^+$ 487, found 487. $^1$H NMR (499 MHz, DMSO-d$_6$) δ 11.83 (s, 1H), 8.71 (s, 1H), 8.66-8.54 (m, 2H), 8.44-8.25 (m, 1H), 8.19-8.03 (m, 2H), 7.71 (d, J=7.6 Hz, 1H), 7.61 (d, J=8.0 Hz, 1H), 7.57 (t, J=7.6 Hz, 1H), 7.54-7.45 (m, 1H), 7.32 (t, J=7.6 Hz, 1H), 6.87 (s, 1H), 6.67 (d, J=7.9 Hz, 1H), 3.80 (s, 3H), 3.39 (d, J=12.2 Hz, 2H), 3.00 (dd, J=12.4 Hz, 2H), 2.82 (ddd, J=15.2, 10.4, 3.3 Hz, 1H), 1.94 (d, J=13.4 Hz, 2H), 1.85-1.73 (m, 2H).

TABLE 8

Compounds listed in the table below were prepared using the synthetic methods described in the aforementioned Example 8-1. The table provides the compound structure, the name, the calculated and observed masses, and Prep procedure details in the Prep Column.

| Example | Structure | Name | Exact Mass $[M + H]^+$ & Prep |
|---|---|---|---|
| 8-1 | 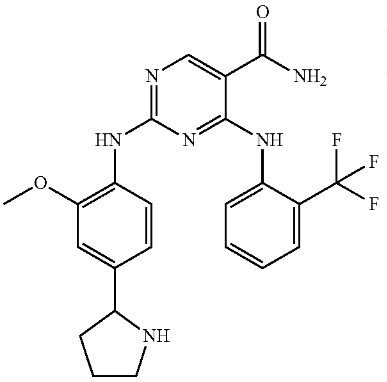 [SMILES: COc1cc(C2CCCN2)ccc1Nc1ncc(C(N)=O)c(Nc2ccccc2C(F)(F)F)n1] | 2-{[2-methoxy-4-(pyrrolidin-2-yl)phenyl]amino}-4-{[2-(trifluoromethyl)phenyl]amino} pyrimidine-5-carboxamide | Calc'd 473, found 473 (Prep 2a) |
| 8-2 | 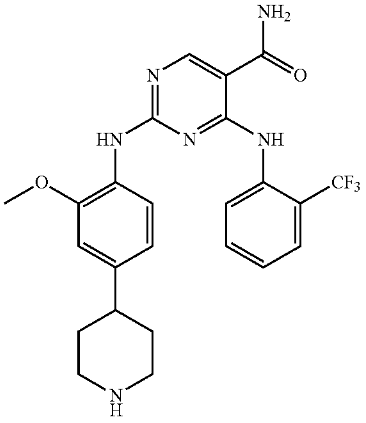 [SMILES: COc1cc(C2CCNCC2)ccc1Nc1ncc(C(N)=O)c(Nc2ccccc2C(F)(F)F)n1] | 2-((2-methoxy-4-(piperidin-4-yl)phenyl)amino)-4-((2-(trifluoro-methyl)phenyl)amino)pyrimi-dine-5-carboxamide | Calc'd 487, found 487 (Prep 2b) |
| 8-3 | 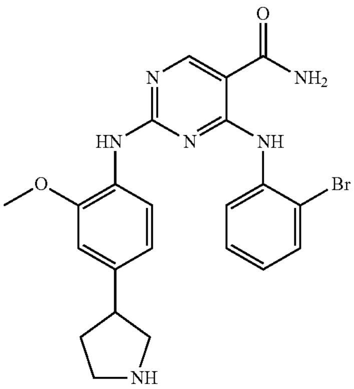 [SMILES: COc1cc(C2CCNC2)ccc1Nc1ncc(C(N)=O)c(Nc2ccccc2Br)n1] | 4-((2-bromophenyl)amino)-2-((2-methoxy-4-(pyrrolidin-3-yl)phenyl)amino)pyrimidine-5-carboxamide | Calc'd 483, found 483 (Prep 2b) |

TABLE 8-continued

| Compounds listed in the table below were prepared using the synthetic methods described in the aforementioned Example 8-1. The table provides the compound structure, the name, the calculated and observed masses, and Prep procedure details in the Prep Column. | | | |
|---|---|---|---|
| Example | Structure | Name | Exact Mass $[M + H]^+$ & Prep |
| 8-4 | 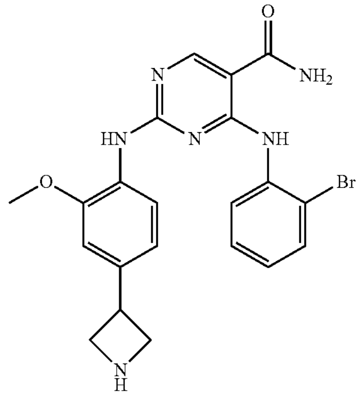 [SMILES: COc1cc(C2CNC2)ccc1Nc1ncc(C(N)=O)c(Nc2ccccc2Br)n1] | 2-((4-(azetidin-3-yl)-2-methoxyphenyl)amino)-4-((2-bromophenyl)amino)pyrimidine-5-carboxamide | Calc'd 469, found 469 (Prep 2b) |

Example 2-1 and 9-2. 4-(Bromphenyl)amino)-2(6-methoxy-2-(oxetan-3-yl)-1,2,3,4-tetrahydroisoquinolin-7-yl)amino)pyrimidine-5-carboxamide

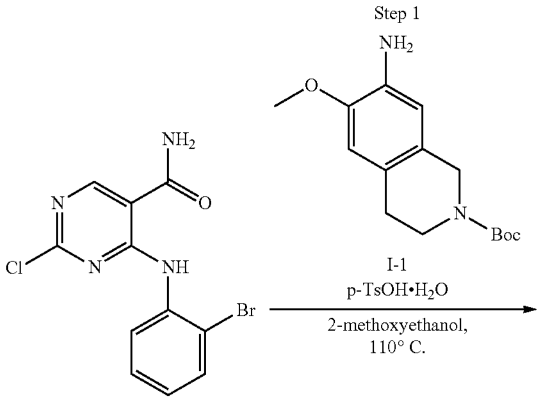

I-9

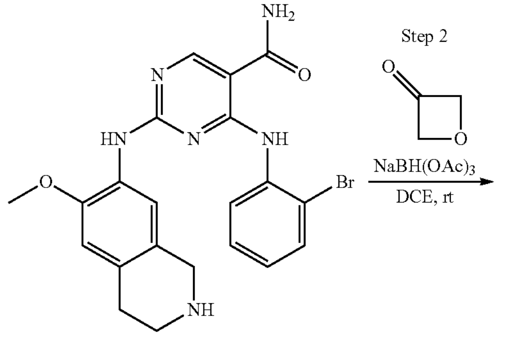

9-1

-continued

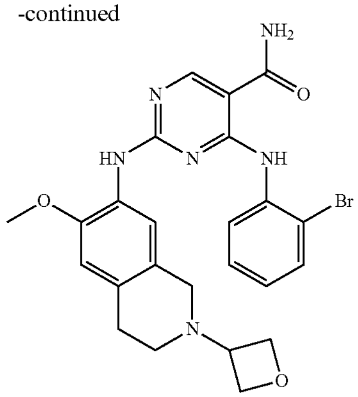

9-2

Step 1. Tosic acid (4.02 g, 21.2 mmol), 4-((2-bromophenyl)amino)-2-chloropyrimidine-5-carboxamide (1-9) (4.62 g, 14.1 mmol) and tert-butyl 7-amino-6-methoxy-3,4-dihydroisoquinoline-2(1H)-carboxylate (1-1) (4.32 g, 15.5 mmol) were charged in a 3-neck 500 mL round bottomed flask fitted with reflux condenser, stir bar and 2 septa. 2-methoxyethanol (80 mL) was added and the reaction was refluxed for 5 h. LCMS indicated complete conversion to the desired product. The reaction was cooled to room temperature and neutralized with 1M NaOH (litmus test) a precipitate was formed. Water (100 mL) was added to further precipitation and the reaction was stirred for 10 minutes. A solid precipitated and was collected and dried under a stream of nitrogen. This provided 4-((2-bromophenyl)amino)-2-((6-methoxy-1,2,3,4-tetrahydroisoquinolin-7-yl)amino)pyrimidine-5-carboxamide (9-1). MS (ESI) m/z calc'd for $C_{21}H_{22}BrN_6O_2[M+H]^+$ 469, found 469. $^1H$ NMR (600 MHz, DMSO-$d_6$) δ 11.70 (s, 1H), 9.11 (s, 2H), 8.72 (s, 1H), 8.43 (s, 1H), 8.23 (s, 1H), 8.07 (s, 1H), 7.68 (dd, J=8.0, 1.2 Hz, 1H), 7.57 (s, 1H), 7.46-7.38 (m, 1H), 7.35 (t, J=7.3 Hz, 1H), 7.06-7.01 (m, 1H), 6.91 (s, 1H), 3.98 (s, 2H), 3.80 (s, 3H), 3.37-3.26 (m, 2H), 2.96 (t, J=6.1 Hz, 2H).

Step 2. Sodium triacetoxy borohydride (148 mg, 0.7 mmol) was added to a solution of 4-((2-bromophenyl)amino)-2-((6-methoxy-1,2,3,4-tetrahydroisoquinolin-7-yl)amino)pyrimidine-5-carboxamide (47 mg, 0.1 mmol) and oxetan-3-one (16 mg, 14 μL, 0.22 mmol) in DCE (2 mL) at room temperature and the reaction was stirred overnight. The reaction was diluted with DCM (2 mL), quenched with $NaOH_{(aq)}$ (2 mL, 1 M) and stirred for 5 minutes. The organic layer was separated using a phase separator with a hydrophobic frit. The filtrate was concentrated, diluted with DMSO (2 mL), filtered and purified via mass directed reverse-phase prep-HPLC (Purification Method A). This provided 4-((2-bromophenyl)amino)-2-((6-methoxy-2-(oxetan-3-yl)-1,2,3,4-tetrahydroisoquinolin-7-yl)amino)pyrimidine-5-carboxamide (9-2). MS (ESI) m/z calc'd for $C_2H_{26}BrN_6O_3$ $[M+H]^+$ 525, found 525. $^1H$ NMR (500 MHz, DMSO-$d_6$) δ 11.64 (s, 1H), 8.69 (s, 1H), 8.31 (s, 1H), 8.16 (s, 1H), 8.03 (s, 1H), 7.66 (dd, J=8.0, 1.3 Hz, 1H), 7.45 (s, 1H), 7.43-7.35 (m, 1H), 7.27 (t, J=7.7 Hz, 1H), 7.07-7.01 (m, 1H), 6.79 (s, 1H), 4.63 (t, J=6.5 Hz, 2H), 4.51 (t, J=6.1 Hz, 2H), 3.77 (s, 3H), 3.55 (p, J=6.4 Hz, 1H), 3.39-3.23 (m, 4H), 2.79 (t, J=5.6 Hz, 2H)

TABLE 9

Compounds listed in the table below were prepared using the synthetic methods described in the aforementioned Example 9-1. The table provides the compound structure, the name, the calculated and observed masses.

| Example | Structure | Name | Exact Mass $[M + H]^+$ |
|---|---|---|---|
| 9-1 | 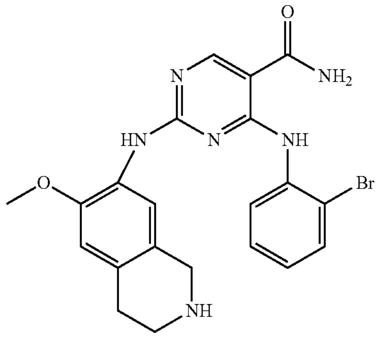 [SMILES: COc1cc2c(cc1Nc1ncc(C(N)=O)c(Nc3ccccc3Br)n1)CNCC2] | 4-[(2-bromophenyl)amino]-2-[(6-methoxy-1,2,3,4-tetrahydroisoquinolin-7-yl)amino]pyrimidine-5-carboxamide | Calc'd 469, found 469 |
| 9-2 | 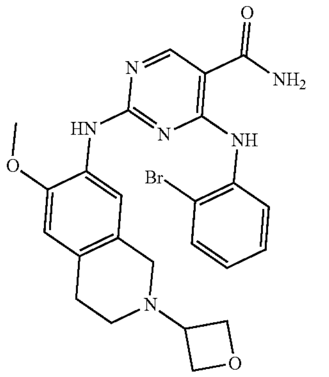 [SMILES: COc1cc2c(cc1Nc1ncc(C(N)=O)c(Nc3ccccc3Br)n1)CN(C1COC1)CC2] | 4-[(2-bromophenyl)amino]-2-{[6-methoxy-2-(oxetan-3-yl)-1,2,3,4-tetrahydroisoquinolin-7-yl]amino}pyrimidine-5-carboxamide | Calc'd 525, found 525 |
| 9-3 | 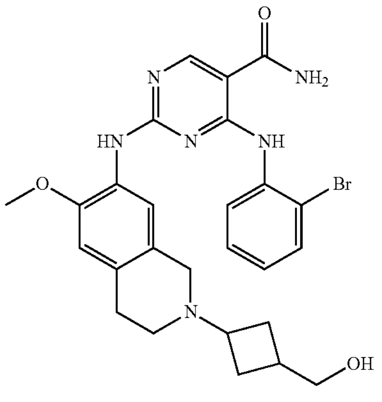 [SMILES: COc1cc2c(cc1Nc1ncc(C(N)=O)c(Nc3ccccc3Br)n1)CN(C1CC(CO)C1)CC2] | 4-((2-bromophenyl)amino)-2-((2-(3-(hydroxymethyl)cyclobutyl)-6-methoxy-1,2,3,4-tetrahydroisoquinolin-7-yl)amino)pyrimidine-5-carboxamide (peak 1) | Calc'd 553, found 553 |

TABLE 9-continued

Compounds listed in the table below were prepared using the synthetic methods described in the aforementioned Example 9-1. The table provides the compound structure, the name, the calculated and observed masses.

| Example | Structure | Name | Exact Mass [M + H]$^+$ |
|---|---|---|---|
| 9-4 | 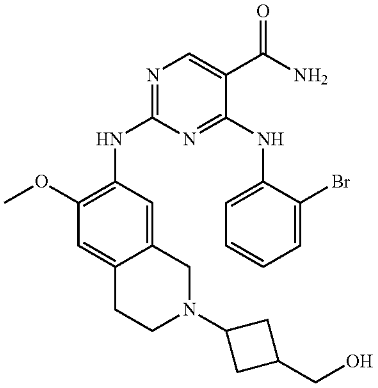 [SMILES: COc1cc2c(cc1Nc1ncc(C(N)=O)c(Nc3ccccc3Br)n1)CN(C1CC(CO)C1)CC2] | 4-((2-bromophenyl)amino)-2-((2-(3-(hydroxymethyl)cyclobutyl)-6-methoxy-1,2,3,4-tetrahydroisoquinolin-7-yl)amino)pyrimidine-5-carboxamide (peak 2) | Calc'd 553, found 553 |
| 9-5 | 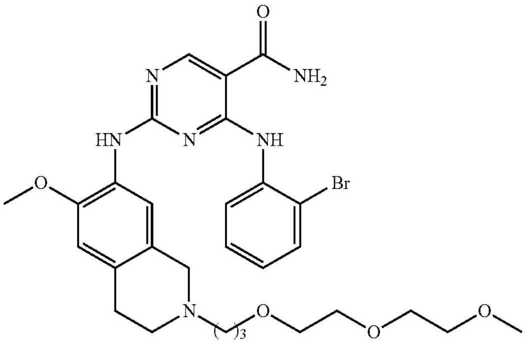 | 4-((2-bromophenyl)amino)-2-((6-methoxy-2-(3-(2-(2-methoxyethoxy)ethoxy)propyl)-1,2,3,4-tetrahydroisoquinolin-7-yl)amino)pyrimidine-5-carboxamide | Calc'd 629, found 629 |
| 9-6 | 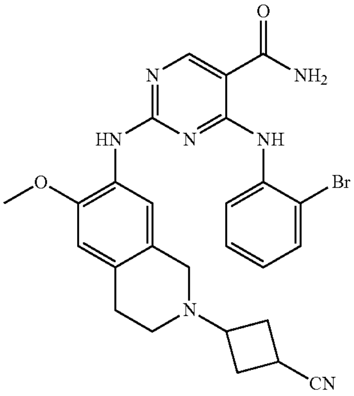 [SMILES: COc1cc2c(cc1Nc1ncc(C(N)=O)c(Nc3ccccc3Br)n1)CN(C1CC(C#N)C1)CC2] | 4-((2-bromophenyl)amino)-2-((2-(3-cyanocyclobutyl)-6-methoxy-1,2,3,4-tetrahydroisoquinolin-7-yl)amino)pyrimidine-5-carboxamide | Calc'd 548, found 548 |

TABLE 9-continued

Compounds listed in the table below were prepared using the synthetic methods described in the aforementioned Example 9-1. The table provides the compound structure, the name, the calculated and observed masses.

| Example | Structure | Name | Exact Mass $[M + H]^+$ |
| --- | --- | --- | --- |
| 9-7 | 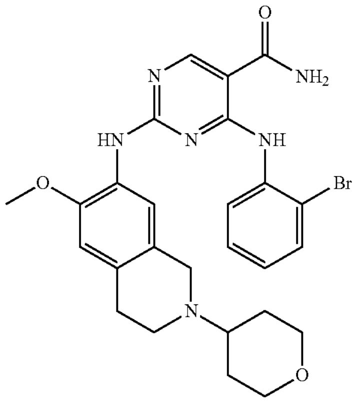 [SMILES: COc1cc2c(cc1Nc1ncc(C(N)=O)c(Nc3ccccc3Br)n1)CN(C1CCOCC1)CC2] | 4-[(2-bromophenyl)amino]-2-{[6-methoxy-2-(oxan-4-yl)-1,2,3,4-tetrahydroisoquinolin-7-yl]amino}pyrimidine-5-carboxamide | Calc'd 553, found 553 |
| 9-8 | 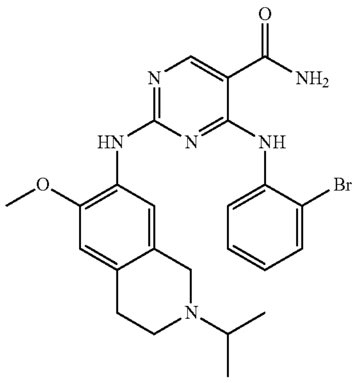 [SMILES: COc1cc2c(cc1Nc1ncc(C(N)=O)c(Nc3ccccc3Br)n1)CN(C(C)C)CC2] | 4-[(2-bromophenyl)amino]-2-{[6-methoxy-2-(propan-2-yl)-1,2,3,4-tetrahydroisoquinolin-7-yl]amino}pyrimidine-5-carboxamide | Calc'd 511, found 511 |
| 9-9 | 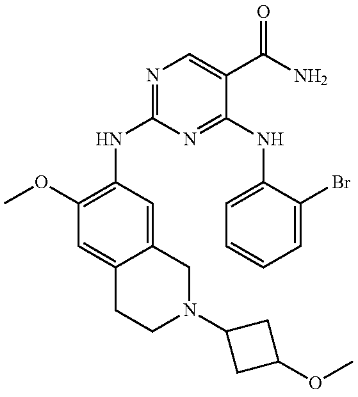 | 4-[(2-bromophenyl)amino]-2-{[6-methoxy-2-(3-methoxycyclobutyl)-1,2,3,4-tetrahydroisoquinolin-7-yl]amino}pyrimidine-5-carboxamide | Calc'd 553, found 553 |

TABLE 9-continued

Compounds listed in the table below were prepared using the synthetic methods described in the aforementioned Example 9-1. The table provides the compound structure, the name, the calculated and observed masses.

| Example | Structure | Name | Exact Mass [M + H]$^+$ |
|---|---|---|---|
| 9-10 | 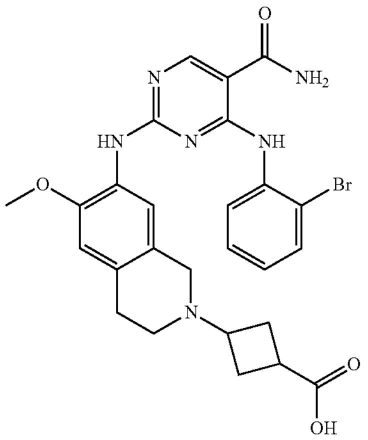 [SMILES: COc1cc2c(cc1Nc1ncc(C(N)=O)c(Nc3ccccc3Br)n1)CN(C1CC(C(=O)O)C1)CC2] | 3-[7-({4-[(2-bromophenyl)amino]-5-carbamoylpyrimidin-2-yl}amino)-6-methoxy-3,4-dihydroisoquinolin-2(1H)-yl]cyclobutane-1-carboxylic acid | Calc'd 567, found 567 |
| 9-11 | 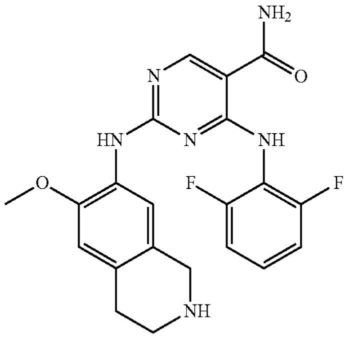 [SMILES: COc1cc2c(cc1Nc1ncc(C(N)=O)c(Nc3c(F)cccc3F)n1)CNCC2] | 4-(2,6-difluoroanilino)-2-[(6-methoxy-1,2,3,4-tetrahydroisoquinolin-7-yl)amino]pyrimidine-5-carboxamide | Calc'd 427, found 427 |
| 9-12 | 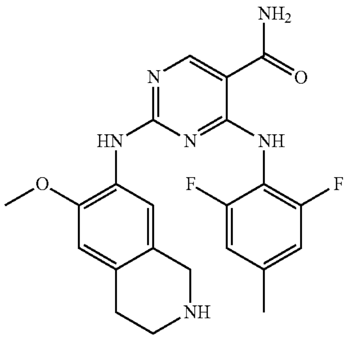 [SMILES: COc1cc2c(cc1Nc1ncc(C(N)=O)c(Nc3c(F)cc(C)cc3F)n1)CNCC2] | 4-(2,6-difluoro-4-iodoanilino)-2-[(6-methoxy-1,2,3,4-tetrahydroisoquinolin-7-yl)amino]pyrimidine-5-carboxamide | Calc'd 553, found 553 |

Example 3-1. 2-((2-Methoxy-4-(pyrrolidin-3-yl)phenyl)amino)-4-((2-(trifluoromethyl)phenyl)amino)pyrimidine-5-carboxamide

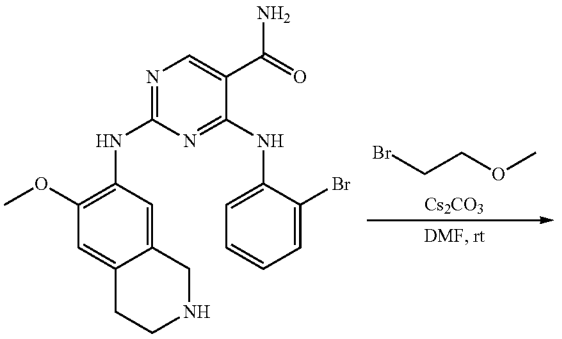

9-1

-continued

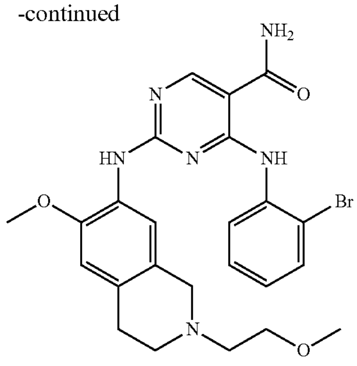

10-1

1-Bromo-2-methoxyethane (16.3 mg, 0.117 mmol) was added to a solution of 4-((2-bromophenyl)amino)-2-((6-methoxy-1,2,3,4-tetrahydroisoquinolin-7-yl)amino)pyrimidine-5-carboxamide (9-1) (50 mg, 0.11 mmol) and cesium carbonate (52 mg, 0.16 mmol) in DMF (1 mL) at room temperature. The reaction was stirred overnight filtered and purified via mass directed reverse-phase prep-HPLC (Purification Method A). This provided 4-((2-bromophenyl)amino)-2-((6-methoxy-2-(2-methoxyethyl)-1,2,3,4-tetrahydroisoquinolin-7-yl)amino)pyrimidine-5-carboxamide. MS (ESI) m/z calc'd for $C_{24}H_{28}BrN_6O_3$ $[M+H]^+$ 528, found 527. $^1H$ NMR (499 MHz, DMSO-d6) δ 11.79 (s, 1H), 10.09 (s, 1H), 8.73 (s, 2H), 8.26-8.01 (m, 2H), 7.70 (d, J=8.0 Hz, 1H), 7.59-7.46 (m, 2H), 7.36 (t, J=7.5 Hz, 1H), 7.09 (t, J=7.6 Hz, 1H), 6.96 (s, 1H), 4.26-4.08 (m, 2H), 3.81 (s, 3H), 3.74 (s, 3H), 3.50-3.35 (m, 5H), 3.21-3.08 (m, 2H), 3.06-2.97 (m, 1H).

TABLE 10

Compounds listed in the table below were prepared using the synthetic methods described in the aforementioned Example 10-1. The table provides the compound structure, the name, the calculated and observed masses.

| Example | Structure | Name | Exact Mass $[M + H]^+$ |
|---|---|---|---|
| 10-1 | 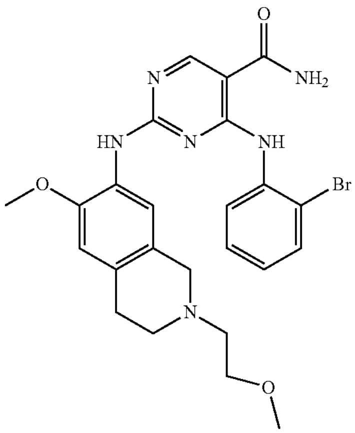 [SMILES: COCCN1CCc2cc(OC)c(Nc3ncc(C(N)=O)c(Nc4ccccc4Br)n3)cc2C1] | 4-[(2-bromophenyl)amino]-2-{[6-methoxy-2-(2-methoxyethyl)-1,2,3,4-tetrahydroisoquinolin-7-yl]amino}pyrimidine-5-carboxamide | Calc'd 527, found 527 |

TABLE 10-continued

| Compounds listed in the table below were prepared using the synthetic methods described in the aforementioned Example 10-1. The table provides the compound structure, the name, the calculated and observed masses. | | | |
|---|---|---|---|
| Example | Structure | Name | Exact Mass [M + H]$^+$ |
| 10-2 | 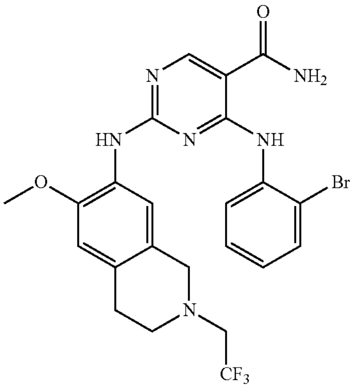 [SMILES: COc1cc2c(cc1Nc1ncc(C(N)=O)c(Nc3ccccc3Br)n1)CN(CC(F)(F)F)CC2] | 4-((2-bromophenyl)amino)-2-((6-methoxy-2-(2,2,2--trifluoroethyl)-1,2,3,4-tetrahydroisoquinolin-7-yl)amino)pyrimidine-5-carboxamide | Calc'd 552, found 551 |
| 10-3 | 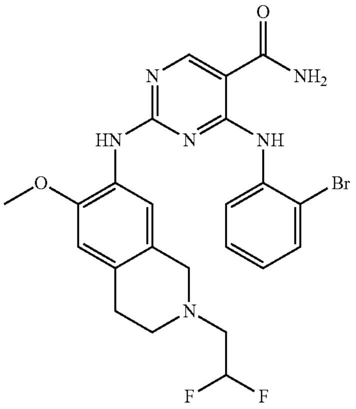 [SMILES: COc1cc2c(cc1Nc1ncc(C(N)=O)c(Nc3ccccc3Br)n1)CN(CC(F)F)CC2] | 4-((2-bromophenyl)amino)-2-((2-(2,2-difluoroethyl)-6-methoxy-1,2,3,4-tetrahydroisoquinolin-7-yl)amino)pyrimidine-5-carboxamide | Calc'd 533, found 533 |
| 10-4 | 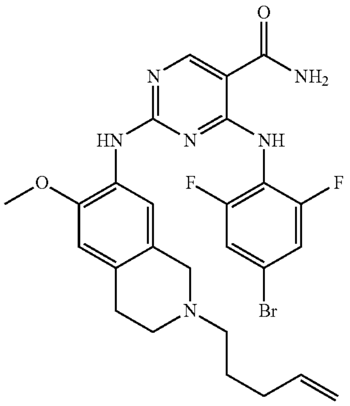 [SMILES: C=CCCCN1CCc2cc(OC)c(Nc3ncc(C(N)=O)c(Nc4c(F)cc(Br)cc4F)n3)cc2C1] | 4-(4-bromo-2,6-difluoroanilino)-2-{[6-methoxy-2-(pent-4-en-1-yl)-1,2,3,4-tetrahydroisoquinolin-7-yl]amino}pyrimidine-5-carboxamide | Calc'd 573, found 573 |

TABLE 10-continued

Compounds listed in the table below were prepared using the synthetic methods described in the aforementioned Example 10-1. The table provides the compound structure, the name, the calculated and observed masses.

| Example | Structure | Name | Exact Mass $[M + H]^+$ |
|---|---|---|---|
| 10-5 | 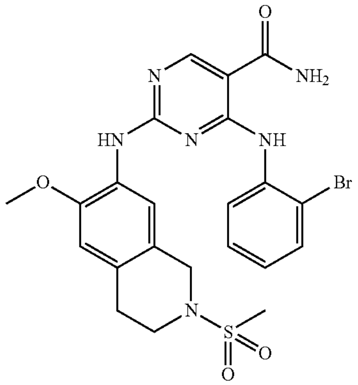 [SMILES: COc1cc2c(cc1Nc1ncc(C(N)=O)c(Nc3ccccc3Br)n1)CN(S(C)(=O)=O)CC2] | 4-[(2-bromophenyl)amino]-2-{[6-methoxy-2-(methylsulfonyl)-1,2,3,4-tetrahydroisoquinolin-7-yl]amino}pyrimidine-5-carboxamide | Calc'd 547, found 547 |
| 10-6 | 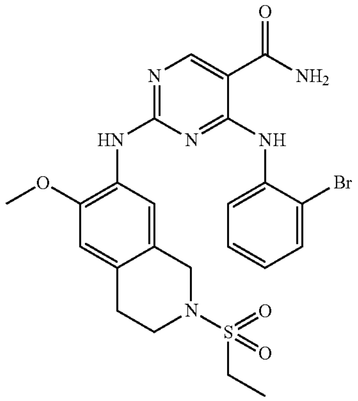 [SMILES: CCS(=O)(=O)N1CCc2cc(OC)c(Nc3ncc(C(N)=O)c(Nc4ccccc4Br)n3)cc2C1] | 4-[(2-bromophenyl)amino]-2-{[2-(ethylsulfonyl)-6-methoxy-1,2,3,4-tetrahydroisoquinolin-7-yl]amino}pyrimidine-5-carboxamide | Calc'd 561, found 561 |
| 10-7 | 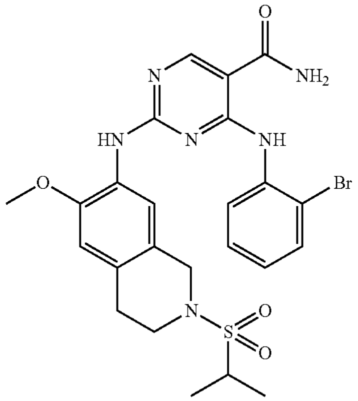 [SMILES: COc1cc2c(cc1Nc1ncc(C(N)=O)c(Nc3ccccc3Br)n1)CN(S(=O)(=O)C(C)C)CC2] | 4-[(2-bromophenyl)amino]-2-({6-methoxy-2-[(propan-2-yl)sulfonyl]-1,2,3,4-tetrahydroisoquinolin-7-yl}amino)pyrimidine-5-carboxamide | Calc'd 575, found 575 |

TABLE 10-continued

| Compounds listed in the table below were prepared using the synthetic methods described in the aforementioned Example 10-1. The table provides the compound structure, the name, the calculated and observed masses. | | | |
|---|---|---|---|
| Example | Structure | Name | Exact Mass [M + H]+ |
| 10-8 | 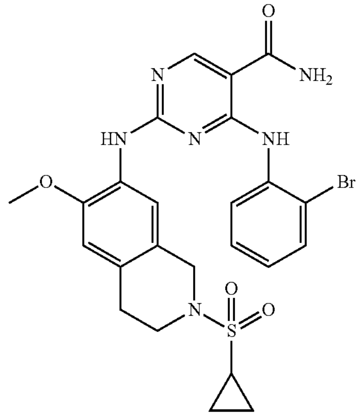 [SMILES: COc1cc2c(cc1Nc1ncc(C(N)=O)c(Nc3ccccc3Br)n1)CN(S(=O)(=O)C1CC1)CC2] | 4-[(2-bromophenyl)amino]-2-{[2-(cyclopropylsulfonyl)-6-methoxy-1,2,3,4-tetrahydroisoquinolin-7-yl]amino}pyrimidine-5-carboxamide | Calc'd 573, found 573 |

Example 4-1. 2-((2-Methoxy-4-(4-methylpiperazine-1-carbonyl)phenyl)amino)-4-((2-trifluoromethyl)phenyl)amino)pyrimidine-5-carboxamide

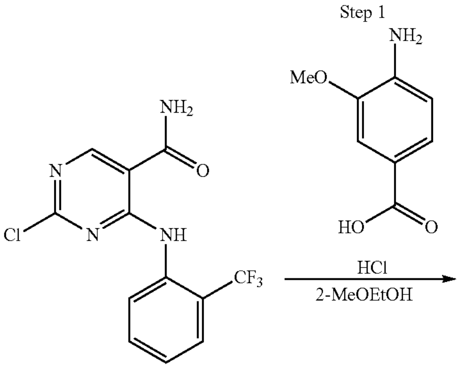

I-10

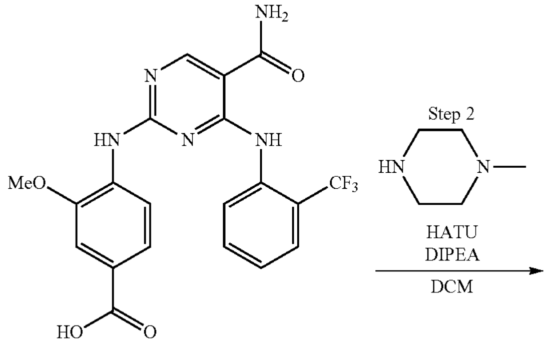

-continued

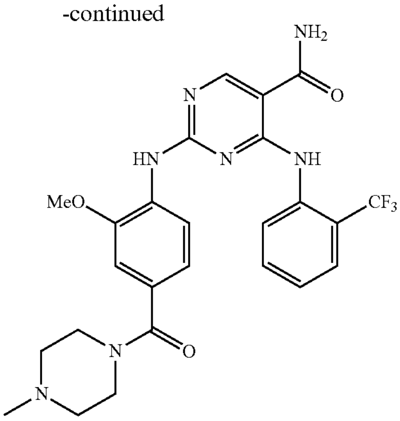

11-1

Step 1. 4-amino-3-methoxybenzoic acid (317 mg, 1.90 mmol), 2-chloro-4-((2-(trifluoromethyl)phenyl)amino)pyrimidine-5-carboxamide (1-10) (500 mg, 1.58 mmol) and hydrochloric acid (987 μl, 3.95 mmol, 4M in dioxane) in 2-methoxyethanol (6.3 mL) were heated to 110° C. overnight. The reaction was concentrated, diluted with DMSO (2 mL), filtered and purified via mass directed reverse-phase prep-HPLC (Purification Method A). This provided give 4-((5-carbamoyl-4-((2-(trifluoromethyl)phenyl)amino)pyrimidin-2-yl)amino)-3-methoxybenzoic acid. MS (ESI) m/z calc'd for $C_{20}H_{17}F_{3}N_{5}O_{4}$ $[M+H]^{+}$ 448, found 448.

Step 2. HATU (26.2 mg, 0.069 mmol) was added to a solution of 4-((5-carbamoyl-4-((2-(trifluoromethyl)phenyl) amino)pyrimidin-2-yl)amino)-3-methoxybenzoic acid (28 mg, 0.063 mmol), 1-methylpiperazine (7.5 mg, 0.075 mmol), and Hunig's Base (0.022 mL, 0.13 mmol) in DMF (2 mL) at room temperature. The reaction was stirred overnight, filtered and purified via mass directed reverse-phase prep-HPLC (Purification Method A). This provided 2-((2-methoxy-4-(4-methylpiperazine-1-carbonyl)phenyl) amino)-4-((2-(trifluoromethyl)phenyl)amino)pyrimidine-5-carboxamide. MS (ESI) m/z calc'd for $C_{25}H_{27}F_3N_7O_3[M+H]^+$ 530, found 530. $^1H$ NMR (499 MHz, DMSO-d6) (reported as observed solvent obscures some peaks) δ 11.76 (s, 1H), 9.74 (s, 1H), 8.76 (s, 1H), 8.50 (s, 1H), 8.12 (s, 1H), 8.09 (d, J=8.4 Hz, 1H), 7.89 (d, J=8.1 Hz, 1H), 7.74 (d, J=8.1 Hz, 1H), 7.67 (t, J=7.7 Hz, 1H), 7.60-7.47 (m, 11H), 7.37 (t, J=7.5 Hz, 1H), 7.08 (s, 1H), 6.87 (d, J=8.1 Hz, 1H), 3.86 (s, 3H), 3.13-3.03 (m, 2H), 2.87 (s, 3H).

TABLE 11

Compounds listed in the table below were prepared using the synthetic methods described in the aforementioned Example 11-1. The table provides the compound structure, the name, the calculated and observed masses.

| Example | Structure | Name | Exact Mass $[M + H]^+$ |
| --- | --- | --- | --- |
| 11-1 | 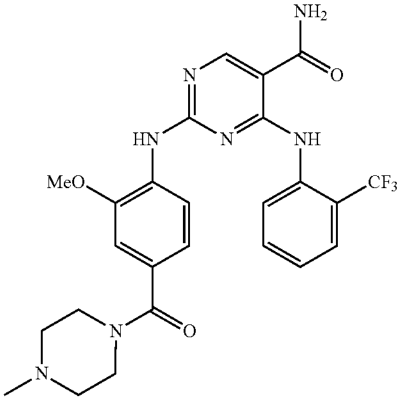 [SMILES: COc1cc(C(=O)N2CCN(C)CC2)ccc1Nc1ncc(C(N)=O)c(Nc2ccccc2C(F)(F)F)n1] | 2-((2-methoxy-4-(4-methylpiperazine-1-carbonyl)phenyl)amino)-4-((2-(trifluoromethyl)phenyl)amino) pyrimidine-5-carboxamide | Calcd'd 530, found 530 |
| 11-2 | 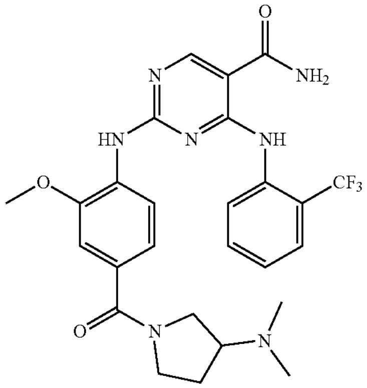 [SMILES: COc1cc(C(=O)N2CCC(N(C)C)C2)ccc1Nc1ncc(C(N)=O)c(Nc2ccccc2C(F)(F)F)n1] | 2-((4-(3-(dimethylamino)pyrrolidine-1-carbonyl)-2-methoxyphenyl)amino)-4-((2-(trifluoromethyl)phenyl)amino) pyrimidine-5-carboxamide | Calc'd 544 found 544 |

Example 5-1. 4-((2-Bromophenyl)amino)-2-((6-methoxy-2-(2-(2-(2-methoxyethoxy)ethoxy)acetyl)-1,2,3,4-tetrahydroisoquinolin-7-yl)amino)pyrimidine-5-carboxamide

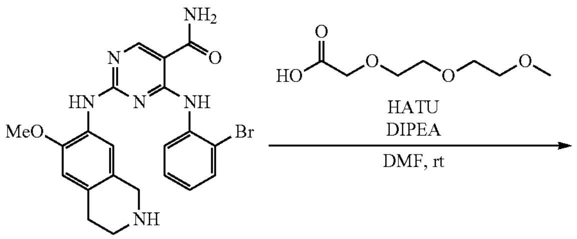

9-1

-continued

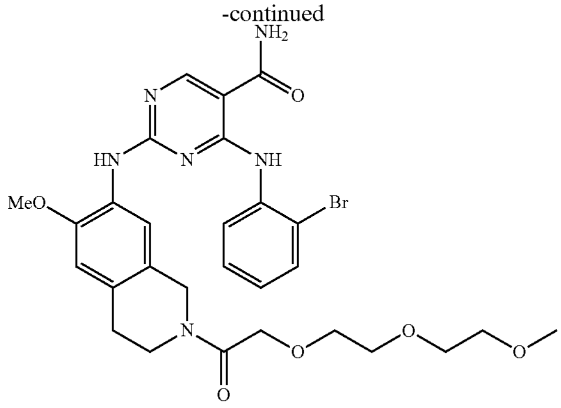

12-1

HATU (37 mg, 0.098 mmol) was added to a solution of 2-[2-(2-methoxyethoxy)ethoxy]acetic acid (17 mg, 0.095 mmol), 4-((2-bromophenyl)amino)-2-((6-methoxy-1,2,3,4-tetrahydroisoquinolin-7-yl)amino)pyrimidine-5-carboxamide (Ex. 9-1) (38.5 mg, 0.082 mmol) and Hunig's Base (0.029 mL, 0.16 mmol) in DMF (2.5 mL) at room temperature. The reaction was stirred for 24 h, filtered and purified via mass directed reverse-phase prep-HPLC (Purification Method A). This provided 4-((2-bromophenyl)amino)-2-((6-methoxy-2-(2-methoxyethyl)-1,2,3,4-tetrahydroisoquinolin-7-yl)amino)pyrimidine-5-carboxamide. MS (ESI) m/z calc'd for $C_{28}H_{34}BrN_6O6$ $[M+H]^+$ 630 found 629. $^1$H NMR (499 MHz, DMSO-d6) δ 11.81 (s, 1H), 8.85-8.55 (m, 2H), 8.31-7.97 (m, 2H), 7.69 (d, J=8.0 Hz, 1H), 7.63-7.42 (m, 2H), 7.32 (t, J=7.6 Hz, 1H), 7.14-7.02 (m, 1H), 6.88 (s, 1H), 4.38 (s, 2H), 4.24 (s, 1H), 4.19 (s, 1H), 3.79 (s, 3H), 3.75-3.34 (m, 10H), 3.24 (s, 2H), 3.18 (s, 1H), 2.89-2.81 (m, 1H), 2.81-2.71 (m, 1H).

TABLE 12

Compounds listed in the table below were prepared using the synthetic methods described in the aforementioned Example 12-1. The table provides the compound structure, the name, the calculated and observed masses.

| Example | Structure | Name | Exact Mass $[M + H]^+$ |
|---|---|---|---|
| 12-1 | 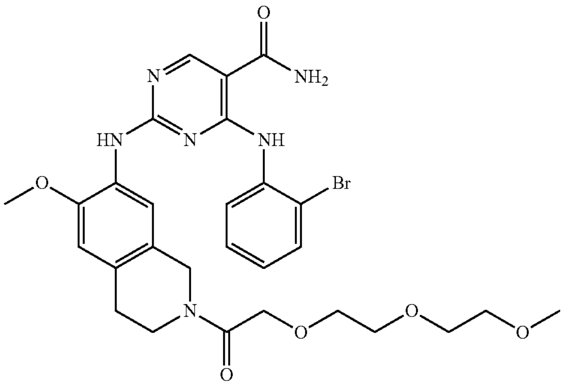 | 4-[(2-bromophenyl)amino]-2-[(6-methoxy-2-{[2-(2-methoxyethoxy)ethoxy)accetyl}-1,2,3,4-tetrahydroisoquinolin-7-yl)amino]pyrimidine-5-carboxamide | Calc'd 629, found 629 |
| 12-2 | 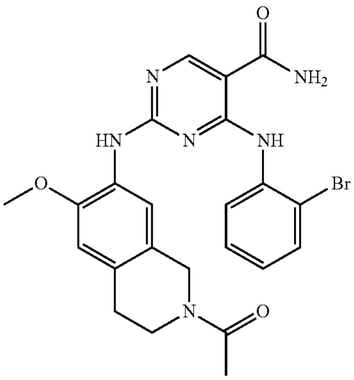 [SMILES: COc1cc2c(cc1Nc1ncc(C(N)=O)c(Nc3ccccc3Br)n1)CN(C(C)=O)CC2] | 2-[(2-acetyl-6-methoxy-1,2,3,4-tetrahydroisoquinolin-7-yl)amino]-4-[(2-bromophenyl)amino]pyrimidine-5-carboxamide | Calc'd 511, found 511 |

TABLE 12-continued

Compounds listed in the table below were prepared using the synthetic methods described in the aforementioned Example 12-1. The table provides the compound structure, the name, the calculated and observed masses.

| Example | Structure | Name | Exact Mass [M + H]+ |
|---|---|---|---|
| 12-3 | 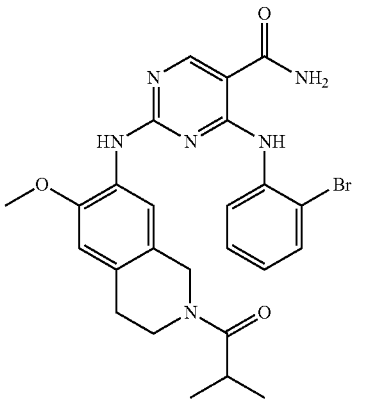 [SMILES: COc1cc2c(cc1Nc1ncc(C(N)=O)c(Nc3ccccc3Br)n1)CN(C(=O)C(C)C)CC2] | 4-[(2-bromophenyl)amino]-2-{[6-methoxy-2-(2-methylpropanoyl)-1,2,3,4-tetrahydroisoquinolin-7-yl]amino}pyrimidine-5-carboxamide | Calc'd 539, found 539 |
| 12-4 | 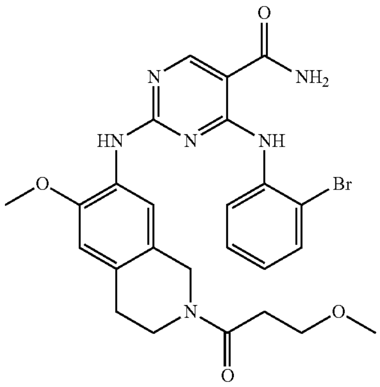 | 4-[(2-bromophenyl)amino]-2-{[6-methoxy-2-(3-methoxypropanoyl)-1,2,3,4-tetrahydroisoquinolin-7-yl]amino}pyrimidine-5-carboxamide | Calc'd 555, found 555 |
| 12-5 | 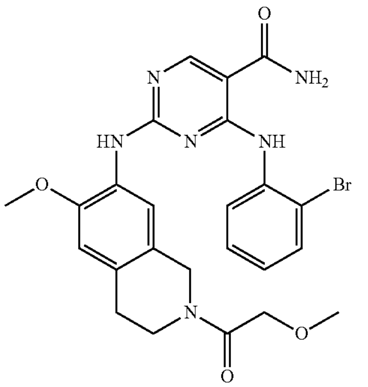 | 4-[(2-bromophenyl)amino]-2-{[6-methoxy-2-(methoxyacetyl)-1,2,3,4-tetrahydroisoquinolin-7-yl]amino}pyrimidine-5-carboxamide | Calc'd 541, found 541 |

TABLE 12-continued

Compounds listed in the table below were prepared using the synthetic methods described in the aforementioned Example 12-1. The table provides the compound structure, the name, the calculated and observed masses.

| Example | Structure | Name | Exact Mass [M + H]$^+$ |
| --- | --- | --- | --- |
| 12-6 | 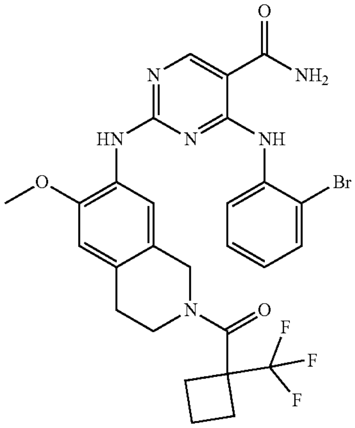 [SMILES: COc1cc2c(cc1Nc1ncc(C(N)=O)c(Nc3ccccc3Br)n1)CN(C(=O)C1(C(F)(F)F)CCC1)CC2] | 4-[(2-bromophenyl)amino]-2-({6-methoxy-2-[1-(trifluoromethyl)cyclobutane-1-carbonyl]-1,2,3,4-tetrahydroisoquinolin-7-yl}amino)pyrimidine-5-carboxamide | Calc'd 619, found 619 |
| 12-7 | 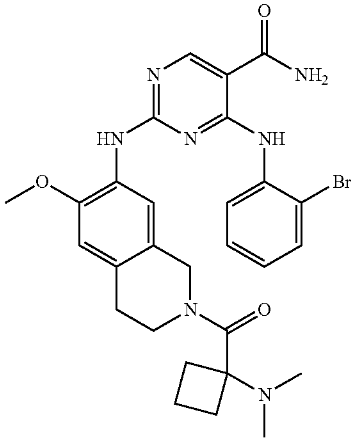 [SMILES: COc1cc2c(cc1Nc1ncc(C(N)=O)c(Nc3ccccc3Br)n1)CN(C(=O)C1(N(C)C)CCC1)CC2] | 4-[(2-bromophenyl)amino]-2-({2-[1-(dimethylamino)cyclobutane-1-carbonyl]-6-methoxy-1,2,3,4-tetrahydroisoquinolin-7-yl}amino)pyrimidine-5-carboxamide | Calc'd 594, found 594 |
| 12-8 | 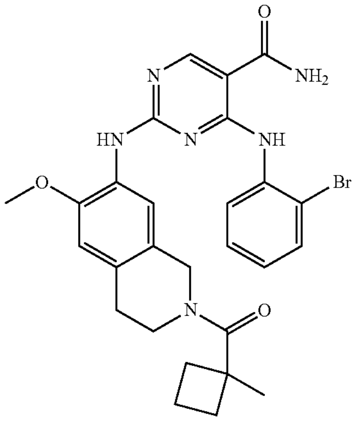 [SMILES: COc1cc2c(cc1Nc1ncc(C(N)=O)c(Nc3ccccc3Br)n1)CN(C(=O)C1(C)CCC1)CC2] | 4-[(2-bromophenyl)amino]-2-{[6-methoxy-2-(1-methylcyclobutane-1-carbonyl)-1,2,3,4-tetrahydroisoquinolin-7-yl]amino}pyrimidine-5-carboxamide | Calc'd 565, found 565 |

TABLE 12-continued

| Compounds listed in the table below were prepared using the synthetic methods described in the aforementioned Example 12-1. The table provides the compound structure, the name, the calculated and observed masses. | | | |
|---|---|---|---|
| Example | Structure | Name | Exact Mass $[M + H]^+$ |
| 12-9 | 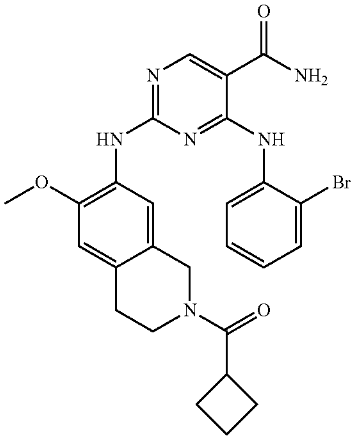 [SMILES: COc1cc2c(cc1Nc1ncc(C(N)=O)c(Nc3ccccc3Br)n1)CN(C(=O)C1CCC1)CC2] | 4-[(2-bromophenyl)amino]-2-{[2-(cyclobutanecarbonyl)-6-methoxy-1,2,3,4-tetrahydroisoquinolin-7-yl]amino}pyrimidine-5-carboxamide | Calc'd 551, found 551 |
| 12-10 | 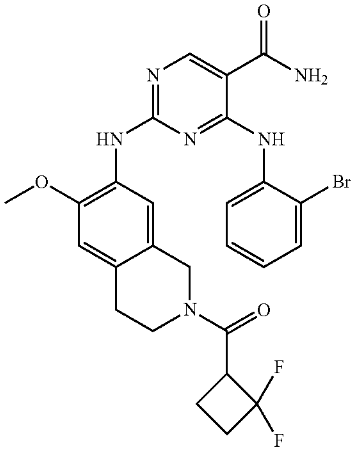 [SMILES: COc1cc2c(cc1Nc1ncc(C(N)=O)c(Nc3ccccc3Br)n1)CN(C(=O)C1CCC1(F)F)CC2] | 4-[(2-bromophenyl)amino]-2-{[2-(2,2-difluorocyclobutane-1-carbonyl)-6-methoxy-1,2,3,4-tetrahydroisoquinolin-7-yl]amino}pyrimidine-5-carboxamide | Calc'd 587, found 587 |

TABLE 12-continued

Compounds listed in the table below were prepared using the synthetic methods described in the aforementioned Example 12-1. The table provides the compound structure, the name, the calculated and observed masses.

| Example | Structure | Name | Exact Mass [M + H]+ |
|---|---|---|---|
| 12-11 | 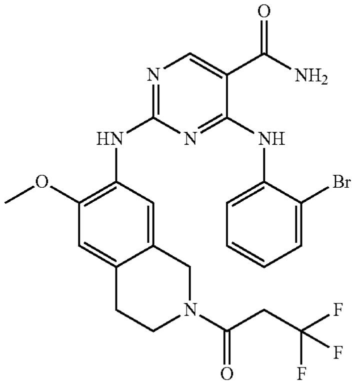 [SMILES: COc1cc2c(cc1Nc1ncc(C(N)=O)c(Nc3ccccc3Br)n1)CN(C(=O)CC(F)(F)F)CC2] | 4-[(2-bromophenyl)amino]-2-{[6-methoxy-2-(3,3,3-trifluoropropanoyl)-1,2,3,4-tetrahydroisoquinolin-7-yl]amino}pyrimidine-5-carboxamide | Calc'd 579, found 579 |
| 12-12 | 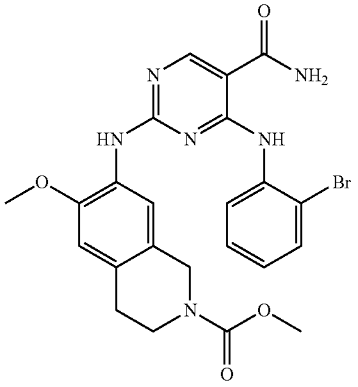 [SMILES: COC(=O)N1CCc2cc(OC)c(Nc3ncc(C(N)=O)c(Nc4ccccc4Br)n3)cc2C1] | methyl 7-({4-[(2-bromophenyl)amino]-5-carbamoylpyrimidin-2-yl}amino)-6-methoxy-3,4-dihydroisoquinoline-2(1H)-carboxylate | Calc'd 572, found 527 |

Example 13-1. 4-((2-Cyclohexylphenyl)amino)-2-((6-methoxy-2-methyl-1,2,3,4-tetrahydroisoquinolin-7-yl)amino)pyrimidine-5-carboxamide 2,2,2-trifluoroacetate

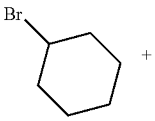

-continued

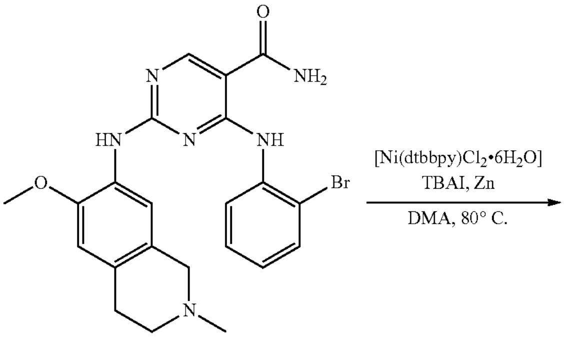

Ex. 7-3

-continued

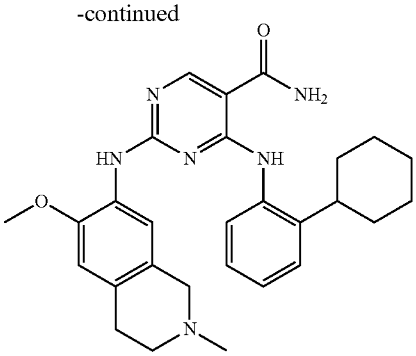

13-1

A vial was charged with 4-((2-bromophenyl)amino)-2-((6-methoxy-2-methyl-1,2,3,4-tetrahydroisoquinolin-7-yl)

amino)pyrimidine-5-carboxamide (Ex. 7-3) (20 mg, 0.041 mmol), [Ni(dtbbpy)$Cl_2$·$6H_2O$] (1.945 mg, 4.14 μmol), TBAI (3.82 mg, 10.34 μmol), zinc (8.12 mg, 0.124 mmol), and lastly bromocyclohexane (13.49 mg, 0.083 mmol), to which a stir bar and DMA (414 μl) was added, capped, flushed 3× with argon and heated to 80° C. After 18 h LCMS aliquot suggested product and mixture was diluted to 2 mL with DMSO and purified directly by reverse-phase HPLC Acetonitrile/Water (0.1% TFA) to afford product 4-((2-cyclohexylphenyl)amino)-2-((6-methoxy-2-methyl-1,2,3,4-tetrahydroisoquinolin-7-yl)amino)pyrimidine-5-carboxamide 2,2,2-trifluoroacetate. MS (ESI) m/z calc'd for $C_{28}H_{35}N_6O_2$ [M+H] 487, found 487. $^1$H NMR (499 MHz, DMSO-$d_6$) δ 11.46 (s, 1H), 9.80 (s, 1H), 8.68 (s, 1H), 8.28 (s, 1H), 8.10 (s, 1H), 7.81 (s, 1H), 7.63 (s, 1H), 7.54 (s, 1H), 7.42-7.18 (m, 3H), 6.93 (s, 1H), 4.02 (s, 2H), 3.83 (s, 3H), 3.71-2.60 (m, 7H), 11.87-1.19 (m, 10H).

TABLE 13

Compounds listed in the table below were prepared using the synthetic methods described in the aforementioned Example 13-1. The table provides the compound structure, the name, the calculated and observed masses.

| Example | Structure | Name | Exact Mass $[M + H]^+$ |
| --- | --- | --- | --- |
| 13-1 | 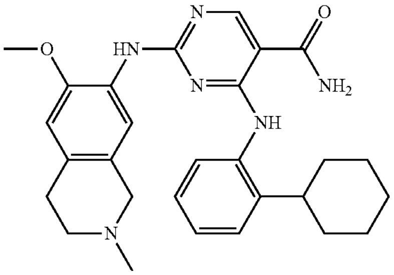 [SMILES: COc1cc2c(cc1Nc1ncc(C(N)=O)c(Nc3ccccc3C3CCCCC3)n1)CN(C)CC2] | 4-[(2-cyclohexylphenyl)amino]-2-[(6-methoxy-2-methyl-1,2,3,4-tetrahydroisoquinolin-7-yl)amino]pyrimidine-5-carboxamide | Calc'd 487, found 487 |
| 13-2 | 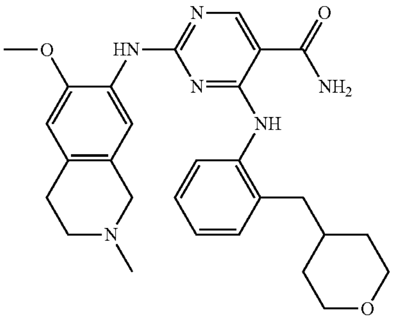 | 2-[(6-methoxy-2-methyl-1,2,3,4-tetrahydroisoquinolin-7-yl)amino]-4-({2-[(oxan-4-yl)methyl]phenyl}amino)pyrimidine-5-carboxamide | Calc'd 503, found 503 |
| 13-3 | 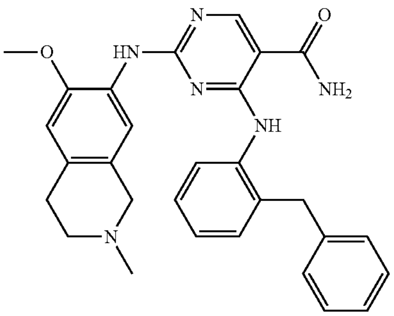 [SMILES: COc1cc2c(cc1Nc1ncc(C(N)=O)c(Nc3ccccc3Cc3ccccc3)n1)CN(C)CC2] | 4-[(2-benzylphenyl)amino]-2-[(6-methoxy-2-methyl-1,2,3,4-tetrahydroisoquinolin-7-yl)amino]pyrimidine-5-carboxamide | Calc'd 495, found 495 |

TABLE 13-continued

Compounds listed in the table below were prepared using the synthetic methods described in the aforementioned Example 13-1. The table provides the compound structure, the name, the calculated and observed masses.

| Example | Structure | Name | Exact Mass [M + H]+ |
| --- | --- | --- | --- |
| 13-4 | 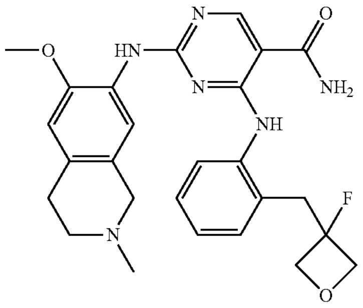 [SMILES: COc1cc2c(cc1Nc1ncc(C(N)=O)c(Nc3ccccc3CC3(F)COC3)n1)CN(C)CC2] | 4-({2-[(3-fluorooxetan-3-yl)methyl]phenyl}amino)-2-[(6-methoxy-2-methyl-1,2,3,4-tetrahydroisoquinolin-7-yl)amino]pyrimidine-5-carboxamide | Calc'd 493, found 493 |
| 13-5 | 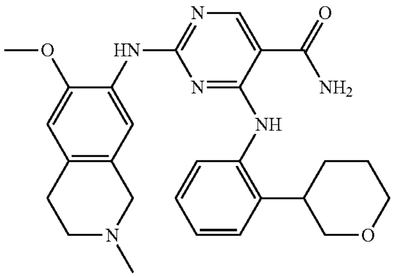 [SMILES: COc1cc2c(cc1Nc1ncc(C(N)=O)c(Nc3ccccc3C3CCCOC3)n1)CN(C)CC2] | 2-[(6-methoxy-2-methyl-1,2,3,4-tetrahydroisoquinolin-7-yl)amino]-4-{[2-(oxan-3-yl)phenyl]amino}pyrimidine-5-carboxamide | Calc'd 489, found 489 |
| 13-6 | 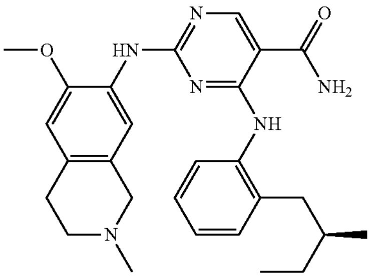 [SMILES: CC[C@H](C)Cc1ccccc1Nc1nc(Nc2cc3c(cc2OC)CCN(C)C3)ncc1C(N)=O] | 2-[(6-methoxy-2-methyl-1,2,3,4-tetrahydroisoquinolin-7-yl)amino]-4-({2-[(2S)-2-methylbutyl]phenyl}amino)pyrimidine-5-carboxamide | Calc'd 475, found 475 |
| 13-7 | 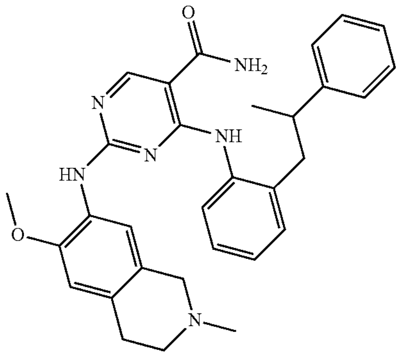 [SMILES: COc1cc2c(cc1Nc1ncc(C(N)=O)c(Nc3ccccc3CC(C)c3ccccc3)n1)CN(C)CC2] | 2-[(6-methoxy-2-methyl-1,2,3,4-tetrahydroisoquinolin-7-yl)amino]-4-{[2-(2-phenylpropyl)phenyl]amino}pyrimidine-5-carboxamide | Calc'd 523, found 523 |

TABLE 13-continued

Compounds listed in the table below were prepared using the synthetic methods described in the aforementioned Example 13-1. The table provides the compound structure, the name, the calculated and observed masses.

| Example | Structure | Name | Exact Mass [M + H]$^+$ |
|---|---|---|---|
| 13-8 | 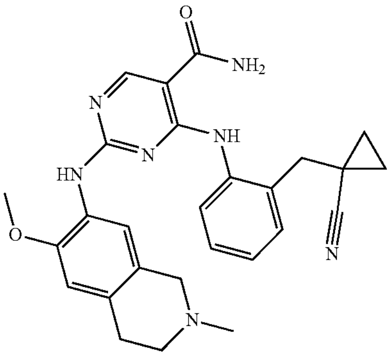 [SMILES: COc1cc2c(cc1Nc1ncc(C(N)=O)c(Nc3ccccc3CC3(C#N)CC3)n1)CN(C)CC2] | 4-({2-[(1-cyanocyclopropyl)methyl]phenyl}amino)-2-[(6-methoxy-2-methyl-1,2,3,4-tetrahydroisoquinolin-7-yl)amino]pyrimidine-5-carboxamide | Calc'd 484, found 484 |
| 13-9 | 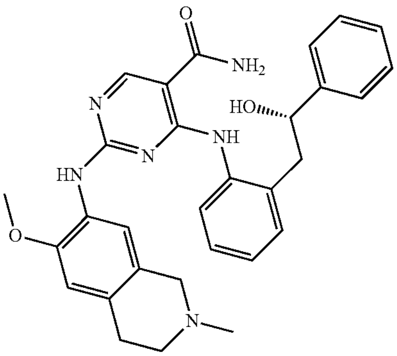 [SMILES: COc1cc2c(cc1Nc1ncc(C(N)=O)c(Nc3ccccc3C[C@H](O)c3ccccc3)n1)CN(C)CC2] | 4-({2-[(2S)-2-hydroxy-2-phenylethyl]phenyl}amino)-2-[(6-methoxy-2-methyl-1,2,3,4-tetrahydroisoquinolin-7-yl)amino]pyrimidine-5-carboxamide | Calc'd 525, found 525 |
| 13-10 | 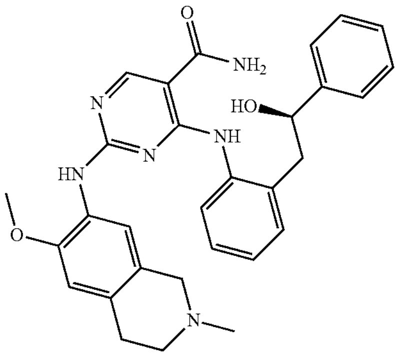 [SMILES: COc1cc2c(cc1Nc1ncc(C(N)=O)c(Nc3ccccc3C[C@@H](O)c3ccccc3)n1)CN(C)CC2] | 4-({2-[(2R)-2-hydroxy-2-phenylethyl]phenyl}amino)-2-[(6-methoxy-2-methyl-1,2,3,4-tetrahydroisoquinolin-7-yl)amino]pyrimidine-5-carboxamide | Calc'd 525, found 525 |
| 13-11 | 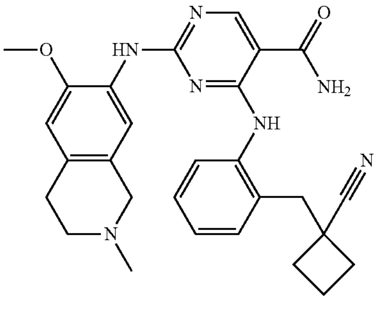 [SMILES: COc1cc2c(cc1Nc1ncc(C(N)=O)c(Nc3ccccc3CC3(C#N)CCC3)n1)CN(C)CC2] | 4-({2-[(1-cyanocyclobutyl)methyl]phenyl}amino)-2-[(6-methoxy-2-methyl-1,2,3,4-tetrahydroisoquinolin-7-yl)amino]pyrimidine-5-carboxamide | Calc'd 498, found 498 |

TABLE 13-continued

Compounds listed in the table below were prepared using the synthetic methods described in the aforementioned Example 13-1. The table provides the compound structure, the name, the calculated and observed masses.

| Example | Structure | Name | Exact Mass $[M + H]^+$ |
|---|---|---|---|
| 13-12 | 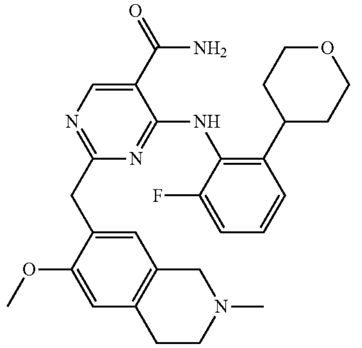 [SMILES: COc1cc2c(cc1Cc1ncc(C(N)=O)c(Nc3c(F)cccc3C3CCOCC3)n1)CN(C)CC2] | 4-{[2-fluoro-6-(oxan-4-yl)phenyl]amino}-2-[(6-methoxy-2-methyl-1,2,3,4-tetrahydroisoquinolin-7-yl)amino]pyrimidine-5-carboxamide | Calc'd 507, found 507 |
| 13-13 | 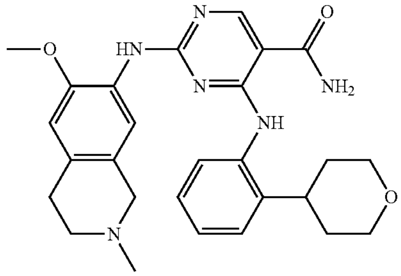 [SMILES: COc1cc2c(cc1Nc1ncc(C(N)=O)c(Nc3ccccc3C3CCOCC3)n1)CN(C)CC2] | 2-[(6-methoxy-2-methyl-1,2,3,4-tetrahydroisoquinolin-7-yl)amino]-4-{[2-(oxan-4-yl)phenyl]amino}pyrimidine-5-carboxamide | Calc'd 489, found 489 |

Example 6-1. 2-((6-Methoxy-2-methyl-1,2,3,4-tetrahydroisoquinolin-7-yl)amino)-4-((2-(thiazol-5-yl)phenyl)amino)pyrimidine-5-carboxamide

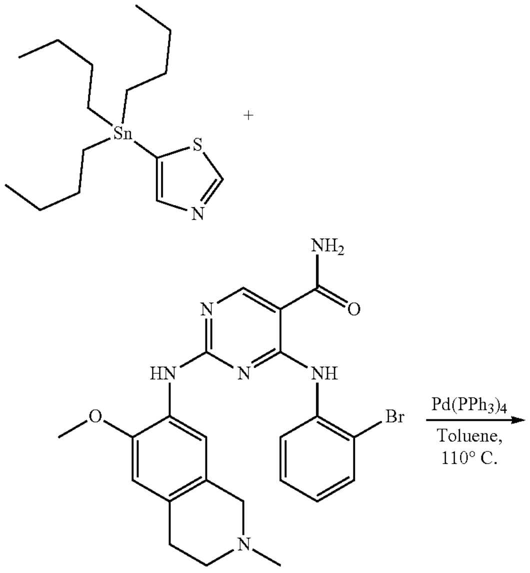

Ex. 7-3

-continued

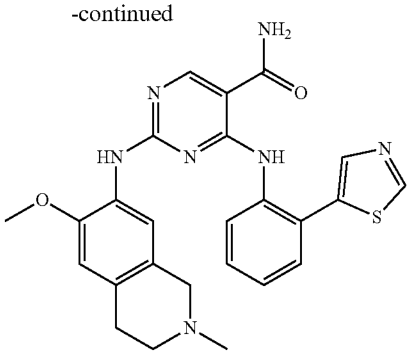

14-1

A microwave vial was charged with 5-(tributylstannyl) thiazole (31.0 mg, 0.083 mmol), 4-((2-bromophenyl) amino)-2-((6-methoxy-2-methyl-1,2,3,4-tetrahydroisoquinolin-7-yl)amino)pyrimidine-5-carboxamide (Ex. 7-3) (20 mg, 0.041 mmol), Pd Tetrakis (4.78 mg, 4.14 μmol), and DMF (414 μl) was added. The vial was capped, flushed 3× with Ar, and heated to 110° C. stirring overnight. LCMS suggested presence of product after 15 h and the mixture was directly purified by column by reverse-phase HPLC Acetonitrile/Water (0.1% TFA) to afford product 2-((6-methoxy-2-methyl-1,2,3,4-tetrahydroisoquinolin-7-yl) amino)-4-((2-(thiazol-5-yl)phenyl)amino)pyrimidine-5-carboxamide 2,2,2-trifluoroacetate, TFA. MS (ESI) m/z calc'd for $C_{25}H_{26}N_7O_2S$ $[M+H]^+$ 488, found 488. $^1H$ NMR (499 MHz, DMSO-dc) S 11.28 (s, 1H), 9.75 (s, 1H), 9.09 (s, 1H), 8.68 (s, 1H), 8.12 (s, 2H), 7.95-7.69 (m, 2H), 7.69-7.22 (m, 4H), 6.91 (s, 1H), 3.83 (s, 3H), 2.50-4.50 (m, 6H), 2.96 (s, 3H)

TABLE 14

Compounds listed in the table below were prepared using the synthetic methods described in the aforementioned Example 14-1. The table provides the compound structure, the name, the calculated and observed masses.

| Example | Structure | Name | Exact Mass [M + H]+ |
|---|---|---|---|
| 14-1 | 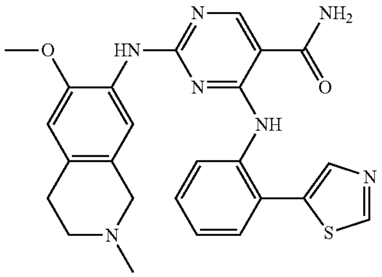 [SMILES: COc1cc2c(cc1Nc1ncc(C(N)=O)c(Nc3ccccc3-c3cncs3)n1)CN(C)CC2] | 2-[(6-methoxy-2-methyl-1,2,3,4-tetrahydroisoquinolin-7-yl)amino]-4-{[2-(1,3-thiazol-5-yl)phenyl]amino}pyrimidine-5-carboxamide | Calc'd 488, found 488 |
| 14-2 | 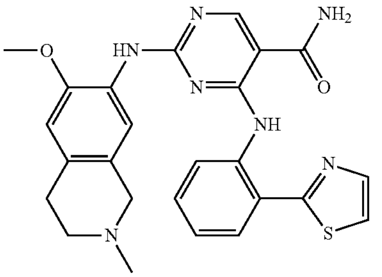 [SMILES: COc1cc2c(cc1Nc1ncc(C(N)=O)c(Nc3ccccc3-c3nccs3)n1)CN(C)CC2] | 2-[(6-methoxy-2-methyl-1,2,3,4-tetrahydroisoquinolin-7-yl)amino]-4-{[2-(1,3-thiazol-2-yl)phenyl]amino}pyrimidine-5-carboxamide | Calc'd 488, found 488 |
| 14-3 | 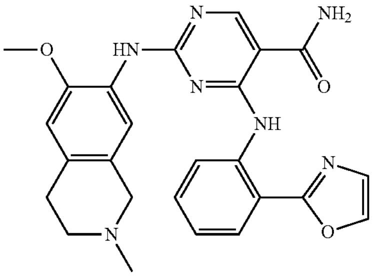 [SMILES: COc1cc2c(cc1Nc1ncc(C(N)=O)c(Nc3ccccc3-c3ncco3)n1)CN(C)CC2] | 2-[(6-methoxy-2-methyl-1,2,3,4-tetrahydroisoquinolin-7-yl)amino]-4-{[2-(1,3-oxazol-2-yl)phenyl]amino}pyrimidine-5-carboxamide | Calc'd 472, found 472 |

Example 7-1. 4-((2-Acetyl-1,2,3,4-tetrahydroisoquinolin-5-yl)amino)-2-((6-methoxy-2-methyl-1,2,3,4-tetrahydroisoquinolin-7-yl)amino)pyrimidine-5-carboxamide

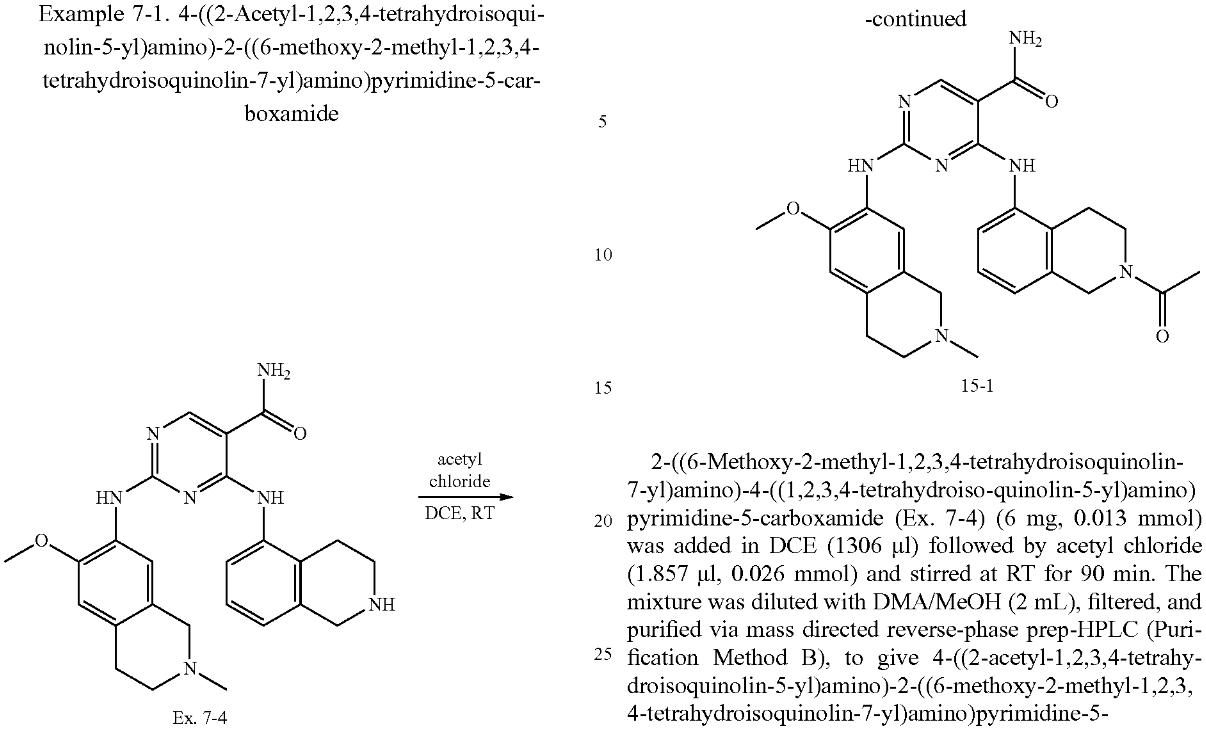

Ex. 7-4

-continued 15-1

2-((6-Methoxy-2-methyl-1,2,3,4-tetrahydroisoquinolin-7-yl)amino)-4-((1,2,3,4-tetrahydroiso-quinolin-5-yl)amino) pyrimidine-5-carboxamide (Ex. 7-4) (6 mg, 0.013 mmol) was added in DCE (1306 μl) followed by acetyl chloride (1.857 μl, 0.026 mmol) and stirred at RT for 90 min. The mixture was diluted with DMA/MeOH (2 mL), filtered, and purified via mass directed reverse-phase prep-HPLC (Purification Method B), to give 4-((2-acetyl-1,2,3,4-tetrahydroisoquinolin-5-yl)amino)-2-((6-methoxy-2-methyl-1,2,3,4-tetrahydroisoquinolin-7-yl)amino)pyrimidine-5-carboxamide as a solid after dry down. MS (ESI) m/z calc'd for $C_{27}H_{32}N_7O_3$ $[M+H]^+$ 502, found 502. $^1$H NMR (499 MHz, DMSO-d6) δ 11.31 (br s, 1H), 8.68 (s, 1H), 8.19-7.91 (m, 2H), 7.79 (d, J=35.0 Hz, 1H), 7.41 (d, J=41.5 Hz, 2H), 7.16 (t, J=7.0 Hz, 1H), 7.02 (d, J=7.1 Hz, 1H), 6.74 (s, 1H), 4.62 (br s, 1H), 3.78 (s, 3H), 3.67 (m, 2H), 3.17 (m, 2H), 2.76 (m, 3H), 2.63 (s, 1H), 2.54 (d, J=5.5 Hz, 3H), 2.32 (s, 3H), 2.06 (br s, 3H).

TABLE 15

Compounds listed in the table below were prepared using the synthetic methods described in the aforementioned Example 15-1. The table provides the compound structure, the name, the calculated and observed masses.

| Example | Structure | Name | Exact Mass $[M + H]^+$ |
|---|---|---|---|
| 15-1 | 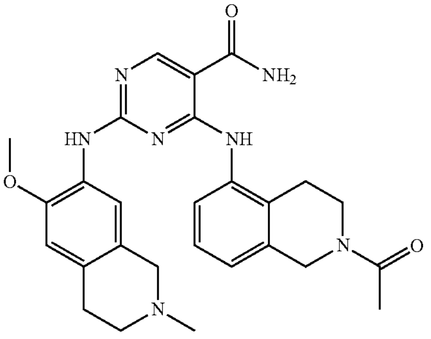 [SMILES: COc1cc2c(cc1Nc1ncc(C(N)=O)c(Nc3cccc4c3CCN(C(C)=O)C4)n1)CN(C)CC2] | 4-[(2-acetyl-1,2,3,4-tetrahydroisoquinolin-5-yl)amino]-2-[(6-methoxy-2-methyl-1,2,3,4-tetrahydroisoquinolin-7-yl)amino]pyrimidine-5-carboxamide | Calc'd 502, found 502 |

Example 16-1. 2-((6-Methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide

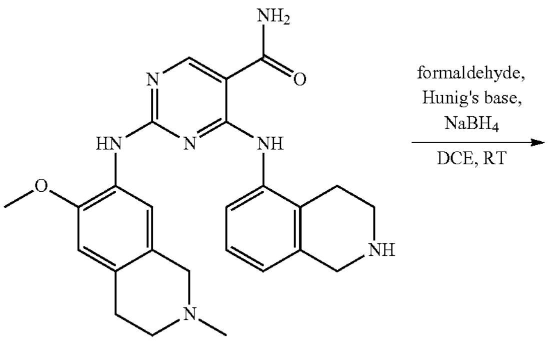

Ex. 7-4

-continued

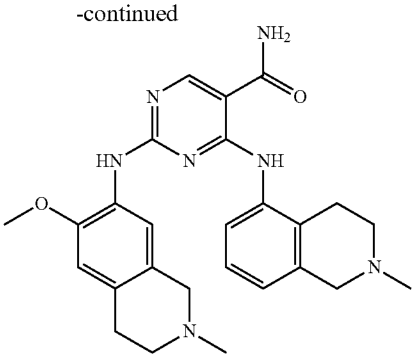

16-1

2-((6-Methoxy-2-methyl-1,2,3,4-tetrahydroisoquinolin-7-yl)amino)-4-((1,2,3,4-tetrahydroisoquinolin-5-yl)amino)pyrimidine-5-carboxamide (Ex. 7-4) (21 mg, 0.046 mmol) was added to a 2 dram vial containing Hunig's Base (15.96 μl, 0.091 mmol) in DCE (457 μl). Formaldehyde (37% in $H_2O$)(10.21 μl, 0.137 mmol) and then $NaBH_4$ (10.37 mg, 0.274 mmol) was added and the mixture was stirred at 24° C. overnight. Upon completion, the mixture was diluted with MeOH (1 mL) and stirred for 10 min at RT. The mixture was diluted with DMSO (1.5 mL) and filtered. The residue was purified via mass directed reverse-phase prep-HPLC (Purification Method B), to give 2-((6-methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide as a colorless solid following dry down. MS (ESI) m/z calc'd for $C_{26}H_{32}N_7O_2$ $[M+H]^+$ 474, found 474. $^1H$ NMR (499 MHz, DMSO-d6) δ 11.31 (br s, 1H), 8.68 (s, 1H), 8.19-7.91 (m, 2H), 7.79 (d, J=35.0 Hz, 1H), 7.41 (d, J=41.5 Hz, 2H), 7.16 (t, J=7.0 Hz, 1H), 7.02 (d, J=7.1 Hz, 1H), 6.74 (s, 1H), 4.62 (br s, 1H), 3.78 (s, 3H), 3.67 (m, 2H), 3.17 (m, 2H), 2.76 (m, 3H), 2.63 (s, 1H), 2.54 (d, J=5.5 Hz, 3H), 2.32 (s, 3H), 2.06 (br s, 3H).

TABLE 16

Compounds listed in the table below were prepared using the synthetic methods described in the aforementioned Example 16-1. The table provides the compound structure, the name, the calculated and observed masses.

| Example | Structure | Name | Exact Mass $[M + H]^+$ |
|---|---|---|---|
| 16-1 | 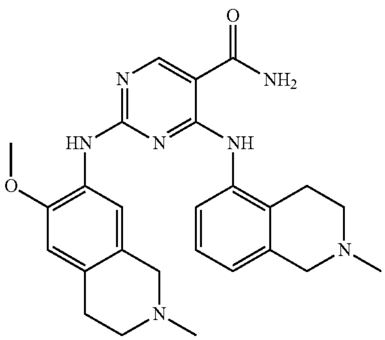 [SMILES: COc1cc2c(cc1Nc1ncc(C(N)=O)c(Nc3cccc4c3CCN(C)C4)n1)CN(C)CC2] | 2-((6-methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide | Calc'd 474, found 474 |

Example 8-1. 4-((2-(2-Hydroxypropan-2-yl)phenyl)amino)-2-((6-methoxy-2-methyl-1,2,3,4-tetrahydroisoquinolin-7-yl)amino)pyrimidine-5-carboxamide

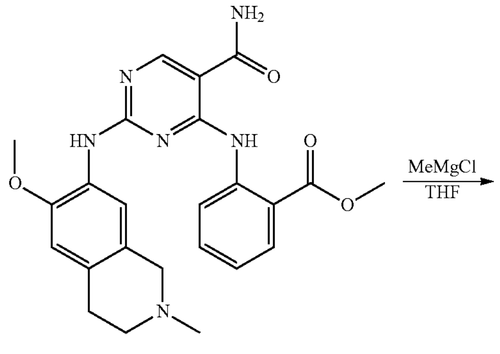

7-94

-continued

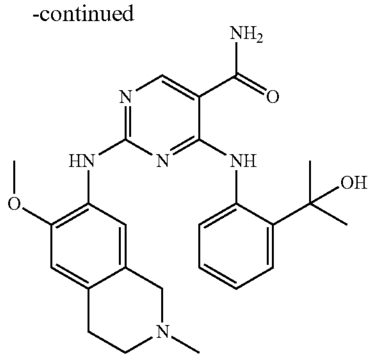

17-1

To a solution of methyl 2-((5-carbamoyl-2-((6-methoxy-2-methyl-1,2,3,4-tetrahydroisoquinolin-7-yl)amino)pyrimidin-4-yl)amino)benzoate (Ex. 7-94) (50.0 mg, 0.108 mmol) in THF (2000 μl) was cooled to 0° C. (internal temp) by ice bath then was added methylmagnesium chloride (180 μl, 0.541 mmol). The solution was stirred for 12 h. The reaction mixture was quenched with a small amount of sat aq $NH_4Cl$, diluted with EtOAc and brine. Separated the layers and extracted the aqueous portion with EtOAc (2×). Dried the combined organic portions with $Na_2SO_4$ and concentrated in vacuo to dryness. The crude material was purified by mass-directed reverse phase chromatography (Purification Method B) to give 4-((2-(2-hydroxypropan-2-yl)phenyl)amino)-2-((6-methoxy-2-methyl-1,2,3,4-tetrahydroisoquinolin-7-yl)amino)pyrimidine-5-carboxamide. MS (ESI) m/z calc'd for $C_{25}H_{30}N_6O_3$ $[M+H]^+$ 463, found 463. $^1H$ NMR (499 MHz, DMSO-d6) δ 11.86 (s, 1H), 9.94 (s, 1H), 8.89 (s, 1H), 8.67 (s, 1H), 7.70-7.54 (m, 2H), 7.51-7.26 (m, 2H), 7.24 (d, J=9.3 Hz, 1H), 7.07 (d, J=51.0 Hz, 1H), 6.94 (s, 1H), 3.88-3.79 (m, 3H), 3.64 (s, 2H), 3.30 (s, 2H), 2.94 (s, 2H), 2.59-2.53 (m, 3H), 1.46 (s, 6H).

TABLE 17

Compounds listed in the table below were prepared using the synthetic methods described in the aforementioned Example 17-1. The table provides the compound structure, the name, the calculated and observed masses.

| Example | Structure | Name | Exact Mass $[M + H]^+$ |
|---|---|---|---|
| 17-1 | 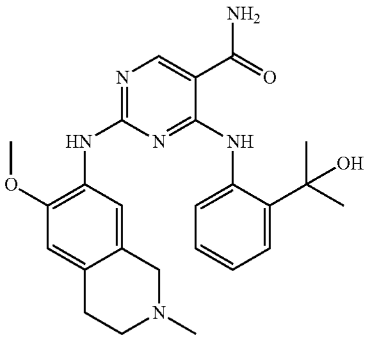 [SMILES: COc1cc2c(cc1Nc1ncc(C(N)=O)c(Nc3ccccc3C(C)(C)O)n1)CN(C)CC2] | 4-{[2-(2-hydroxypropan-2-yl)phenyl]amino}-2-[(6-methoxy-2-methyl-1,2,3,4-tetrahydroisoquinolin-7-yl)amino]pyrimidine-5-carboxamide | Calc'd 463, found 463 |

Example 18-1. 2-((6-Methoxy-2-methyl-1,2,3,4-tetrahydroisoquinolin-7-yl)amino)-4-(phenylamino)pyrimidine-5-carbohydrazide

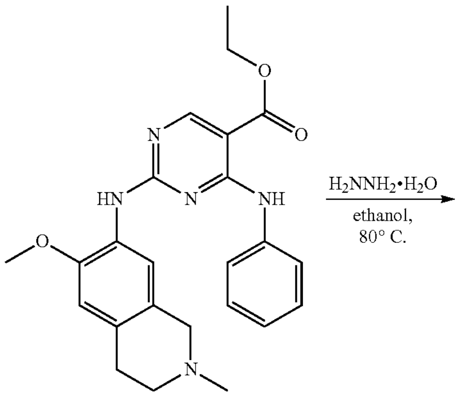

from Ex. 6-1

-continued

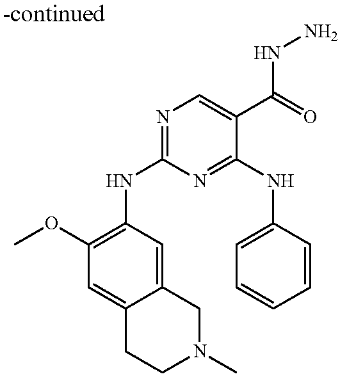

18-1

Ethyl 2-((6-methoxy-2-methyl-1,2,3,4-tetrahydroisoquinolin-7-yl)amino)-4-(phenylamino)pyrimidine-5-carboxylate (Intermediate from Ex. 6-1) (34 mg, 0.078 mmol) added to a 2 dram vial in ethanol (157 μl). Hydrazine monohydrate (64% $H_2NNH_2$ in water) (36.5 μl, 1.176 mmol) was added via syringe and the mixture was heated to 80° C. for 3 h. The mixture was cooled and diluted with DMA/MeOH (2 mL), filtered through a frit, and the mixture was purified via mass directed reverse-phase prep-HPLC (Purification Method B), to give 2-((6-methoxy-2-methyl-1,2,3,4-tetrahydroisoquinolin-7-yl)amino)-4-(phenylamino)pyrimidine-5-carbohydrazide as a solid after dry down. MS (ESI) m/z calc'd for $C_{22}H_{26}N_7O_2$ $[M+H]^+$ 420, found 420. $^1$H NMR (499 MHz, DMSO-d6) δ 11.22 (s, 1H), 9.76 (s, 1H), 8.56 (s, 1H), 8.30 (s, 1H), 7.57 (br s, 2H), 7.46 (s, 1H), 7.28 (t, J=7.8 Hz, 2H), 7.06 (t, J=7.4 Hz, 1H), 6.79 (s, 1H), 4.47 (br s, 2H), 3.77 (s, 3H), 3.32 (m, 2H), 2.81 (t, J=5.7 Hz, 2H), 2.58 (t, J=5.9 Hz, 2H), 2.33 (s, 3H).

TABLE 18

Compounds listed in the table below were prepared using the synthetic methods described in the aforementioned Example 18-1. The table provides the compound structure, the name, the calculated and observed masses.

| Example | Structure | Name | Exact Mass $[M + H]^+$ |
|---|---|---|---|
| 18-1 | 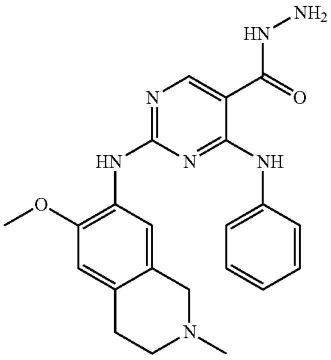 [SMILES: COc1cc2c(cc1Nc1ncc(C(=O)NN)c(Nc3ccccc3)n1)CN(C)CC2] | 2-((6-methoxy-2-methyl-1,2,3,4-tetrahydroisoquinolin-7-yl)amino)-4-(phenylamino)pyrimidine-5-carbohydrazide | Calc'd 420, found 420 |

Example 9-1. 52,56-Difluoro-16-methoxy-11,12,13,14-tetrahydro-2,4-diaza-1(7,2)-isoquinolina-3(2,4)-pyrimidina-5(1,4)-benzenacyclodecaphane-35-carboxamide

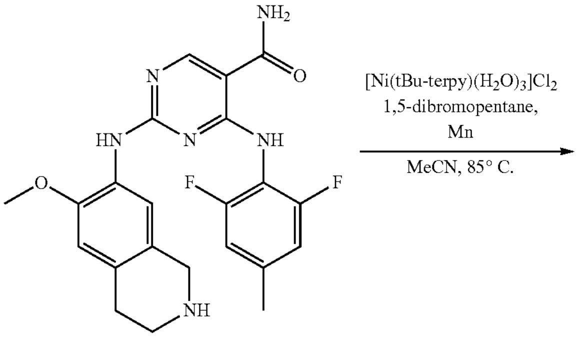

Ex. 9-12

-continued

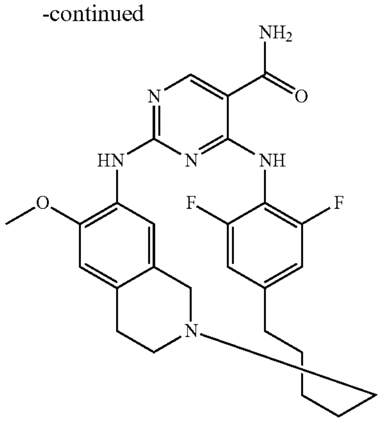

19-1

4-((2,6-Difluoro-4-iodophenyl)amino)-2-((6-methoxy-1,2,3,4-tetrahydroisoquinolin-7-yl)amino)pyrimidine-5-carboxamide, HCl (Ex. 9-12) (30 mg, 0.051 mmol) was added to a 2 dram vial, followed by 1,5-dibromopentane (23.43 mg, 0.102 mmol), $[NiCBu\text{-}terpy)(H_2O)_3]Cl_2$ precat (1.629 mg, 2.55 μmol), and Mn (8.40 mg, 0.153 mmol). Dry Acetonitrile (1019 μl) (contents not fully soluble) was added to the capped mixture and $N_2$ was bubbled through the solution for 3 min. The vessel was sealed and heated to 85° C. overnight. The mixture was cooled, concentrated, diluted in DMA/MeOH (2 mL), and filtered. The residue was purified via mass directed reverse-phase prep-HPLC (Purification Method B), to give 2-((6-methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide as a solid following dry down. MS (ESI) m/z calc'd for $C_{26}H_{29}F_2N_6O_2[M+H]^+$ 495, found 495. $^1H$ NMR (600 MHz, DMSO-d6) δ 10.90 (s, 1H), 8.70 (s, 1H), 8.08 (s, 1H), 7.86 (s, 1H), 7.44 (s, 2H), 7.18 (d, J=9.4 Hz, 2H), 6.70 (s, 1H), 3.80 (s, 3H), 2.99 (s, 2H), 2.76-2.63 (m, 4H), 2.53 (d, J=5.8 Hz, 2H), 2.48-2.42 (m, 2H), 1.85-1.78 (m, 2H), 1.62-1.52 (m, 2H), 1.31-1.18 (m, 2H).

TABLE 19

Compounds listed in the table below were prepared using the synthetic methods described in the aforementioned Example 19-1. The table provides the compound structure, the name, the calculated and observed masses.

| Example | Structure | Name | Exact Mass $[M + H]^+$ |
|---|---|---|---|
| 19-1 | 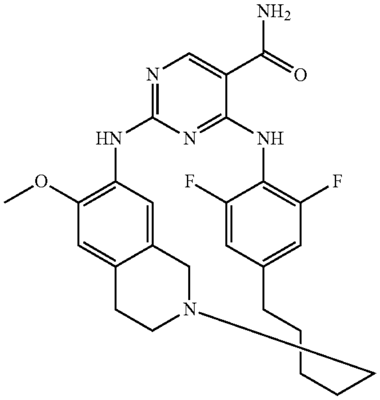 [SMILES: COc1cc2c3cc1Nc1ncc(C(N)=O)c(n1)Nc1c(F)cc(cc1F)CCCCCN(CC2)C3] | 10,28-difluoro-23-methoxy-2,4,8,18,29-pentaazapentacyclo [16.5.3.2~9,12~.1~3,7~.0~21,25~] nonacosa-1(23),3(29),4,6,9,11,21,24,27-nonaene-6-carboxamide (non-preferred name) | Calc'd 495, found 495 |

Example 20-1 and 20-2. 2-((1-Cyclopropyl-6-methoxy-2-methyl-1,2,3,4-tetrahydroisoquinolin-7-yl)amino)-4-((2-(trifluoromethyl)phenyl)amino)pyrimidine-5-carboxamide and 2-((1-Cyclopropyl-6-methoxy-2-methyl-1,2,3,4-tetrahydroisoquinolin-7-yl)amino)-4-((2-(trifluoromethyl)phenyl)amino) pyrimidine-5-carboxamide

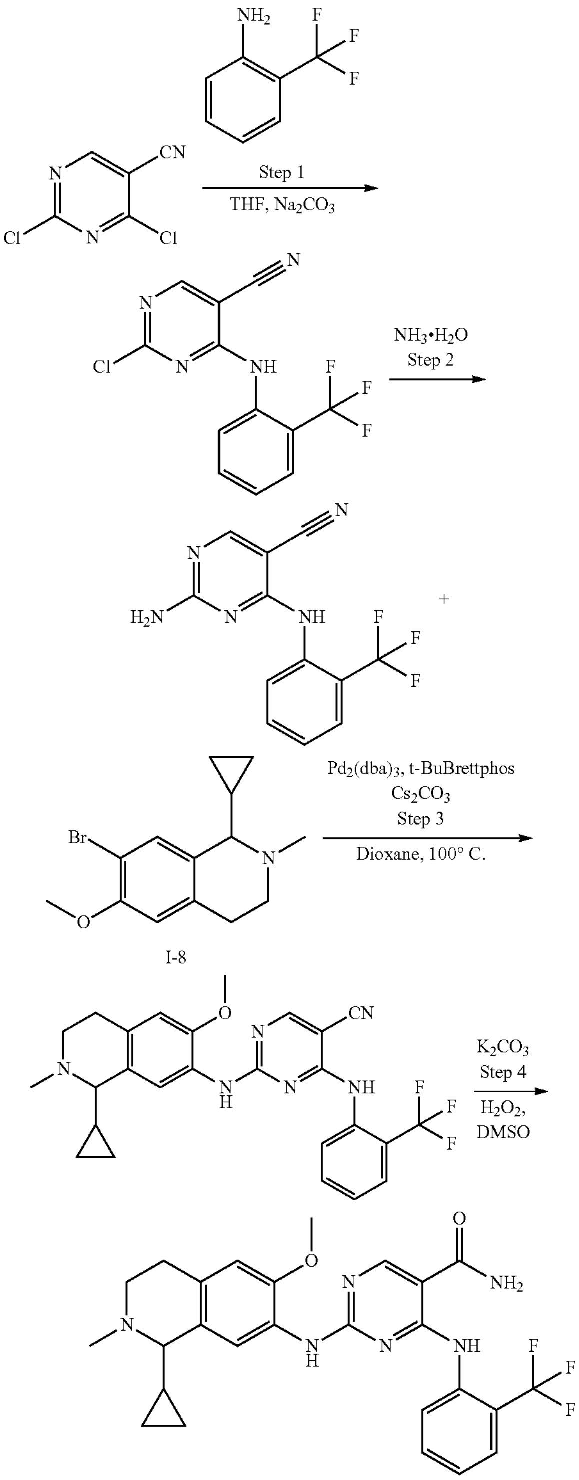

I-8

-continued

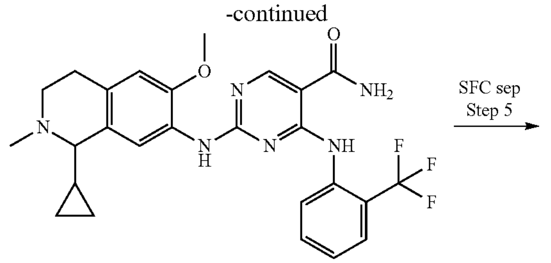

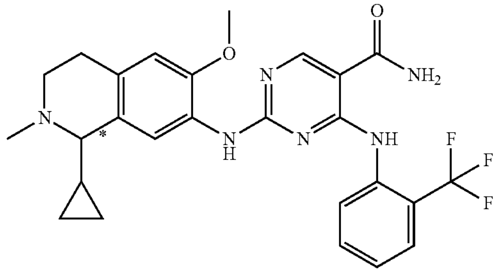 [SMILES: COc1cc2c(cc1Nc1ncc(C(N)=O)c(Nc3ccccc3C(F)(F)F)n1)C(C1CC1)N(C)CC2]

20-1

20-2

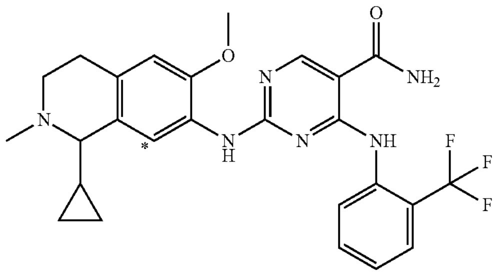 [SMILES: COc1cc2c(cc1Nc1ncc(C(N)=O)c(Nc3ccccc3C(F)(F)F)n1)C(C1CC1)N(C)CC2]

Step 1. To a solution of 2,4-dichloropyrimidine-5-carbonitrile (2 g, 11.50 mmol) in THF (20 ml) was added 2-(trifluoromethyl)aniline (1.852 g, 11.50 mmol) and $Na_2CO_3$ (3.66 g, 34.5 mmol). It was stirred at 60° C. for 12 h. LCMS and TLC showed desired product was formed. Water (50 mL) and EtOAc (50 mL) were added. The organic layer was separated and the aqueous was re-extracted with EtOAc (50 mL×3). The combined organic layers were washed with brine (50 mL), dried ($Na_2SO_4$), filtered and concentrated. The residue was purified by Prep-TLC (silica gel, pet. ether/ethyl acetate=5/1], v/v, Rf=0.3) to give 2-chloro-4-((2-(trifluoromethyl)phenyl)amino)pyrimidine-5-carbonitrile. MS (ESI) m/z calc'd for $C_{12}H_7ClF_3N_4$ [M+H$^+$] 299, found 299.

Step 2. A solution of 2-chloro-4-((2-(trifluoromethyl) phenyl)amino)pyrimidine-5-carbonitrile (300 mg, 1.005 mmol) in Dioxane (3 mL) was added ammonium hydroxide (1.397 ml, 10.05 mmol) and stirred at 60° C. for 3 h. LCMS showed the product was formed. The mixture was quenched with water (20 mL), extracted with EtOAc (20 mL×3). The combined organic layers were dried ($Na_2SO_4$), filtered and the filtrate was concentrated in vacuo and purified by Prep-TLC (silica gel, pet. ether/ethyl acetate=1/21, v/v, Rf=0.4) to give 2-amino-4-((2-(trifluoromethyl)phenyl) amino)pyrimidine-5-carbonitrile. MS (ESI) m/z calc'd for $C_{12}H_9F_3N_5$ (M+H$^+$) 280, found 280.

Step 3. To a mixture of 7-bromo-1-cyclopropyl-6-methoxy-2-methyl-1,2,3,4-tetrahydroisoquinoline (1-8) (60 mg, 0.203 mmol), 2-amino-44(2-(trifluoromethyl)phenyl) amino)pyrimidine-5-carbonitrile (56.6 mg, 0.203 mmol) and $Cs_2CO_3$ (132 mg, 0.405 mmol) in Dioxane (1 mL) was added di-tert-butyl(2',4',6'-triisopropyl-3,6-dimethoxy-[1,1'- biphenyl]-2-yl)phosphine (29.5 mg, 0.061 mmol) and $Pd_2(dba)_3$ (18.55 mg, 0.020 mmol) under $N_2$. The mixture was stirred at 100° C. under $N_2$ for 4 h. LCMS showed desired product was formed. Water (5 mL) and EtOAc (5 mL) were added. The organic layer was separated and the aqueous was re-extracted with EtOAc (5 mL×3). The combined organic layers were washed with brine (5 mL), dried ($Na_2SO_4$), filtered and concentrated. The mixture was purified by Prep-TLC (silica gel, $CH_2Cl_2$/MeOH=10/1], v/v, Rf=0.4) to give desire product 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carbonitrile. MS (ESI) m calc'd for $C_{26}H_{26}F_3N_6O$ (M+H$^+$) 495, found 495.

Step 4. To a solution of 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carbonitrile (100 mg, 0.149 mmol) in DMSO (0.5 mL) was added $K_2CO_3$ (41.3 mg, 0.299 mmol) and hydrogen peroxide (0.044 mL, 0.448 mmol). Then it was stirred at 0° C. for 30 min. LCMS showed the desired product. Water (10 mL) and EtOAc (10 mL) were added. The organic layer was separated and the aqueous was re-extracted with EtOAc (10 mL×3). The combined organic layers were washed with brine (5 mL), dried ($Na_2SO_4$), filtered and concentrated in vacuum to give crude product, which was purified by Pre-HPLC (Column Agela DuraShell C18 150*25 mm*5 um Condition water (0.04% $NH_3H_2O$+10 mM $NH_4HCO_3$)-ACN Begin B 50 End B 80 Gradient Time (min) 10 100% B Hold Time (min) 2 FlowRate (ml/min) 25 Injections 5) to give 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide. MS (ESI) m/z calc'd for $C_{26}H_{28}F_3N_6O_2$ (M+H$^+$) 513, found 513.

Step 5. 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide (30 mg, 0.059 mmol) was separated by SFC (Column: Phenomenex-Cellulose-2 (250 mm*30 mm, 5 um), Condition: 0.05% DEA MEOH, Mobile phase: A: $CO_2$ B: methanol (0.05% DEA), Gradient: from 5% to 40% of B in 5.5 min and hold 40% for 3 min, then 5% of B for 1.5 min, Flow rate: 2.8 mL/min, Column temp: 35° C.) to give 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide (Peak 1. Rt=6.242 min, UV=220 nm, EE=100%). 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide (Peak 2, Rt=6.124 min, UV=220 nm, EE=96.16%), both as solid. MS (ESI) m/z calc'd for $C_{16}H_{28}F_3N_6O_2$ (M+H$^+$) 513, found 513.

Ex. 20-1: $^1$H NMR (500 MHz, $CDCl_3$) δ 11.21 (s, 1H), 8.42 (s, 1H), 7.99 (d, J=7.5 Hz, 2H), 7.72 (d, J=7.5 Hz, 2H), 7.42-7.57 (m, 1H), 6.56 (s, 1H), 5.66 (s, 2H), 3.85 (s, 3H), 3.25 (s, 1H), 2.83-2.92 (m, 1H), 2.79 (d, J=6.5 Hz, 1H), 2.69 (d, J=16.5 Hz, 1H), 2.54 (s, 3H), 1.18-1.38 (m, 2H), 0.69-0.93 (m, 1H), −0.05-0.55 (m, 3H).

Ex. 20-2: $^1$H NMR (500 MHz, $CDCl_3$) δ 11.21 (s, 1H), 8.42 (s, 1H), 7.99 (d, J=7.5 Hz, 2H), 7.71 (d, J=7.5 Hz, 2H), 7.42-7.57 (m, 1H), 6.56 (s, 1H), 5.66 (s, 2H), 3.85 (s, 3H), 3.23 (s, 1H), 2.83-2.96 (m, 1H), 2.79 (d, J=6.5 Hz, 1H), 2.70 (d, J=16.5 Hz, 1H), 2.54 (s, 3H), 1.19-1.35 (m, 2H), 0.69-0.93 (m, 1H), −0.05-0.55 (m, 3H)

TABLE 20

Compounds listed in the table below were prepared using the synthetic methods described in the aforementioned Example 20-1. The table provides the compound structure, the name, the calculated and observed masses.

| Example | Structure | Name | Exact Mass [M + H]$^+$ |
|---|---|---|---|
| 20-1 | 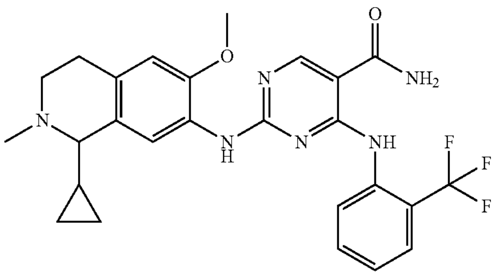 | 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide | Calc'd 513, found 513 |
| 20-2 | 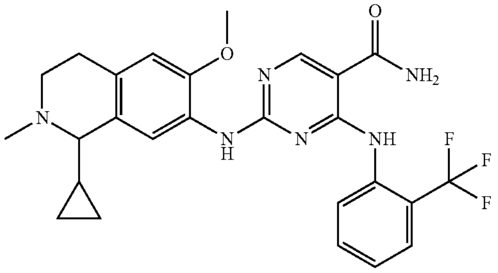 | 2-((1-cyclopropyl-6-methoxy-2-methyl-1,2,3,4-tetrahydroisoquinolin-7-yl)amino)-4-((2-(trifluoromethyl)phenyl)amino)pyrimidine-5-carboxamide | Calc'd 513, found 513 |

Example 10-1. 4-((2-Fluoro-6-(trifluoromethyl)phenyl)amino)-2-((6'-methoxy-2'-methyl-2',3'-dihydro-1'H-spiro[cyclopropane-1,4'-isoquinolin]-7'-yl)amino)pyrimidine-5-carboxamide

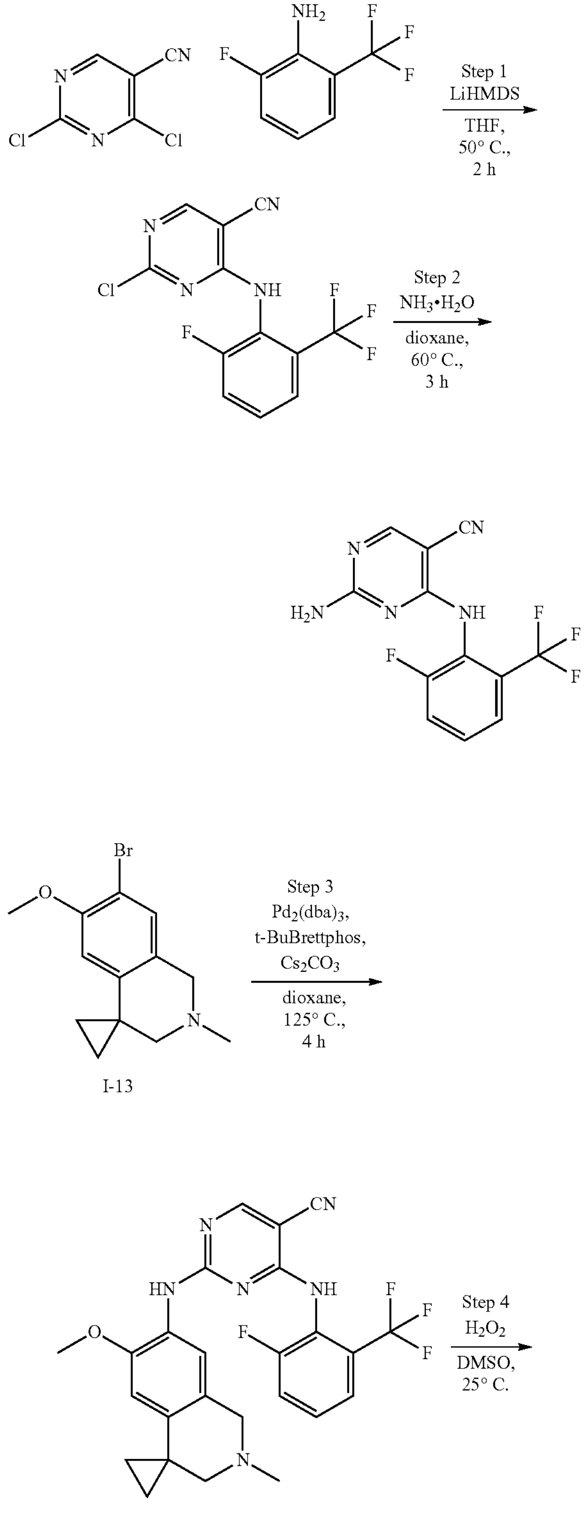

I-13

-continued

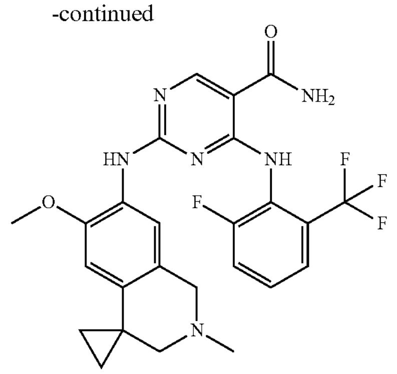

21-1

Step 1. To a solution of 2,4-dichloropyrimidine-5-carbonitrile (2 g, 11.50 mmol), 2-fluoro-6-(trifluoromethyl)aniline (1.935 g, 10.81 mmol) in THF (18 mL) was added LiHMDS (22.99 mL, 22.99 mmol) at 25° C. The reaction was stirred at 50° C. for 2 h. LCMS showed the reaction was completed. Water (40 mL) was added, the resulting mixture was added DCM (20 mL). The organic layer was separated and the aqueous was re-extracted with DCM (30 mL×3). The combined organic layers were washed with brine (40 mL), dried ($Na_2SO_4$), filtered, and concentrated to give a residue which was purified by flash silica gel chromatography (ISCO®; 12 g Agela® Silica Flash Column, Eluent of 0~10% EtOAc/Pet. ether gradient @ 30 mL/min) and reversed MPLC (Biotage; 120 g Agela, C18, 20~35 μm, Eluent of 44% MeCN\H$_2$O (0.5‰ TFA) gradient d) 50 mL/min) to give 2-chloro-4-((2-fluoro-6-(trifluoromethyl)phenyl)amino)pyrimidine-5-carbonitrile. MS (ESI): m/z $[M+H]^+$ 317, found 317.

Step 2. To a solution of 2-chloro-4-((2-fluoro-6-(trifluoromethyl)phenyl)amino)pyrimidine-5-carbonitrile (500 mg, 1.500 mmol) in Dioxane (6 mL) was added ammonium hydroxide (2 mL) and stirred at 60° C. for 3 h. LCMS showed the product was formed. The mixture was quenched with water (20 mL), extracted with EtOAc (20 mL×3). The combined organic layers were dried ($Na_2SO_4$), filtered, and concentrated in vacuo to give a residue which was purified by flash silica gel chromatography (ISCO®; 4 g Agela® Silica Flash Column, Eluent of 0~19.8% EtOAc/Pet. ether gradient @ 20 mL/min) to give 2-amino-4-((2-fluoro-6-(trifluoromethyl)phenyl)amino)pyrimidine-5-carbonitrile. MS (ESI): m/z $[M+H]^+$ 298, found 298.

Step 3. To a solution of 2-amino-4-((2-fluoro-6-(trifluoromethyl)phenyl)amino)pyrimidine-5-carbonitrile (30 mg, 0.101 mmol) in Toluene (I mL) was added $Cs_2CO_3$ (99 mg, 0.303 mmol), 7'-bromo-6'-methoxy-2'-methyl-2',3'-dihydro-1'H-spiro[cyclopropane-1,4'-isoquinoline] (1-13) (42.7 mg, 0.151 mmol), di-tert-butyl(2',4',6'-triisopropyl-3,6-dimethoxy-[1,1'-biphenyl]-2-yl)phosphine (24.46 mg, 0.050 mmol) and $Pd_2(dba)_3$ (18.49 mg, 0.020 mmol) at 25° C. under $N_2$ atmosphere. The mixture was stirred at 125° C. under $N_2$ atmosphere for 4 h. The mixture was cooled and the solvent was evaporated under reduced pressure to give the crude product. The residue was purified by reverse preparative HPLC (Column: Waters XSELECT C18 150*30 mm*5 um; Condition: water (0.1% TFA)-MeCN: Begin B—End B: 21-41; Gradient Time (min): 10; 100% B Hold Time (min): 1; Flow rate (mL/min): 25) to give 4-((2-fluoro-6-(trifluoromethyl)phenyl)amino)-2-((6'-methoxy-2'-methyl-2',3'-dihydro-1'H-spiro[cyclopropane-1,4'-isoquinolin]-7'-yl)aminopyrimidine-5-carbonitrile. MS (ESI) m/z $[M+H]^+$ 499, found 499.

Step 4. To a solution of 4-((2-fluoro-6-(trifluoromethyl) phenyl)amino)-2-((6'-methoxy-2'-methyl-2',3'-dihydro-1'H-spiro[cyclopropane-1,4'-isoquinolin]-7'-yl)amino)pyrimidine-5-carbonitrile (80 mg, 0.160 mmol) in DMSO (3 mL) was added $K_2CO_3$ (44.4 mg, 0.321 mmol) and $H_2O_2$ (0.141 mL, 1.605 mmol) at 25° C. under $N_2$ atmosphere. The mixture was stirred at 25° C. for 10 min. The mixture was filtered and the solvent was purification by HPLC. The residue was purified by reverse preparative HPLC (Column: Waters XSELECT C18 150*30 mm*5 um; Condition: water (0.1% TFA)-MeCN; Begin B—End B: 21-41; Gradient Time (min): 10; 100% B Hold Time (min): 1; FlowRate (mL/min): 25) to give 4-((2-fluoro-6-(trifluoromethyl)phenyl)amino)-2-((6'-methoxy-2'-methyl-2',3'-dihydro-1'H-spiro[cyclopropane-1,4'-isoquinolin]-7'-yl)amino)pyrimidine-5-carboxamide. MS (ESI) m/z $[M+H]^+$ 517, found 517. $^1H$ NMR (400 MHz, MeOD-$d_4$) δ 8.64 (s, 1H), 7.58-7.74 (m, 3H), 7.48 (s, 1H), 6.36 (s, 1H), 3.90-4.10 (m, 2H), 3.84 (s, 3H), 3.49-3.60 (m, 1H), 3.15 (d, J=10.8 Hz, 1H), 3.02 (s, 3H), 1.43 (br s, 1H), 0.98-1.20 (m, 3H).

TABLE 21

Compounds listed in the table below were prepared using the synthetic methods described in the aforementioned Example 21-1. The table provides the compound structure, the name, the calculated and observed masses.

| Example | Structure | Name | Exact Mass $[M + H]^+$ |
|---|---|---|---|
| 21-1 | 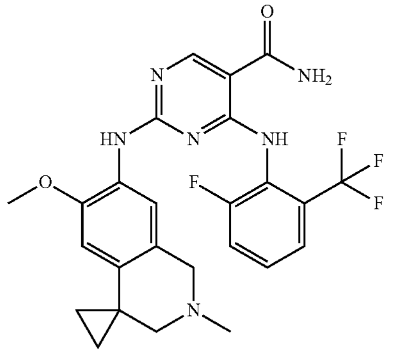 [SMILES: COc1cc2c(cc1Nc1ncc(C(N)=O)c(Nc3c(F)cccc3C(F)(F)F)n1)CN(C)CC21CC1] | 4-((2-fluoro-6-(trifluoromethyl)phenyl) amino)-2-((6'-methoxy-2'-methyl-2',3'-dihydro-1'H-spiro[cyclopropane-1,4'-isoquinolin]-7'-yl)amino) pyrimidine-5-carboxamide | Calc'd 517, found 517 |

Example 11-1. 4-((2-Bromophenyl)amino)-2-((trans)-2-(1-methyl-1H-pyrazol-4-yl)cyclopropane-1-carboxamido)pyrimidine-5-carboxamide (racemic)

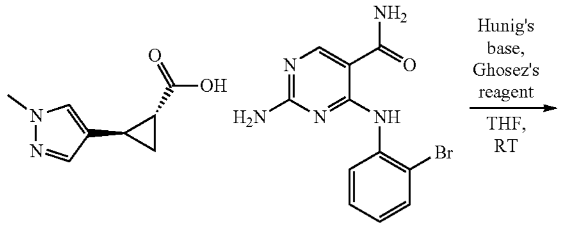

from Ex. 21-1

-continued

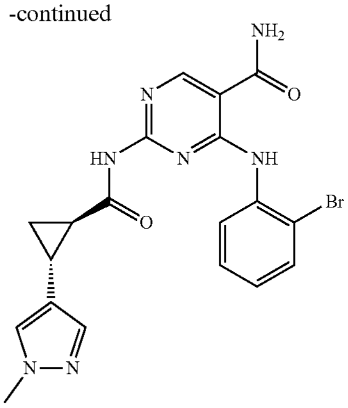

22-1

(trans)-2-(1-Methyl-1H-pyrazol-4-yl)cyclopropane-1-carboxylic acid (9.71 mg, 0.058 mmol) was added to a 2 dram vial. Dry THF (389 µl) was added, followed by 1-chloro-N,N,2-trimethylprop-1-en-1-amine (Ghosez's Reagent, 23.18 µl, 0.175 mmol) and stirred (mixture slowly went into solution over 5 min). 2-Amino-4-((2-bromophenyl)amino)pyrimidine-5-carboxamide (prepared analogous to intermediate in Ex. 21-1) (18 mg, 0.058 mmol) was added in one portion after 5 min at RT followed by N-ethyl-N-isopropylpropan-2-amine (19.61 µl, 0.117 mmol), and mixture was stirred at RT overnight. Upon completion, the solvent was evaporated. The residue was diluted with DMA/MeOH (3 mL), filtered through a frit, and the mixture was purified via reverse-phase prep-HPLC (Purification Method B), to give 4-((2-bromophenyl)amino)-2-((trans)-2-(1-methyl-1H-pyrazol-4-yl)cyclopropane-1-carboxamido)pyrimidine-5-carboxamide (trans. racemic) following dry down. MS (ESI) m/z calc'd for $C_{19}H_{19}BrN_7O_2$ $[M+H]^+$ 456, found 456. $^1H$ NMR (499 MHz, DMSO-d6) δ 11.87 (s, 1H), 10.91 (s, 1H), 9.15 (d, J=8.4 Hz, 1H), 8.85 (s, 1H), 8.25 (s, 1H), 7.65 (dd, J=8.0, 1.3 Hz, 2H), 7.53 (s, 1H), 7.35 (t, J=7.8 Hz, 1H), 7.27 (s, 1H), 7.06-6.93 (m, 1H), 3.76 (s, 3H), 2.30 (m, 1H), 2.23 (ddd, J=10.1, 6.4, 4.0 Hz, 1H), 1.41 (ddd, J=10.1, 6.0, 4.0 Hz, 1H), 1.19 (m, 1H).

TABLE 22

Compounds listed in the table below were prepared using the synthetic methods described in the aforementioned Example 22-1. The table provides the compound structure, the name, the calculated and observed masses.

| Example | Structure | Name | Exact Mass $[M + H]^+$ |
|---|---|---|---|
| 22-1 | 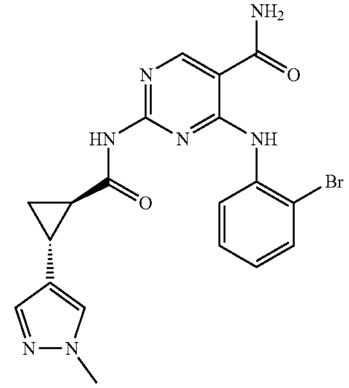 [SMILES: Cn1cc([C@@H]2C[C@H]2C(=O)Nc2ncc(C(N)=O)c(Nc3ccccc3Br)n2)cn1] | 4-((2-bromophenyl)amino)-2-((trans)-2-(1-methyl-1H-pyrazol-4-yl)cyclopropane-1-carboxamido)pyrimidine-5-carboxamide | Calc'd 456, found 456 |
| 22-2 | 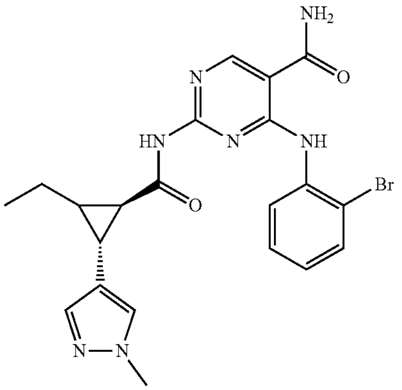 [SMILES: CCC1[C@@H](C(=O)Nc2ncc(C(N)=O)c(Nc3ccccc3Br)n2)[C@@H]1c1cnn(C)c1] | 4-[(2-bromophenyl)amino]-2-{[(1R,3R)-2-ethyl-3-(1-methyl-1H-pyrazol-4-yl)cyclopropane-1-carbonyl]amino}pyrimidine-5-carboxamide | Calc'd 484, found 484 |

Example 12-1. 4-((2-Fluoro-6-(1-methoxyethyl)phenyl)amino)-2-((6-methoxy-2-methyl-1,2,3,4-tetrahydroisoquinolin-7-yl)amino)pyrimidine-5-carboxamide

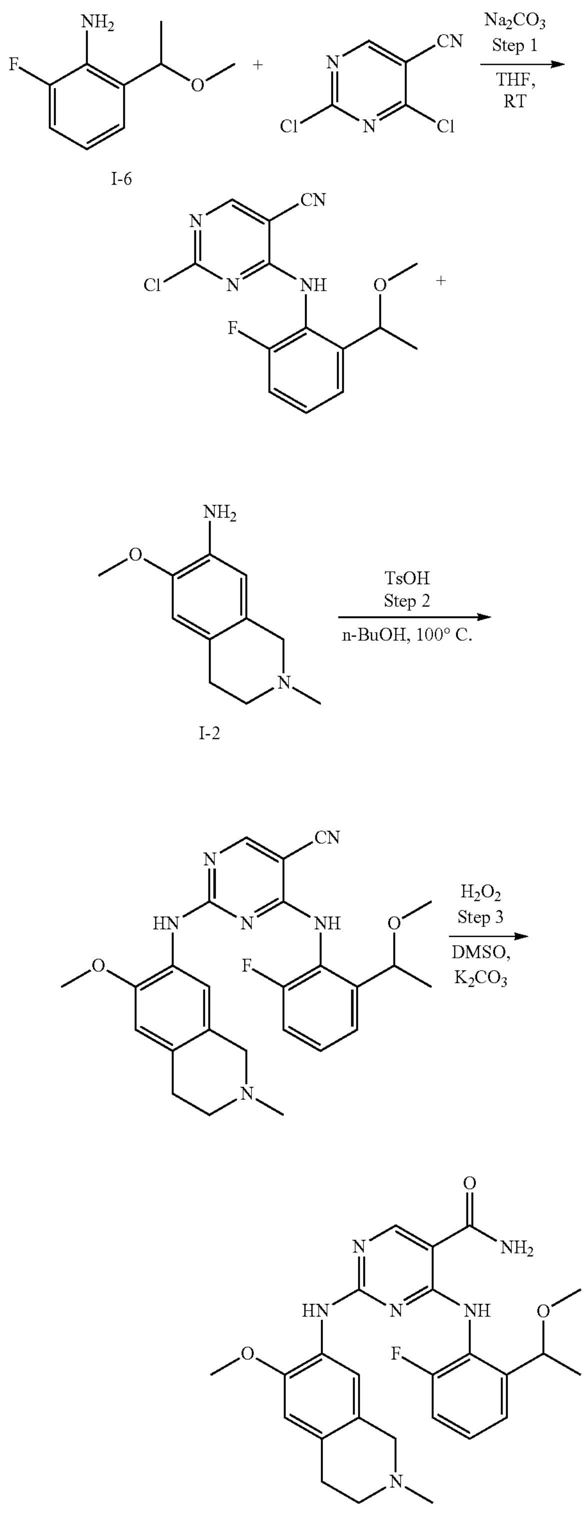

I-6

I-2

23-1

Step 1. A mixture of 2,4-dichloropyrimidine-5-carbonitrile (70 mg, 0.402 mmol), 2-fluoro-6-(1-methoxyethyl)aniline (71.5 mg, 0.422 mmol) in THF (2 mL) was added $Na_2CO_3$ (128 mg, 1.207 mmol) at 25° C. The reaction was stirred at 25° C. for 40 h. The mixture turned yellow turbid. Lcms showed the reaction was completed. Water (10 mL) was added, the resulting mixture was added EtOAc (10 mL). The organic layer was separated and the aqueous was re-extracted with EtOAc (10 mL×3). The combined organic layers were washed with brine (10 mL), dried over anhydrous $Na_2SO_4$, filtered and concentrated to give a residue which was purified by Pre-HPLC (Instrument ee; Method Column YMC-Actus Triart C18 150*30 mm*5 um; Condition water (0.1% TFA)-ACN Begin B 30 End B 60 Gradient Time (min) 11; 100% B Hold Time (min) 1.1 FlowRate (mL/min) 40; Injections 1) to give 2-chloro-4-((2-fluoro-6-(1-methoxyethyl)phenyl)amino)pyrimidine-5-carbonitrile. MS (ESI): m/z $[M+H]^+$ 307, found 307.

Step 2. To a stirred solution of 2-chloro-4-((2-fluoro-6-(1-methoxyethyl)phenyl)amino)-pyrimidine-5-carbonitrile (15.95 mg, 0.052 mmol) in Dioxane (0.6 mL) was added 6-methoxy-2-methyl-1,2,3,4-tetrahydroisoquinolin-7-amine (I-2) (10 mg, 0.052 mmol) and 4-methylbenzenesulfonic acid (17.91 mg, 0.104 mmol) at 20° C. The reaction was stirred at 100° C. for 4 h. Water (10 mL) and EtOAc (10 mL) was added. The organic layer was separated and the aqueous was re-extracted with EtOAc (10 mL×3). The combined organic layers were washed with brine (20 mL), dried over anhydrous $Na_2SO_4$, filtered, and concentrated. The residue was purified by Prep-Hplc (Instrument ed; Method Column Agela DuraShell C18 150*25 mm*5 um; Condition water (0.04% $NH_3H_2O$+10 mM $NH_4HCO$+ACN Begin B 40 End B 70 Gradient Time (min) 10; 100% B Hold Time (min) 2 FlowRate (mL/min) 25; Injections 1) to give 4-((2-fluoro-6-(1-methoxyethyl)phenyl)amino)-2-((6-methoxy-2-methyl-1,2,3,4-tetrahydroisoquinolin-7-yl)amino)pyrimidine-5-carbonitrile. MS (ESI): m/z $[M+H]^+$ 463, found 463.

Step 3. To a solution of 4-((2-fluoro-6-(1-methoxyethyl)phenyl)amino)-2-((6-methoxy-2-methyl-1,2,3,4-tetrahydroisoquinolin-7-yl)amino)pyrimidine-5-carbonitrile (7 mg, 0.013 mmol) in DMSO (0.5 mL) was added $K_2CO_3$ (5.58 mg, 0.040 mmol) and hydrogen peroxide (6.55 μL, 0.067 mmol). The reaction was stirred at 25° C. for 1.5 h. The mixture was purified by Prep-Hplc (Instrument ed; Method Column Agela DuraShell C18 150*25 mm*5 um; Condition water (0.04% $NH_3H_2O$+10 mM $NH_4HCO_3$)-ACN Begin B 35 End B 65 Gradient Time (min) 10; 100% B Hold Time (min) 2 FlowRate (mL/min) 25; Injections 1) to give (RAC)-4-((2-fluoro-6-(1-methoxyethyl)phenyl)amino)-2-((6-methoxy-2-methyl-1,2,3,4-tetrahydroisoquinolin-7-yl)amino)pyrimidine-5-carboxamide. MS (ESI): m/z $[M+H]^+$ 481, found 481. $^1H$ NMR (400 MHz, MeOD-$d_4$): δ 8.57 (s, 1H), 7.41-7.52 (m, 2H), 7.35 (br d, J=7.6 Hz, 1H), 7.21 (t, J=8.0 Hz, 1H), 6.65 (s, 1H), 4.52-4.54 (m, 1H), 3.83 (s, 3H), 3.07-3.22 (m, 3H), 2.98-3.00 (m, 2H), 2.75-2.84 (m, 2H), 2.59-2.69 (m, 2H), 2.42 (s, 3H), 1.33 (br d, J=6.0 Hz, 3H).

TABLE 23

Compounds listed in the table below were prepared using the synthetic methods described in the aforementioned Example 23-1. The table provides the compound structure, the name, the calculated and observed masses.

| Example | Structure | Name | Exact Mass $[M + H]^+$ |
|---|---|---|---|
| 23-1 | 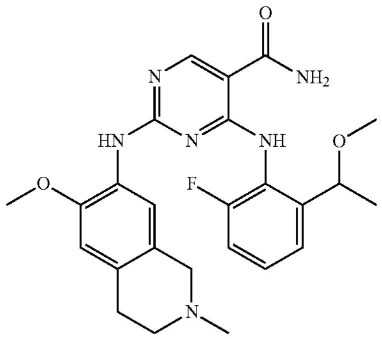 | (RAC)-4-((2-fluoro-6-(1-methoxyethyl)phenyl)amino)-2-((6-methoxy-2-methyl-1,2,3,4-tetrahydroisoquinolin-7-yl)amino)pyrimidine-5-carboxamide | Calc'd 481, found 481 |
| 23-2 | 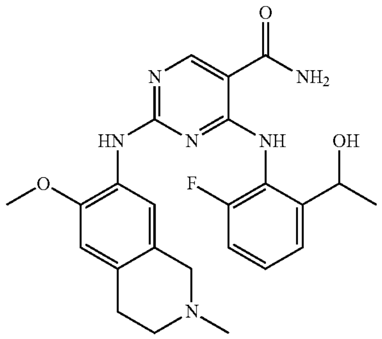 [SMILES: COc1cc2c(cc1Nc1ncc(C(N)=O)c(Nc3c(F)cccc3C(C)O)n1)CN(C)CC2] | (RAC)-4-((2-fluoro-6-(1-hydroxyethyl)phenyl)amino)-2-((6-methoxy-2-methyl-1,2,3,4-tetrahydroisoquinolin-7-yl)amino)pyrimidine-5-carboxamide | Calc'd 467, found 467 |
| 23-3 | 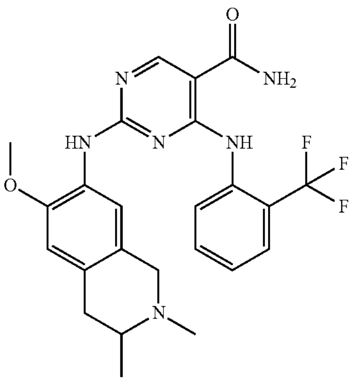 [SMILES: COc1cc2c(cc1Nc1ncc(C(N)=O)c(Nc3ccccc3C(F)(F)F)n1)CN(C)C(C)C2] | (RAC)-2-((6-methoxy-2,3-dimethyl-1,2,3,4-tetrahydroisoquinolin-7-yl)amino)-4-((2-(trifluoromethyl)phenyl)amino)pyrimidine-5-carboxamide | Calc'd 487, found 487 |

Example 13-1. 2-((6-Isopropyl-5-oxo-5,6,7,8-tetrahydro-4H-pyrazolo[1,5-d][1,4]diazepin-2-yl)amino)-4-((1,2,3,4-tetrahydroisoquinolin-5-yl)amino)pyrimidine-5-carboxamide

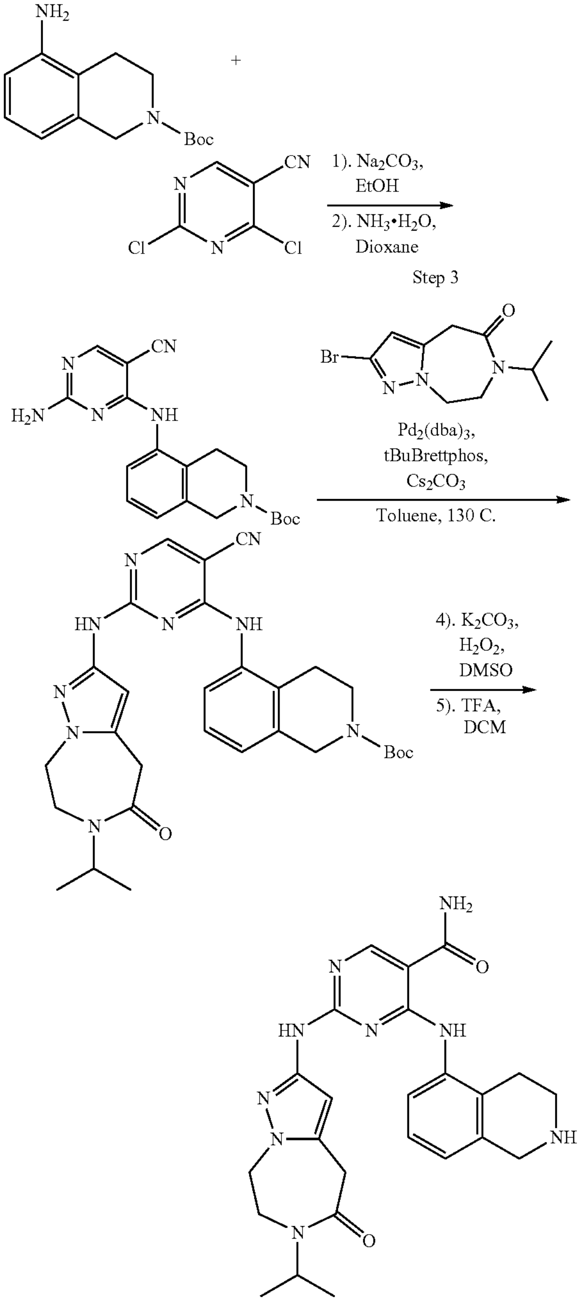

24-1

Step 1. To a mixture of 2,4-dichloropyrimidine-5-carbonitrile (140 mg, 0.805 mmol) and $Na_2CO_3$ (256 mg, 2.414 mmol) in EtOH (3 mL) was added tert-butyl 5-amino-3,4-dihydroisoquinoline-2(1H)-carboxylate (200 mg, 0.805 mmol) at 25'° C. Then the mixture was stirred at 25° C. for 5 h. LCMS showed desired was formed. The mixture was filtered and the filtrate was concentrated in vacuo. The residue was purified by pre-TLC (Pet. ether:EtOAc=3:1) to afford tert-butyl 5-((2-chloro-5-cyanopyrimidin-4-yl)amino)-3,4-dihydroisoquinoline-2(1H)-carboxylate. MS (ESI): m/z $[M+H-56]^+$ 330. found 330.

Step 2. A mixture of tert-butyl 5-((2-chloro-5-cyanopyrimidin-4-yl)amino)-3,4-dihydroisoquinoline-2(1H)-carboxylate (200 mg, 0.518 mmol) and ammonium hydroxide (0.721 mL) in Dioxane (5 mL) were stirred at 60° C. for 13 h. LCMS showed the starting material was consumed up and the target was formed. The reaction mixture was concentrated in vacuum and purified by Pre-TLC (Pet. ether: EtOAc=1:3) to give tert-butyl 5-((2-amino-5-cyanopyrimidin-4-yl)amino)-3,4-dihydroisoquinoline-2(1H)-carboxylate. MS (ESI): m/z $[M+H]^+$ 367, found 367

Step 3. To a mixture of 2-bromo-6-isopropyl-7,8-dihydro-4H-pyrazolo[1,5-d][1,4]diazepin-5(6H)-one (29.7 mg, 0.109 mmol) [prepared as disclosed by: Chan, et al., "ISOQUINOLINES AS INHIBITORS OF HPK1," PCT Patent Publication WO 2018183964 A1; published Oct. 4, 20181, tert-butyl 5-((2-amino-5-cyanopyrimidin-4-yl)amino)-3,4-dihydroisoquinoline-2(1H)-carboxylate (40 mg, 0.109 mmol), $Cs_2CO_3$ (107 mg, 0.327 mmol) in Toluene (1.5 mL) was added di-tert-butyl(2',4',6'-triisopropyl-3,6-dimethoxy-[1,1'-biphenyl]-2-yl)phosphine (26.5 mg, 0.055 mmol) and $Pd_2(dba)_3$ (19.99 mg, 0.022 mmol). Then it was stirred at 130° C. under $N_2$ for 3 h. LCMS showed desired product was formed. The mixture was purified by prep-TLC (EtOAc) to give tert-butyl 5-((5-cyano-2-((6-isopropyl-5-oxo-5,6,7,8-tetrahydro-4H-pyrazolo[1,5-d][1,4]diazepin-2-yl)amino)pyrimidin-4-yl)amino)-3,4-dihydroisoquinoline-2(1H)-carboxylate. MS (ESI): m/z $[M+H]^+$ 558, found 558.

Step 4. To a mixture of tert-butyl 5-((5-cyano-2-((6-isopropyl-5-oxo-5,6,7,8-tetrahydro-4H-pyrazolo[1,5-d][1,4]diazepin-2-yl)amino)pyrimidin-4-yl)amino)-3,4-dihydroisoquinoline-2(1H)-carboxylate (50 mg, 0.090 mmol) and $K_2CO_3$ (62.0 mg, 0.448 mmol) in DMSO (1 mL) was added $H_2O_2$ (0.079 mL, 0.897 mmol) at 25° C. The mixture was stirred at 25° C. for 2 h. LCMS showed the product was formed. The mixture was quenched with water (15 mL), extracted with EtOAc:MeOH=10:1 (10 mL*2). The combined organic layers were washed with brine, dried over $Na_2SO_4$, filtered and concentrated in vacuo to afford crude tert-butyl 5-((5-carbamoyl-2-((6-isopropyl-5-oxo-5,6,7,8-tetrahydro-4H-pyrazolo[1,5-d][1,4]diazepin-2-yl)amino)pyrimidin-4-yl)amino)-3,4-dihydroisoquinoline-2(1H)-carboxylate, which was used directly in next step without further purification. MS (ESI): m/z $[M+H]^+$ 576, found 576.

Step 5. A solution of tert-butyl 5-((5-carbamoyl-2-((6-isopropyl-5-oxo-5,6,7,8-tetrahydro-4H-pyrazolo[1,5-d][1,4]diazepin-2-yl)amino)pyrimidin-4-yl)amino)-3,4-dihydroisoquinoline-2(1H)-carboxylate (45 mg, crude) in DCM (1 mL) and TFA (1 mL) was stirred at 25° C. for 1 h. LCMS showed the product was formed. The mixture was concentrated in vacuo, the residue was purified by pre-HPLC (Column YMC-Actus Triart C18 150*30 mm*5 um, Condition water (0.1% TFA)-ACN Begin B 3. End B 33 Gradient Time (min) 11, 100% B Hold Time (min) 1.1 FlowRate (ml/min) 40, Injections 2) to afford 2-((6-isopropyl-5-oxo-5,6,7,8-tetrahydro-4H-pyrazolo[1,5-d][1,4]diazepin-2-yl)amino)-4-((1,2,3,4-tetrahydroisoquinolin-5-yl)amino)pyrimidine-5-carboxamide. MS (ESI): m/z calc'd for $C_{24}H_{30}N_9O_2$ $[M+H]^+$ 476, found 476. $^1H$ NMR (400 MHz, MeOD-$d_4$) δ ppm 8.62 (s, 1H), 7.89 (br s, 1H), 7.42 (br t, J=7.6 Hz, 1H), 7.23 (br d, J=7.2 Hz, 1H), 5.92 (br s, 1H), 4.71-4.78 (m, 1H), 4.45 (s, 2H), 4.21-4.25 (m, 2H), 3.95-4.01 (m, 2H), 3.82-3.85 (m, 2H), 3.51-3.53 (m, 2H), 3.04-3.06 (m, 2H), 1.21 (d, J=7.2 Hz, 6H).

TABLE 24

| Example | Structure | Name | Exact Mass [M + H]+ |
|---|---|---|---|
| Compounds listed in the table below were prepared using the synthetic methods described in the aforementioned Example 24-1. The table provides the compound structure, the name, the calculated and observed masses. | | | |
| 24-1 | 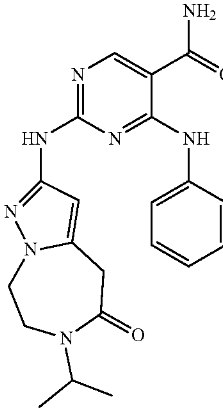 | 2-((6-isopropyl-5-oxo-5,6,7,8-tetrahydro-4H-pyrazolo[1,5-d][1,4]diazepin-2-yl)amino)-4-((1,2,3,4-tetrahydroisoquinolin-5-yl)amino)pyrimidine-5-carboxamide | Calc'd 476, found 476 |

Example 14-1. 4-((1-Oxo-1,2,3,4-tetrahydroisoquinolin-5-yl)amino)-2-(phenylamino)pyrimidine-5-carboxamide, and related compounds

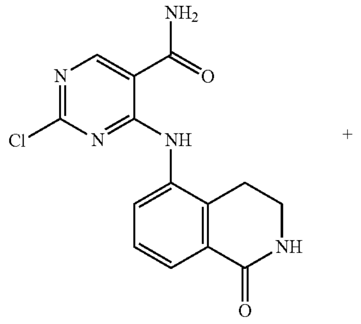

from Ex. 7-1

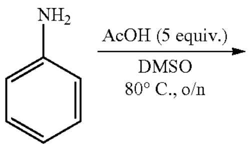

-continued

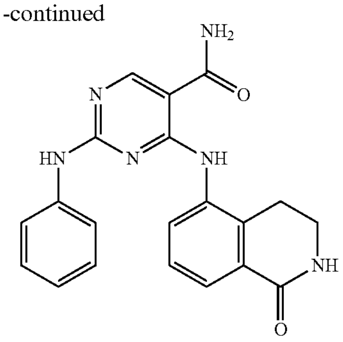

25-1

A stock solution of 2-chloro-4-((1-oxo-1,2,3,4-tetrahydroisoquinolin-5-yl)amino)pyrimidine-5-carboxamide (from Ex. 7-1) (10 mg, 0.032 mmol) in DMSO (25 ul) was dispensed into 96. 1 mL glass vials across a 96 well-plate array, containing the amine (aniline: 6.0 mg, 0.064 mmol) in DMSO (25 μl). Acetic acid (9.3 μl, 0.16 mmol) was added to each well via pipette and plate was capped and sealed shut (screws). The plate(s) was stirred at 80° C. overnight. Upon completion the vials were diluted with DMSO (100 ul) and purified by high-throughput micro-isolation to afford the desired compound with sufficient purity. MS (ESI): m/z calc'd for $C_{20}H_{19}N_6O_2$ [M+H]+ 375, found 375. $^1H$ NMR (600 MHz, DMSO-d6) δ 1H NMR (600 MHz, DMSO-d6) δ 1H NMR (499 MHz, DMSO-d6) δ 11.62 (s, 1H), 10.43 (br s, 1H), 8.77 (s, 1H), 8.33 (s, 1H), 8.00 (m, 2H), 7.93-7.81 (m, 2H), 7.49-7.35 (m, 3H), 7.18 (m, 1H), 7.05 (d, J=7.3 Hz, 1H), 3.42-3.35 (m, 1H), 3.32 (dt, J=6.5, 3.1 Hz, 2H), 2.81 (t, J=6.5 Hz, 2H).

TABLE 25

| Compounds listed in the table below were prepared using the synthetic methods described in the aforementioned Example 25-1. The table provides the compound structure, the name, the calculated and observed masses. | | | |
|---|---|---|---|
| Example | Structure | Name | Exact Mass [M + H]$^+$ |
| 25-1 | 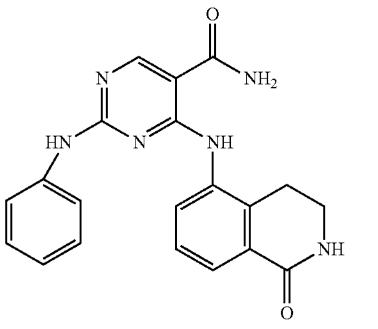 [SMILES: NC(=O)c1cnc(Nc2ccccc2)nc1Nc1cccc2c1CCNC2=O] | 4-[(1-oxo-1,2,3,4-tetrahydroisoquinolin-5-yl)amino]-2-(phenylamino)pyrimidine-5-carboxamide | Calc'd 375, found 375 |
| 25-2 | 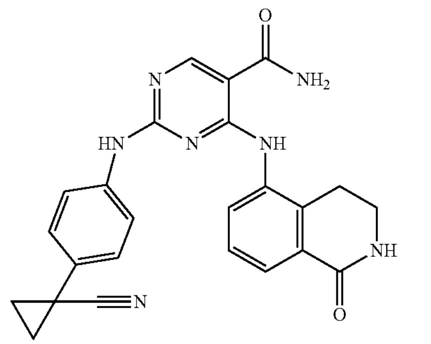 [SMILES: N#CC1(c2ccc(Nc3ncc(C(N)=O)c(Nc4cccc5c4CCNC5=O)n3)cc2)CC1] | 2-{[4-(1-cyanocyclopropyl)phenyl]amino}-4-[(1-oxo-1,2,3,4-tetrahydroisoquinolin-5-yl)amino]pyrimidine-5-carboxamide | Calc'd 440, found 440 |
| 25-3 | 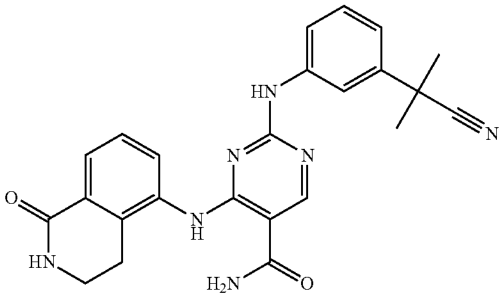 [SMILES: CC(C)(C#N)c1cccc(Nc2ncc(C(N)=O)c(Nc3cccc4c3CCNC4=O)n2)c1] | 2-{[3-(2-cyanopropan-2-yl)phenyl]amino}-4-[(1-oxo-1,2,3,4-tetrahydroisoquinolin-5-yl)amino]pyrimidine-5-carboxamide | Calc'd 442, found 442 |
| 25-4 | 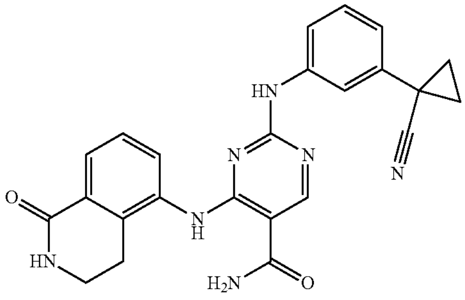 [SMILES: N#CC1(c2cccc(Nc3ncc(C(N)=O)c(Nc4cccc5c4CCNC5=O)n3)c2)CC1] | 2-{[3-(1-cyanocyclopropyl)phenyl]amino}-4-[(1-oxo-1,2,3,4-tetrahydroisoquinolin-5-yl)amino]pyrimidine-5-carboxamide | Calc'd 440, found 440 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass $[M + H]^+$ |
|---|---|---|---|
| 25-5 | 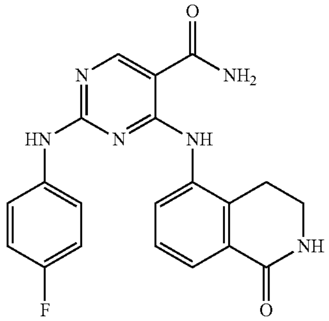 [SMILES: NC(=O)c1cnc(Nc2ccc(F)cc2)nc1Nc1cccc2c1CCNC2=O] | 2-[(4-fluorophenyl)amino]-4-[(1-oxo-1,2,3,4-tetrahydroisoquinolin-5-yl)amino]pyrimidine-5-carboxamide | Calc'd 393, found 393 |
| 25-6 | 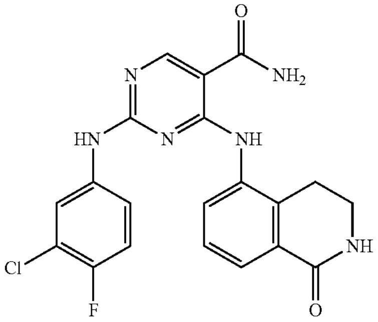 [SMILES: NC(=O)c1cnc(Nc2ccc(F)c(Cl)c2)nc1Nc1cccc2c1CCNC2=O] | 2-[(3-chloro-4-fluorophenyl)amino]-4-[(1-oxo-1,2,3,4-tetrahydroisoquinolin-5-yl)amino]pyrimidine-S-carboxamide | Calc'd 427, found 427 |
| 25-7 | 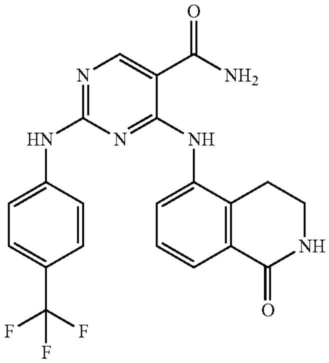 [SMILES: NC(=O)c1cnc(Nc2ccc(C(F)(F)F)cc2)nc1Nc1cccc2c1CCNC2=O] | 4-[(1-oxo-1,2,3,4-tetrahydroisoquinolin-5-yl)amino]-2-{[4-(trifluoromethyl)phenyl]amino}pyrimidine-5-carboxamide | Calc'd 443, found 443 |
| 25-8 | 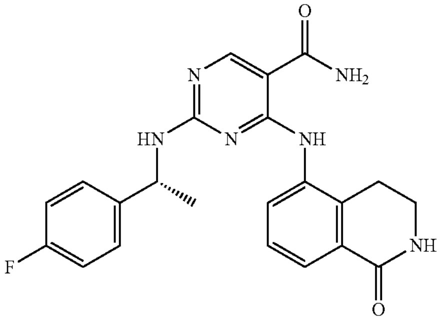 [SMILES: C[C@@H](Nc1ncc(C(N)=O)c(Nc2cccc3c2CCNC3=O)n1)c1ccc(F)cc1] | 2-{[(1R)-1-(4-fluorophenyl)ethyl]amino}-4-[(1-oxo-1,2,3,4-tetrahydroisoquinolin-5-yl)amino]pyrimidine-5-carboxamide | Calc'd 421, found 421 |

TABLE 25-continued

| Compounds listed in the table below were prepared using the synthetic methods described in the aforementioned Example 25-1. The table provides the compound structure, the name, the calculated and observed masses. | | | |
|---|---|---|---|
| Example | Structure | Name | Exact Mass $[M + H]^+$ |
| 25-9 | 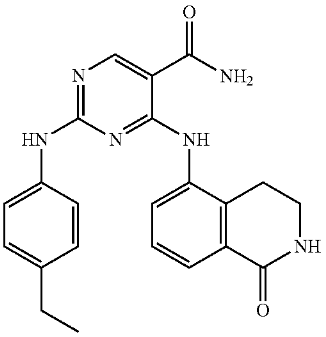 [SMILES: CCc1ccc(Nc2ncc(C(N)=O)c(Nc3cccc4c3CCNC4=O)n2)cc1] | 2-[(4-ethylphenyl)amino]-4-[(1-oxo-1,2,3,4-tetrahydroisoquinolin-5-yl)amino]pyrimidine-5-carboxamide | Calc'd 403, found 403 |
| 25-10 | 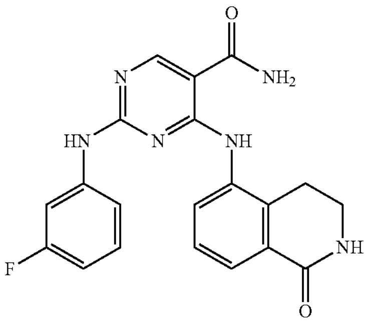 [SMILES: NC(=O)c1cnc(Nc2cccc(F)c2)nc1Nc1cccc2c1CCNC2=O] | 2-[(3-fluorophenyl)amino]-4-[(1-oxo-1,2,3,4-tetrahydroisoquinolin-5-yl)amino]pyrimidine-5-carboxamide | Calc'd 393, found 393 |
| 25-11 | 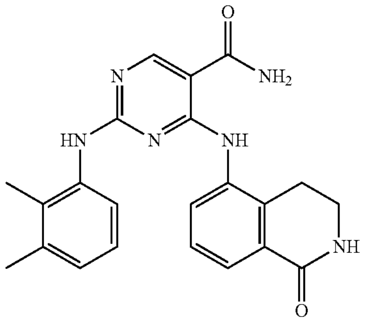 [SMILES: Cc1cccc(Nc2ncc(C(N)=O)c(Nc3cccc4c3CCNC4=O)n2)c1C] | 2-[(2,3-dimethylphenyl)amino]-4-[(1-oxo-1,2,3,4-tetrahydroisoquinolin-5-yl)amino]pyrimidine-5-carboxamide | Calc'd 403, found 403 |
| 25-12 | 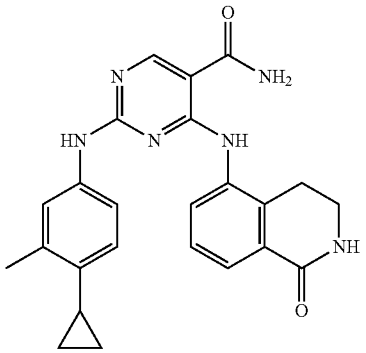 [SMILES: Cc1cc(Nc2ncc(C(N)=O)c(Nc3cccc4c3CCNC4=O)n2)ccc1C1CC1] | 2-[(4-cyclopropyl-3-methylphenyl)amino]-4-[(1-oxo-1,2,3,4-tetrahydroisoquinolin-5-yl)amino]pyrimidine-5-carboxamide | Calc'd 429, found 429 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass $[M + H]^+$ |
|---|---|---|---|
| 25-13 | 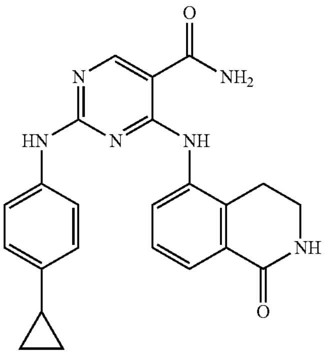 [SMILES: NC(=O)c1cnc(Nc2ccc(C3CC3)cc2)nc1Nc1cccc2c1CCNC2=O] | 2-[(4-cyclopropylphenyl)amino]-4-[(1-oxo-1,2,3,4-tetrahydroisoquinolin-5-yl)amino]pyrimidine-5-carboxamide | Calc'd 415, found 415 |
| 25-14 | 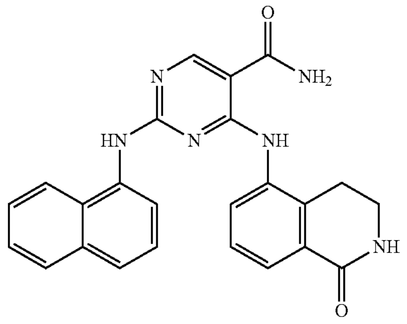 [SMILES: NC(=O)c1cnc(Nc2cccc3ccccc23)nc1Nc1cccc2c1CCNC2=O] | 2-[(naphthalen-1-yl)amino]-4-[(1-oxo-1,2,3,4-tetrahydroisoquinolin-5-yl)amino]pyrimidine-5-carboxamide | Calc'd 425, found 425 |
| 25-15 | 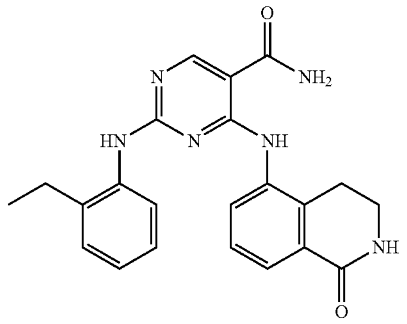 [SMILES: CCc1ccccc1Nc1ncc(C(N)=O)c(Nc2cccc3c2CCNC3=O)n1] | 2-[(2-ethylphenyl)amino]-4-[(1-oxo-1,2,3,4-tetrahydroisoquinolin-5-yl)amino]pyrimidine-5-carboxamide | Calc'd 403, found 403 |
| 25-16 | 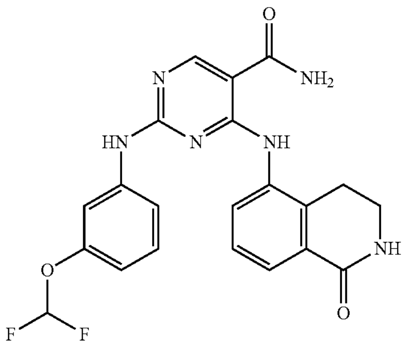 [SMILES: NC(=O)c1cnc(Nc2cccc(OC(F)F)c2)nc1Nc1cccc2c1CCNC2=O] | 2-{[3-(difluoromethoxy)phenyl]amino}-4-[(1-oxo-1,2,3,4-tetrahydroisoquinolin-5-yl)amino]pyrimidine-5-carboxamide | Calc'd 441, found 441 |

TABLE 25-continued

| Compounds listed in the table below were prepared using the synthetic methods described in the aforementioned Example 25-1. The table provides the compound structure, the name, the calculated and observed masses. | | | |
|---|---|---|---|
| Example | Structure | Name | Exact Mass $[M + H]^+$ |
| 25-17 | 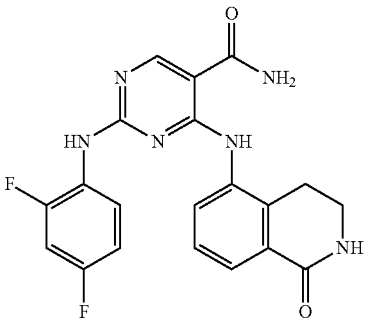 [SMILES: NC(=O)c1cnc(Nc2ccc(F)cc2F)nc1Nc1cccc2c1CCNC2=O] | 2-[(2,4-difluorophenyl)amino]-4-[(1-oxo-1,2,3,4-tetrahydroisoquinolin-5-yl)amino]pyrimidine-5-carboxamide | Calc'd 411, found 411 |
| 25-18 | 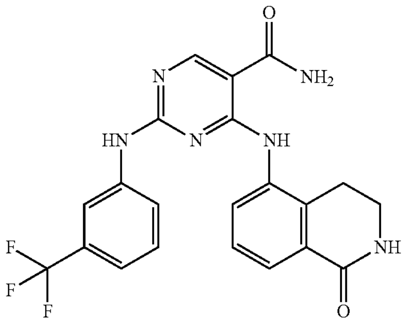 [SMILES: NC(=O)c1cnc(Nc2cccc(C(F)(F)F)c2)nc1Nc1cccc2c1CCNC2=O] | 4-[(1-oxo-1,2,3,4-tetrahydroisoquinolin-5-yl)amino]-2-{[3-(trifluoromethyl)phenyl]amino}pyrimidine-5-carboxamide | Calc'd 443, found 443 |
| 25-19 | 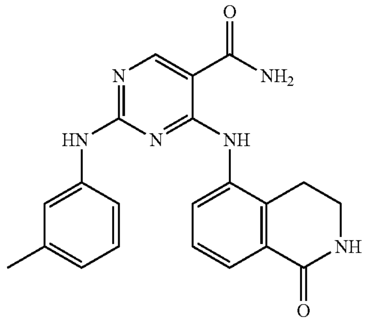 [SMILES: Cc1cccc(Nc2ncc(C(N)=O)c(Nc3cccc4c3CCNC4=O)n2)c1] | 2-[(3-methylphenyl)amino]-4-[(1-oxo-1,2,3,4-tetrahydroisoquinolin-5-yl)amino]pyrimidine-5-carboxamide | Calc'd 389, found 389 |
| 25-20 | 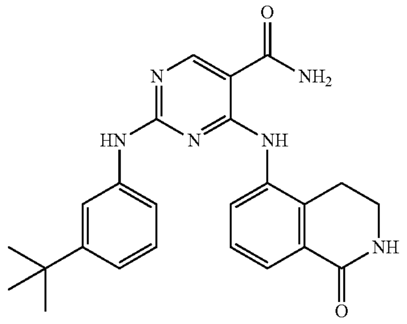 [SMILES: CC(C)(C)c1cccc(Nc2ncc(C(N)=O)c(Nc3cccc4c3CCNC4=O)n2)c1] | 2-[(3-tert-butylphenyl)amino]-4-[(1-oxo-1,2,3,4-tetrahydroisoquinolin-5-yl)amino]pyrimidine-5-carboxamide | Calc'd 431, found 431 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass [M + H]$^+$ |
|---|---|---|---|
| 25-21 | 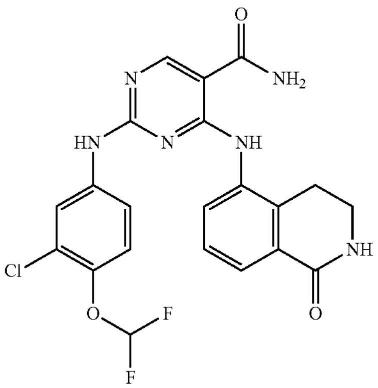 [SMILES: NC(=O)c1cnc(Nc2ccc(OC(F)F)c(Cl)c2)nc1Nc1cccc2c1CCNC2=O] | 2-{[3-chloro-4-(difluoromethoxy)phenyl]amino}-4-[(1-oxo-1,2,3,4-tetrahydroisoquinolin-5-yl)amino]pyrimidine-5-carboxamide | Calc'd 475, found 475 |
| 25-22 | 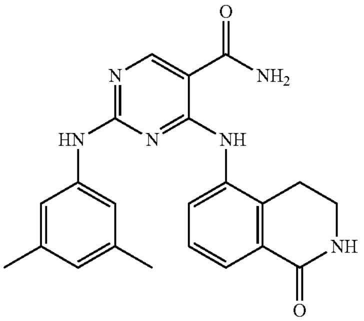 [SMILES: Cc1cc(C)cc(Nc2ncc(C(N)=O)c(Nc3cccc4c3CCNC4=O)n2)c1] | 2-[(3,5-dimethylphenyl)amino]-4-[(1-oxo-1,2,3,4-tetrahydroisoquinolin-5-yl)amino]pyrimidine-5-carboxamide | Calc'd 403, found 403 |
| 25-23 | 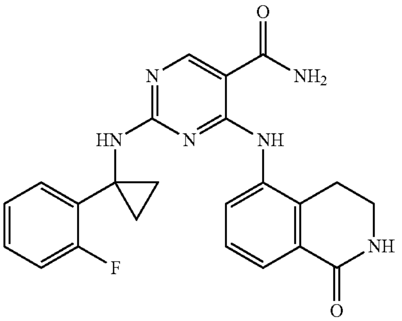 [SMILES: NC(=O)c1cnc(NC2(c3ccccc3F)CC2)nc1Nc1cccc2c1CCNC2=O] | 2-{[1-(2-fluorophenyl)cyclopropyl]amino}-4-[(1-oxo-1,2,3,4-tetrahydroisoquinolin-5-yl)amino]pyrimidine-5-carboxamide | Calc'd 433, found 433 |
| 25-24 | 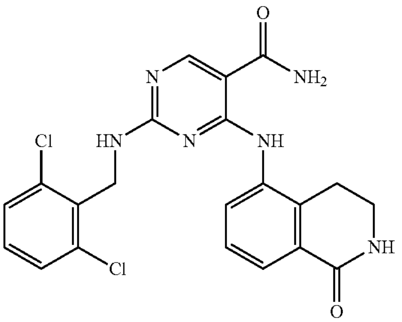 [SMILES: NC(=O)c1cnc(NCc2c(Cl)cccc2Cl)nc1Nc1cccc2c1CCNC2=O] | 2-{[(2,6-dichlorophenyl)methyl]amino}-4-[(1-oxo-1,2,3,4-tetrahydroisoquinolin-5-yl)amino]pyrimidine-5-carboxamide | Calc'd 457, found 457 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass $[M + H]^+$ |
|---|---|---|---|
| 25-25 | 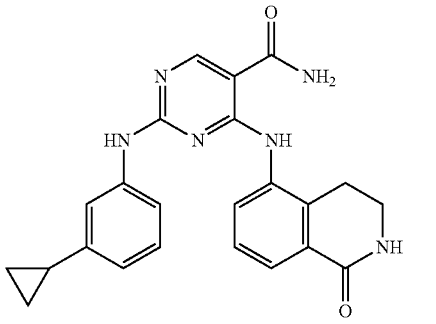 [SMILES: NC(=O)c1cnc(Nc2cccc(C3CC3)c2)nc1Nc1cccc2c1CCNC2=O] | 2-[(3-cyclopropylphenyl)amino]-4-[(1-oxo-1,2,3,4-tetrahydroisoquinolin-5-yl)amino]pyrimidine-5-carboxamide | Calc'd 415, found 415 |
| 25-26 | 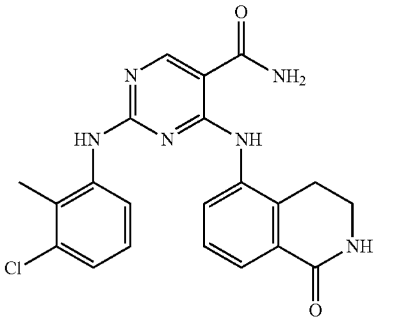 [SMILES: Cc1c(Cl)cccc1Nc1ncc(C(N)=O)c(Nc2cccc3c2CCNC3=O)n1] | 2-[(3-chloro-2-methylphenyl)amino]-4-[(1-oxo-1,2,3,4-tetrahydroisoquinolin-5-yl)amino]pyrimidine-5-carboxamide | Calc'd 423, found 423 |
| 25-27 | 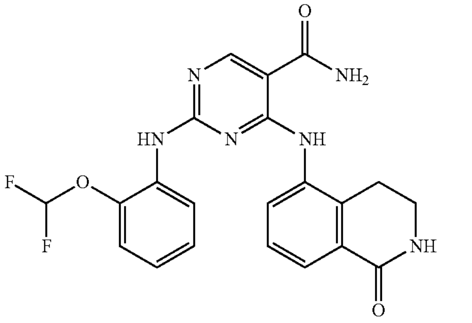 [SMILES: NC(=O)c1cnc(Nc2ccccc2OC(F)F)nc1Nc1cccc2c1CCNC2=O] | 2-{[2-(difluoromethoxy)phenyl]amino}-4-[(1-oxo-1,2,3,4-tetrahydroisoquinolin-5-yl)amino]pyrimidine-5-carboxamide | Calc'd 441, found 441 |
| 25-28 | 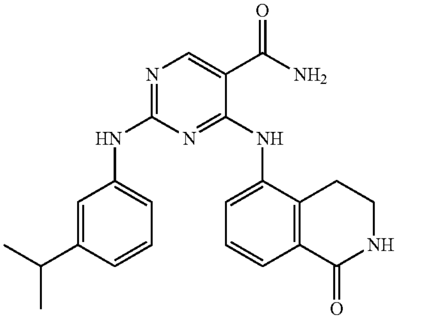 [SMILES: CC(C)c1cccc(Nc2ncc(C(N)=O)c(Nc3cccc4c3CCNC4=O)n2)c1] | 4-[(1-oxo-1,2,3,4-tetrahydroisoquinolin-5-yl)amino]-2-{[3-(propan-2-yl)phenyl]amino}pyrimidine-5-carboxamide | Calc'd 417, found 417 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass $[M + H]^+$ |
|---|---|---|---|
| 25-29 | 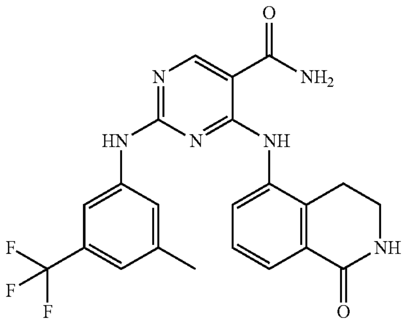 [SMILES: Cc1cc(Nc2ncc(C(N)=O)c(Nc3cccc4c3CCNC4=O)n2)cc(C(F)(F)F)c1] | 2-{[3-methyl-5-(trifluoromethyl)phenyl]amino}-4-[(1-oxo-1,2,3,4-tetrahydroisoquinolin-5-yl)amino]pyrimidine-5-carboxamide | Calc'd 457, found 457 |
| 25-30 | 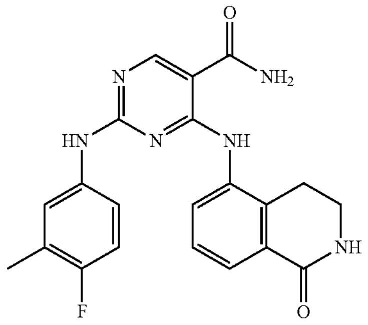 [SMILES: Cc1cc(Nc2ncc(C(N)=O)c(Nc3cccc4c3CCNC4=O)n2)ccc1F] | 2-[(4-fluoro-3-methylphenyl)amino]-4-[(1-oxo-1,2,3,4-tetrahydroisoquinolin-5-yl)amino]pyrimidine-5-carboxamide | Calc'd 407, found 407 |
| 25-31 | 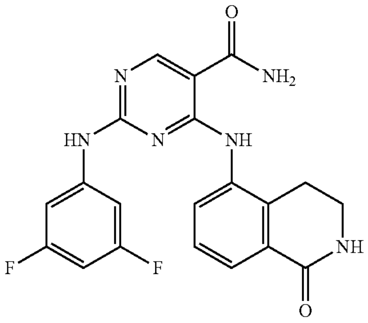 [SMILES: NC(=O)c1cnc(Nc2cc(F)cc(F)c2)nc1Nc1cccc2c1CCNC2=O] | 2-[(3,5-difluorophenyl)amino]-4-[(1-oxo-1,2,3,4-tetrahydroisoquinolin-5-yl)amino]pyrimidine-5-carboxamide | Calc'd 411, found 411 |
| 25-32 | 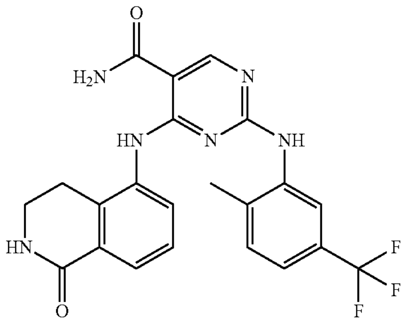 [SMILES: Cc1ccc(C(F)(F)F)cc1Nc1ncc(C(N)=O)c(Nc2cccc3c2CCNC3=O)n1] | 2-{[2-methyl-5-(trifluoromethyl)phenyl]amino}-4-[(1-oxo-1,2,3,4-tetrahydroisoquinolin-5-yl)amino]pyrimidine-5-carboxamide | Calc'd 457, found 457 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass $[M + H]^+$ |
|---|---|---|---|
| 25-33 | 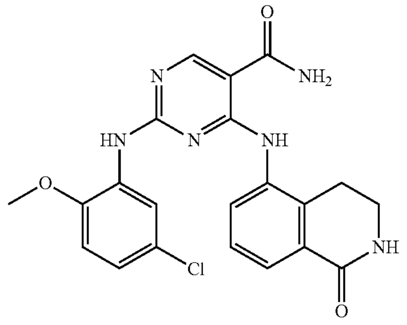 [SMILES: COc1ccc(Cl)cc1Nc1ncc(C(N)=O)c(Nc2cccc3c2CCNC3=O)n1] | 2-[(5-chloro-2-methoxyphenyl)amino]-4-[(1-oxo-1,2,3,4-tetrahydroisoquinolin-5-yl)amino]pyrimidine-5-carboxamide | Calc'd 439, found 439 |
| 25-34 | 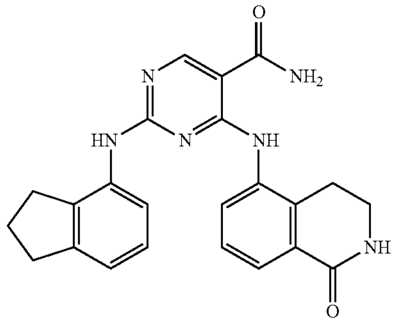 | 2-[(2,3-dihydro-1H-inden-4-yl)amino]-4-[(1-oxo-1,2,3,4-tetrahydroisoquinolin-5-yl)amino]pyrimidine-5-carboxamide | Calc'd 415, found 415 |
| 25-35 | 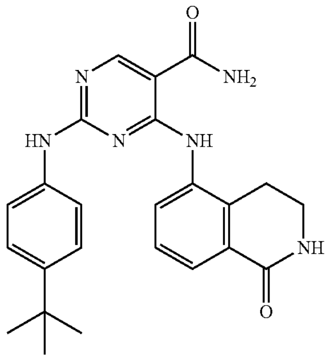 [SMILES: CC(C)(C)c1ccc(Nc2ncc(C(N)=O)c(Nc3cccc4c3CCNC4=O)n2)cc1] | 2-[(4-tert-butylphenyl)amino]-4-[(1-oxo-1,2,3,4-tetrahydroisoquinolin-5-yl)amino]pyrimidine-5-carboxamide | Calc'd 431, found 431 |
| 25-36 | 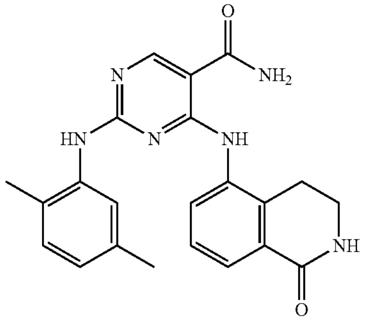 [SMILES: Cc1ccc(C)c(Nc2ncc(C(N)=O)c(Nc3cccc4c3CCNC4=O)n2)c1] | 2-[(2,5-dimethylphenyl)amino]-4-[(1-oxo-1,2,3,4-tetrahydroisoquinolin-5-yl)amino]pyrimidine-5-carboxamide | Calc'd 403, found 403 |

TABLE 25-continued

| Compounds listed in the table below were prepared using the synthetic methods described in the aforementioned Example 25-1. The table provides the compound structure, the name, the calculated and observed masses. | | | |
|---|---|---|---|
| Example | Structure | Name | Exact Mass $[M + H]^+$ |
| 25-37 | 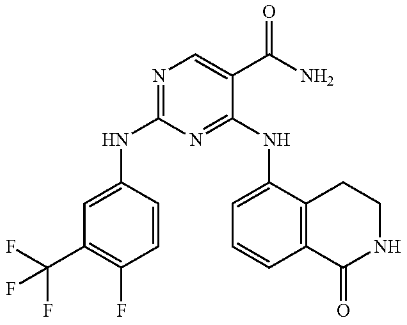 [SMILES: NC(=O)c1cnc(Nc2ccc(F)c(C(F)(F)F)c2)nc1Nc1cccc2c1CCNC2=O] | 2-{[4-fluoro-3-(trifluoromethyl)phenyl]amino}-4-[(1-oxo-1,2,3,4-tetrahydroisoquinolin-5-yl)amino]pyrimidine-5-carboxamide | Calc'd 461, found 461 |
| 25-38 | 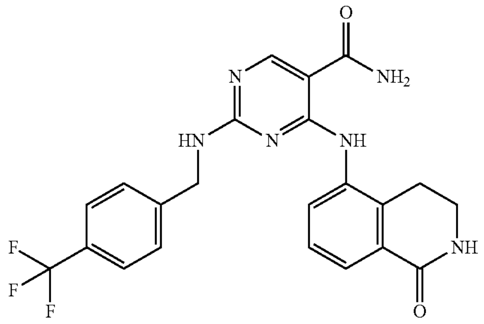 [SMILES: NC(=O)c1cnc(NCc2ccc(C(F)(F)F)cc2)nc1Nc1cccc2c1CCNC2=O] | 4-[(1-oxo-1,2,3,4-tetrahydroisoquinolin-5-yl)amino]-2-({[4-(trifluoromethyl)phenyl]methyl}amino)pyrimidine-5-carboxamide | Calc'd 457, found 457 |
| 25-39 | 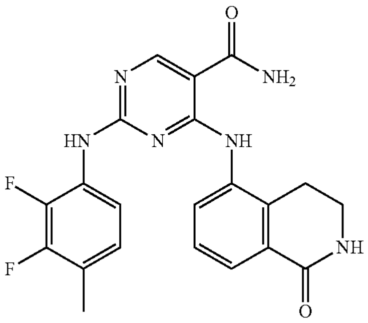 [SMILES: Cc1ccc(Nc2ncc(C(N)=O)c(Nc3cccc4c3CCNC4=O)n2)c(F)c1F] | 2-[(2,3-difluoro-4-methylphenyl)amino]-4-[(1-oxo-1,2,3,4-tetrahydroisoquinolin-5-yl)amino]pyrimidine-5-carboxamide | Calc'd 425, found 425 |
| 25-40 | 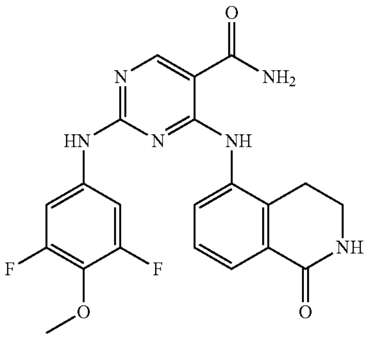 [SMILES: COc1c(F)cc(Nc2ncc(C(N)=O)c(Nc3cccc4c3CCNC4=O)n2)cc1F] | 2-[(3,5-difluoro-4-methoxyphenyl)amino]-4-[(1-oxo-1,2,3,4-tetrahydroisoquinolin-5-yl)amino]pyrimidine-5-carboxamide | Calc'd 441, found 441 |

TABLE 25-continued

Compounds listed in the table below were prepared using the synthetic methods described in the aforementioned Example 25-1. The table provides the compound structure, the name, the calculated and observed masses.

| Example | Structure | Name | Exact Mass [M + H]+ |
|---|---|---|---|
| 25-41 | 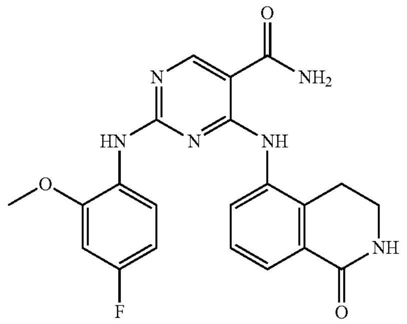 [SMILES: COc1cc(F)ccc1Nc1ncc(C(N)=O)c(Nc2cccc3c2CCNC3=O)n1] | 2-[(4-fluoro-2-methoxyphenyl)amino]-4-[(1-oxo-1,2,3,4-tetrahydroisoquinolin-5-yl)amino]pyrimidine-5-carboxamide | Calc'd 423, found 423 |
| 25-42 | 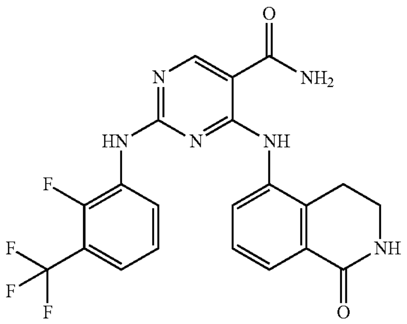 [SMILES: NC(=O)c1cnc(Nc2cccc(C(F)(F)F)c2F)nc1Nc1cccc2c1CCNC2=O] | 2-{[2-fluoro-3-(trifluoromethyl)phenyl]amino}-4-[(1-oxo-1,2,3,4-tetrahydroisoquinolin-5-yl)amino]pyrimidine-5-carboxamide | Calc'd 461, found 461 |
| 25-43 | 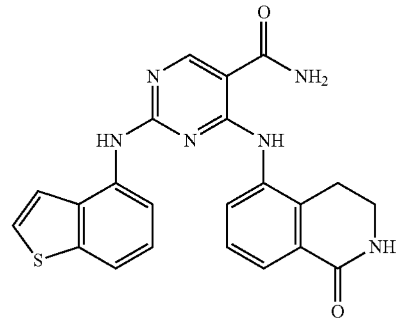 [SMILES: NC(=O)c1cnc(Nc2cccc3sccc23)nc1Nc1cccc2c1CCNC2=O] | 2-[(1-benzothiophen-4-yl)amino]-4-[(1-oxo-1,2,3,4-tetrahydroisoquinolin-5-yl)amino]pyrimidine-5-carboxamide | Calc'd 431, found 431 |
| 25-44 | 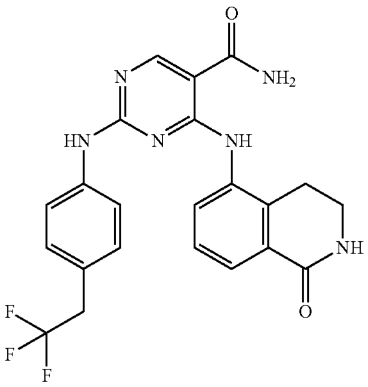 [SMILES: NC(=O)c1cnc(Nc2ccc(CC(F)(F)F)cc2)nc1Nc1cccc2c1CCNC2=O] | 4-[(1-oxo-1,2,3,4-tetrahydroisoquinolin-5-yl)amino]-2-{[4-(2,2,2-trifluoroethyl)phenyl]amino}pyrimidine-5-carboxamide | Calc'd 457, found 457 |

TABLE 25-continued

| Example | Structure | Name | Exact Mass [M + H]$^+$ |
|---|---|---|---|
| | Compounds listed in the table below were prepared using the synthetic methods described in the aforementioned Example 25-1. The table provides the compound structure, the name, the calculated and observed masses. | | |
| 25-45 | 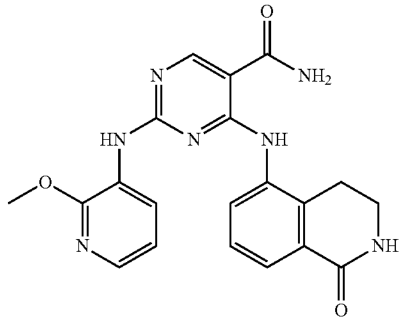 [SMILES: COc1ncccc1Nc1ncc(C(N)=O)c(Nc2cccc3c2CCNC3=O)n1] | 2-[(2-methoxypyridin-3-yl)amino]-4-[(1-oxo-1,2,3,4-tetrahydroisoquinolin-5-yl)amino]pyrimidine-S-carboxamide | Calc'd 406, found 406 |

Example 15-1. 4-(Cycloheptylamino)-2-((6-methoxy-2-methyl-1,2,3,4-tetrahydro-isoquinolin-7-yl)amino)pyrimidine-5-carboxamide

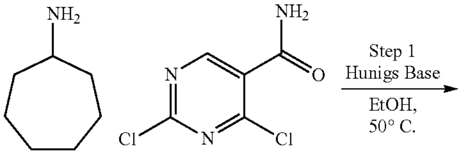

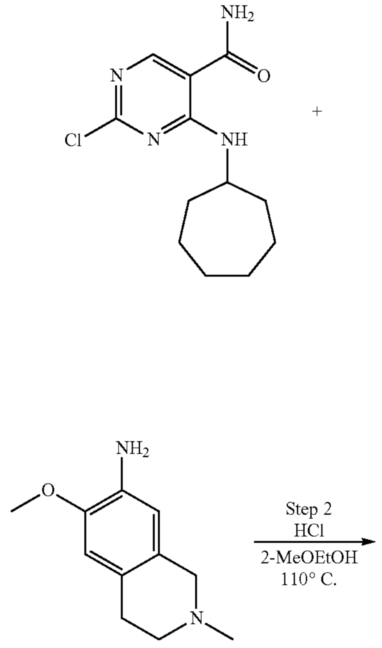

I-2

-continued

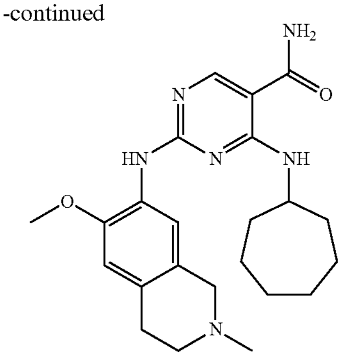

26-1

Step 1. To a 2 dram vial with a stirbar. N-Ethyl-N-isopropylpropan-2-amine (40.9 μl, 0.234 mmol) was added to a solution of cycloheptanamine (17.69 mg, 0.156 mmol) and 2,4-dichloropyrimidine-5-carboxamide (30 mg, 0.156 mmol) in Ethanol (446 μl). The mixture was capped and stirred at 50° C. for 3 h. The mixture was diluted with DCM (2 mL) and water (2 mL), capped, and stirred vigorously for 5 min. The mixture was filtered through a phase separator and the organics were concentrated to afford 2-chloro-4-(cycloheptylamino)pyrimidine-5-carboxamide as a yellow oil. The compound was sufficiently pure and carried on crude to the subsequent reaction. MS (ESI): m/z calc'd for $C_{12}H_{18}ClN_4O$ [M+H]$^+$ 269. found 269.

Step 2. 2-Chloro-4-(cycloheptylamino)pyrimidine-5-carboxamide (23 mg, 0.086 mmol) was added to a vial containing 6-methoxy-2-methyl-1,2,3,4-tetrahydroisoquinolin-7-amine (1-2) (18.10 mg, 0.094 mmol) in 2-Methoxymethanol (245 μl). HCl in Ethanol (1.25M) (171 μl, 0.214 mmol) was added via syringe and the mixture was stirred at 110° C. for 3 h. Upon completion as observed by LCMS analysis, the mixture was cooled, diluted with DMA (2 mL), filtered, and purified by reverse phase preparative HPLC (Purification Method A or Purification Method B, depending on final compound properties), to afford 4-(cycloheptylamino)-2-((6-methoxy-2-methyl-1,2,3,4-tetrahydroisoquinolin-7-yl)amino)pyrimidine-5-carboxamide as a solid. MS (ESI): m/z calc'd for $C_{23}H_{33}N_6O_2$ [M+H]$^+$ 425, found 425. $^1$H NMR (600 MHz, DMSO-d6) δ 1H NMR (600

MHz, DMSO-d6) δ 10.26 (s, 1H), 9.82 (s, 1H), 8.52 (s, 1H), 8.06 (s, 1H), 7.82 (s, 1H), 7.51 (s, 1H), 7.01 (s, 1H), 4.40 (d, J=14.6 Hz, 1H), 4.23 (s, 1H), 4.17-4.06 (m, 1H), 3.86 (s, 3H), 3.67 (s, 1H), 3.34 (s, 1H), 3.13 (d, J=8.0 Hz, 1H), 3.04 (d, J=16.9 Hz, 1H), 2.94 (s, 3H), 1.89 (s, 2H), 1.61-1.55 (m, 8H), 1.49 (s, 2H).

TABLE 26

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
|---|---|---|---|
| 26-1 | 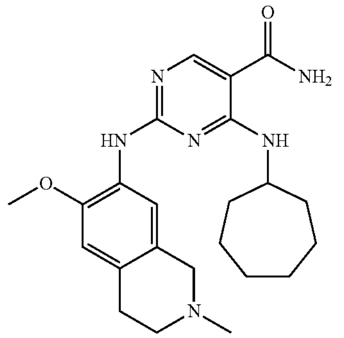 [SMILES: COc1cc2c(cc1Nc1ncc(C(N)=O)c(NC3CCCCCC3)n1)CN(C)CC2] | 4-(cycloheptylamino)-2-[(6-methoxy-2-methyl-1,2,3,4-tetrahydroisoquinolin-7-yl)amino]pyrimidine-5-carboxamide | Calc'd 425, found 425 |
| 26-2 | 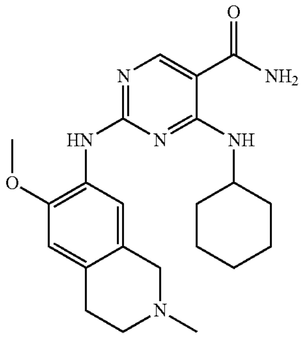 [SMILES: COc1cc2c(cc1Nc1ncc(C(N)=O)c(NC3CCCCC3)n1)CN(C)CC2] | 4-(cyclohexylamino)-2-[(6-methoxy-2-methyl-1,2,3,4-tetrahydroisoquinolin-7-yl)amino]pyrimidine-5-carboxamide | Calc'd 411, found 411 |
| 26-3 | 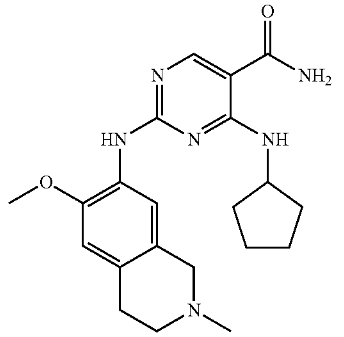 [SMILES: COc1cc2c(cc1Nc1ncc(C(N)=O)c(NC3CCCC3)n1)CN(C)CC2] | 4-(cyclopentylamino)-2-[(6-methoxy-2-methyl-1,2,3,4-tetrahydroisoquinolin-7-yl)amino]pyrimidine-5-carboxamide | Calc'd 397, found 397 |
| 26-4 | 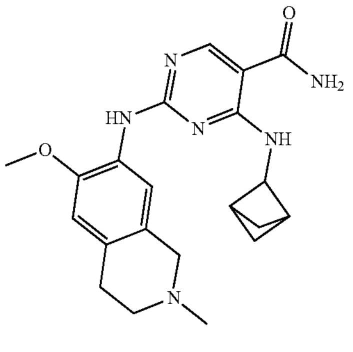 [SMILES: COc1cc2c(cc1Nc1ncc(C(N)=O)c(NC3C4CC3C4)n1)CN(C)CC2] | 4-[(bicyclo[1.1.1]pentan-2-yl)amino]-2-[(6-methoxy-2-methyl-1,2,3,4-tetrahydroisoquinolin-7-yl)amino]pyrimidine-5-carboxamide | Calc'd 395, found 395 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]$^+$ |
|---|---|---|---|
| 26-5 | 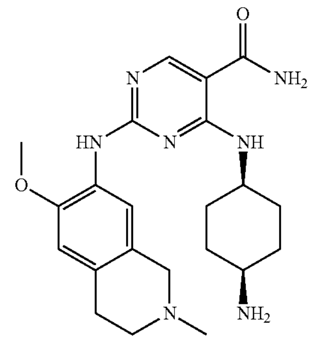 [SMILES: COc1cc2c(cc1Nc1ncc(C(N)=O)c(N[C@H]3CC[C@@H](N)CC3)n1)CN(C)CC2] | 4-[(cis-4-aminocyclohexyl)amino]-2-[(6-methoxy-2-methyl-1,2,3,4-tetrahydroisoquinolin-7-yl)amino]pyrimidine-5-carboxamide | Calc'd 426, found 426 |
| 26-6 | 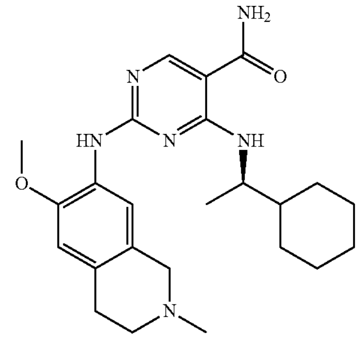 [SMILES: COc1cc2c(cc1Nc1ncc(C(N)=O)c(N[C@H](C)C3CCCCC3)n1)CN(C)CC2] | 4-{[(1R)-1-cyclohexylethyl]amino}-2-[(6-methoxy-2-methyl-1,2,3,4-tetrahydroisoquinolin-7-yl)amino]pyrimidine-5-carboxamide | Calc'd 439, found 439 |
| 26-7 | 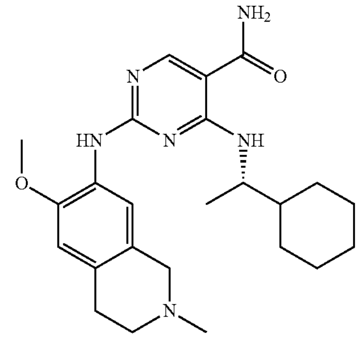 [SMILES: COc1cc2c(cc1Nc1ncc(C(N)=O)c(N[C@@H](C)C3CCCCC3)n1)CN(C)CC2] | 4-{[(1S)-1-cyclohexylethyl]amino}-2-[(6-methoxy-2-methyl-1,2,3,4-tetrahydroisoquinolin-7-yl)amino]pyrimidine-5-carboxamide | Calc'd 439, found 439 |
| 26-8 | 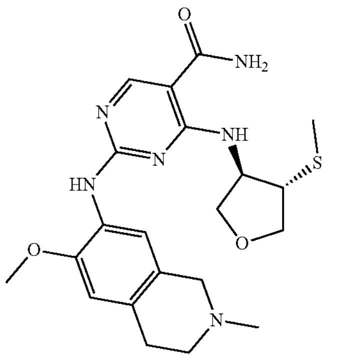 [SMILES: COc1cc2c(cc1Nc1ncc(C(N)=O)c(N[C@@H]3COC[C@H]3SC)n1)CN(C)CC2] | 2-[(6-methoxy-2-methyl-1,2,3,4-tetrahydroisoquinolin-7-yl)amino]-4-{[(3R,4S)-4-(methylsulfanyl)oxolan-3-yl]amino}pyrimidine-5-carboxamide | Calc'd 445, found 445 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]$^+$ |
|---|---|---|---|
| 26-9 | 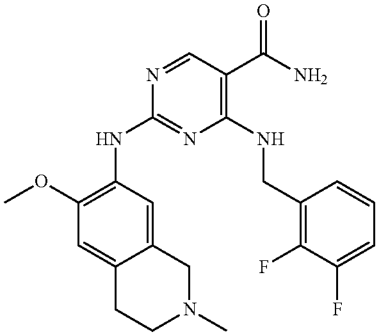 [SMILES: COc1cc2c(cc1Nc1ncc(C(N)=O)c(NCc3cccc(F)c3F)n1)CN(C)CC2] | 4-{[(2,3-difluorophenyl)methyl]amino}-2-[(6-methoxy-2-methyl-1,2,3,4-tetrahydroisoquinolin-7-yl)amino]pyrimidine-5-carboxamide | Calc'd 455, found 455 |
| 26-10 | 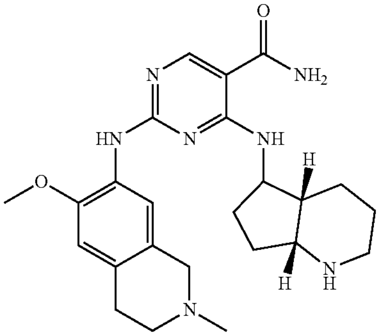 [SMILES: COc1cc2c(cc1Nc1ncc(C(N)=O)c(NC3CC[C@H]4NCCC[C@@H]34)n1)CN(C)CC2] | 2-[(6-methoxy-2-methyl-1,2,3,4-tetrahydroisoquinolin-7-yl)amino]-4-{[(4aR,7aR)-octahydro-1H-cyclopenta[b]pyridin-5-yl]amino}pyrimidine-5-carboxamide | Calc'd 452, found 452 |
| 26-11 | 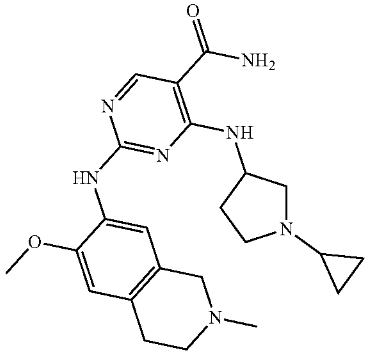 [SMILES: COc1cc2c(cc1Nc1ncc(C(N)=O)c(NC3CCN(C4CC4)C3)n1)CN(C)CC2] | 4-[(1-cyclopropylpyrrolidin-3-yl)amino]-2-[(6-methoxy-2-methyl-1,2,3,4-tetrahydroisoquinolin-7-yl)amino]pyrimidine-5-carboxamide | Calc'd 438, found 438 |
| 26-12 | 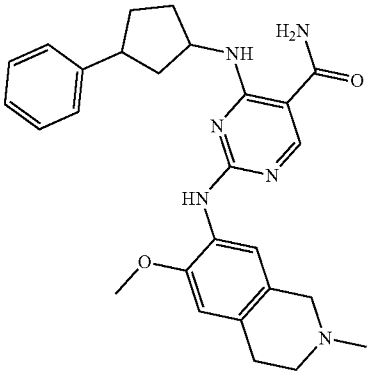 [SMILES: COc1cc2c(cc1Nc1ncc(C(N)=O)c(NC3CCC(c4ccccc4)C3)n1)CN(C)CC2] | 2-[(6-methoxy-2-methyl-1,2,3,4-tetrahydroisoquinolin-7-yl)amino]-4-[(3-phenylcyclopentyl)amino]pyrimidine-5-carboxamide | Calc'd 473, found 473 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
| --- | --- | --- | --- |
| 26-13 | 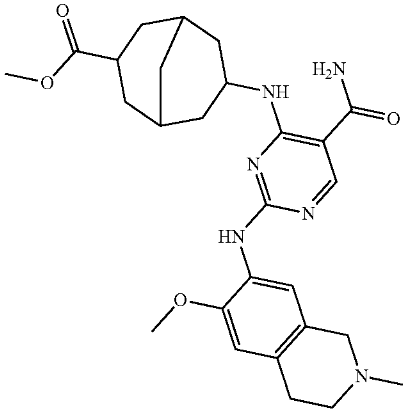 | methyl 7-({5-carbamoyl-2-[(6-methoxy-2-methyl-1,2,3,4-tetrahydroisoquinolin-7-yl)amino]pyrimidin-4-yl}amino)bicyclo[3.3.1]nonane-3-carboxylate | Calc'd 509, found 509 |
| 26-14 | 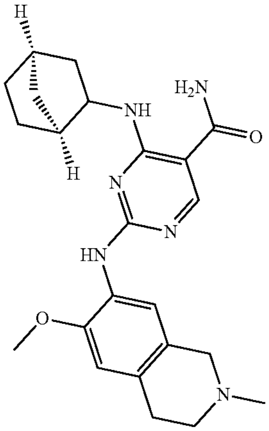 [SMILES: COc1cc2c(cc1Nc1ncc(C(N)=O)c(NC3C[C@@H]4CC[C@H]3C4)n1)CN(C)CC2] | 4-{[(1S,4R)-bicyclo[2.2.1]heptan-2-yl]amino}-2-[(6-methoxy-2-methyl-1,2,3,4-tetrahydroisoquinolin-7-yl)amino]pyrimidine-5-carboxamide | Calc'd 423, found 423 |
| 26-15 | 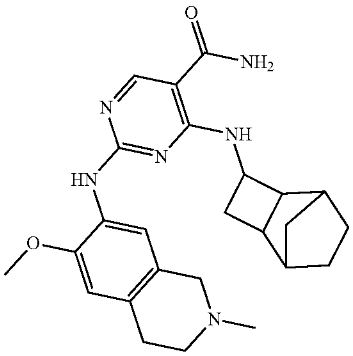 [SMILES: COc1cc2c(cc1Nc1ncc(C(N)=O)c(NC3CC4C5CCC(C5)C34)n1)CN(C)CC2] | 2-[(6-methoxy-2-methyl-1,2,3,4-tetrahydroisoquinolin-7-yl)amino]-4-[(tricyclo[4.2.1.0~2,5~]nonan-3-yl)amino]pyrimidine-5-carboxamide | Calc'd 449, found 449 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]+ |
|---|---|---|---|
| 26-16 | 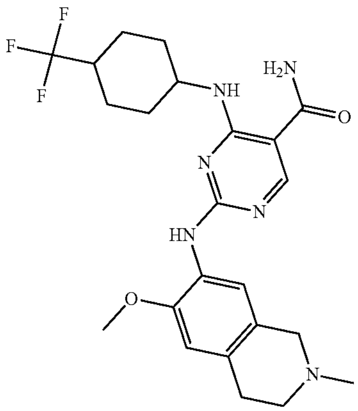 [SMILES: COc1cc2c(cc1Nc1ncc(C(N)=O)c(NC3CCC(C(F)(F)F)CC3)n1)CN(C)CC2] | 2-[(6-methoxy-2-methyl-1,2,3,4-tetrahydroisoquinolin-7-yl)amino]-4-{[4-(trifluoromethyl)cyclohexyl]amino}pyrimidine-5-carboxamide | Calc'd 479, found 479 |
| 26-17 | 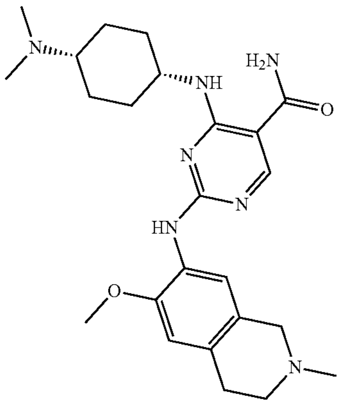 | 4-{[cis-4-(dimethylamino)cyclohexyl]amino}-2-[(6-methoxy-2-methyl-1,2,3,4-tetrahydroisoquinolin-7-yl)amino]pyrimidine-5-carboxamide | Calc'd 454, found 454 |
| 26-18 | 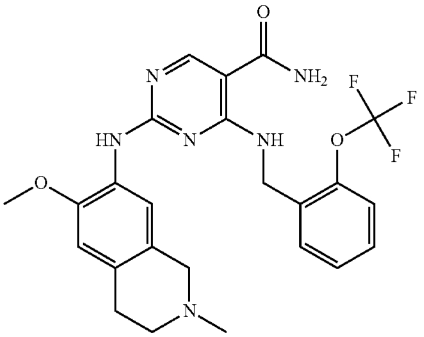 [SMILES: COc1cc2c(cc1Nc1ncc(C(N)=O)c(NCc3ccccc3OC(F)(F)F)n1)CN(C)CC2] | 2-[(6-methoxy-2-methyl-1,2,3,4-tetrahydroisoquinolin-7-yl)amino]-4-({[2-(trifluoromethoxy)phenyl]methyl}amino)pyrimidine-5-carboxamide | Calc'd 503, found 503 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
|---|---|---|---|
| 26-19 | 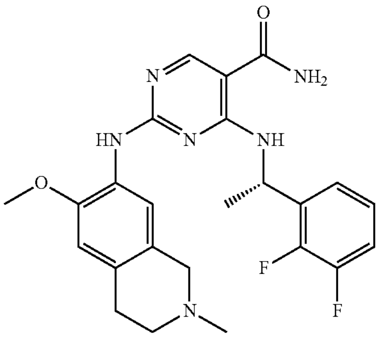 [SMILES: COc1cc2c(cc1Nc1ncc(C(N)=O)c(N[C@@H](C)c3cccc(F)c3F)n1)CN(C)CC2] | 4-{[(1S)-1-(2,3-difluorophenyl)ethyl]amino}-2-[(6-methoxy-2-methyl-1,2,3,4-tetrahydroisoquinolin-7-yl)amino]pyrimidine-5-carboxamide | Calc'd 469, found 469 |
| 26-20 | 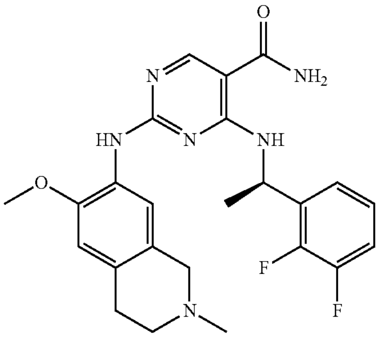 [SMILES: COc1cc2c(cc1Nc1ncc(C(N)=O)c(N[C@H](C)c3cccc(F)c3F)n1)CN(C)CC2] | 4-{[(1R)-1-(2,3-difluorophenyl)ethyl]amino}-2-[(6-methoxy-2-methyl-1,2,3,4-tetrahydroisoquinolin-7-yl)amino]pyrimidine-5-carboxamide | Calc'd 469, found 469 |
| 26-21 | 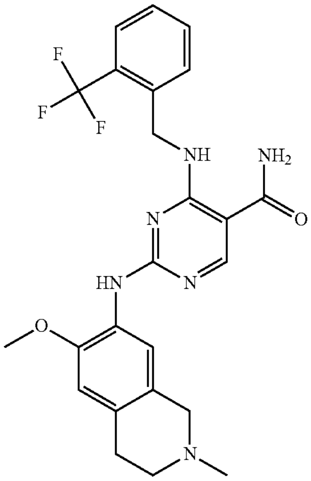 [SMILES: COc1cc2c(cc1Nc1ncc(C(N)=O)c(NCc3ccccc3C(F)(F)F)n1)CN(C)CC2] | 2-[(6-methoxy-2-methyl-1,2,3,4-tetrahydroisoquinolin-7-yl)amino]-4-({[2-(trifluoromethyl)phenyl]methyl}amino)pyrimidine-5-carboxamide | Calc'd 487, found 487 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
|---|---|---|---|
| 26-22 | 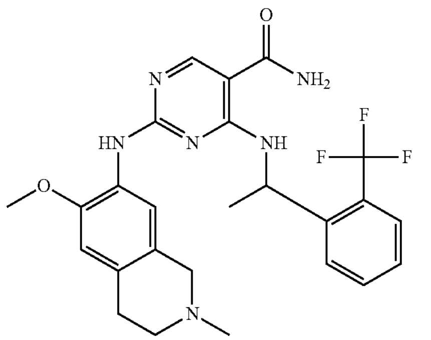 [SMILES: COc1cc2c(cc1Nc1ncc(C(N)=O)c(NC(C)c3ccccc3C(F)(F)F)n1)CN(C)CC2] | 2-[(6-methoxy-2-methyl-1,2,3,4-tetrahydroisoquinolin-7-yl)amino]-4-({1-[2-(trifluoromethyl)phenyl]ethyl}amino) pyrimidine-5-carboxamide | Calc'd 501, found 501 |
| 26-23 | 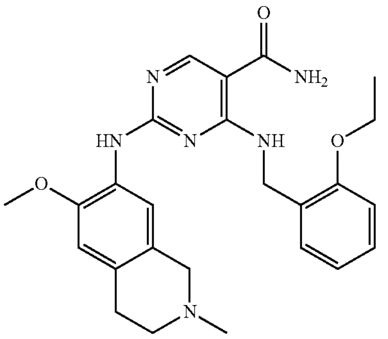 [SMILES: CCOc1ccccc1CNc1nc(Nc2cc3c(cc2OC)CCN(C)C3)ncc1C(N)=O] | 4-{[(2-ethoxyphenyl)methyl]amino}-2-[(6-methoxy-2-methyl-1,2,3,4-tetrahydroisoquinolin-7-yl)amino]pyrimidine-5-carboxamide | Calc'd 463, found 463 |
| 26-24 | 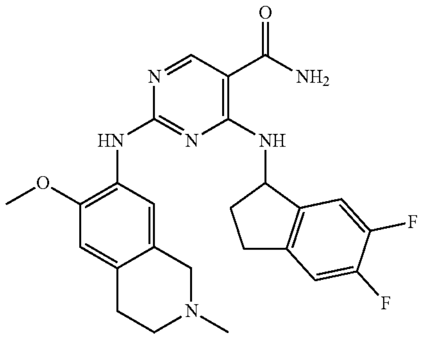 [SMILES: COc1cc2c(cc1Nc1ncc(C(N)=O)c(NC3CCc4cc(F)c(F)cc43)n1)CN(C)CC2] | 4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 481, found 481 |
| 26-25 | 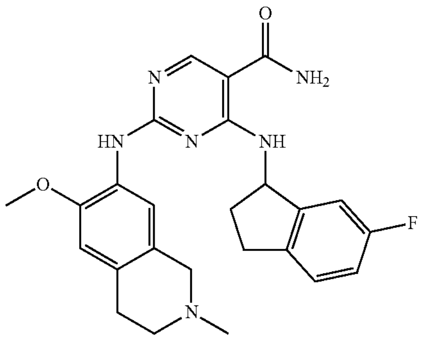 [SMILES: COc1cc2c(cc1Nc1ncc(C(N)=O)c(NC3CCc4ccc(F)cc43)n1)CN(C)CC2] | 4-[(6-fluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 463, found 463 |

TABLE 26-continued

| Compounds listed in the table below were prepared using the synthetic methods described in the aforementioned Example 26-1. The table provides the compound structure, the name, the calculated and observed masses. | | | |
|---|---|---|---|
| Example | Structure | Name | Exact Mass $[M + H]^+$ |
| 26-26 | 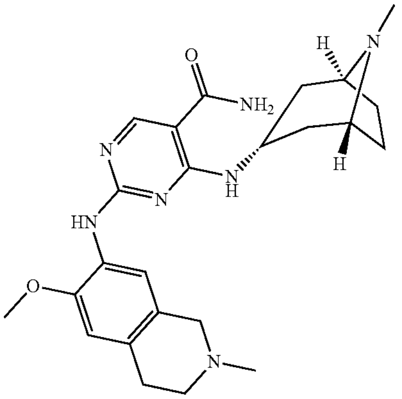 | 2-[(6-methoxy-2-methyl-1,2,3,4-tetrahydroisoquinolin-7-yl)amino]-4-{[(1R,3r,5S)-8-methyl-8-azabicyclo[3.2.1]octan-3-yl]amino}pyrimidine-5-carboxamide | Calc'd 452, found 452 |
| 26-27 | 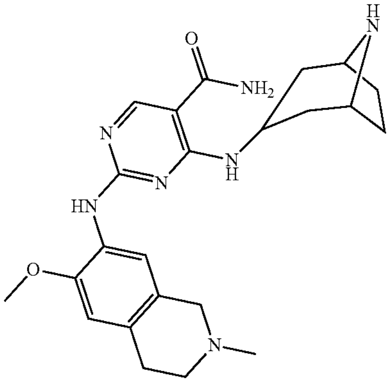 [SMILES: COc1cc2c(cc1Nc1ncc(C(N)=O)c(NC3CC4CCC(C3)N4)n1)CN(C)CC2] | 4-[(8-azabicyclo[3.2.1]octan-3-yl)amino]-2-[(6-methoxy-2-methyl-1,2,3,4-tetrahydroisoquinolin-7-yl)amino]pyrimidine-5-carboxamide | Calc'd 438, found 438 |
| 26-28 | 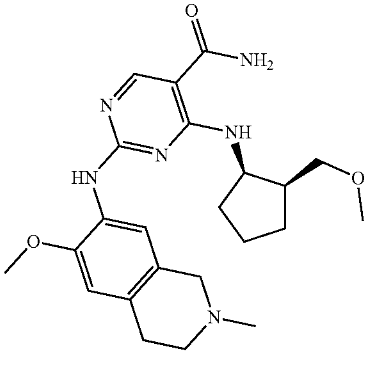 | 4-{[(1R,2S)-2-(methoxymethyl)cyclopentyl]amino}-2-[(6-methoxy-2-methyl-1,2,3,4-tetrahydroisoquinolin-7-yl)amino]pyrimidine-5-carboxamide | Calc'd 441, found 441 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]$^+$ |
| --- | --- | --- | --- |
| 26-29 | 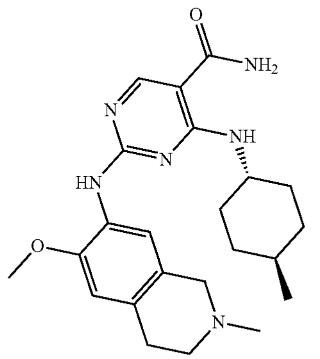 [SMILES: COc1cc2c(cc1Nc1ncc(C(N)=O)c(N[C@H]3CC[C@H](C)CC3)n1)CN(C)CC2] | 2-[(6-methoxy-2-methyl-1,2,3,4-tetrahydroisoquinolin-7-yl)amino]-4-[(trans-4-methylcyclohexyl)amino]pyrimidine-5-carboxamide | Calc'd 425, found 425 |
| 26-30 | 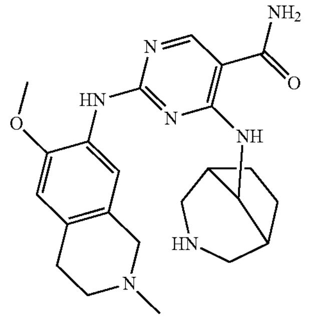 [SMILES: COc1cc2c(cc1Nc1ncc(C(N)=O)c(NC3C4CCC3CNC4)n1)CN(C)CC2] | 4-[(3-azabicyclo[3.2.1]octan-8-yl)amino]-2-[(6-methoxy-2-methyl-1,2,3,4-tetrahydroisoquinolin-7-yl)amino]pyrimidine-5-carboxamide | Calc'd 438, found 438 |
| 26-31 | 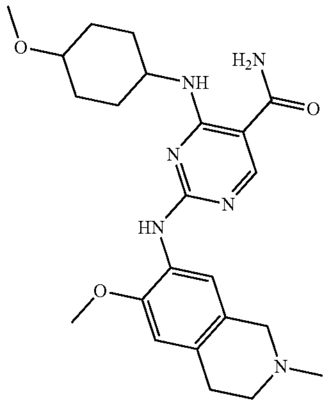 | 4-[(4-methoxycyclohexyl)amino]-2-[(6-methoxy-2-methyl-1,2,3,4-tetrahydroisoquinolin-7-yl)amino]pyrimidine-5-carboxamide | Calc'd 441, found 441 |
| 26-32 | 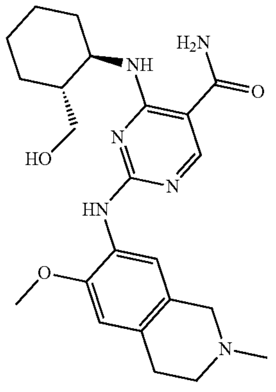 [SMILES: COc1cc2c(cc1Nc1ncc(C(N)=O)c(N[C@@H]3CCCC[C@H]3CO)n1)CN(C)CC2] | 4-{[(1R,2R)-2-(hydroxymethyl)cyclohexyl]amino}-2-[(6-methoxy-2-methyl-1,2,3,4-tetrahydroisoquinolin-7-yl)amino]pyrimidine-5-carboxamide | Calc'd 441, found 441 |

TABLE 26-continued

| Compounds listed in the table below were prepared using the synthetic methods described in the aforementioned Example 26-1. The table provides the compound structure, the name, the calculated and observed masses. | | | |
|---|---|---|---|
| Example | Structure | Name | Exact Mass [M + H]$^+$ |
| 26-33 | 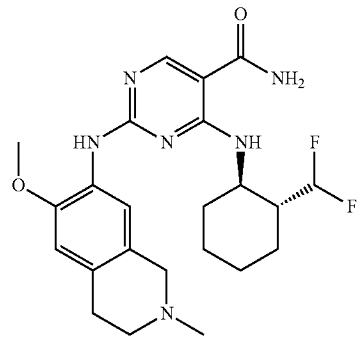 [SMILES: COc1cc2c(cc1Nc1ncc(C(N)=O)c(N[C@@H]3CCCC[C@H]3C(F)F)n1)CN(C)CC2] | 4-{[(1R,2R)-2-(difluoromethyl)cyclohexyl]amino}-2-[(6-methoxy-2-methyl-1,2,3,4-tetrahydroisoquinolin-7-yl)amino]pyrimidine-5-carboxamide | Calc'd 461, found 461 |
| 26-34 | 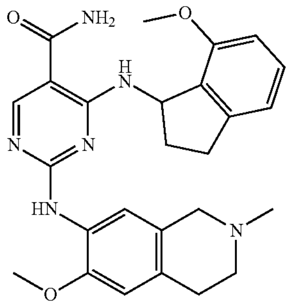 [SMILES: COc1cc2c(cc1Nc1ncc(C(N)=O)c(NC3CCc4cccc(OC)c43)n1)CN(C)CC2] | 4-[(7-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 475, found 475 |
| 26-35 | 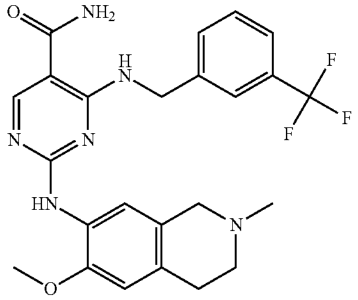 [SMILES: COc1cc2c(cc1Nc1ncc(C(N)=O)c(NCc3cccc(C(F)(F)F)c3)n1)CN(C)CC2] | 2-[(6-methoxy-2-methyl-1,2,3,4-tetrahydroisoquinolin-7-yl)amino]-4-({[3-(trifluoromethyl)phenyl]methyl}amino)pyrimidine-5-carboxamide | Calc'd 487, found 487 |
| 26-36 | 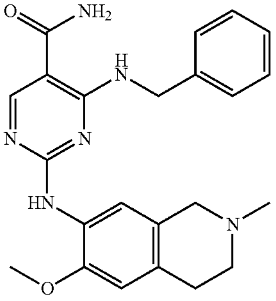 [SMILES: COc1cc2c(cc1Nc1ncc(C(N)=O)c(NCc3ccccc3)n1)CN(C)CC2] | 4-(benzylamino)-2-[(6-methoxy-2-methyl-1,2,3,4-tetrahydroisoquinolin-7-yl)amino]pyrimidine-5-carboxamide | Calc'd 419, found 419 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]+ |
|---|---|---|---|
| 26-37 | 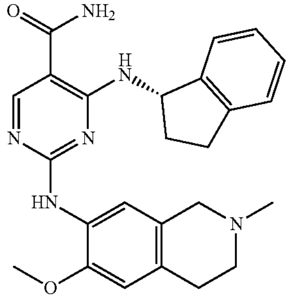 [SMILES: COc1cc2c(cc1Nc1ncc(C(N)=O)c(N[C@H]3CCc4ccccc43)n1)CN(C)CC2] | 4-{[(1S)-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 445, found 445 |
| 26-38 | 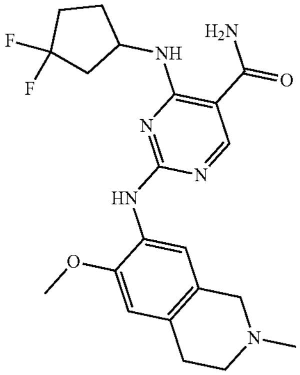 [SMILES: COc1cc2c(cc1Nc1ncc(C(N)=O)c(NC3CCC(F)(F)C3)n1)CN(C)CC2] | 4-[(3,3-difluorocyclopentyl)amino]-2-[(6-methoxy-2-methyl-1,2,3,4-tetrahydroisoquinolin-7-yl)amino]pyrimidine-5-carboxamide | Calc'd 433, found 433 |
| 26-39 | 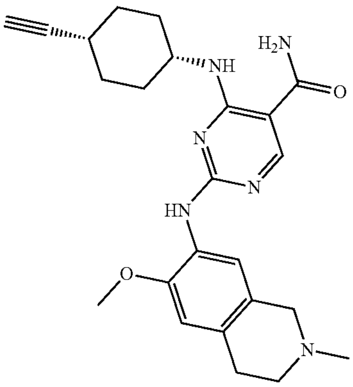 [SMILES: C#C[C@H]1CC[C@@H](Nc2nc(Nc3cc4c(cc3OC)CCN(C)C4)ncc2C(N)=O)CC1] | 4-[(cis-4-ethynylcyclohexyl)amino]-2-[(6-methoxy-2-methyl-1,2,3,4-tetrahydroisoquinolin-7-yl)amino]pyrimidine-5-carboxamide | Calc'd 435, found 435 |
| 26-40 | 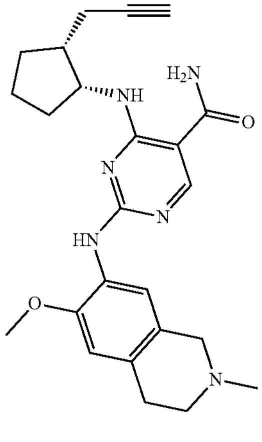 | 2-[(6-methoxy-2-methyl-1,2,3,4-tetrahydroisoquinolin-7-yl)amino]-4-{[(1R,2R)-2-(prop-2-yn-1-yl)cyclopentyl]amino}pyrimidine-5-carboxamide | Calc'd 435, found 435 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]+ |
|---|---|---|---|
| 26-41 | 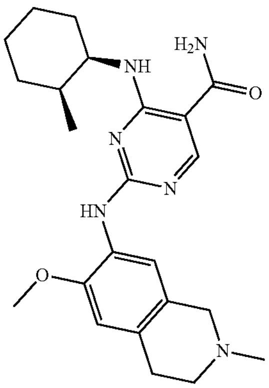 [SMILES: COc1cc2c(cc1Nc1ncc(C(N)=O)c(N[C@@H]3CCCC[C@@H]3C)n1)CN(C)CC2] | 2-[(6-methoxy-2-methyl-1,2,3,4-tetrahydroisoquinolin-7-yl)amino]-4-{[(1R,2S)-2-methylcyclohexyl]amino}pyrimidine-5-carboxamide | Calc'd 425, found 425 |
| 26-42 | 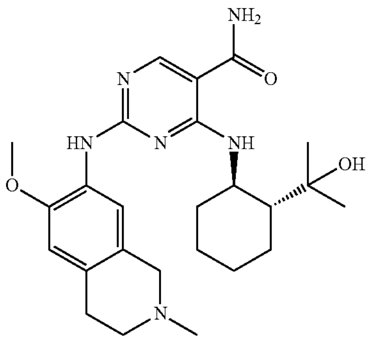 [SMILES: COc1cc2c(cc1Nc1ncc(C(N)=O)c(N[C@@H]3CCCC[C@H]3C(C)(C)O)n1)CN(C)CC2] | 4-{[(1R,2R)-2-(2-hydroxypropan-2-yl)cyclohexyl]amino}-2-[(6-methoxy-2-methyl-1,2,3,4-tetrahydroisoquinolin-7-yl)amino]pyrimidine-5-carboxamide | Calc'd 469, found 469 |
| 26-43 | 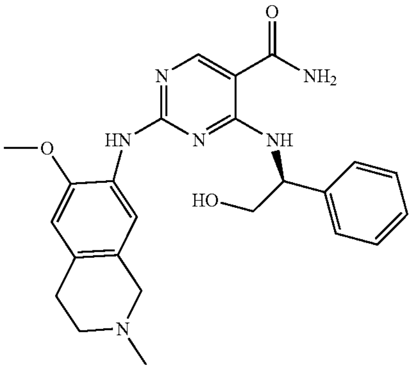 [SMILES: COc1cc2c(cc1Nc1ncc(C(N)=O)c(N[C@H](CO)c3ccccc3)n1)CN(C)CC2] | 4-{[(1S)-2-hydroxy-1-phenylethyl]amino}-2-[(6-methoxy-2-methyl-1,2,3,4-tetrahydroisoquinolin-7-yl)amino]pyrimidine-5-carboxamide | Calc'd 449, found 449 |
| 26-44 | 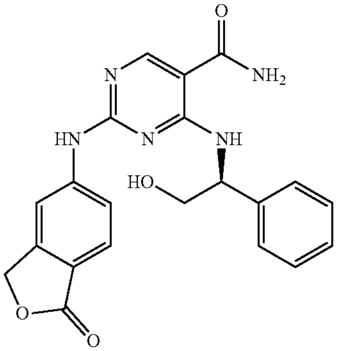 [SMILES: NC(=O)c1cnc(Nc2ccc3c(c2)COC3=O)nc1N[C@H](CO)c1ccccc1] | 4-{[(1S)-2-hydroxy-1-phenylethyl]amino}-2-[(1-oxo-1,3-dihydro-2-benzofuran-5-yl)amino]pyrimidine-5-carboxamide | Calc'd 406, found 406 |

TABLE 26-continued

| Compounds listed in the table below were prepared using the synthetic methods described in the aforementioned Example 26-1. The table provides the compound structure, the name, the calculated and observed masses. | | | |
|---|---|---|---|
| Example | Structure | Name | Exact Mass $[M + H]^+$ |
| 26-45 | 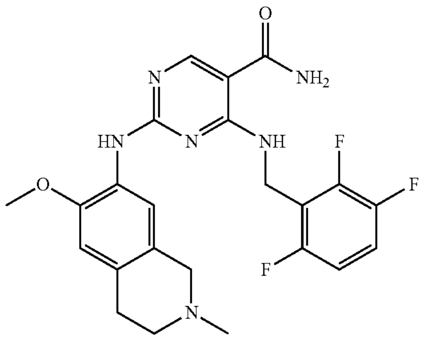 [SMILES: COc1cc2c(cc1Nc1ncc(C(N)=O)c(NCc3c(F)ccc(F)c3F)n1)CN(C)CC2] | 2-[(6-methoxy-2-methyl-1,2,3,4-tetrahydroisoquinolin-7-yl)amino]-4-{[(2,3,6-trifluorophenyl)methyl]amino}py-rimidine-5-carboxamide | Calc'd 473, found 473 |
| 26-46 | 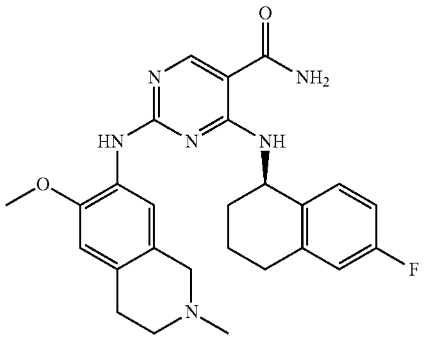 [SMILES: COc1cc2c(cc1Nc1ncc(C(N)=O)c(N[C@@H]3CCCc4cc(F)ccc43)n1)CN(C)CC2] | 4-{[(1R)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide | Calc'd 477, found 477 |
| 26-47 | 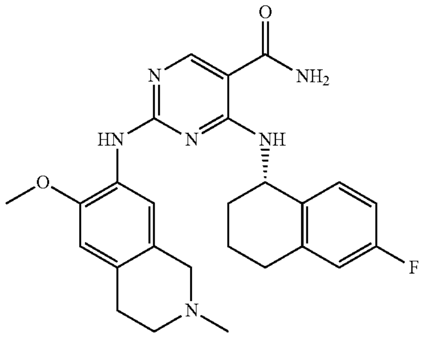 [SMILES: COc1cc2c(cc1Nc1ncc(C(N)=O)c(N[C@H]3CCCc4cc(F)ccc43)n1)CN(C)CC2] | 4-{[(1S)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide | Calc'd 477, found 477 |
| 26-48 | 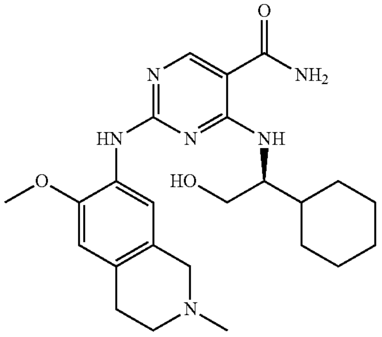 [SMILES: COc1cc2c(cc1Nc1ncc(C(N)=O)c(N[C@H](CO)C3CCCCC3)n1)CN(C)CC2] | 4-{[(1S)-1-cyclohexyl-2-hydroxyethyl]amino}-2-[(6-methoxy-2-methyl-1,2,3,4-tetrahydroisoquinolin-7-yl)amino]pyrimidine-5-carboxamide | Calc'd 455, found 455 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
| --- | --- | --- | --- |
| 26-49 | 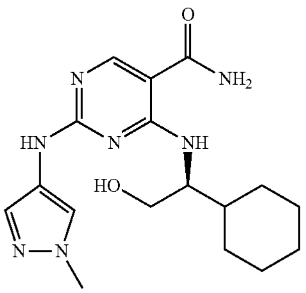 [SMILES: Cn1cc(Nc2ncc(C(N)=O)c(N[C@H](CO)C3CCCCC3)n2)cn1] | 4-{[(1S)-1-cyclohexyl-2-hydroxyethyl]amino}-2-[(1-methyl-1H-pyrazol-4-yl)amino]pyrimidine-5-carboxamide | Calc'd 360, found 360 |
| 26-50 | 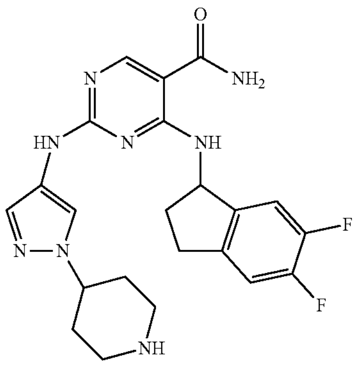 [SMILES: NC(=O)c1cnc(Nc2cnn(C3CCNCC3)c2)nc1NC1CCc2cc(F)c(F)cc21] | 4-[(5,6-difluoro-2,3-dihydro-1H-inden-1-yl)amino]-2-{[1-(piperidin-4-yl)-1H-pyrazol-4-yl]amino}pyrimidine-5-carboxamide | Calc'd 455, found 455 |
| 26-51 | 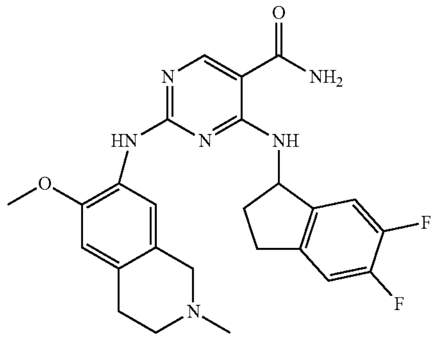 [SMILES: COc1cc2c(cc1Nc1ncc(C(N)=O)c(NC3CCc4cc(F)c(F)cc43)n1)CN(C)CC2] | 4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 481, found 481 |
| 26-52 | 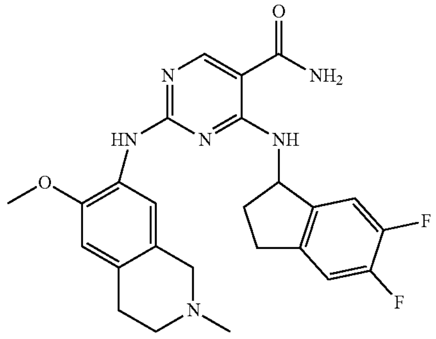 [SMILES: COc1cc2c(cc1Nc1ncc(C(N)=O)c(NC3CCc4cc(F)c(F)cc43)n1)CN(C)CC2] | 4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 481, found 481 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
| --- | --- | --- | --- |
| 26-53 | 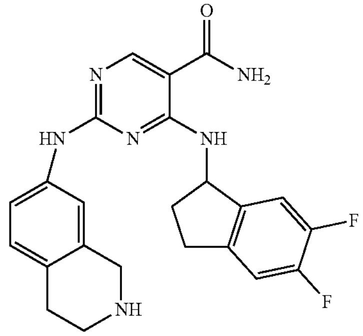 [SMILES: NC(=O)c1cnc(Nc2ccc3c(c2)CNCC3)nc1NC1CCc2cc(F)c(F)cc21] | 4-[(5,6-difluoro-2,3-dihydro-1H-inden-1-yl)amino]-2-[(1,2,3,4-tetrahydroisoquinolin-7-yl)amino]pyrimidine-5-carboxamide | Calc'd 437, found 437 |
| 26-54 | 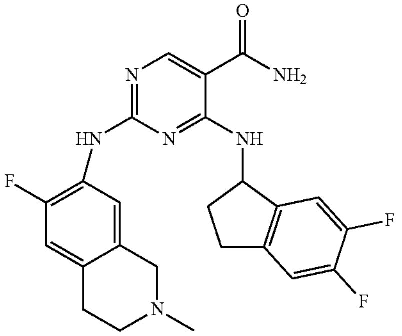 [SMILES: CN1CCc2cc(F)c(Nc3ncc(C(N)=O)c(NC4CCc5cc(F)c(F)cc54)n3)cc2C1] | 4-[(5,6-difluoro-2,3-dihydro-1H-inden-1-yl)amino]-2-[(6-fluoro-2-methyl-1,2,3,4-tetrahydroisoquinolin-7-yl)amino]pyrimidine-5-carboxamide | Calc'd 469, found 469 |
| 26-55 | 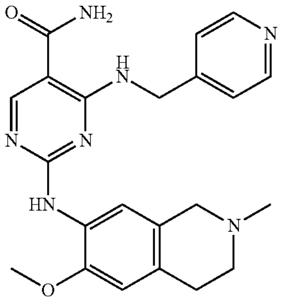 [SMILES: COc1cc2c(cc1Nc1ncc(C(N)=O)c(NCc3ccncc3)n1)CN(C)CC2] | 2-[(6-methoxy-2-methyl-1,2,3,4-tetrahydroisoquinolin-7-yl)amino]-4-{[(pyridin-4-yl)methyl]amino}pyrimidine-5-carboxamide | Calc'd 420, found 420 |
| 26-56 | 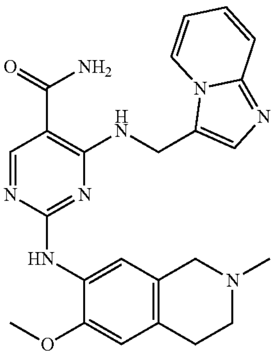 | 4-{[(imidazo[1,2-a]pyridin-3-yl)methyl]amino}-2-[(6-methoxy-2-methyl-1,2,3,4-tetrahydroisoquinolin-7-yl)amino]pyrimidine-5-carboxamide | Calc'd 459, found 459 |

TABLE 26-continued

| Compounds listed in the table below were prepared using the synthetic methods described in the aforementioned Example 26-1. The table provides the compound structure, the name, the calculated and observed masses. | | | |
|---|---|---|---|
| Example | Structure | Name | Exact Mass [M + H]$^+$ |
| 26-57 | 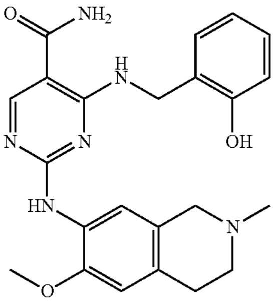 [SMILES: COc1cc2c(cc1Nc1ncc(C(N)=O)c(NCc3ccccc3O)n1)CN(C)CC2] | 4-{[(2-hydroxyphenyl)methyl]amino}-2-[(6-methoxy-2-methyl-1,2,3,4-tetrahydroisoquinolin-7-yl)amino]pyrimidine-5-carboxamide | Calc'd 435, found 435 |
| 26-58 | 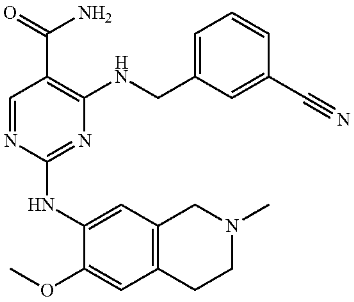 [SMILES: COc1cc2c(cc1Nc1ncc(C(N)=O)c(NCc3cccc(C#N)c3)n1)CN(C)CC2] | 4-{[(3-cyanophenyl)methyl]amino}-2-[(6-methoxy-2-methyl-1,2,3,4-tetrahydroisoquinolin-7-yl)amino]pyrimidine-5-carboxamide | Calc'd 444, found 444 |
| 26-59 | 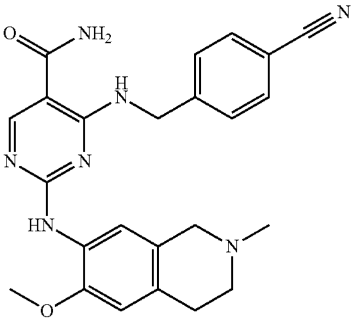 [SMILES: COc1cc2c(cc1Nc1ncc(C(N)=O)c(NCc3ccc(C#N)cc3)n1)CN(C)CC2] | 4-{[(4-cyanophenyl)methyl]amino}-2-[(6-methoxy-2-methyl-1,2,3,4-tetrahydroisoquinolin-7-yl)amino]pyrimidine-5-carboxamide | Calc'd 444, found 444 |
| 26-60 | 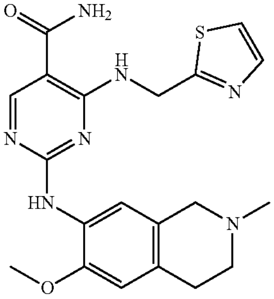 | 2-[(6-methoxy-2-methyl-1,2,3,4-tetrahydroisoquinolin-7-yl)amino]-4-{[(1,3-thiazol-2-yl)methyl]amino}pyrimidine-5-carboxamide | Calc'd 426, found 426 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass $[M + H]^+$ |
|---|---|---|---|
| 26-61 | 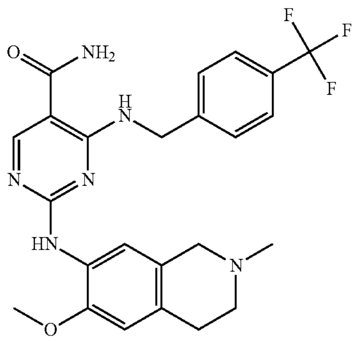 [SMILES: COc1cc2c(cc1Nc1ncc(C(N)=O)c(NCc3ccc(C(F)(F)F)cc3)n1)CN(C)CC2] | 2-[(6-methoxy-2-methyl-1,2,3,4-tetrahydroisoquinolin-7-yl)amino]-4-({[4-(trifluoromethyl)phenyl]methyl}amino)pyrimidine-5-carboxamide | Calc'd 487, found 487 |
| 26-62 | 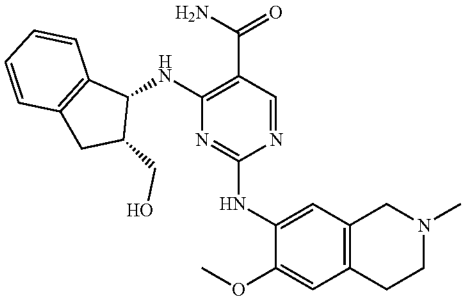 [SMILES: COc1cc2c(cc1Nc1ncc(C(N)=O)c(N[C@H]3c4ccccc4C[C@H]3CO)n1)CN(C)CC2] | 4-{[(1R,2R)-2-(hydroxymethyl)-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 475, found 475 |
| 26-63 | 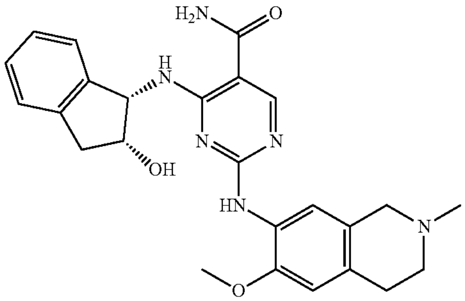 [SMILES: COc1cc2c(cc1Nc1ncc(C(N)=O)c(N[C@H]3c4ccccc4C[C@H]3O)n1)CN(C)CC2] | 4-{[(1S,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 461, found 461 |
| 26-64 | 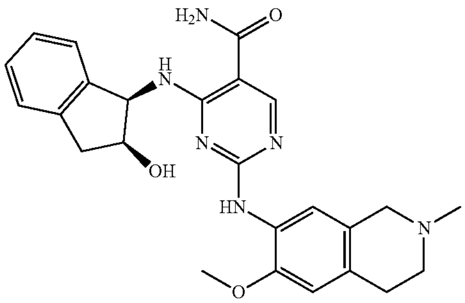 [SMILES: COc1cc2c(cc1Nc1ncc(C(N)=O)c(N[C@@H]3c4ccccc4C[C@@H]3O)n1)CN(C)CC2] | 4-{[(1R,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 461, found 461 |

TABLE 26-continued

| Compounds listed in the table below were prepared using the synthetic methods described in the aforementioned Example 26-1. The table provides the compound structure, the name, the calculated and observed masses. | | | |
|---|---|---|---|
| Example | Structure | Name | Exact Mass $[M + H]^+$ |
| 26-65 | 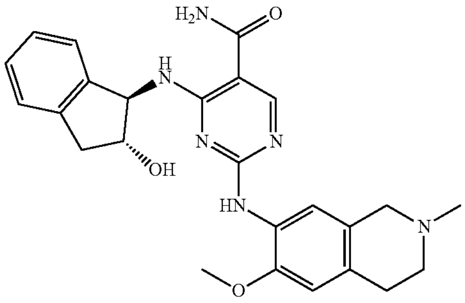 [SMILES: COc1cc2c(cc1Nc1ncc(C(N)=O)c(N[C@@H]3c4ccccc4C[C@H]3O)n1)CN(C)CC2] | 4-{[(1R,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 461, found 461 |
| 26-66 | 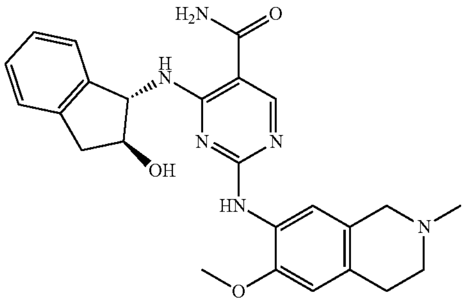 [SMILES: COc1cc2c(cc1Nc1ncc(C(N)=O)c(N[C@H]3c4ccccc4C[C@@H]3O)n1)CN(C)CC2] | 4-{[(1S,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 461, found 461 |
| 26-67 | 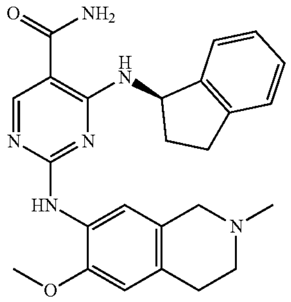 [SMILES: COc1cc2c(cc1Nc1ncc(C(N)=O)c(N[C@@H]3CCc4ccccc43)n1)CN(C)CC2] | 4-{[(1R)-2,3-dihydro-1H-inden-1-yl]amino}-2-[(6-methoxy-2-methyl-1,2,3,4-tetrahydroisoquinolin-7-yl)amino]pyrimidine-5-carboxamide | Calc'd 445, found 445 |
| 26-68 | 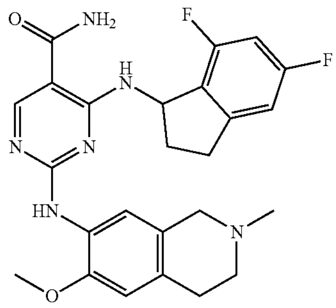 [SMILES: COc1cc2c(cc1Nc1ncc(C(N)=O)c(NC3CCc4cc(F)cc(F)c43)n1)CN(C)CC2] | 4-[(5,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 481, found 481 |

TABLE 26-continued

Compounds listed in the table below were prepared using the synthetic methods described in the aforementioned Example 26-1. The table provides the compound structure, the name, the calculated and observed masses.

| Example | Structure | Name | Exact Mass [M + H]$^+$ |
|---|---|---|---|
| 26-69 | 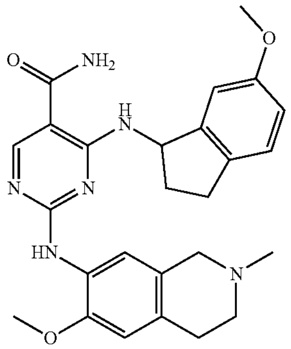 [SMILES: COc1ccc2c(c1)C(Nc1nc(Nc3cc4c(cc3OC)CCN(C)C4)ncc1C(N)=O)CC2] | 4-[(6-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 475, found 475 |
| 26-70 | 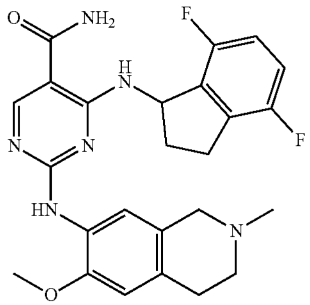 [SMILES: COc1cc2c(cc1Nc1ncc(C(N)=O)c(NC3CCc4c(F)ccc(F)c43)n1)CN(C)CC2] | 4-[(4,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide | Calc'd 481, found 481 |
| 26-71 | 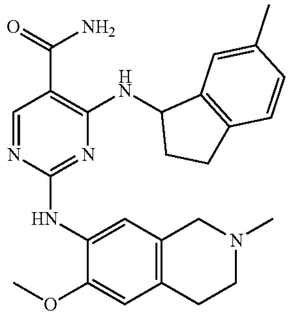 [SMILES: COc1cc2c(cc1Nc1ncc(C(N)=O)c(NC3CCc4ccc(C)cc43)n1)CN(C)CC2] | 2-[(6-methoxy-2-methyl-1,2,3,4-tetrahydroisoquinolin-7-yl)amino]-4-[(6-methyl-2,3-dihydro-1H-inden-1-yl)amino]pyrimidine-5-carboxamide | Calc'd 459, found 459 |
| 26-72 | 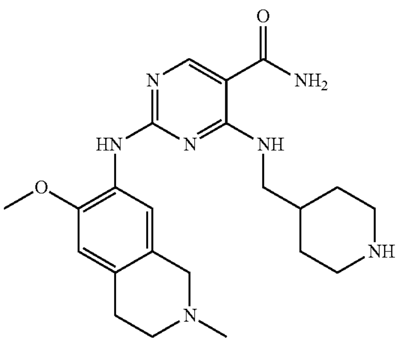 [SMILES: COc1cc2c(cc1Nc1ncc(C(N)=O)c(NCC3CCNCC3)n1)CN(C)CC2] | 2-[(6-methoxy-2-methyl-1,2,3,4-tetrahydroisoquinolin-7-yl)amino]-4-{[(piperidin-4-yl)methyl]amino}pyrimidine-5-carboxamide | Calc'd 426, found 426 |

Reverse Phase Prep-HPLC Methods

Purification Method A—TFA Modifier

Reverse-phase Prep-HPLC [Waters SunFire OBD C18, 19 mm×150 mm (5 μm); gradient elution, $MeCN/H_2O/0.1\%$ TFA]. Electrospray (ESI) Mass-triggered fraction collected was employed using positive ion polarity scanning to monitor for the target mass.

HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Purification Method B—$NH_4OH$ Modifier reverse-phase Prep-HPLC [Waters XBridge OBD C18, 19 mm×150 mm (5 μm); gradient elution. $MeCN/H_2O/0.1\%$ $NH_4OH$]. Electrospray (ESI) Mass-triggered fraction collected was employed using positive ion polarity scanning to monitor for the target mass

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 12 | 25 | 0.2 |

HPK1-SLP76 TR-FRET Assay

Assay Principle:

HPK1-Catalytic domain enzyme is preincubated for 30 minutes with varying concentrations of investigational test compounds, or DMSO reference. HPK1 activity is initiated by the addition of ATP and results in phosphorylation of a His-tagged SLP-76 protein substrate. Following a 60-minute reaction time, the reaction is quenched and FRET partners Eu-anti-His Ab and phospho-SLP-76 (Ser376) (D7S1K) XP Rabbit mAb (AF 647 Conjugate) are added to detect the phosphorylated His-tagged SLP-76 product.

Instrumentation:

Labcyte Echo

Beckman Coulter BioRaptr

Perkin Elmer Envision

Final Assay Conditions:

HPK1-Kinase Domain: 0.075 nM

Full length SLP-76: 10 nM

ATP: 10 μM

Eu-anti-His Tag: 0.75 nM pSLP76(Ser376)-AF647: 0.75 nM

Preincubation Time: 30 minutes

Kinase Reaction Time: 60 minutes

Temperature: Ambient Room Temperature

Reaction Volume: 7.5 μL

Total Volume: 10.0 μL

Materials:

Assay Plate: Black Corning NBS 384-well microplate #3820

Kinase: Human HPK1, catalytic domain [1-346 amino acids of accession number NP_009112.1]

Substrate: Full Length SLP76, C-Terminal 8× His-tag

ATP: 100 mM

BSA: 10%

Reaction Buffer: 50 mM HEPES (pH 7.5), 10 mM $MgCl_2$, 1 mM EGTA, 0.01% Brij-35, 0.05% BSA and 0.5 mM TCEP.

Detection Solution: Reaction Buffer with LANCE Eu-W1024 Anti-6×His Ab. Phospho-SLP-76 (Ser376) (D7S1K) XP Rabbit mAb (AF 647 Conjugate)(Cell Signaling Technologies) and 10 mM EDTA.

General Assay Procedure:

To each well of black Corning #3820 384-well plate, an ECHO was used to dispense 7.5 nL of DMSO or Test compound in DMSO. A 1.5× kinase solution, 5 μL/well, was added and preincubated for 30 minutes before 2.5 μL/well of 3× substrate solution was added. The reaction solution incubated for 60 minutes and quenched with 2.5 μL of 4× detection solution. The solutions were incubated for an additional 60 minutes prior to reading on a Perkin Elmer Envision. The TR-FRET signal was measured at both 615 and 665 nm. The calculated emission ratio of 665/615 was used to determine the percent effect for each compound concentration.

Detailed HPK1 Assay Protocol.

Compounds are serially diluted (3-fold in 100% DMSO) across a 384-well polypropylene source plated from column 3 to column 12 and column 13 to column 22, to yield 10 concentration dose responses for each test compound. Columns 1, 2, 23 and 24 contain either only DMSO or a pharmacological known control inhibitor. Once titrations are made, 7.5 nL of the compounds on 384 well plates are transferred by acoustic dispersion into a 384-well assay plate (Corning 3820) to assay the HPK1 enzyme.

The HPK1 kinase biochemical assay was developed using commercially available HTRF reagents. The assay contains the following reagents: 1) Assay Buffer: 50 mM HEPES (pH 7.5), 10 mM $MgCl_2$, 1 mM EGTA, 0.01% Brij-35, 0.05% BSA and 0.5 mM TCEP; 2) Enzyme Solution: HPK1 (Carna); 3) Substrate Solution: ATP and Full Length SLP76 with His-Tag; 4) Stop and Detection Solution: EDTA, LANCE Eu-W1024 Anti-6×His Ab (Perkin Elmer) and Phospho-SLP-76 (Ser376) (D7S1K) XP Rabbit mAb (AF 647 Conjugate)(Cell Signaling Technologies).

Enzyme, Substrate and Stop/Detection solutions are prepared in assay buffer. Enzyme solution (75 pM HPK1 Final), 5 μL/well, is added to 384-well assay plate and incubated with 7.5 nL of compound or DMSO for 30 minutes. Kinase reaction is initiated with addition of 2.5 μL of substrate solution (ATP 10 uM and SLP76 10 nM Final) and allowed to proceed for 60 minutes.

Enzyme addition and compound pre-incubation are initiated by the addition of 5 μL of HPK1 enzyme solution (at one and a half times its final concentration of 75 pM) to all wells using a BioRaptr. Plates are incubated at room temperature for 30 minutes. Reactions are initiated by addition of 2.5 μL of 3× substrate solution (10 nM SLP76 and 10 uM ATP Final) using BioRaptr. Plates are incubated at room temperature for one hour. Reactions are quenched, and activity detected by addition of 2.5 μL of 4× stop and detection solution (10 mM EDTA, 0.75 nM LANCE Eu-W1024 Anti-6×His Ab and 0.75 nM Phospho-SLP-76 (Ser376) (D7S1K) XP Rabbit mAb (AF 647 Conjugate)

Final) to all wells using the BioRaptr. Following a one-hour incubation, the HTRF signal is measured on the Envision plate reader set for 320 nm excitation and dual emission detection at 615 nM (Eu) and 665 nM (AF647).

Data Analysis:

The loss of the HTRF signal is due to the inhibition of HPK1 activity and decreased phosphorylation of SLP76 substrate. All data were calculated using the ratio of acceptor (AF647) to donor (Europium) fluorescence in each well of the assay plate. The percent effect for each compound concentration was calculated as follows: % Effect=100×(Emission ratio−Minimum Effect Control)/(Maximum Effect Control−Minimum Effect Control) where Minimum Effect Control=HPK1+DMSO and Maximum Effect Control=HPK1 Kinase reaction+known reference inhibitor. An $EC_{50}$ was then calculated fitting the % effect data. Dose response data were analyzed using the 4 parameter logistic nonlinear regression model: Y=Bottom+(Top−Bottom)/(1+10^((Log($EC_{50}$)−X)*Hill Slope)). Where: Y=% E (percent effect) described above; X=base 10 logarithm of molar drug concentration; Bottom=lower limit of dose response (minimum % E); Top=upper limit of dose response (maximum % E); $EC_{50}$=concentration at which 50%; effect is achieved; Hill Slope=Hill slope coefficient; slope of curve at $EC_{50}$.

HPK1—SLP76 TR-FRET Assay Data

The following table provides biological data for specific compounds of the present invention. The biological data was collected using the methodology described above. For each compound. HPK1 $IC_{50}$ values are listed in nanomolar (nM) concentration units.

| Example Number | IC50 (nM) |
|---|---|
| 1-1 | 0.35 |
| 2-1 | 1.59 |
| 2-2 | 0.34 |
| 2-3 | 1.64 |
| 2-4 | 0.63 |
| 2-5 | 0.25 |
| 2-6 | 0.54 |
| 2-7 | 0.24 |
| 3-1 | 0.56 |
| 4-1 | 0.16 |
| 4-2 | 14.38 |
| 4-3 | 0.30 |
| 4-4 | 0.12 |
| 4-5 | 0.61 |
| 4-6 | 0.11 |
| 4-7 | 0.26 |
| 4-8 | 0.25 |
| 4-9 | 5.65 |
| 4-10 | 1.34 |
| 4-11 | 0.55 |
| 4-12 | 0.65 |
| 4-13 | 2.40 |
| 4-14 | 0.18 |
| 4-15 | 0.53 |
| 4-16 | 0.10 |
| 4-17 | 1.01 |
| 4-18 | 0.48 |
| 4-19 | 0.38 |
| 4-20 | 0.21 |
| 4-21 | 0.45 |
| 4-22 | 383.9 |
| 4-23 | 443.3 |
| 4-24 | 593.6 |
| 4-25 | 81.6 |
| 4-26 | 0.17 |
| 4-27 | 0.08 |
| 4-28 | 0.26 |
| 4-29 | 0.20 |

-continued

| Example Number | IC50 (nM) |
|---|---|
| 4-30 | 0.42 |
| 4-31 | 0.20 |
| 4-32 | 1.13 |
| 4-33 | 0.44 |
| 4-34 | 65.1 |
| 4-35 | 158.1 |
| 5-1 | 2.97 |
| 5-2 | 2.54 |
| 6-1 | 0.88 |
| 7-1 | 0.66 |
| 7-2 | 0.15 |
| 7-3 | 0.09 |
| 7-4 | 0.07 |
| 7-5 | 0.50 |
| 7-6 | 70.5 |
| 7-7 | 0.03 |
| 7-8 | 1.48 |
| 7-9 | 1.17 |
| 7-10 | 34.19 |
| 7-11 | 110.8 |
| 7-12 | 1.86 |
| 7-13 | 0.46 |
| 7-14 | 0.19 |
| 7-15 | 0.13 |
| 7-16 | 0.14 |
| 7-17 | 0.86 |
| 7-18 | 0.29 |
| 7-19 | 0.11 |
| 7-20 | 0.20 |
| 7-21 | 0.51 |
| 7-22 | 0.81 |
| 7-23 | 0.17 |
| 7-24 | 0.40 |
| 7-25 | 1.04 |
| 7-26 | 15.0 |
| 7-27 | 0.13 |
| 7-28 | 0.51 |
| 7-29 | 0.35 |
| 7-30 | 2.38 |
| 7-31 | 0.15 |
| 7-32 | 0.41 |
| 7-33 | 0.06 |
| 7-34 | 2.43 |
| 7-35 | 1.49 |
| 7-36 | 0.37 |
| 7-37 | 0.21 |
| 7-38 | 7.77 |
| 7-39 | 57.36 |
| 7-40 | 8.32 |
| 7-41 | 8.85 |
| 7-42 | 0.12 |
| 7-43 | 4.25 |
| 7-44 | 4.69 |
| 7-45 | 19.54 |
| 7-46 | 0.28 |
| 7-47 | 3.57 |
| 7-48 | 1.29 |
| 7-49 | 0.34 |
| 7-50 | 6.24 |
| 7-51 | 4.21 |
| 7-52 | 0.55 |
| 7-53 | 3.94 |
| 7-54 | 82.50 |
| 7-55 | 15.29 |
| 7-56 | 248.5 |
| 7-57 | 1.31 |
| 7-58 | 3.65 |
| 7-59 | 2.15 |
| 7-60 | 0.51 |
| 7-61 | 108.4 |
| 7-62 | 56.0 |
| 7-63 | 103.0 |
| 7-64 | 3.65 |
| 7-65 | 91.5 |
| 7-66 | 0.15 |
| 7-67 | 0.04 |
| 7-68 | 14.0 |

-continued

| Example Number | IC50 (nM) |
|---|---|
| 7-69 | 0.04 |
| 7-70 | 0.15 |
| 7-71 | 1.49 |
| 7-72 | 1.52 |
| 7-73 | 0.13 |
| 7-74 | 0.59 |
| 7-75 | 0.99 |
| 7-76 | 0.22 |
| 7-77 | 0.23 |
| 7-78 | 0.05 |
| 7-79 | 105.5 |
| 7-80 | 0.91 |
| 7-81 | 3.08 |
| 7-82 | 650.8 |
| 7-83 | 4.84 |
| 7-84 | 5.66 |
| 7-85 | 9.29 |
| 7-86 | 11.8 |
| 7-87 | 4.78 |
| 7-88 | 9.16 |
| 7-89 | 172.8 |
| 7-90 | 1.44 |
| 7-91 | 38.57 |
| 7-92 | 10.87 |
| 7-93 | 18.52 |
| 7-94 | 0.88 |
| 7-95 | 548.0 |
| 7-96 | 712.9 |
| 7-97 | 0.23 |
| 7-98 | 0.07 |
| 7-99 | 1.44 |
| 7-100 | 30.0 |
| 7-101 | 0.03 |
| 7-102 | 0.61 |
| 7-103 | 188.4 |
| 7-104 | 0.01 |
| 7-105 | 344.5 |
| 7-106 | 63.81 |
| 7-107 | 55.04 |
| 7-108 | 4.17 |
| 7-109 | 0.16 |
| 7-110 | 0.07 |
| 7-111 | 0.26 |
| 7-112 | 0.03 |
| 7-113 | 0.13 |
| 7-114 | 0.09 |
| 7-115 | 0.20 |
| 7-116 | 282.5 |
| 7-117 | 54.8 |
| 7-118 | 2.74 |
| 8-1 | 1.26 |
| 8-2 | 11.69 |
| 8-3 | 9.48 |
| 8-4 | 13.9 |
| 9-1 | 0.09 |
| 9-2 | 1.42 |
| 9-3 | 0.33 |
| 9-4 | 0.18 |
| 9-5 | 0.71 |
| 9-6 | 4.57 |
| 9-7 | 0.84 |
| 9-8 | 16.45 |
| 9-9 | 3.27 |
| 9-10 | 1.60 |
| 9-11 | 0.79 |
| 9-12 | 1.83 |
| 10-1 | 0.44 |
| 10-2 | 245.5 |
| 10-3 | 28.94 |
| 10-4 | 67.11 |
| 10-5 | 43.24 |
| 10-6 | 41.63 |
| 10-7 | 52.64 |
| 10-8 | 844.6 |
| 11-1 | 868.8 |
| 11-2 | 199.2 |
| 12-1 | 117.3 |

-continued

| Example Number | IC50 (nM) |
|---|---|
| 12-2 | 243.9 |
| 12-3 | 598.0 |
| 12-4 | 379.6 |
| 12-5 | 111.9 |
| 12-6 | 27.73 |
| 12-7 | 1.96 |
| 12-8 | 343.7 |
| 12-9 | 172.5 |
| 12-10 | 186.1 |
| 12-11 | 11.14 |
| 12-12 | 283.6 |
| 13-1 | 5.83 |
| 13-2 | 0.92 |
| 13-3 | 30.62 |
| 13-4 | 0.66 |
| 13-5 | 0.69 |
| 13-6 | 596.9 |
| 13-7 | 214.6 |
| 13-8 | 229.5 |
| 13-9 | 312.4 |
| 13-10 | 325.8 |
| 13-11 | 0.40 |
| 13-12 | 0.12 |
| 13-13 | 1.09 |
| 14-1 | 2.75 |
| 14-2 | 0.26 |
| 14-3 | 0.64 |
| 15-1 | 0.48 |
| 16-1 | 0.09 |
| 17-1 | 11.41 |
| 18-1 | 23.6 |
| 19-1 | 3.01 |
| 20-1 | 1.62 |
| 20-2 | 0.12 |
| 21-1 | 0.21 |
| 22-1 | 370.2 |
| 22-2 | 467.8 |
| 23-1 | 0.22 |
| 23-2 | 0.82 |
| 23-3 | 0.28 |
| 24-1 | 5.05 |
| 25-1 | 24.36 |
| 25-2 | 14.26 |
| 25-3 | 1.14 |
| 25-4 | 2.78 |
| 25-5 | 216.9 |
| 25-6 | 579.6 |
| 25-7 | 473.9 |
| 25-8 | 175.8 |
| 25-9 | 12.06 |
| 25-10 | 1.22 |
| 25-11 | 71.0 |
| 25-12 | 0.57 |
| 25-13 | 14.04 |
| 25-14 | 135.9 |
| 25-15 | 209.7 |
| 25-16 | 14.54 |
| 25-17 | 333.3 |
| 25-18 | 20.07 |
| 25-19 | 2.61 |
| 25-20 | 3.31 |
| 25-21 | 45.03 |
| 25-22 | 2.98 |
| 25-23 | 345.5 |
| 25-24 | 230.1 |
| 25-25 | 1.23 |
| 25-26 | 203.5 |
| 25-27 | 880.8 |
| 25-28 | 3.72 |
| 25-29 | 65.18 |
| 25-30 | 0.72 |
| 25-31 | 29.59 |
| 25-32 | 454.9 |
| 25-33 | 187.1 |
| 25-34 | 24.56 |
| 25-35 | 0.30 |
| 25-36 | 169.5 |

-continued

| Example Number | IC50 (nM) |
|---|---|
| 25-37 | 69.01 |
| 25-38 | 403.8 |
| 25-39 | 19.4 |
| 25-40 | 38.7 |
| 25-41 | 733.4 |
| 25-42 | 89.9 |
| 25-43 | 77.8 |
| 25-44 | 1.95 |
| 25-45 | 41.3 |
| 26-1 | 0.26 |
| 26-2 | 0.60 |
| 26-3 | 0.29 |
| 26-4 | 1.33 |
| 26-5 | 9.79 |
| 26-6 | 1.32 |
| 26-7 | 12.00 |
| 26-8 | 0.95 |
| 26-9 | 0.95 |
| 26-10 | 1.06 |
| 26-11 | 26.0 |
| 26-12 | 18.1 |
| 26-13 | 0.60 |
| 26-14 | 0.14 |
| 26-15 | 0.25 |
| 26-16 | 11.87 |
| 26-17 | 60.18 |
| 26-18 | 0.57 |
| 26-19 | 2.49 |
| 26-20 | 0.45 |
| 26-21 | 0.22 |
| 26-22 | 1.43 |
| 26-23 | 3.69 |
| 26-24 | 0.23 |
| 26-25 | 0.22 |
| 26-26 | 3.31 |
| 26-27 | 106.0 |
| 26-28 | 4.92 |
| 26-29 | 1.43 |
| 26-30 | 28.57 |
| 26-31 | 5.18 |
| 26-32 | 1.02 |
| 26-33 | 0.46 |
| 26-34 | 9.66 |
| 26-35 | 52.75 |
| 26-36 | 6.05 |
| 26-37 | 0.38 |
| 26-38 | 1.07 |
| 26-39 | 0.34 |
| 26-40 | 2.08 |
| 26-41 | 0.14 |
| 26-42 | 205.2 |
| 26-43 | 6.59 |
| 26-44 | 92.11 |
| 26-45 | 0.51 |
| 26-46 | 29.7 |
| 26-47 | 3.01 |
| 26-48 | 22.82 |
| 26-49 | 78.77 |
| 26-50 | 40.58 |
| 26-51 | 12.89 |
| 26-52 | 0.32 |
| 26-53 | 0.23 |
| 26-54 | 0.97 |
| 26-55 | 223.5 |
| 26-56 | 776.6 |
| 26-57 | 3.19 |
| 26-58 | 9.83 |
| 26-59 | 48.31 |
| 26-60 | 4.89 |
| 26-61 | 145.7 |
| 26-62 | 15.62 |
| 26-63 | 109.1 |
| 26-64 | 0.86 |
| 26-65 | 17.77 |
| 26-66 | 193.2 |
| 26-67 | 4.74 |
| 26-68 | 2.62 |

-continued

| Example Number | IC50 (nM) |
|---|---|
| 26-69 | 42.5 |
| 26-70 | 2.71 |
| 26-71 | 32.84 |
| 26-72 | 1.23 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula (Ib):

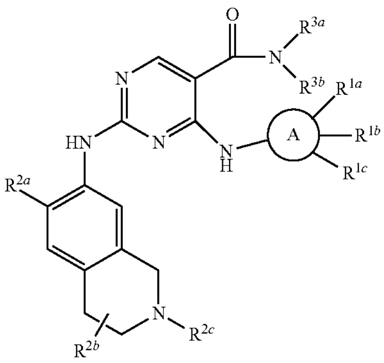

II wherein:

A is a phenyl, cycloalkyl, or heterocyclyl ring;

$R^{1a}$, $R^{1b}$ and $R^{1c}$ as are present are independently selected from:

(1) hydrogen, (2) halogen, (3) hydroxyl, (4) $C_{1-6}$alkyl, which is unsubstituted or substituted with substituents selected from: hydroxy, —O—$C_{1-6}$alkyl, —$NH_2$, —NH($C_{1-6}$alkyl), —N($C_{1-6}$alkyl)$_2$, —CN, —(CO)NH($C_{1-6}$alkyl), —(CO)NH($C_{1-6}$alkyl)$_2$, —(CO)NH($C_{1-6}$alkyl-$CO_2$H), phenyl, and fluoro, (5) —O—$C_{1-6}$alkyl, which is unsubstituted or substituted with substituents selected from: hydroxy, methoxy, —(CO)NH($C_{1-6}$alkyl), —(CO)O($C_{1-6}$alkyl), —CN, and fluoro, (6) —$C_{3-10}$cycloalkyl, which is unsubstituted or substituted with substituents selected from: hydroxy, methoxy, —$C_{1-6}$alkyl, —$C_{2-6}$alkenyl, —$C_{2-6}$alkynyl, —(CO)NH($C_{1-6}$alkyl), —(CO)O($C_{1-6}$alkyl), —CN, and fluoro, (7) $C_{2-6}$alkynyl, (8) —$NH_2$, (9) —NH($C_{1-6}$alkyl),

(10) —N($C_{1-6}$alkyl)$_2$,

(11) —(CO)($C_{1-6}$alkyl),

(12) —(CO)$NH_2$,

(13) —(CO)NH($C_{1-6}$alkyl),

(14) —(CO)NH($C_{3-6}$cycloalkyl),

(15) —NH(CO)($C_{1-6}$alky),

(16) —S—$C_{1-6}$alkyl,

(17) —$SO_2$—$C_{1-6}$alkyl,

(18) —$SO_2NH_2$,
(19) —CN,
(20) keto,
(21) -phenyl,
(22) -pyridyl,
(23) -diazolyl,
(24) -morpholinyl,
(25) -oxazolyl,
(26) -oxadiazolyl,
(27) -piperazinyl,
(28) -piperidinyl,
(29) -pyrazolyl,
(30) -thiazolyl, and
(31) -triazolyl, or $R^{1a}$ and $R^{1b}$ may be joined to form a phenyl, 1,4-dioxanyl, 1,3-dioxolanyl, morpholinyl, oxazolyl, piperidinyl, pyrazolyl, pyrrolidinyl, tetrahydrofuranyl, tetrahydropyranyl, tetrahydroquinolinyl, or thiazolyl ring, which is unsubstituted or substituted with $C_{1-6}$alkyl, or one of $R^{1a}$, $R^{1b}$ and $R^{1c}$ may be joined by a $C_{3-6}$alkyl to one of $R^{2a}$, $R^{2b}$ and $R^{2c}$;

$R^{2a}$, $R^{2b}$ and $R^{2c}$ as are present are independently selected from:
(1) hydrogen,
(2) halogen,
(3) hydroxyl,
(4) $C_{1-6}$alkyl, which is unsubstituted or substituted with substituents selected from: hydroxy, fluoro, —(CO)NH($C_{1-6}$alkyl), —(CO)O($C_{1-6}$alkyl), —$SO_2$—$C_{1-6}$ alkyl, $C_{3-6}$cycloalkyl, —CN, —O—$C_{1-6}$alkyl, —(O—$C_{1-6}$alkyl-)$_3$, —$C_{3-6}$cycloalkyl, $C_{2-6}$alkenyl, phenyl, and pyrazolyl which is unsubstituted or substituted with $C_{1-6}$alkyl,
(5) —O—$C_{1-6}$alkyl, which is unsubstituted or substituted with fluoro,
(6) —$C_{3-6}$cycloalkyl, which is unsubstituted or substituted with substituents selected from: hydroxy, methoxy, —$C_{1-6}$alkyl, —$C_{1-6}$alkyl-OH, —(CO)NH($C_{1-6}$alkyl), —(CO)O($C_{1-6}$alkyl), —CN, and fluoro
(7) —$NH_2$,
(8) —NH($C_{1-6}$alkyl),
(9) —N($C_{1-6}$alkyl)$_2$,
(10) —(CO)$C_{1-6}$alkyl,
(10) —(CO)$C_{1-6}$alkyl-fluoro,
(11) —(CO)$C_{1-6}$alkyl-O—$C_{1-6}$alkyl,
(11) —(CO)$C_{1-6}$alkyl-O—$C_{1-6}$alkyl-O—$C_{1-6}$alkyl-O—$C_{1-6}$alkyl,
(12) —(CO)$C_{3-6}$cycloalkyl-$C_{1-6}$alkyl,
(13) —(CO)$C_{3-6}$cycloalkyl-$C_{1-6}$alkyl-fluoro,
(14) —(CO)$C_{3-6}$cycloalkyl-$C_{1-6}$alkyl-amino,
(15) —(CO)$NH_2$,
(16) —(CO)NH($C_{1-6}$alkyl),
(17) —NH(CO)($C_{1-6}$alkyl),
(18) —$SO_2$—$C_{1-6}$alkyl,
(19) —$SO_2$—NH($C_{1-6}$alkyl),
(20) —$SO_2$—N($C_{1-6}$alkyl)$_2$,
(21) azaspiro[3.3]heptanyl, which is unsubstituted or substituted with —$C_{1-6}$alkyl or oxetanyl, which is unsubstituted or substituted with —$C_{1-6}$alkyl,
(22) azetidinyl, which is unsubstituted or substituted with —$C_{1-6}$alkyl or —(CO)O($C_{1-6}$ alkyl),
(23)bicyclopentyl, which is unsubstituted or substituted with —$C_{1-6}$alkyl or —(CO)O($C_{1-6}$alkyl),
(24) oxazolyl,
(25) oxadiazolyl,
(26) oxetanyl, which is unsubstituted or substituted with —$C_{1-6}$alkyl,
(27) piperidinyl, which is unsubstituted or substituted with —$C_{1-6}$alkyl or oxetanyl, which is unsubstituted or substituted with —$C_{1-6}$alkyl,
(28) pyrrolidinyl, which is unsubstituted or substituted with oxo or —$C_{1-6}$alkyl, and
(29) thiazolyl,
(30) keto, or $R^{2b}$ and $R^{2c}$ may be joined to form a pyrrolyl, dihydrospiro[1,4'-pyrazolo[1,5-d][1,4]diazepin]-7'(8'H)-one, or dihydro-4H-pyrazolo[1,5-d][1,4]diazepin-one ring, which is unsubstituted or substituted with —$C_{1-6}$alkyl, —$C_{1-6}$alkyl-OH or —$C_{3-6}$cycloalkyl;

$R^{3a}$ and $R^{3b}$ are independently selected from:
(1) hydrogen,
(2) $C_{1-6}$alkyl, and
(3) —$NH_2$;

or a pharmaceutically acceptable salt thereof.

2. The compound of claim 1, or a pharmaceutically acceptable salt thereof, wherein A is a phenyl, pyridyl, indenyl, tetrahydronaphthalenyl, tetrahydroisoquinolinyl, pyrazolyl, or 2,3-dihydro-1H-pyrido[2,3-b][1,4]oxazin-7-yl ring.

3. The compound of claim 1, or a pharmaceutically acceptable salt thereof, wherein $R^{1a}$, $R^{1b}$ and $R^{1c}$ as are present are independently selected from:
(1) hydrogen,
(2) fluoro,
(3) chloro,
(4) bromo,
(5) hydroxyl,
(6) $C_{1-6}$alkyl, which is unsubstituted or substituted with hydroxy, amidoalkyl, amino, aminomethyl, carboxyl, methoxy, phenyl, or one or more fluoro,
(7) —O—$C_{1-6}$alkyl, which is unsubstituted or substituted with one or more fluoro,
(8) $C_{3-6}$cycloalkyl, which is unsubstituted or substituted with cyano, or one or more fluoro,
(9) —S—$C_{1-3}$alkyl,
(10) —$NH_2$,
(11) —NH($C_{1-3}$alkyl),
(12) —N($C_{1-3}$alkyl)$_2$,
(13) —(CO)$NH_2$,
(14) —(CO)NH—$C_{1-6}$alkyl,
(15) keto, and
(16) -phenyl.

4. The compound of claim 3, or a pharmaceutically acceptable salt thereof, wherein $R^{1e}$ is hydrogen and $R^{1a}$ and $R^{1b}$, as are present, are independently selected from:
(1) hydrogen,
(2) fluoro,
(3) bromo,
(4) chloro,
(5) hydroxyl,
(6) —$CH_3$,
(7) —$CHF_2$,
(8) —$CF_3$,
(9) —CN,
(10) —$CH_2OH$,
(11) —$CH_2NH_2$,
(12) —$CH_2CH_3$,
(13) —$CH(CH_3)$ OH,
(14) —$CH(CH_3)$ $OCH_3$,
(15) —$CH(CH_3)$ $NH_2$,
(16) —$CH_2CH_2OH$,

(17) —$C(CH_3)_3$,
(18) —$CH_2NH(CH_3)$,
(19) —$CH_2NH(CO)O$—$C(CH_3)_3$,
(20) —$CH_2N(CH_3)CH_2CO_2H$,
(21) —$CH(OCH_3)CH_3$,
(22) —$(CO)NH_2$,
(23) —$(CO)NHCH_3$,
(24) —$OCH_3$,
(25) —$OCF_3$,
(26) —$OCHF_2$,
(27) —$OCH(CH_3)_2$,
(28) —$OCH_2CH_2F$,
(29) —$SCH_3$,
(30) —$N(CH_3)_2$,
(31)cyclopropyl, which is unsubstituted or substituted with —CN, and
(32) phenyl.

5. The compound of claim 4, or a pharmaceutically acceptable salt thereof, wherein $R^{2a}$ is hydrogen, $R^{2b}$ is hydrogen or —$C_{1-6}$alkyl, and $R^{2c}$ is independently selected from:
(1) $C_{1-6}$alkyl, which is unsubstituted or substituted with substituents selected from: hydroxy, —(CO)NH($C_{1-6}$ alkyl), —(CO)O($C_{1-6}$alkyl), —$C_{3-6}$cycloalkyl, phenyl and fluoro,
(2) —O—$C_{1-6}$alkyl, which is unsubstituted or substituted with fluoro,
(3) —$C_{3-6}$cycloalkyl, which is unsubstituted or substituted with substituents selected from: hydroxy, methoxy, —$C_{1-6}$alkyl, —(CO)NH($C_{1-6}$alkyl), —(CO)O($C_{1-6}$alkyl), and fluoro,
(4) azaspiro[3.3]heptanyl, which is unsubstituted or substituted with —$C_{1-6}$alkyl or oxetanyl, which is unsubstituted or substituted with —$C_{1-6}$alkyl,
(5) azetidinyl, which is unsubstituted or substituted with —$C_{1-6}$alkyl or —(CO)O($C_{1-6}$alkyl),
(6)bicyclopentyl, which is unsubstituted or substituted with —$C_{1-6}$alkyl or —(CO)O($C_{1-6}$alkyl),
(7) oxazolyl,
(8) oxadiazolyl,
(9) oxetanyl, which is unsubstituted or substituted with —$C_{1-6}$alkyl,
(10) piperidinyl, which is unsubstituted or substituted with —$C_{1-6}$alkyl or oxetanyl, which is unsubstituted or substituted with —$C_{1-6}$alkyl,
(11) pyrrolidinyl, which is unsubstituted or substituted with oxo or —$C_{1-6}$alkyl, and
(12) thiazolyl.

6. The compound of claim 5, or a pharmaceutically acceptable salt thereof, wherein $R^{2a}$ is hydrogen, $R^{2b}$ is hydrogen or —$C_{1-6}$alkyl, and $R^{2c}$ is independently selected from:
(1) hydrogen,
(2) fluoro,
(3) hydroxyl,
(4) $C_{1-6}$alkyl, and
(5) —O—$C_{1-6}$alkyl.

7. The compound of claim 6, or a pharmaceutically acceptable salt thereof, wherein $R^{3a}$ is hydrogen and $R^{3b}$ is hydrogen.

8. A compound which is selected from the group consisting of:
4-((3-(hydroxymethyl)phenyl)amino)-2-((6-methoxy-2-methyl-1,2,3,4-tetrahydroisoquinolin-7-yl)amino)pyrimidine-5-carboxamide;
tert-butyl {[3-({5-carbamoyl-2-[(6-methoxy-2-methyl-1,2,3,4-tetrahydroisoquinolin-7-yl)amino]pyrimidin-4-yl}amino)phenyl]methyl}carbamate;
4-{[3-(aminomethyl)phenyl]amino}-2-[(6-methoxy-2-methyl-1,2,3,4-tetrahydroisoquinolin-7-yl)amino]pyrimidine-5-carboxamide;
4-{[2-(aminomethyl)phenyl]amino}-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-({2-[(methylamino)methyl] phenyl}aminopyrimidine-5-carboxamide;
4-{[3-(1-aminoethyl)phenyl]amino}-2-[(6-methoxy-2-methyl-1,2,3,4-tetrahydroisoquinolin-7-yl)amino]pyrimidine-5-carboxamide;
4-{[3-(1-aminoethyl)phenyl]amino}-2-[(6-chloro-2-methyl-1,2,3,4-tetrahydroisoquinolin-7-yl)amino]pyrimidine-5-carboxamide;
4-{[3-(1-aminoethyl)phenyl]amino}-2-[(6-fluoro-2-methyl-1,2,3,4-tetrahydroisoquinolin-7-yl)amino]pyrimidine-5-carboxamide;
4-[(3-{[(1-fluorocyclopropane-1-carbonyl)amino] methyl}phenyl)amino]-2-[(6-methoxy-2-methyl-1,2,3,4-tetrahydroisoquinolin-7-yl)amino]pyrimidine-5-carboxamide;
4-((2,6-difluorophenyl)amino)-2-((6-methoxy-2-methyl-1,2,3,4-tetrahydroisoquinolin-7-yl)amino)pyrimidine-5-carboxamide;
4-[(2,6-dimethylphenyl)amino]-2-[(6-methoxy-2-methyl-1,2,3,4-tetrahydroisoquinolin-7-yl)amino]pyrimidine-5-carboxamide;
4-[(2-fluoro-6-methylphenyl)amino]-2-[(6-methoxy-2-methyl-1,2,3,4-tetrahydroisoquinolin-7-yl)amino]pyrimidine-5-carboxamide;
4-[(2-bromo-6-fluorophenyl)amino]-2-[(6-methoxy-2-methyl-1,2,3,4-tetrahydroisoquinolin-7-yl)amino]pyrimidine-5-carboxamide;
2-[(6-chloro-2-methyl-1,2,3,4-tetrahydroisoquinolin-7-yl)amino]-4-[(2-fluoro-6-methylphenyl)amino]pyrimidine-5-carboxamide;
4-[(2-fluoro-6-methylphenyl)amino]-2-[(6-fluoro-2-methyl-1,2,3,4-tetrahydroisoquinolin-7-yl)amino]pyrimidine-5-carboxamide;
4-[(2-fluoro-6-methylphenyl)amino]-2-[(6-methoxy-1,2,3,4-tetrahydroisoquinolin-7-yl)amino]pyrimidine-5-carboxamide;
4-{[2-fluoro-6-(trifluoromethyl)phenyl]amino}-2-[(6-methoxy-2-methyl-1,2,3,4-tetrahydroisoquinolin-7-yl)amino]pyrimidine-5-carboxamide;
4-[(2-cyano-6-fluorophenyl)amino]-2-[(6-methoxy-2-methyl-1,2,3,4-tetrahydroisoquinolin-7-yl)amino]pyrimidine-5-carboxamide;
4-[(2,4-difluorophenyl)amino]-2-[(6-methoxy-2-methyl-1,2,3,4-tetrahydroisoquinolin-7-yl)amino]pyrimidine-5-carboxamide;
4-[(2,5-difluorophenyl)amino]-2-[(6-methoxy-2-methyl-1,2,3,4-tetrahydroisoquinolin-7-yl)amino]pyrimidine-5-carboxamide;
4-[(3-chloro-2-fluorophenyl)amino]-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-[(2,3,4-trifluorophenyl)amino]pyrimidine-5-carboxamide;
4-[(2-fluoro-3-methylphenyl)amino]-2-[(6-methoxy-2-methyl-1,2,3,4-tetrahydroisoquinolin-7-yl)amino]pyrimidine-5-carboxamide;

4-[(2,6-difluoro-4-methoxyphenyl)amino]-2-[(6-methoxy-2-methyl-1,2,3,4-tetrahydroisoquinolin-7-yl)amino]pyrimidine-5-carboxamide;

4-[(2-chloro-6-fluoro-3-methylphenyl)amino]-2-[(6-methoxy-2-methyl-1,2,3,4-tetrahydroisoquinolin-7-yl)amino]pyrimidine-5-carboxamide;

4-[(2-fluoro-6-hydroxyphenyl)amino]-2-[(6-methoxy-2-methyl-1,2,3,4-tetrahydroisoquinolin-7-yl)amino]pyrimidine-5-carboxamide;

4-[(2-chloro-5-methylphenyl)amino]-2-[(6-methoxy-2-methyl-1,2,3,4-tetrahydroisoquinolin-7-yl)amino]pyrimidine-5-carboxamide;

4-[(2-chloro-4-methylphenyl)amino]-2-[(6-methoxy-2-methyl-1,2,3,4-tetrahydroisoquinolin-7-yl)amino]pyrimidine-5-carboxamide;

4-[(6-chloro-2-fluoro-3-methylphenyl)amino]-2-[(6-methoxy-2-methyl-1,2,3,4-tetrahydroisoquinolin-7-yl)amino]pyrimidine-5-carboxamide;

4-[(2-chloro-4,6-difluorophenyl)amino]-2-[(6-methoxy-2-methyl-1,2,3,4-tetrahydroisoquinolin-7-yl)amino]pyrimidine-5-carboxamide;

2-{[1-(cyclopropylmethyl)-1H-pyrazol-4-yl]amino}-4-[(2-fluoro-6-methylphenyl)amino]pyrimidine-5-carboxamide;

4-[(2-fluoro-6-methylphenyl)amino]-2-{[1-(2-hydroxy-2-methylpropyl)-1H-pyrazol-4-yl]amino}pyrimidine-5-carboxamide;

4-[(2-fluoro-6-methylphenyl)amino]-2-{[1-(2,2,2-trifluoroethyl)-1H-pyrazol-4-yl]amino}pyrimidine-5-carboxamide;

4-[(2-fluoro-6-methylphenyl)amino]-2-{[4-(methylsulfonyl)phenyl]amino}pyrimidine-5-carboxamide;

4-[(2-cyclopropylphenyl)amino]-2-[(6-methoxy-2-methyl-1,2,3,4-tetrahydroisoquinolin-7-yl)amino]pyrimidine-5-carboxamide;

4-[(2-ethylphenyl)amino]-2-[(6-methoxy-2-methyl-1,2,3,4-tetrahydroisoquinolin-7-yl)amino]pyrimidine-5-carboxamide;

4-[(2-tert-butylphenyl)amino]-2-[(6-methoxy-2-methyl-1,2,3,4-tetrahydroisoquinolin-7-yl)amino]pyrimidine-5-carboxamide;

2-[(6-fluoro-2-methyl-1,2,3,4-tetrahydroisoquinolin-7-yl)amino]-4-{[2-fluoro-6-(trifluoromethyl)phenyl]amino}pyrimidine-5-carboxamide;

4-[(4-bromo-2,6-difluorophenyl)amino]-2-[(6-methoxy-2-methyl-1,2,3,4-tetrahydroisoquinolin-7-yl)amino]pyrimidine-5-carboxamide;

4-{[2-(difluoromethoxy)-6-fluorophenyl]amino}-2-[(6-methoxy-2-methyl-1,2,3,4-tetrahydroisoquinolin-7-yl)amino]pyrimidine-5-carboxamide;

4-[(2,2-dimethyl-2,3-dihydro-1-benzofuran-7-yl)amino]-2-[(6-fluoro-2-methyl-1,2,3,4-tetrahydroisoquinolin-7-yl)amino]pyrimidine-5-carboxamide;

4-[(4-cyano-2-fluoro-6-methylphenyl)amino]-2-[(6-methoxy-2-methyl-1,2,3,4-tetrahydroisoquinolin-7-yl)amino]pyrimidine-5-carboxamide;

2-[(3,5-dimethyl-1H-pyrazol-4-yl)amino]-4-[(2-fluoro-6-methylphenyl)amino]pyrimidine-5-carboxamide;

4-[(2-fluoro-6-methylphenyl)amino]-2-[(1-methyl-1H-pyrazol-4-yl)amino]pyrimidine-5-carboxamide;

4-{[2-fluoro-6-(trifluoromethyl)phenyl]amino}-2-{[2-(2-hydroxy-2-methylpropyl)-6-methoxy-1,2,3,4-tetrahydroisoquinolin-7-yl]amino}pyrimidine-5-carboxamide;

4-[(2-fluoro-6-methylphenyl)amino]-2-{[2-(2-hydroxy-2-methylpropyl)-6-methoxy-1,2,3,4-tetrahydroisoquinolin-7-yl]amino}pyrimidine-5-carboxamide;

2-[(6-methoxy-2-methyl-1,2,3,4-tetrahydroisoquinolin-7-yl)amino]-4-(phenylaminopyrimidine-5-carboxamide;

2-{[4-(methylsulfonyl)phenyl]amino}-4-[(1,2,3,4-tetrahydroisoquinolin-5-yl)amino]pyrimidine-5-carboxamide;

2-[(6-methoxy-2-methyl-1,2,3,4-tetrahydroisoquinolin-7-yl)amino]-4-({2-[(4S)-4-methyl-2-oxo-1,3-oxazolidin-3-yl]phenyl}aminopyrimidine-5-carboxamide;

4-[(2-bromophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(1,2,3,4-tetrahydroisoquinolin-5-yl)amino]pyrimidine-5-carboxamide;

4-[(1H-benzotriazol-7-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-methylcinnolin-5-yl)amino]pyrimidine-5-carboxamide;

4-[(2,3-dihydro-1-benzofuran-7-yl)amino]-2-[(6-methoxy-2-methyl-1,2,3,4-tetrahydroisoquinolin-7-yl)amino]pyrimidine-5-carboxamide;

2-{[1-(cyclopropylmethyl)-1H-pyrazol-4-yl]amino}-4-[(1,2,3,4-tetrahydroisoquinolin-5-yl)amino]pyrimidine-5-carboxamide;

2-[(3-methoxy-1-methyl-1H-pyrazol-4-yl)amino]-4-[(1,2,3,4-tetrahydroisoquinolin-5-yl)amino]pyrimidine-5-carboxamide;

4-[(2-bromophenyl)amino]-2-{[2-methoxy-4-(piperazin-1-yl)phenyl]amino}pyrimidine-5-carboxamide;

2-[(1-methyl-3-oxo-2,3-dihydro-1H-pyrazol-4-yl)amino]-4-[(1,2,3,4-tetrahydroisoquinolin-5-yl)amino]pyrimidine-5-carboxamide;

2-[(1-methyl-1H-pyrazol-4-yl)amino]-4-[(1,2,3,4-tetrahydroisoquinolin-5-yl)amino]pyrimidine-5-carboxamide;

4-{[2-fluoro-6-(hydroxymethyl)phenyl]amino}-2-[(6-methoxy-2-methyl-1,2,3,4-tetrahydroisoquinolin-7-yl)amino]pyrimidine-5-carboxamide;

4-[(2,2-dimethyl-2,3-dihydro-1-benzofuran-7-yl)amino]-2-[(6-methoxy-2-methyl-1,2,3,4-tetrahydroisoquinolin-7-yl)amino]pyrimidine-5-carboxamide;

2-{[4-(1-cyanocyclopropyl)phenyl]amino}-4-[(1,2,3,4-tetrahydroisoquinolin-5-yl)amino]pyrimidine-5-carboxamide;

2-[(3,4-dihydro-1H-2-benzopyran-7-yl)amino]-4-[(1,2,3,4-tetrahydroisoquinolin-5-yl)amino]pyrimidine-5-carboxamide;

2-{[4-(1-cyanocyclopropyl)phenyl]amino}-4-[(1-oxo-1,2,3,4-tetrahydroisoquinolin-5-yl)amino]pyrimidine-5-carboxamide;

4-[(3-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(trifluoromethyl)phenyl]amino}pyrimidine-5-carboxamide;

2-[(6-methoxy-2-methyl-1,2,3,4-tetrahydroisoquinolin-7-yl)amino]-4-[(2-methylphenyl)amino]pyrimidine-5-carboxamide;

4-[(4-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-methylphenyl)amino]pyrimidine-5-carboxamide;

4-{[2-(butan-2-yl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(4-methylphenyl)amino]pyrimidine-5-carboxamide;

4-[(3-chlorophenyl)amino]-2-[(6-methoxy-2-methyl-1,2,3,4-tetrahydroisoquinolin-7-yl)amino]pyrimidine-5-carboxamide;

4-[(3-cyano-4-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

4-{[2-(2-hydroxy-2-methylpropyl)-1,2,3,4-tetrahydroisoquinolin-5-yl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(2,2,2-trifluoroethyl)-1,2,3,4-tetrahydroisoquinolin-5-yl]amino}pyrimidine-5-carboxamide;

4-[(3-cyano-2-fluorophenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(methylsulfonyl)-1,2,3,4-tetrahydroisoquinolin-5-yl]amino}pyrimidine-5-carboxamide;

4-{[3-(1-cyanocyclopropyl)phenyl]amino}-2-[(6-methoxy-2-methyl-1,2,3,4-tetrahydroisoquinolin-7-yl)amino]pyrimidine-5-carboxamide;

4-{[2-(hydroxymethyl)phenyl]amino}-2-[(6-methoxy-2-methyl-1,2,3,4-tetrahydroisoquinolin-7-yl)amino]pyrimidine-5-carboxamide;

N-{[3-({5-carbamoyl-2-[(6-methoxy-2-methyl-1,2,3,4-tetrahydroisoquinolin-7-yl)amino]pyrimidin-4-yl}amino)phenyl methyl}-N-methylglycine 2-[(6-methoxy-2-methyl-1,2,3,4-tetrahydroisoquinolin-7-yl)amino]-4-[(2-methyl-1-oxo-1,2,3,4-tetrahydroisoquinolin-5-yl)amino]pyrimidine-5-carboxamide;

2-[(6-chloro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

2-[(6-fluoro-2-methyl-1,2,3,4-tetrahydroisoquinolin-7-yl)amino]-4-[(1-oxo-1,2,3,4-tetrahydroisoquinolin-5-yl)amino]pyrimidine-5-carboxamide;

2-[(6-methoxy-2-methyl-1,2,3,4-tetrahydroisoquinolin-7-yl)amino]-4-{[3-(methylcarbamoyl)phenyl]amino}pyrimidine-5-carboxamide;

2-[(6-chloro-2-methyl-1,2,3,4-tetrahydroisoquinolin-7-yl)amino]-4-{[3-(methylcarbamoyl)phenyl]amino}pyrimidine-5-carboxamide;

4-[(2-bromo-6-methylphenyl)amino]-2-[(6-methoxy-2-methyl-1,2,3,4-tetrahydroisoquinolin-7-yl)amino]pyrimidine-5-carboxamide;

2-[(6-fluoro-2-methyl-1,2,3,4-tetrahydroisoquinolin-7-yl)amino]-4-{[3-(methylcarbamoyl)phenyl]amino}pyrimidine-5-carboxamide;

2-[(6-fluoro-2-methyl-1,2,3,4-tetrahydroisoquinolin-7-yl)amino]-4-{[2-(hydroxymethyl)phenyl]amino}pyrimidine-5-carboxamide;

2-{[1-(cyclopropylmethyl)-1H-pyrazol-4-yl]amino}-4-[(1-oxo-1,2,3,4-tetrahydroisoquinolin-5-yl)amino]pyrimidine-5-carboxamide;

2-[(1-methyl-1H-pyrazol-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[1-(2,2,2-trifluoroethyl)-1H-pyrazol-4-yl]amino}pyrimidine-5-carboxamide;

2-{[1-(1-cyclopropylethyl)-1H-pyrazol-4-yl]amino}-4-[(1-oxo-1,2,3,4-tetrahydroisoquinolin-5-yl)amino]pyrimidine-5-carboxamide;

2-[(3-methoxy-1-methyl-1H-pyrazol-4-yl)amino]-4-[(1-oxo-1,2,3,4-tetrahydroisoquinolin-5-yl)amino]pyrimidine-5-carboxamide;

2-{[4-(methylsulfonyl)phenyl]amino}-4-[(1-oxo-1,2,3,4-tetrahydroisoquinolin-5-yl)amino]pyrimidine-5-carboxamide;

4-[(2-cyanophenyl)amino]-2-[(6-methoxy-2-methyl-1,2,3,4-tetrahydroisoquinolin-7-yl)amino]pyrimidine-5-carboxamide;

4-[(1-oxo-1,2,3,4-tetrahydroisoquinolin-5-yl)amino]-2-{[1-(propan-2-yl)-1H-pyrazol-4-yl]amino}pyrimidine-5-carboxamide;

2-[(1-cyclobutyl-1H-pyrazol-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[1-(piperidin-4-yl)-1H-pyrazol-4-yl]amino}pyrimidine-5-carboxamide;

4-[(1-oxo-1,2,3,4-tetrahydroisoquinolin-5-yl)amino]-2-[(4,5,6,7-tetrahydropyrazolo[1,5-a]pyridin-3-yl)amino]pyrimidine-5-carboxamide;

2-{[5-(difluoromethyl)-1-methyl-1H-pyrazol-4-yl]amino}-4-[(1-oxo-1,2,3,4-tetrahydroisoquinolin-5-yl)amino]pyrimidine-5-carboxamide;

2-{[3-(2,2-difluoroethoxy)-1-methyl-1H-pyrazol-4-yl]amino}-4-[(1-oxo-1,2,3,4-tetrahydroisoquinolin-5-yl)amino]pyrimidine-5-carboxamide;

2-{[1-methyl-5-(trifluoromethyl)-1H-pyrazol-4-yl]amino}-4-[(1-oxo-1,2,3,4-tetrahydroisoquinolin-5-yl)amino]pyrimidine-5-carboxamide;

2-[(6,7-dihydro-5H-pyrazolo[5,1-b][1,3]oxazin-3-yl)amino]-4-[(1-oxo-1,2,3,4-tetrahydroisoquinolin-5-yl)amino]pyrimidine-5-carboxamide;

2-[(5,6-dihydro-4H-pyrrolo[1,2-b]pyrazol-2-yl)amino]-4-[(1-oxo-1,2,3,4-tetrahydroisoquinolin-5-yl)amino]pyrimidine-5-carboxamide;

2-({4-[(methylsulfonyl)methyl]phenyl}amino)-4-[(1-oxo-1,2,3,4-tetrahydroisoquinolin-5-yl)amino]pyrimidine-5-carboxamide;

2-({4-[2-(methylsulfonyl) propan-2-yl]phenyl}amino)-4-[(1-oxo-1,2,3,4-tetrahydroisoquinolin-5-yl)amino]pyrimidine-5-carboxamide;

2-{[2-methoxy-5-(methylsulfonyl)phenyl]amino}-4-[(2-methyl-1,2,3,4-tetrahydroisoquinolin-5-yl)amino]pyrimidine-5-carboxamide;

2-{[3-methoxy-1-(2,2,2-trifluoroethyl)-1H-pyrazol-4-yl]amino}-4-[(2-methyl-1,2,3,4-tetrahydroisoquinolin-5-yl)amino]pyrimidine-5-carboxamide;

2-{[2-methoxy-5-(methylsulfonyl)phenyl]amino}-4-[(1,2,3,4-tetrahydroisoquinolin-5-yl)amino]pyrimidine-5-carboxamide;

2-[(2-methyl-3-oxo-2,3-dihydro-1H-isoindol-5-yl)amino]-4-[(1,2,3,4-tetrahydroisoquinolin-5-yl)amino]pyrimidine-5-carboxamide;

4-{[2-fluoro-6-(hydroxymethyl)phenyl]amino}-2-{[4-(methylsulfonyl)phenyl]amino}pyrimidine-5-carboxamide;

2-[(6-methoxy-2-methyl-1,2,3,4-tetrahydroisoquinolin-7-yl)amino]-4-{[7-(trifluoromethyl)-1,2,3,4-tetrahydroisoquinolin-5-yl]amino}pyrimidine-5-carboxamide;

4-({2-[(1S)-1-methoxyethyl]phenyl}amino)-2-[(6-methoxy-2-methyl-1,2,3,4-tetrahydroisoquinolin-7-yl)amino]pyrimidine-5-carboxamide;

4-{[2-(hydroxymethyl)phenyl]amino}-2-({4-[(methylsulfonyl)methyl]phenyl}-aminopyrimidine-5-carboxamide;

4-({2-[(1R)-1-methoxyethyl]phenyl}amino)-2-[(6-methoxy-2-methyl-1,2,3,4-tetrahydroisoquinolin-7-yl)amino]pyrimidine-5-carboxamide;

4-[(2-iodophenyl)amino]-2-[(6-methoxy-2-methyl-1,2,3,4-tetrahydroisoquinolin-7-yl)amino]pyrimidine-5-carboxamide;

4-[(3-bromophenyl)amino]-2-[(6-methoxy-2-methyl-1,2,3,4-tetrahydroisoquinolin-7-yl)amino]pyrimidine-5-carboxamide;

4-[(4-bromophenyl)amino]-2-[(6-methoxy-2-methyl-1,2,3,4-tetrahydroisoquinolin-7-yl)amino]pyrimidine-5-carboxamide;

4-[(2-chlorophenyl)amino]-2-[(6-methoxy-2-methyl-1,2,3,4-tetrahydroisoquinolin-7-yl)amino]pyrimidine-5-carboxamide;

4-[(2-fluorophenyl)amino]-2-[(6-methoxy-2-methyl-1,2,3,4-tetrahydroisoquinolin-7-yl)amino]pyrimidine-5-carboxamide;

4-{[3-(2-hydroxyethyl)phenyl]amino}-2-[(6-methoxy-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-((2-(2-oxooxazolidin-3-yl)phenyl)amino-pyrimidine-5-carboxamide;

2-[(6-methoxy-2-methyl-1,2,3,4-tetrahydroisoquinolin-7-yl)amino]-4-{[2-(1H-1,2,3-triazol-1-yl)phenyl]amino}pyrimidine-5-carboxamide;

2-[(6-methoxy-2-methyl-1,2,3,4-tetrahydroisoquinolin-7-yl)amino]-4-[(2-sulfamoylphenyl)amino]pyrimidine-5-carboxamide;

4-((1-ethyl-3-methyl-1H-pyrazol-5-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((1,3,5-trimethyl-1H-pyrazol-4-yl)amino)pyrimidine-5-carboxamide;

4-((3-cyclopropyl-1-methyl-1H-pyrazol-4-yl)amino)-2-((6-methoxy-2-methyl-1,2,3,4-tetrahydroisoquinolin-7-yl)amino)pyrimidine-5-carboxamide;

4-((3-cyclopropyl-1-methyl-1H-pyrazol-5-yl)amino)-2-((6-methoxy-2-methyl-1,2,3,4-tetrahydroisoquinolin-7-yl)amino)pyrimidine-5-carboxamide;

4-((3,5-dimethylisoxazol-4-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((2-methyl-2,4,5,6-tetrahydrocyclopenta[c]pyrazol-3-yl)amino)pyrimidine-5-carboxamide;

2-((6-methoxy-2-methyl-1,2,3,4-tetrahydroisoquinolin-7-yl)amino)-4-((2-(3-methylisoxazol-5-yl)phenyl)aminopyrimidine-5-carboxamide;

2-((6-methoxy-2-methyl-1,2,3,4-tetrahydroisoquinolin-7-yl)amino)-4-((1-methyl-3-(trifluoromethyl)-1H-pyrazol-4-yl)amino)pyrimidine-5-carboxamide;

4-((4-chloro-1-ethyl-1H-pyrazol-3-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((1-methyl-1H-pyrazol-5-yl)amino)pyrimidine-5-carboxamide;

4-((3-(tert-butyl)-1-methyl-1H-pyrazol-5-yl)amino)-2-((6-methoxy-2-methyl-1,2,3,4-tetrahydroisoquinolin-7-yl)amino)pyrimidine-5-carboxamide;

4-((1-(2-hydroxyethyl)-3-methyl-1H-pyrazol-5-yl)amino)-2-((6-methoxy-2-methyl-1,2,3,4-tetrahydroisoquinolin-7-yl)amino)pyrimidine-5-carboxamide;

4-((1-benzyl-3-methyl-1H-pyrazol-5-yl)amino)-2-((6-methoxy-2-methyl-1,2,3,4-tetrahydroisoquinolin-7-yl)amino)pyrimidine-5-carboxamide;

2-((6-methoxy-2-methyl-1,2,3,4-tetrahydroisoquinolin-7-yl)amino)-4-((3-methyl-1-phenyl-1H-pyrazol-5-yl)amino)pyrimidine-5-carboxamide;

4-((1-ethyl-4-methyl-1H-pyrazol-5-yl)amino)-2-((6-methoxy-2-methyl-1,2,3,4-tetrahydroisoquinolin-7-yl)amino)pyrimidine-5-carboxamide;

methyl 2-({5-carbamoyl-2-[(6-methoxy-2-methyl-1,2,3,4-tetrahydroisoquinolin-7-yl)amino]pyrimidin-4-yl}amino)benzoate 4-[(2-bromophenyl)amino]-2-[(5-carbamoyl-2-methoxyphenyl)amino]pyrimidine-5-carboxamide;

4-[(2-bromophenyl)amino]-2-[(2,3-dihydro-1-benzofuran-7-yl)amino]pyrimidine-5-carboxamide;

4-{[2-(1,1,1,3,3,3-hexafluoro-2-hydroxypropan-2-yl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(2,2,2-trifluoroethyl)phenyl]amino}pyrimidine-5-carboxamide;

2-[(6-methoxy-2-methyl-1,2,3,4-tetrahydroisoquinolin-7-yl)amino]-4-({2-[(morpholin-4-yl)methyl]phenyl}aminopyrimidine-5-carboxamide;

4-[(2-bromophenyl)amino]-2-{[4-(1-cyanocyclopropyl)phenyl]amino}pyrimidine-5-carboxamide;

4-{[2-(1,1-difluoroethyl)phenyl]amino}-2-[(6-methoxy-2-methyl-1,2,3,4-tetrahydroisoquinolin-7-yl)amino]pyrimidine-5-carboxamide;

4-[(2-ethynylphenyl)amino]-2-[(6-methoxy-2-methyl-1,2,3,4-tetrahydroisoquinolin-7-yl)amino]pyrimidine-5-carboxamide;

4-[(2-bromophenyl)amino]-2-[(1-oxo-1,3-dihydro-2-benzofuran-5-yl)amino]pyrimidine-5-carboxamide;

2-[(6-methoxy-2-methyl-1,2,3,4-tetrahydroisoquinolin-7-yl)amino]-4-[(2-methoxyphenyl)amino]pyrimidine-5-carboxamide;

4-[(2-bromophenyl)amino]-2-(phenylaminopyrimidine-5-carboxamide;

4-[(2-bromophenyl)amino]-2-[(1-oxo-3,4-dihydro-1H-2-benzopyran-7-yl)amino]pyrimidine-5-carboxamide;

4-[(2-bromophenyl)amino]-2-[(3,4-dihydro-1H-2-benzopyran-7-yl)amino]pyrimidine-5-carboxamide;

2-{[4-(1-cyanocyclopropyl)phenyl]amino}-4-{[2-(hydroxymethyl)phenyl]amino}pyrimidine-5-carboxamide;

2-((6-methoxy-2-methyl-1,2,3,4-tetrahydroisoquinolin-7-yl)amino)-4-((2-(tetrahydrofuran-2-yl)phenyl)amino-pyrimidine-5-carboxamide;

4-{[2-(1-methoxyethyl)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({2-[(propan-2-yl)oxy]phenyl}aminopyrimidine-5-carboxamide;

4-[(2-ethoxyphenyl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({2-[(trifluoromethyl) sulfanyl]phenyl}aminopyrimidine-5-carboxamide;

4-{[2-(difluoromethoxy)phenyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[2-(trifluoromethoxy)phenyl]amino}pyrimidine-5-carboxamide;

4-[(2-bromophenyl)amino]-2-({2-methoxy-4-[4-(morpholin-4-yl) piperidin-1-yl]phenyl}aminopyrimidine-5-carboxamide;

2-((6-methoxy-2-methyl-1,2,3,4-tetrahydroisoquinolin-7-yl)amino)-4-((2-(phenylcarbamoyl)phenyl)aminopyrimidine-5-carboxamide;

4-((2-(cyclopropylcarbamoyl)phenyl)amino)-2-((6-methoxy-2-methyl-1,2,3,4-tetrahydroisoquinolin-7-yl)amino)pyrimidine-5-carboxamide;

4-[(2-acetyl-1,2,3,4-tetrahydroisoquinolin-5-yl)amino]-2-[(6-methoxy-2-methyl-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-((2-methyl-1,2,3,4-tetrahydroisoquinolin-5-yl)amino)pyrimidine-5-carboxamide;

4-{[2-(2-hydroxypropan-2-yl)phenyl]amino}-2-[(6-methoxy-2-methyl-1,2,3,4-tetrahydroisoquinolin-7-yl)amino]pyrimidine-5-carboxamide;

2-((6-methoxy-2-methyl-1,2,3,4-tetrahydroisoquinolin-7-yl)amino)-4-(phenylaminopyrimidine-5-carbohydrazide;

10,28-difluoro-23-methoxy-2,4,8,18,29-pentaazapentacyclo-[16.5.3.2~9,12~.1~3,7~.0~21,25~]nonacosa-1(23),3(29),4,6,9,11,21,24,27-nonaene-6-carboxamide;

2-((1-cyclopropyl-6-methoxy-2-methyl-1,2,3,4-tetrahydroisoquinolin-7-yl)amino)-4-((2-(trifluoromethyl)phenyl)aminopyrimidine-5-carboxamide;

2-((1-cyclopropyl-6-methoxy-2-methyl-1,2,3,4-tetrahydroisoquinolin-7-yl)amino)-4-((2-(trifluoromethyl)phenyl)aminopyrimidine-5-carboxamide;

4-((2-fluoro-6-(trifluoromethyl)phenyl)amino)-2-((6'-methoxy-2'-methyl-2',3'-dihydro-1H-spiro[cyclopropane-1,4'-isoquinolin]-7'-yl)amino)pyrimidine-5-carboxamide;

4-((2-bromophenyl)amino)-2-((trans)-2-(1-methyl-1H-pyrazol-4-yl)cyclopropane-1-carboxamido)pyrimidine-5-carboxamide;

4-[(2-bromophenyl)amino]-2-{[(1R,3R)-2-ethyl-3-(1-methyl-1H-pyrazol-4-yl)cyclopropane-1-carbonyl]amino}pyrimidine-5-carboxamide;

4-((2-fluoro-6-(1-methoxyethyl)phenyl)amino)-2-((6-methoxy-2-methyl-1,2,3,4-tetrahydroisoquinolin-7-yl)amino)pyrimidine-5-carboxamide;

4-((2-fluoro-6-(1-hydroxyethyl)phenyl)amino)-2-((6-methoxy-2-methyl-1,2,3,4-tetrahydroisoquinolin-7-yl)amino)pyrimidine-5-carboxamide;

2-((6-methoxy-2,3-dimethyl-1,2,3,4-tetrahydroisoquinolin-7-yl)amino)-4-((2-(trifluoromethyl)phenyl)amino-pyrimidine-5-carboxamide;

2-((6-isopropyl-5-oxo-5,6,7,8-tetrahydro-4H-pyrazolo[1,5-d][1,4]diazepin-2-yl)amino)-4-((1,2,3,4-tetrahydroisoquinolin-5-yl)amino)pyrimidine-5-carboxamide;

4-[(1-oxo-1,2,3,4-tetrahydroisoquinolin-5-yl)amino]-2-(phenylaminopyrimidine-5-carboxamide;

2-{[4-(1-cyanocyclopropyl)phenyl]amino}-4-[(1-oxo-1,2,3,4-tetrahydroisoquinolin-5-yl)amino]pyrimidine-5-carboxamide;

2-{[3-(2-cyanopropan-2-yl)phenyl]amino}-4-[(1-oxo-1,2,3,4-tetrahydroisoquinolin-5-yl)amino]pyrimidine-5-carboxamide;

2-{[3-(1-cyanocyclopropyl)phenyl]amino}-4-[(1-oxo-1,2,3,4-tetrahydroisoquinolin-5-yl)amino]pyrimidine-5-carboxamide;

2-[(4-fluorophenyl)amino]-4-[(1-oxo-1,2,3,4-tetrahydroisoquinolin-5-yl)amino]pyrimidine-5-carboxamide;

2-[(3-chloro-4-fluorophenyl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[4-(trifluoromethyl)phenyl]amino}pyrimidine-5-carboxamide;

2-{[(1R)-1-(4-fluorophenyl)ethyl]amino}-4-[(1-oxo-1,2,3,4-tetrahydroisoquinolin-5-yl)amino]pyrimidine-5-carboxamide;

2-[(4-ethylphenyl)amino]-4-[(1-oxo-1,2,3,4-tetrahydroisoquinolin-5-yl)amino]pyrimidine-5-carboxamide;

2-[(3-fluorophenyl)amino]-4-[(1-oxo-1,2,3,4-tetrahydroisoquinolin-5-yl)amino]pyrimidine-5-carboxamide;

2-[(2,3-dimethylphenyl)amino]-4-[(1-oxo-1,2,3,4-tetrahydroisoquinolin-5-yl)amino]pyrimidine-5-carboxamide;

2-[(4-cyclopropyl-3-methylphenyl)amino]-4-[(1-oxo-1,2,3,4-tetrahydroisoquinolin-5-yl)amino]pyrimidine-5-carboxamide;

2-[(4-cyclopropylphenyl)amino]-4-[(1-oxo-1,2,3,4-tetrahydroisoquinolin-5-yl)amino]pyrimidine-5-carboxamide;

2-[(naphthalen-1-yl)amino]-4-[(1-oxo-1,2,3,4-tetrahydroisoquinolin-5-yl)amino]pyrimidine-5-carboxamide;

2-[(2-ethylphenyl)amino]-4-[(1-oxo-1,2,3,4-tetrahydroisoquinolin-5-yl)amino]pyrimidine-5-carboxamide;

2-{[3-(difluoromethoxy)phenyl]amino}-4-[(1-oxo-1,2,3,4-tetrahydroisoquinolin-5-yl)amino]pyrimidine-5-carboxamide;

2-[(2,4-difluorophenyl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[3-(trifluoromethyl)phenyl]amino}pyrimidine-5-carboxamide;

2-[(3-methylphenyl)amino]-4-[(1-oxo-1,2,3,4-tetrahydroisoquinolin-5-yl)amino]pyrimidine-5-carboxamide;

2-[(3-tert-butylphenyl)amino]-4-[(1-oxo-1,2,3,4-tetrahydroisoquinolin-5-yl)amino]pyrimidine-5-carboxamide;

2-{[3-chloro-4-(difluoromethoxy)phenyl]amino}-4-[(1-oxo-1,2,3,4-tetrahydroisoquinolin-5-yl)amino]pyrimidine-5-carboxamide;

2-[(3,5-dimethylphenyl)amino]-4-[(1-oxo-1,2,3,4-tetrahydroisoquinolin-5-yl)amino]pyrimidine-5-carboxamide;

2-{[1-(2-fluorophenyl)cyclopropyl]amino}-4-[(1-oxo-1,2,3,4-tetrahydroisoquinolin-5-yl)amino]pyrimidine-5-carboxamide;

2-{[(2,6-dichlorophenyl)methyl]amino}-4-[(1-oxo-1,2,3,4-tetrahydroisoquinolin-5-yl)amino]pyrimidine-5-carboxamide;

2-[(3-cyclopropylphenyl)amino]-4-[(1-oxo-1,2,3,4-tetrahydroisoquinolin-5-yl)amino]pyrimidine-5-carboxamide;

2-[(3-chloro-2-methylphenyl)amino]-4-[(1-oxo-1,2,3,4-tetrahydroisoquinolin-5-yl)amino]pyrimidine-5-carboxamide;

2-{[2-(difluoromethoxy)phenyl]amino}-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[3-(propan-2-yl)phenyl]amino}pyrimidine-5-carboxamide;

2-{[3-methyl-5-(trifluoromethyl)phenyl]amino}-4-[(1-oxo-1,2,3,4-tetrahydroisoquinolin-5-yl)amino]pyrimidine-5-carboxamide;

2-[(4-fluoro-3-methylphenyl)amino]-1-oxo-1,2,3,4-tetrahydroisoquinolin-5-yl)amino]pyrimidine-5-carboxamide;

2-[(3,5-difluorophenyl)amino]-4-[(1-oxo-1,2,3,4-tetrahydroisoquinolin-5-yl)amino]pyrimidine-5-carboxamide;

2-{[2-methyl-5-(trifluoromethyl)phenyl]amino}-4-[(1-oxo-1,2,3,4-tetrahydroisoquinolin-5-yl)amino]pyrimidine-5-carboxamide;

2-[(5-chloro-2-methoxyphenyl)amino]-4-[(1-oxo-1,2,3,4-tetrahydroisoquinolin-5-yl)amino]pyrimidine-5-carboxamide;

2-[(2,3-dihydro-1H-inden-4-yl)amino]-4-[(1-oxo-1,2,3,4-tetrahydroisoquinolin-5-yl)amino]pyrimidine-5-carboxamide;

2-[(4-tert-butylphenyl)amino]-4-[(1-oxo-1,2,3,4-tetrahydroisoquinolin-5-yl)amino]pyrimidine-5-carboxamide;

2-[(2,5-dimethylphenyl)amino]-4-[(1-oxo-1,2,3,4-tetrahydroisoquinolin-5-yl)amino]pyrimidine-5-carboxamide;

2-{[4-fluoro-3-(trifluoromethyl)phenyl]amino}-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-({[4-(trifluoromethyl)phenyl]-methyl}aminopyrimidine-5-carboxamide;

2-[(2,3-difluoro-4-methylphenyl)amino]-4-[(1-oxo-1,2,3,4-tetrahydroisoquinolin-5-yl)amino]pyrimidine-5-carboxamide;

2-[(3,5-difluoro-4-methoxyphenyl)amino]-4-[(1-oxo-1,2,3,4-tetrahydroisoquinolin-5-yl)amino]pyrimidine-5-carboxamide;

2-[(4-fluoro-2-methoxyphenyl)amino]-4-[(1-oxo-1,2,3,4-tetrahydroisoquinolin-5-yl)amino]pyrimidine-5-carboxamide;

2-{[2-fluoro-3-(trifluoromethyl)phenyl]amino}-4-[(1-oxo-1,2,3,4-tetrahydroisoquinolin-5-yl)amino]pyrimidine-5-carboxamide;

2-[(1-benzothiophen-4-yl)amino]-4-[(1-oxo-1,2,3,4-tetrahydroisoquinolin-5-yl)amino]pyrimidine-5-carboxamide;

4-[(1-oxo-1,2,3,4-tetrahydroisoquinolin-5-yl)amino]-2-{[4-(2,2,2-trifluoroethyl)phenyl]-amino}pyrimidine-5-carboxamide;

2-[(2-methoxypyridin-3-yl)amino]-4-[(1-oxo-1,2,3,4-tetrahydroisoquinolin-5-yl)amino]pyrimidine-5-carboxamide;

4-(cycloheptylamino)-2-[(6-methoxy-2-methyl-1,2,3,4-tetrahydroisoquinolin-7-yl)amino]pyrimidine-5-carboxamide;

4-(cyclohexylamino)-2-[(6-methoxy-2-methyl-1,2,3,4-tetrahydroisoquinolin-7-yl)amino]pyrimidine-5-carboxamide;

4-(cyclopentylamino)-2-[(6-methoxy-2-methyl-1,2,3,4-tetrahydroisoquinolin-7-yl)amino]pyrimidine-5-carboxamide;

4-[(bicyclo[1.1.1]pentan-2-yl)amino]-2-[(6-methoxy-2-methyl-1,2,3,4-tetrahydroisoquinolin-7-yl)amino]pyrimidine-5-carboxamide;

4-[(cis-4-aminocyclohexyl)amino]-2-[(6-methoxy-2-methyl-1,2,3,4-tetrahydroisoquinolin-7-yl)amino]pyrimidine-5-carboxamide;

4-{[(1R)-1-cyclohexylethyl]amino}-2-[(6-methoxy-2-methyl-1,2,3,4-tetrahydroisoquinolin-7-yl)amino]pyrimidine-5-carboxamide;

4-{[(1S)-1-cyclohexylethyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(3R,4S)-4-(methylsulfanyl)oxolan-3-yl]amino}pyrimidine-5-carboxamide;

4-{[(2,3-difluorophenyl)methyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(4aR,7aR)-octahydro-1H-cyclopenta[b]pyridin-5-yl]amino}pyrimidine-5-carboxamide;

4-[(1-cyclopropylpyrrolidin-3-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(3-phenylcyclopentyl)amino]pyrimidine-5-carboxamide;

methyl 7-({5-carbamoyl-2-[(6-methoxy-2-methyl-1,2,3,4-tetrahydroisoquinolin-7-yl)amino]pyrimidin-4-yl}amino)bicyclo[3.3.1]nonane-3-carboxylate;

4-{[(1S,4R)-bicyclo[2.2.1]heptan-2-yl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(tricyclo[4.2.1.0~2,5~]nonan-3-yl)amino]pyrimidine-5-carboxamide;

2-[(6-methoxy-2-methyl-1,2,3,4-tetrahydroisoquinolin-7-yl)amino]-4-{[4-(trifluoromethyl)cyclohexyl]amino}pyrimidine-5-carboxamide;

4-{[cis-4-(dimethylamino)cyclohexyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({[2-(trifluoromethoxy)phenyl]methyl}aminopyrimidine-5-carboxamide;

4-{[(1S)-1-(2,3-difluorophenyl)ethyl]amino}-2-[(6-methoxy-2-methyl-1,2,3,4-tetrahydroisoquinolin-7-yl)amino]pyrimidine-5-carboxamide;

4-{[(1R)-1-(2,3-difluorophenyl)ethyl]amino}-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-({[2-(trifluoromethyl)phenyl]methyl}aminopyrimidine-5-carboxamide;

2-[(6-methoxy-2-methyl-1,2,3,4-tetrahydroisoquinolin-7-yl)amino]-4-({1-[2-(trifluoromethyl)phenyl]ethyl}aminopyrimidine-5-carboxamide;

4-{[(2-ethoxyphenyl)methyl]amino}-2-[(6-methoxy-2-methyl-1,2,3,4-tetrahydroisoquinolin-7-yl)amino]pyrimidine-5-carboxamide;

4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

4-[(6-fluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-{[(1R,3r,5S)-8-methyl-8-azabicyclo[3.2.1]octan-3-yl]amino}pyrimidine-5-carboxamide;

4-[(8-azabicyclo[3.2.1]octan-3-yl)amino]-2-[(6-methoxy-2-methyl-1,2,3,4-tetrahydroisoquinolin-7-yl)amino]pyrimidine-5-carboxamide;
4-{[(1R,2S)-2-(methoxymethyl)cyclopentyl]amino}-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-[(trans-4-methylcyclohexyl)amino]pyrimidine-5-carboxamide;
4-[(3-azabicyclo[3.2.1]octan-8-yl)amino]-2-[(6-methoxy-2-methyl-1,2,3,4-tetrahydroisoquinolin-7-yl)amino]pyrimidine-5-carboxamide;
4-[(4-methoxycyclohexyl)amino]-2-[(6-methoxy-2-methyl-1,2,3,4-tetrahydroisoquinolin-7-yl)amino]pyrimidine-5-carboxamide;
4-{[(1R,2R)-2-(hydroxymethyl)cyclohexyl]amino}-2-[(6-methoxy-2-methyl-1,2,3,4-tetrahydroisoquinolin-7-yl)amino]pyrimidine-5-carboxamide;
4-{[(1R,2R)-2-(difluoromethyl)cyclohexyl]amino}-2-[(6-methoxy-2-methyl-1,2,3,4-tetrahydroisoquinolin-7-yl)amino]pyrimidine-5-carboxamide;
4-[(7-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-({[3-(trifluoromethyl)phenyl]methyl}aminopyrimidine-5-carboxamide;
4-(benzylamino)-2-[(6-methoxy-2-methyl-1,2,3,4-tetrahydroisoquinolin-7-yl)amino]pyrimidine-5-carboxamide;
4-{[(1S)-2,3-dihydro-1H-inden-1-yl]amino}-2-[(6-methoxy-2-methyl-1,2,3,4-tetrahydroisoquinolin-7-yl)amino]pyrimidine-5-carboxamide;
4-[(3,3-difluorocyclopentyl)amino]-2-[(6-methoxy-2-methyl-1,2,3,4-tetrahydroisoquinolin-7-yl)amino]pyrimidine-5-carboxamide;
4-[(cis-4-ethynylcyclohexyl)amino]-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-{[(1R,2R)-2-(prop-2-yn-1-yl)cyclopentyl]amino}pyrimidine-5-carboxamide;
2-[(6-methoxy-2-methyl-1,2,3,4-tetrahydroisoquinolin-7-yl)amino]-4-{[(1R,2S)-2-methylcyclohexyl]amino}pyrimidine-5-carboxamide;
4-{[(1R,2R)-2-(2-hydroxypropan-2-yl)cyclohexyl]amino}-2-[(6-methoxy-2-methyl-1,2,3,4-tetrahydroisoquinolin-7-yl)amino]pyrimidine-5-carboxamide;
4-{[(1S)-2-hydroxy-1-phenylethyl]amino}-2-[(6-methoxy-2-methyl-1,2,3,4-tetrahydroisoquinolin-7-yl)amino]pyrimidine-5-carboxamide;
4-{[(1S)-2-hydroxy-1-phenylethyl]amino}-2-[(1-oxo-1,3-dihydro-2-benzofuran-5-yl)amino]pyrimidine-5-carboxamide;
2-[(6-methoxy-2-methyl-1,2,3,4-tetrahydroisoquinolin-7-yl)amino]-4-{[(2,3,6-trifluorophenyl)methyl]amino}pyrimidine-5-carboxamide;
4-{[(1R)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide;
4-{[(1S)-6-fluoro-1,2,3,4-tetrahydronaphthalen-1-yl]amino}-2-[(6-methoxy-2-methyl-1,2,3,4-tetrahydroisoquinolin-7-yl)amino]pyrimidine-5-carboxamide;
4-{[(1S)-1-cyclohexyl-2-hydroxyethyl]amino}-2-[(6-methoxy-2-methyl-1,2,3,4-tetrahydroisoquinolin-7-yl)amino]pyrimidine-5-carboxamide;
4-{[(1S)-1-cyclohexyl-2-hydroxyethyl]amino}-2-[(1-methyl-1H-pyrazol-4-yl)amino]pyrimidine-5-carboxamide;
4-[(5,6-difluoro-2,3-dihydro-1H-inden-1-yl)amino]-2-{[1-(piperidin-4-yl)-1H-pyrazol-4-yl]amino}pyrimidine-5-carboxamide;
4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;
4-[(5,6-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;
4-[(5,6-difluoro-2,3-dihydro-1H-inden-1-yl)amino]-2-[(1,2,3,4-tetrahydroisoquinolin-7-yl)amino]pyrimidine-5-carboxamide;
4-[(5,6-difluoro-2,3-dihydro-1H-inden-1-yl)amino]-2-[(6-fluoro-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-{[(pyridin-4-yl)methyl]amino}pyrimidine-5-carboxamide;
4-{[(imidazo[1,2-a]pyridin-3-yl)methyl]amino}-2-[(6-methoxy-2-methyl-1,2,3,4-tetrahydroisoquinolin-7-yl)amino]pyrimidine-5-carboxamide;
4-{[(2-hydroxyphenyl)methyl]amino}-2-[(6-methoxy-2-methyl-1,2,3,4-tetrahydroisoquinolin-7-yl)amino]pyrimidine-5-carboxamide;
4-{[(3-cyanophenyl)methyl]amino}-2-[(6-methoxy-2-methyl-1,2,3,4-tetrahydroisoquinolin-7-yl)amino]pyrimidine-5-carboxamide;
4-{[(4-cyanophenyl)methyl]amino}-2-[(6-methoxy-2-methyl-1,2,3,4-tetrahydroisoquinolin-7-yl)amino]pyrimidine-5-carboxamide;
2-[(6-methoxy-2-methyl-1,2,3,4-tetrahydroisoquinolin-7-yl)amino]-4-{[(1,3-thiazol-2-yl)methyl]amino}pyrimidine-5-carboxamide;
2-[(6-methoxy-2-methyl-1,2,3,4-tetrahydroisoquinolin-7-yl)amino]-4-({[4-(trifluoromethyl)phenyl]methyl}aminopyrimidine-5-carboxamide;
4-{[(1R,2R)-2-(hydroxymethyl)-2,3-dihydro-1H-inden-1-yl]amino}-2-[(6-methoxy-2-methyl-1,2,3,4-tetrahydroisoquinolin-7-yl)amino]pyrimidine-5-carboxamide;
4-{[(1S,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;
4-{[(1R,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;
4-{[(1R,2R)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;
4-{[(1S,2S)-2-hydroxy-2,3-dihydro-1H-inden-1-yl]amino}-2-[(6-methoxy-2-methyl-1,2,3,4-tetrahydroisoquinolin-7-yl)amino]pyrimidine-5-carboxamide;
4-{[(1R)-2,3-dihydro-1H-inden-1-yl]amino}-2-[(6-methoxy-2-methyl-1,2,3,4-tetrahydroisoquinolin-7-yl)amino]pyrimidine-5-carboxamide;
4-[(5,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;
4-[(6-methoxy-2,3-dihydro-1H-inden-1-yl)amino]-2-[(6-methoxy-2-methyl-1,2,3,4-tetrahydroisoquinolin-7-yl)amino]pyrimidine-5-carboxamide;
4-[(4,7-difluoro-2,3-dihydro-1H-inden-1-yl)amino]-2-[(6-methoxy-2-methyl-1,2,3,4-tetrahydroisoquinolin-7-yl)amino]pyrimidine-5-carboxamide;

2-[(6-methoxy-2-methyl-1,2,3,4-tetrahydroisoquinolin-7-yl)amino]-4-[(6-methyl-2,3-dihydro-1H-inden-1-yl)amino]pyrimidine-5-carboxamide; and 2-[(6-methoxy-2-methyl-1,2,3,4-tetrahydroisoquinolin-7-yl)amino]-4-{[(piperidin-4-yl)methyl]amino}pyrimidine-5-carboxamide;

or a pharmaceutically acceptable salt thereof.

9. A pharmaceutical composition which comprises an inert carrier and a compound of claim 1, or a pharmaceutically acceptable salt thereof.

10. A method for treating an HPK1-associated disease or disorder in a mammalian subject which comprises administering to the subject an effective amount of a compound of claim 1, or a pharmaceutically acceptable salt thereof.

11. A method for treating an HPK1-associated disease or disorder in a mammalian subject which comprises administering to the subject an effective amount of a compound of claim 1, or a pharmaceutically acceptable salt thereof in combination with one or more second anti-cancer agent selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents.

12. The method of claim 10 wherein the HPK1-associated disease or disorder is a cancer, metastasis, inflammation and auto-immune pathogenesis.

13. The method of claim 12, wherein the cancer is liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma or diffuse large B-cell lymphoma.

* * * * *